US007968536B2

(12) United States Patent
Cossrow et al.

(10) Patent No.: US 7,968,536 B2
(45) Date of Patent: Jun. 28, 2011

(54) HETEROCYCLIC COMPOUNDS USEFUL AS RAF KINASE INHIBITORS

(75) Inventors: Jennifer Cossrow, San Mateo, CA (US); Bing Guan, Needham, MA (US); Alexey Ishchenko, Somerville, MA (US); John Howard Jones, Framingham, MA (US); Gnanasambandam Kumaravel, Westford, MA (US); Alexey Lugovskoy, Woburn, MA (US); Hairuo Peng, Needham, MA (US); Noel Powell, Westford, MA (US); Brian C. Raimundo, San Francisco, CA (US); Hiroko Tanaka, Foster City, CA (US); Jeffrey Vessels, Marlborough, MA (US); Thomas Wynn, Salem, MA (US); Zhili Xin, Lexington, MA (US)

(73) Assignees: Millennium Pharmaceuticals, Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 365 days.

(21) Appl. No.: 12/164,905

(22) Filed: Jun. 30, 2008

(65) Prior Publication Data

US 2009/0005359 A1    Jan. 1, 2009

Related U.S. Application Data

(60) Provisional application No. 60/947,319, filed on Jun. 29, 2007.

(51) Int. Cl.
*C07D 413/12*        (2006.01)
*C07D 413/14*        (2006.01)
*C07D 417/12*        (2006.01)
*C07D 417/14*        (2006.01)
*A61K 31/505*        (2006.01)

(52) U.S. Cl. ............... 514/212.06; 514/221; 514/234.2; 514/252.03; 514/260.1; 514/261.1; 514/262.1; 514/263.21; 514/265.1; 544/117; 544/118; 544/238; 544/254; 544/255; 544/262; 544/264; 544/278; 544/280; 540/502; 540/521

(58) Field of Classification Search .......... 540/502, 540/521; 544/117, 118, 238, 254, 255, 262, 544/264, 278, 280; 514/212.06, 221, 234.2, 514/252.03, 260.1, 261.1, 262.1, 263.21, 514/265.1
See application file for complete search history.

(56) References Cited

U.S. PATENT DOCUMENTS

| | | | |
|---|---|---|---|
| 5,563,158 A | 10/1996 | DeGrado et al. | |
| 5,691,329 A | 11/1997 | DeGrado et al. | |
| 5,760,028 A | 6/1998 | Jadhav et al. | |
| 5,840,917 A | 11/1998 | Oi et al. | |
| 5,872,136 A | 2/1999 | Anthony et al. | |
| 5,877,182 A | 3/1999 | Nargund et al. | |
| 6,017,925 A | 1/2000 | Duggan | |
| 6,127,382 A | 10/2000 | Beard et al. | |
| 6,214,834 B1 | 4/2001 | Jadhav et al. | |
| 6,242,470 B1 | 6/2001 | Baxter et al. | |
| 6,284,757 B1 | 9/2001 | Sanner | |
| 6,288,078 B1 | 9/2001 | Walsh et al. | |
| 6,369,227 B1 | 4/2002 | Lam et al. | |
| 6,403,583 B1 | 6/2002 | Lam et al. | |
| 6,500,855 B1 | 12/2002 | Lam et al. | |
| 6,602,871 B2 | 8/2003 | Lam et al. | |
| 6,632,823 B1 | 10/2003 | Vernier et al. | |
| 7,709,500 B2* | 5/2010 | Alcaraz et al. ............... 514/318 |
| 2003/0119811 A1* | 6/2003 | Liverton et al. .......... 514/211.08 |
| 2004/0014765 A1 | 1/2004 | Boyle et al. | |
| 2004/0048866 A1 | 3/2004 | Kolasa et al. | |
| 2004/0082627 A1 | 4/2004 | Darrow et al. | |
| 2004/0097531 A1 | 5/2004 | Ledeboer et al. | |
| 2004/0106631 A1 | 6/2004 | Bernardelli et al. | |
| 2005/0070538 A1 | 3/2005 | Cheng et al. | |
| 2005/0171105 A1 | 8/2005 | Chopiuk et al. | |
| 2006/0035908 A1* | 2/2006 | Lew et al. ................. 514/260.1 |
| 2006/0183747 A1 | 8/2006 | Freyne et al. | |
| 2006/0205721 A1 | 9/2006 | Freyne et al. | |
| 2007/0015207 A1 | 1/2007 | Ludovici et al. | |
| 2009/0036419 A1 | 2/2009 | Chen et al. | |

FOREIGN PATENT DOCUMENTS

| | | |
|---|---|---|
| DE | 10328999 | 1/2005 |
| EP | 0847992 | 6/1998 |
| EP | 1547585 | 6/2005 |
| GB | 2361474 | 10/2001 |
| JP | 11209366 | 8/1999 |
| JP | 2004161716 | 6/2004 |
| JP | 2004339159 | 12/2004 |
| WO | WO-9723480 | 7/1997 |
| WO | WO-9736901 | 10/1997 |
| WO | WO-9842323 | 10/1998 |
| WO | WO-0053602 | 9/2000 |
| WO | WO-0058300 | 10/2000 |
| WO | WO-0138309 | 5/2001 |
| WO | WO-0198294 | 12/2001 |

(Continued)

OTHER PUBLICATIONS

Smith et al., "Recent Advances in the Research and Development of RAF Kinase Inhibitors," Current Topics in Medicinal Chemistry 6(11):1071-1089 (2006).

International Search Report for PCT/US2008/068789, mailed on Jun. 23, 2009.

Marchal et al., Bull. Soc. Chim. Belg. 69:177-193 (1960).

(Continued)

*Primary Examiner* — Bruck Kifle
(74) *Attorney, Agent, or Firm* — Choate, Hall & Stewart LLP; Andrea L. C. Robidoux; Emilie Porter Huck

(57) ABSTRACT

The present invention provides compounds useful as inhibitors of protein kinase. The present invention also provides compositions thereof, and methods of treating Raf-mediated diseases.

31 Claims, No Drawings

FOREIGN PATENT DOCUMENTS

| | | |
|---|---|---|
| WO | WO-02080928 | 10/2002 |
| WO | WO-03055491 | 7/2003 |
| WO | WO-2005066156 | 7/2005 |
| WO | WO-2005072733 | 8/2005 |
| WO | WO-2006045010 | 4/2006 |
| WO | WO-2006065703 | 6/2006 |
| WO | WO-2006074057 | 7/2006 |
| WO | WO-2006120573 | 11/2006 |
| WO | WO-2010078408 | 7/2010 |

OTHER PUBLICATIONS

Plouvier et al., "Synthesis of two new thiazole-containing oligopeptides as potential DNA minor groove binding analogs of netropsin," Heterocycles 32:693-701 (1991).

Frimurer et al., "A physicogenetic method to assign ligand-binding relationships between 7TM receptors," Bioorg. Med. Chem. 13:3707-3712 (2005).

* cited by examiner

HETEROCYCLIC COMPOUNDS USEFUL AS RAF KINASE INHIBITORS

CROSS-REFERENCE TO RELATED APPLICATIONS

The present invention claims priority to U.S. provisional patent application Ser. No. 60/947,319, filed Jun. 29, 2007, the entirety of which is hereby incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

Cancer results from the deregulation of the normal processes that control cell division, differentiation and apoptotic cell death. Protein kinases play a critical role in this regulatory process. A partial non-limiting list of such kinases includes ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, p38, PDGFR, PIK, PKC, PYK2, ros, $tie_1$, $tie_2$, TRK, Yes and Zap70. In mammalian biology, such protein kinases comprise mitogen activated protein kinase (MAPK) signalling pathways. MAPK signalling pathways are inappropriately activated by a variety of common disease-associated mechanisms such as mutation of ras genes and deregulation of growth factor receptors (Magnuson et al., Seminars in Cancer Biology; 1994 (5), 247-252).

Additionally, protein kinases have been implicated as targets in central nervous system disorders (such as Alzheimer's), inflammatory disorders (such as psoriasis, arthritis), bone diseases (such as osteoporosis), atherosclerosis, restenosis, thrombosis, metabolic disorders (such as diabetes) and infectious diseases (such as viral and fungal infections).

One of the most commonly studied pathways involving kinase regulation is intracellular signalling from cell surface receptors to the nucleus. One example of this pathway includes a cascade of kinases in which members of the Growth Factor receptor Tyrosine Kinases (such as EGF-R, PDGF-R, VEGF-R, IGF1-R, the Insulin receptor) deliver signals through phosphorylation to other kinases such as Src Tyrosine kinase, and the Raf, Mek and Erk serine/threonine kinase families. Each of these kinases is represented by several family members, which play related, but functionally distinct roles. The loss of regulation of the growth factor signalling pathway is a frequent occurrence in cancer as well as other disease states.

The signals mediated by kinases have also been shown to control growth, death and differentiation in the cell by regulating the processes of the cell cycle. Progression through the eukaryotic cell cycle is controlled by a family of kinases called cyclin dependent kinases (CDKs). The regulation of CDK activation is complex, but requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer.

Raf protein kinases are key components of signal transduction pathways by which specific extracellular stimuli elicit precise cellular responses in mammalian cells. Activated cell surface receptors activate ras/rap proteins at the inner aspect of the plasma membrane which in turn recruit and activate Raf proteins. Activated Raf proteins phosphorylate and activate the intracellular protein kinases MEK1 and MEK2. In turn, activated MEKs catalyze phosphorylation and activation of p42/p44 mitogen-activated protein kinase (MAPK). Various cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g., histiocytic lymphoma, lung adenocarcinoma, small cell lung cancer, and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery, and/or during childbirth.

Accordingly, there is a great need to develop compounds useful as inhibitors of protein kinases. In particular, it would be desirable to develop compounds that are useful as Raf inhibitors.

SUMMARY OF THE INVENTION

It has now been found that compounds of this invention, and pharmaceutically acceptable compositions thereof, are effective as inhibitors of one or more protein kinases. Such compounds are of formula I:

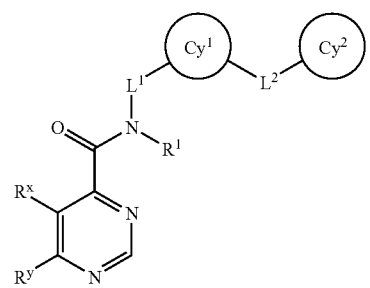

or a pharmaceutically acceptable salt thereof, wherein each of $R^x$, $R^y$, $R^1$, $L^1$, $L^2$, $Cy^1$, and $Cy^2$ are as defined in classes and subclasses herein, and pharmaceutical compositions thereof, as described generally and in subclasses herein, which compounds are useful as inhibitors of protein kinase (e.g., Raf), and thus are useful, for example, for the treatment of Raf-mediated diseases.

In certain other embodiments, the invention provides pharmaceutical compositions comprising a compound of the invention, wherein the compound is present in an amount effective to inhibit Raf activity. In certain other embodiments, the invention provides pharmaceutical compositions comprising a compound of the invention and optionally further comprising an additional therapeutic agent. In yet other embodiments, the additional therapeutic agent is an agent for the treatment of cancer.

In yet another aspect, the present invention provides methods for inhibiting kinase (e.g., Raf) activity in a patient or a biological sample, comprising administering to said patient, or contacting said biological sample with, an effective inhibitory amount of a compound of the invention. In still another aspect, the present invention provides methods for treating any disorder involving Raf activity, comprising administering to a subject in need thereof a therapeutically effective amount of a compound of the invention.

DETAILED DESCRIPTION OF CERTAIN EMBODIMENTS OF THE INVENTION

1. General Description of Compounds of the Invention

In certain embodiments, the present invention provides a compound of formula I:

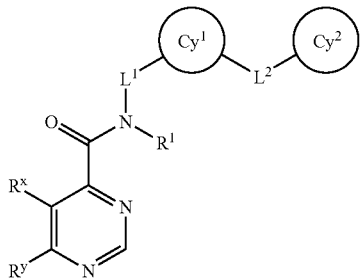

I or a pharmaceutically acceptable salt thereof, wherein:

$Cy^1$ is an optionally substituted phenyl or 5-6 membered saturated, partially unsaturated, or aromatic ring having 1-3 heteroatoms independently selected from nitrogen, oxygen, or sulfur;

$Cy^2$ is an optionally substituted 5-14 membered saturated, partially unsaturated, or aromatic monocyclic, bicyclic, or tricyclic ring having 0-4 heteroatoms, independently selected from nitrogen, oxygen, or sulfur;

$L^1$ is a direct bond or an optionally substituted, straight or branched $C_{1-6}$ alkylene chain;

$L^2$ is a direct bond, or is an optionally substituted, straight or branched $C_{1-6}$ alkylene chain wherein 1 or 2 methylene units of $L^2$ are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or a 3-6 membered cycloalkylene;

each R is independently hydrogen or an optionally substituted $C_{1-6}$ aliphatic group;

$R^1$ is hydrogen or an optionally substituted $C_{1-6}$ aliphatic group; and $R^x$ and $R^y$ are taken together with their intervening atoms to form:
(a) a 5-membered partially unsaturated or aromatic fused ring having 0-3 heteroatoms independently selected from nitrogen, oxygen, or sulfur, or
(b) a 7-membered partially unsaturated fused ring having 0-3 heteroatoms independently selected from nitrogen, oxygen, or sulfur, wherein any substitutable carbon on the ring formed by $R^x$ and $R^y$ is optionally substituted with —$R^2$, oxo, -halo, —NO$_2$, —CN, —OR$^2$, —SR$^2$, —N(R$^3$)$_2$, —C(O)R$^2$, —CO$_2$R$^2$, C(O)C(O)R$^2$, —C(O)CH$_2$C (O)R$^2$, —S(O)R$^2$, —S(O)$_2$R$^2$, C(O)N(R$^3$)$_2$, —SO$_2$N (R$^3$)$_2$, —OC(O)R$^2$, —N(R$^3$)C(O)R$^2$, —N(R$^3$) N(R$^3$)$_2$, —C=NN(R$^3$)$_2$, —C=NOR$^2$, —N(R$^3$)C(O) N(R$^3$)$_2$, —N(R$^3$)SO$_2$N(R$^3$)$_2$, —N(R$^3$)SO$_2$R$^2$, or —OC(O)N(R$^3$)$_2$, and wherein any substitutable nitrogen on the ring formed by $R^x$ and $R^y$ is optionally substituted with —$R^2$, —C(O) R$^2$, —CO$_2$R$^2$, C(O)C(O)R$^2$, —C(O)CH$_2$C(O)R$^2$, —S(O)R$^2$, —S(O)$_2$R$^2$, —C(O)N(R$^3$)$_2$, —SO$_2$N(R$^3$)$_2$, —OC(O)R$^2$, or —OC(O)N(R$^3$)$_2$;

each $R^2$ is independently hydrogen or an optionally substituted group selected from $C_{1-6}$ aliphatic, a $C_{1-10}$ monocyclic or bicyclic aryl ring, or a 5-10 membered saturated, partially unsaturated, or aromatic monocyclic or bicyclic ring having 1-4 heteroatoms independently selected from nitrogen, oxygen, or sulfur; and each $R^3$ is independently $R^2$, or two $R^3$ on the same nitrogen are taken together with the nitrogen to form an optionally substituted 5-8 membered saturated, partially unsaturated, or aromatic ring having 1-4 heteroatoms independently selected from nitrogen, oxygen, or sulfur.

Compounds of this invention include those generally set forth above and described specifically herein, and are illustrated in part by the various classes, subgenera and species disclosed herein. Additionally, the present invention provides pharmaceutically acceptable derivatives of the compounds of the invention, and methods of treating a subject using these compounds, pharmaceutical compositions thereof, or either of these in combination with one or more additional therapeutic agents.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, compounds of the invention and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein, may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

As used herein a "direct bond" or "covalent bond" refers to a single, double or triple bond. In certain embodiments, a "direct bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

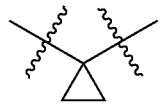

In other embodiments, a cycloalkylene group is a 1,2-cycloalkylene group or a 1,3-cycloalkylene group. Exemplary 1,2-cycloalkylene groups include

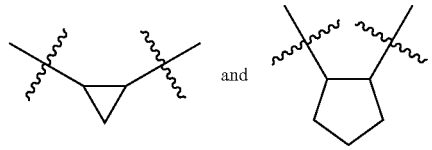

The term "alkyl," as used herein, refers to saturated, straight- or branched-chain hydrocarbon radicals derived from an aliphatic moiety containing between one and six carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl(propargyl), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As defined herein, an alkylene chain also can be optionally replaced by a functional group. An alkylene chain is "replaced" by a functional group when an internal methylene unit is replaced with the functional group. Examples of suitable "interrupting functional groups" are described in the specification and claims herein.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}R°$; —O—$(CH_2)_{0-4}C(O)$OR°; —$(CH_2)_{0-4}CH(OR°)_2$; —$(CH_2)_{0-4}SR°$; —$(CH_2)_{0-4}$Ph, which may be substituted with R°; —$(CH_2)_{0-4}O(CH_2)_{0-4}$Ph which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)$R°; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$;

—(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$R$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$aliphatic, —CH$_2$Ph, —O(CH$_2$)0-1Ph, or a 5-6-membered saturated, partially unsaturated, or aryl ring having 0-4 heteroatoms independently selected from nitrogen, oxygen, or sulfur.

3. Description of Exemplary Compounds

As defined above, $R^x$ and $R^y$ are taken together with their intervening atoms to form: (a) a 5-membered partially unsaturated or aromatic fused ring having 0-3 heteroatoms independently selected from nitrogen, oxygen, or sulfur, or (b) a 7-membered partially unsaturated fused ring having 0-3 heteroatoms independently selected from nitrogen, oxygen, or sulfur, wherein any substitutable carbon on the ring formed by $R^x$ and $R^y$ is optionally substituted with —R$^2$, oxo, -halo, —NO$_2$, —CN, —OR$^2$, —SR$^2$, —N(R$^3$)$_2$, —C(O)R$^2$, —CO$_2$R$^2$, C(O)C(O)R$^2$, —C(O)CH$_2$C(O)R$^2$, —S(O)R$^2$, —S(O)$_2$R$^2$, —C(O)N(R$^3$)$_2$, —SO$_2$N(R$^3$)$_2$, —OC(O)R$^2$, —N(R$^3$)C(O)R$^2$, —N(R$^3$)N(R$^3$)$_2$, —C=NN(R$^3$)$_2$, —C=NOR$^2$, —N(R$^3$)C(O)N(R$^3$)$_2$, —N(R$^3$)SO$_2$N(R$^3$)$_2$, —N(R$^3$)SO$_2$R$^2$, or —OC(O)N(R$^3$)$_2$, wherein any substitutable nitrogen on the ring formed by $R^x$ and $R^y$ is optionally substituted with R$^2$, —C(O)R$^2$, —CO$_2$R$^2$, C(O)C(O)R$^2$, —C(O)CH$_2$C(O)R$^2$, —S(O)R$^2$, —S(O)$_2$R$^2$, —C(O)N(R$^3$)$_2$, —SO$_2$N(R$^3$)$_2$, —OC(O)R$^2$, or —OC(O)N(R$^3$)$_2$, and wherein groups R$^2$ and R$^3$ are as defined above and described herein.

In certain embodiments, $R^x$ and $R^y$ are taken together with their intervening atoms to form a 5-membered partially unsaturated or aromatic fused ring having 0-3 heteroatoms independently selected from nitrogen, oxygen, or sulfur, wherein said ring is optionally substituted as defined above and described herein.

In yet other embodiments, $R^x$ and $R^y$ are taken together with their intervening atoms to form a 5-membered partially unsaturated or aromatic fused carbocyclic ring, wherein said ring is optionally substituted as defined above and described herein. In some embodiments, $R^x$ and $R^y$ are taken together with their intervening atoms to form a 5-membered partially unsaturated fused carbocyclic ring, wherein said ring is optionally substituted as defined above and described herein. In certain embodiments, $R^x$ and $R^y$ are taken together with their intervening atoms to form a 5-membered aromatic fused carbocyclic ring, wherein said ring is optionally substituted as defined above and described herein. In yet other embodiments, $R^x$ and $R^y$ are taken together to form a cyclopentenyl or cyclopentadienyl ring, wherein said ring is optionally substituted as defined above and described herein.

In certain embodiments, $R^x$ and $R^y$ are taken together with their intervening atoms to form a 5-membered partially unsaturated fused ring having 1-3 heteroatoms independently selected from nitrogen, oxygen, or sulfur, wherein said ring is optionally substituted as defined above and described herein. In some embodiments, $R^x$ and $R^y$ are taken together with their intervening atoms to form a 5-membered partially unsaturated fused ring having 1-3 nitrogen heteroatoms, wherein said ring is optionally substituted as defined above and described herein. In other embodiments, $R^x$ and $R^y$ are taken together with their intervening atoms to form a 5-membered partially unsaturated fused ring having 1-2 nitrogen heteroatoms, wherein said ring is optionally substituted as defined above and described herein. In yet other embodiments, $R^x$ and $R^y$ are taken together to form a imidazolidinone, oxazolidinone, or pyrrolidinone ring, wherein said ring is optionally substituted as defined above and described herein. In some embodiments, $R^x$ and $R^y$ are taken together to form a imidazolidinone or pyrrolidinone ring, wherein said ring is optionally substituted as defined above and described herein.

In certain embodiments, $R^x$ and $R^y$ are taken together with their intervening atoms to form a 5-membered aromatic fused ring having 1-3 heteroatoms independently selected from nitrogen, oxygen, or sulfur, wherein said ring is optionally substituted as defined above and described herein. In some embodiments, $R^x$ and $R^y$ are taken together with their intervening atoms to form a 5-membered aromatic fused ring having 1 heteroatom independently selected from nitrogen, oxygen, or sulfur, wherein said ring is optionally substituted as defined above and described herein. In other embodiments, $R^x$ and $R^y$ are taken together with their intervening atoms to form a 5-membered aromatic fused ring having 2 heteroatoms independently selected from nitrogen, oxygen, or sulfur, wherein said ring is optionally substituted as defined above and described herein. According to one aspect, $R^x$ and $R^y$ are taken together with their intervening atoms to form a 5-membered aromatic fused ring having 2 nitrogen atoms, wherein said ring is optionally substituted as defined above and described herein.

In some embodiments, $R^x$ and $R^y$ are taken together with their intervening atoms to form a 5-membered aromatic fused ring having a nitrogen atom and a sulfur atom, wherein said ring is optionally substituted as defined above and described herein. In other embodiments, $R^x$ and $R^y$ are taken together with their intervening atoms to form a 5-membered aromatic fused ring having a nitrogen atom and an oxygen atom, wherein said ring is optionally substituted as defined above and described herein. In yet other embodiments, $R^x$ and $R^y$ are taken together with their intervening atoms to form a 5-membered aromatic fused ring having 3 heteroatoms independently selected from nitrogen, oxygen, or sulfur, wherein said ring is optionally substituted as defined above and described herein. In some embodiments, $R^x$ and $R^y$ are taken together with their intervening atoms to form a 5-membered aromatic fused ring having 3 nitrogen atoms, wherein said ring is optionally substituted as defined above and described herein. In other embodiments, $R^x$ and $R^y$ are taken together to form a pyrrolo, pyrazolo, imidazolo, triazolo, thiopheno, furano, thiazolo, isothiazolo, thiadiazolo, oxazolo, isoxazolo, or oxadiazolo fused ring, wherein said ring is optionally substituted as defined above and described herein. In yet other embodiments, $R^x$ and $R^y$ are taken together to form a pyrrolo, pyrazolo, imidazolo, triazolo, or thiazolo fused ring, wherein said ring is optionally substituted as defined above and described herein.

In certain embodiments, $R^x$ and $R^y$ are taken together with their intervening atoms to form a 7-membered partially unsaturated fused ring having 0-3 heteroatoms independently selected from nitrogen, oxygen, or sulfur, wherein said ring is optionally substituted as defined above and described herein.

In some embodiments, $R^x$ and $R^y$ are taken together with their intervening atoms to form a 7-membered partially unsaturated fused ring, wherein said ring is optionally substituted as defined above and described herein. In certain embodiments, $R^x$ and $R^y$ are taken together to form a cyclohepteno, cycloheptadieno, or cycloheptatrieno fused ring, wherein said ring is optionally substituted as defined above and described herein.

In certain embodiments, $R^x$ and $R^y$ are taken together with their intervening atoms to form a 7-membered partially unsaturated fused ring having 1-3 heteroatoms independently selected from nitrogen, oxygen, or sulfur, wherein said ring is optionally substituted as defined above and described herein. In other embodiments, $R^x$ and $R^y$ are taken together with their intervening atoms to form a 7-membered partially unsaturated fused ring having 1 heteroatom independently selected from nitrogen, oxygen, or sulfur, wherein said ring is optionally substituted as defined above and described herein.

In some embodiments, $R^x$ and $R^y$ are taken together with their intervening atoms to form a 7 membered partially unsaturated fused ring having 2 heteroatoms independently selected from nitrogen, oxygen, or sulfur, wherein said ring is optionally substituted as defined above and described herein. In certain embodiments, $R^x$ and $R^y$ are taken together with their intervening atoms to form a 7 membered partially unsaturated fused ring having 3 heteroatoms independently selected from nitrogen, oxygen, or sulfur, wherein said ring is optionally substituted as defined above and described herein. In certain embodiments, $R^x$ and $R^y$ are taken together to form a oxepino, oxepinono, thiepino, thiepinono, azepino, diazapino, azepinono, or diazepinono fused ring, wherein said ring is optionally substituted as defined above and described herein. In certain embodiments, $R^x$ and $R^y$ are taken together to form a azepino, azepinono, or diazepinono fused ring, wherein said ring is optionally substituted as defined above and described herein.

In certain embodiments, any substitutable carbon on the ring formed by $R^x$ and $R^y$ is optionally substituted with hydrogen, -halo, oxo, or an optionally substituted group selected from $C_{1-6}$ aliphatic, a $C_{6-10}$ monocyclic or bicyclic aryl ring, or a 5-10 membered saturated, partially unsaturated, or aromatic monocyclic or bicyclic ring having 1-4 heteroatoms independently selected from nitrogen, oxygen, or sulfur. In some embodiments, any substitutable carbon on the ring formed by $R^x$ and $R^y$ is optionally substituted with hydrogen, oxo or an optionally substituted $C_{1-6}$ aliphatic group. In other embodiments, any substitutable carbon on the ring formed by $R^x$ and $R^y$ is optionally substituted with hydrogen, oxo or a methyl group.

In certain embodiments, any substitutable nitrogen on the ring formed by $R^x$ and $R^y$ is optionally substituted with hydrogen, an optionally substituted group selected from $C_{1-6}$ aliphatic, a $C_{6-10}$ monocyclic or bicyclic aryl ring, or a 5-10 membered saturated, partially unsaturated, or aromatic monocyclic or bicyclic ring having 1-4 heteroatoms independently selected from nitrogen, oxygen, or sulfur. In some embodiments, any substitutable nitrogen on the ring formed by $R^x$ and $R^y$ is optionally substituted with hydrogen or an optionally substituted $C_{1-6}$ aliphatic group. In other embodiments, any substitutable nitrogen on the ring formed by $R^x$ and $R^y$ is optionally substituted with hydrogen or an optionally substituted methyl, ethyl or n-propyl group. In yet other embodiments, any substitutable nitrogen on the ring formed by $R^x$ and $R^y$ is optionally substituted with hydrogen or a methyl group.

As defined above, $R^1$ is hydrogen or an optionally substituted $C_{1-6}$ aliphatic group. In certain embodiments, $R^1$ is hydrogen. In other embodiments, $R^1$ is an optionally substituted $C_{1-6}$ aliphatic group. In certain embodiments, $R^1$ is an optionally substituted $C_{1-6}$ alkyl group. In some embodiments, $R^1$ is an optionally substituted $C_{1-3}$ alkyl group. In certain aspects, $R^1$ is an optionally substituted methyl or ethyl group. In certain embodiments, $R^1$ is an optionally substituted methyl group.

As defined above, $L^1$ is a direct bond or an optionally substituted, straight or branched $C_{1-6}$ alkylene chain. In some aspects, $L^1$ is a direct bond. In certain embodiments, $L^1$ is an optionally substituted, straight or branched $C_{1-5}$ alkylene chain. In some embodiments, $L^1$ is an optionally substituted, straight or branched $C_{1-4}$ alkylene chain. In other embodiments, $L^1$ is an optionally substituted, straight or branched $C_{1-3}$ alkylene chain. According to some embodiments, $L^1$ is an optionally substituted, straight or branched $C_{1-2}$ alkylene chain.

In certain embodiments, $L^1$ is an optionally substituted, straight or branched $C_1$ alkylene chain. In some embodiments, $L^1$ is an optionally substituted, straight or branched $C_2$ alkylene chain. In other embodiments, $L^1$ is an optionally substituted, straight or branched $C_3$ alkylene chain. According to some embodiments, $L^1$ is an optionally substituted, straight or branched $C_4$ alkylene chain. In certain aspects, $L^1$ is an optionally substituted, straight or branched $C_5$ alkylene chain. In other aspects, $L^1$ is an optionally substituted, straight or branched $C_6$ alkylene chain.

In certain embodiments, $L^1$ is an optionally substituted, straight $C_{1-6}$ alkylene chain. In some embodiments, $L^1$ is a straight $C_{1-6}$ alkylene chain. In other embodiments, $L^1$ is an optionally substituted, branched $C_{1-6}$ alkylene chain. In certain aspects, $L^1$ is a branched $C_{1-6}$ alkylene chain. In certain embodiments, $L^1$ is —CH($C_{1-6}$alkyl)-, —CH($C_{1-5}$alkyl)-, —CH($C_{1-4}$alkyl)-, —CH($C_{1-3}$alkyl)-, or —CH($C_{1-2}$alkyl)-. In certain embodiments, $L^1$ is —CH(CH$_3$)—.

As defined generally above, $Cy^1$ is an optionally substituted phenyl or an optionally substituted 5-6 membered saturated, partially unsaturated, or aromatic ring having 1-3 heteroatoms independently selected from nitrogen, oxygen, or sulfur. In some embodiments, $Cy^1$ is optionally substituted phenyl. In certain embodiments, $Cy^1$ is an optionally substituted 6 membered saturated, partially unsaturated, or aromatic ring having 1-3 heteroatoms independently selected from nitrogen, oxygen, or sulfur. In other embodiments, $Cy^1$ is an optionally substituted 5-membered saturated, partially unsaturated, or aromatic ring having 1-3 heteroatoms independently selected from nitrogen, oxygen, or sulfur. In certain aspects, $Cy^1$ is an optionally substituted 5-membered heteroaryl ring having 2 heteroatoms independently selected from nitrogen, oxygen, or sulfur. In other embodiments, $Cy^1$ is an optionally substituted 5-membered heteroaryl ring having 2 heteroatoms independently selected from nitrogen and oxygen. In some embodiments, $Cy^1$ is an optionally substituted 5-membered heteroaryl ring having 2 heteroatoms independently selected from nitrogen and sulfur.

Exemplary $Cy^1$ groups include an optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group. In certain embodiments, $Cy^1$ is an optionally substituted thiazolyl or isoxazolyl group. In other embodiments, $Cy^1$ is an optionally substituted thiazolyl group. In some embodiments, $Cy^1$ is an unsubstituted thiazolyl group. In certain aspects, $Cy^1$ is an optionally substituted isoxazolyl group. According to another aspect, $Cy^1$ is an unsubstituted isoxazolyl group.

As defined generally above, $L^2$ is a direct bond, or is an optionally substituted, straight or branched $C_{1-6}$ alkylene chain wherein 1 or 2 methylene units of $L^2$ are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or a 3-6 membered cycloalkylene. In certain embodiments, $L^2$ is a direct bond.

In certain embodiments, $L^2$ is an optionally substituted, straight or branched $C_{1-6}$ alkylene chain wherein 1 or 2 methylene units of $L^2$ are replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, or —C(O)O—; wherein each R is as defined above and described herein. In some embodiments, $L^2$ is an optionally substituted, straight or branched $C_{1-4}$ alkylene chain wherein 1 or 2 methylene units of $L^2$ are replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, or —C(O)O—. In other embodiments, $L^2$ is an optionally substituted, straight or branched $C_{1-2}$ alkylene chain wherein 1 methylene unit of $L^2$ is replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, or —C(O)O—. In certain aspects, $L^2$ is —O—, —S—, —N(R)—, —C(O)—, —C(O)N(R)—, —N(R)C(O)—, —SO$_2$—, —SO$_2$N(R)—, —N(R)SO$_2$—, —OC(O)—, or —C(O)O—. In other embodiments, $L^2$ is —C(O)N(R)—, —N(R)C(O)—, —SO$_2$N(R)—, —N(R)SO$_2$—, —OC(O)—, or —C(O)O—. In certain aspects, $L^2$ is —C(O)N(R)— or —N(R)C(O)—. In certain embodiments, $L^2$ is —C(O)N(H)— or —N(H)C(O)—. In certain embodiments, $L^2$ is —C(O)N(H)—.

As defined generally above, $Cy^2$ is an optionally substituted 5-14 membered saturated, partially unsaturated, or aromatic monocyclic, bicyclic, or tricyclic ring having 0-4 heteroatoms, independently selected from nitrogen, oxygen, or sulfur.

In certain embodiments, $Cy^2$ is an optionally substituted 5-10 membered saturated, partially unsaturated, or aromatic monocyclic ring having 1-4 heteroatoms, independently selected from nitrogen, oxygen, or sulfur. In other embodiments, $Cy^2$ is an optionally substituted 5-6 membered saturated, partially unsaturated, or aromatic monocyclic ring having 1-4 heteroatoms, independently selected from nitrogen, oxygen, or sulfur.

In certain embodiments, $Cy^2$ is an optionally substituted 5-membered saturated, partially unsaturated, or aromatic monocyclic ring having 1-3 heteroatoms, independently selected from nitrogen, oxygen, or sulfur. In some embodiments, $Cy^2$ is an optionally substituted 5-membered saturated, partially unsaturated, or aromatic monocyclic ring having 1-2 heteroatoms, independently selected from nitrogen, oxygen, or sulfur. In other embodiments, $Cy^2$ is an optionally substituted 5-membered heteroaryl ring having 1-3 heteroatoms, independently selected from nitrogen, oxygen, or sulfur. In still other embodiments, $Cy^2$ is an optionally substituted 5-membered heteroaryl ring having 1-2 heteroatoms, independently selected from nitrogen. Exemplary $Cy^2$ groups include an optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group.

In certain embodiments, $Cy^2$ is an optionally substituted 6-membered saturated, partially unsaturated, or aromatic monocyclic ring having 1-4 heteroatoms, independently selected from nitrogen, oxygen, or sulfur. In some embodiments, $Cy^2$ is an optionally substituted 6-membered saturated, partially unsaturated, or aromatic monocyclic ring having 1-2 heteroatoms, independently selected from nitrogen, oxygen, or sulfur. In other embodiments, $Cy^2$ is an optionally substituted 6-membered heteroaryl ring having 1-4 nitrogen atoms. In certain aspects, $Cy^2$ is an optionally substituted 6-membered heteroaryl ring having 1-3 nitrogen atoms. In some embodiments, $Cy^2$ is an optionally substituted 6-membered heteroaryl ring having 1-2 nitrogen atoms. Exemplary $Cy^2$ groups include an optionally substituted pyridinyl, pyrimidinyl, pyrazinyl, pyridazinyl, triazinyl, or tetrazinyl group. In some embodiments, $Cy^2$ is an optionally substituted pyridinyl, pyrimidinyl or pyridazinyl group.

In certain embodiments, $Cy^2$ is an optionally substituted 5-10 membered saturated, partially unsaturated, or aromatic bicyclic ring having 1-4 heteroatoms, independently selected from nitrogen, oxygen, or sulfur. In some embodiments, $Cy^2$ is an optionally substituted 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, $Cy^2$ is an optionally substituted 5,5-fused, 5,6-fused, or 6,6-fused heteroaryl ring having 1-4 heteroatoms, independently selected from nitrogen, oxygen, or sulfur. In certain aspects, $Cy^2$ is an optionally substituted 5,5-fused, 5,6-fused, or 6,6-fused heteroaryl ring having 1-4 nitrogen atoms. In other embodiments, $Cy^2$ is an optionally substituted 5,6-fused heteroaryl ring having 1-4 nitrogen atoms. Exemplary $Cy^2$ groups include an optionally substituted pyyrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl group. In certain aspects, $Cy^2$ is an optionally substituted benzimidazolyl, imidazopyridinyl or purinyl group.

In certain embodiments, $Cy^2$ is an optionally substituted 8-10 membered saturated, partially unsaturated, or aromatic monocyclic or bicyclic carbocyclic ring. In some embodiments, $Cy^2$ is an optionally substituted 5-10 membered saturated, partially unsaturated, or aromatic monocyclic or bicyclic carbocyclic ring. In other embodiments, $Cy^2$ is an optionally substituted 5-6 membered saturated, partially unsaturated, or aromatic monocyclic carbocyclic ring. In certain aspects, $Cy^2$ is an optionally substituted 5-membered saturated or partially unsaturated carbocyclic ring. According to one embodiment, $Cy^2$ is an optionally substituted 6 membered saturated, partially unsaturated, or aromatic ring. In still other embodiments, $Cy^2$ is an optionally substituted phenyl group.

In certain embodiments, $Cy^2$ is an optionally substituted 5,5-fused-, 5,6-fused, or 6,6-fused saturated, partially unsaturated, or aromatic bicyclic ring. In some embodiments, $Cy^2$ is an optionally substituted 5,5-fused, 5,6-fused, or 6,6-fused aromatic bicyclic ring. In other embodiments, $Cy^2$ is optionally substituted naphthalenyl, indanyl or indenyl group.

In certain embodiments, $Cy^2$, as described above and herein, is optionally substituted with one or more groups selected from —R°, -halo, —NO$_2$, —CN, —OR°, —SR°, —N(R°)$_2$, —C(O)R°, —CO$_2$R°, —C(O)C(O)R°, —C(O)CH$_2$C(O)R°, —S(O)R°, —S(O)$_2$R°, —C(O)N(R°)$_2$, —SO$_2$N(R°)$_2$, —OC(O)R°, —N(R°)C(O)R°, —N(R°)N (R°)$_2$, —C=NN(R°)$_2$, —C=NOR°, —N(R°)C(O)N(R°)$_2$, —N(R°)SO$_2$N(R°)$_2$, —N(R°)SO$_2$R°, or —OC(O)N(R°)$_2$; wherein R° is as defined above and described herein. In other embodiments, $Cy^2$ is optionally substituted with $C_{1-6}$ aliphatic or halogen. In some embodiments, $Cy^2$ is optionally substituted with Cl, F, CF$_3$, or $C_{1-4}$ alkyl. Exemplary substituents on $Cy^2$ include methyl, tert-butyl, and 1-methylcyclopropyl. In other embodiments, $Cy^2$ is mono- or di-substituted. In certain aspects, $Cy^2$ is optionally substituted at the meta or the para position with any one of the above-mentioned substituents.

According to one aspect, the present invention provides a compound of formula II:

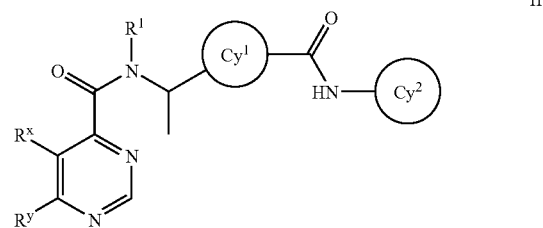

or a pharmaceutically acceptable salt thereof, wherein:
each of $R^1$, $R^x$, and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms.

According to another aspect, the present invention provides a compound of formula II':

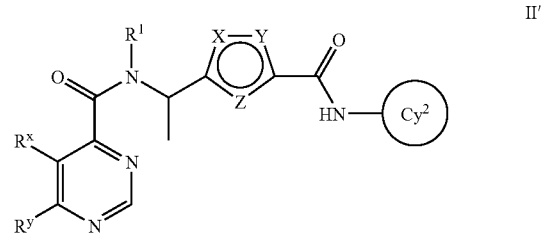

or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
$Cy^2$ is optionally substituted phenyl or an optionally substituted 6-membered aromatic ring having 1-3 nitrogen atoms.

Yet another aspect of the present invention provides a compound of formulae II-a and II-b:

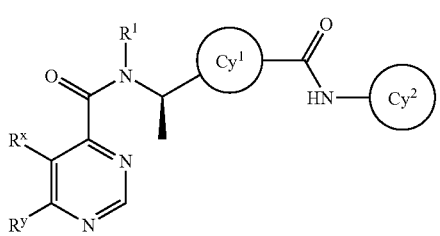

II-a

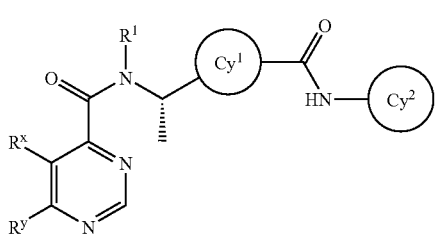

II-b or a pharmaceutically acceptable salt thereof, wherein:
each of $R^1$, $R^x$, and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms.

In certain embodiments, the present invention provides a compound of formulae II-c and II-d:

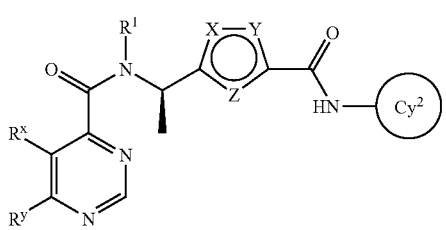

II-c

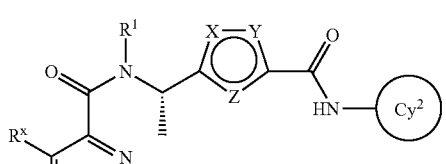

II-d or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
$Cy^2$ is optionally substituted phenyl or an optionally substituted 6-membered aromatic ring having 1-3 nitrogen atoms.

According to another aspect, the present invention provides a compound of formula III:

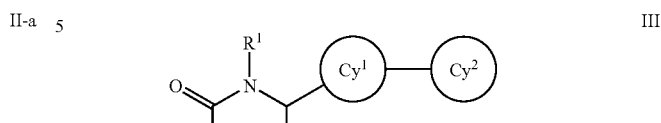

III or a pharmaceutically acceptable salt thereof, wherein:
each of $R^1$, $R^x$, and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and
$Cy^2$ is an optionally substituted 8-10 membered saturated, partially unsaturated, or aromatic bicyclic ring having 1-4 heteroatoms, independently selected from nitrogen, oxygen, or sulfur.

According to certain embodiments, the present invention provides a compound of formula III':

III' or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
$Cy^2$ is optionally substituted phenyl or an optionally substituted 6-membered aromatic ring having 1-4 nitrogen atoms.

In certain aspects, the present invention provides a compound of formulae III-a and III-b:

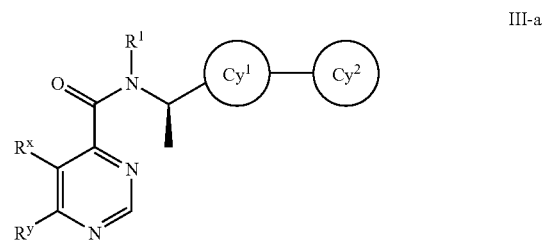

III-a

-continued

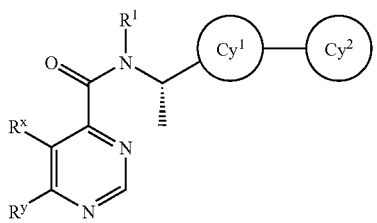

III-b or a pharmaceutically acceptable salt thereof, wherein:
each of $R^1$, $R^x$, and $R^y$ is as defined above and described in classes and subclasses herein;
$Cy^1$ is an optionally substituted 5-membered saturated, partially unsaturated, or aromatic ring having 1-3 heteroatoms independently selected from nitrogen, oxygen, or sulfur; and
$Cy^2$ is an optionally substituted 8-10 membered saturated, partially unsaturated, or aromatic bicyclic ring having 1-4 heteroatoms, independently selected from nitrogen, oxygen, or sulfur.

In certain embodiments, the present invention provides a compound of formulae III-c and III-d:

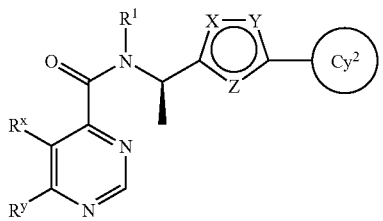

III-c

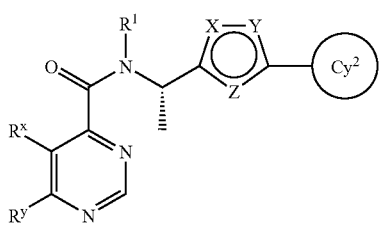

III-d or a pharmaceutically acceptable salt thereof, wherein:
each of $R^1$, $R^x$, and $R^y$ is as defined above and described in classes and subclasses herein;
each of X, Y, and Z is independently —CH—, nitrogen, oxygen, or sulfur, wherein at least one of X, Y, or Z is a heteroatom and the circle depicted within the ring containing X, Y, and Z indicates that said ring is aromatic; and
$Cy^2$ is optionally substituted phenyl or an optionally substituted 6-membered aromatic ring having 1-4 nitrogen atoms.

According to one aspect, the present invention provides a compound of formula IV:

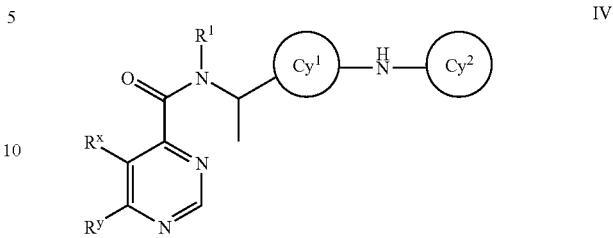

IV or a pharmaceutically acceptable salt thereof, wherein:
each of $R^1$, $R^x$, and $R^y$ is as defined above and described in classes and subclasses herein;
$Cy^1$ is an optionally substituted 5-6 membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms.

Yet another aspect of the present invention provides a compound of formulae IV-a and IV-b:

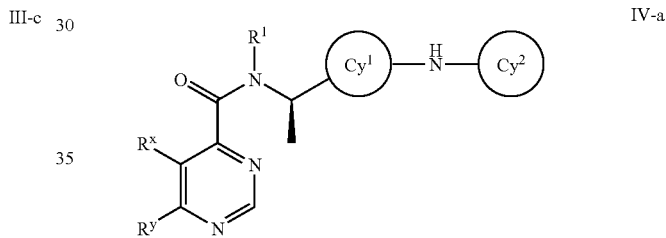

IV-a

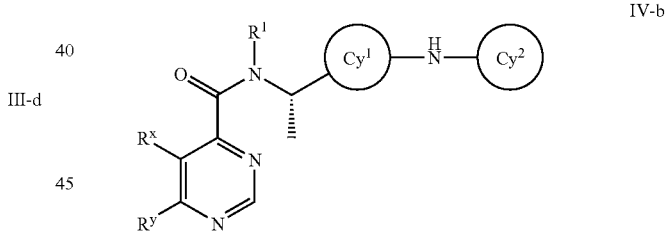

IV-b or a pharmaceutically acceptable salt thereof, wherein:
each of $R^1$, $R^x$, and $R^y$ is as defined above and described in classes and subclasses herein;
$Cy^1$ is an optionally substituted 5-6 membered saturated, partially unsaturated, or aromatic ring having 1-3 heteroatoms independently selected from nitrogen, oxygen, or sulfur; and
$Cy^2$ is optionally substituted phenyl or an optionally substituted 6-membered aromatic ring having 1-3 nitrogen atoms.

In certain embodiments, the present invention provides a compound of formula IV, IV-a, or IV-b wherein $Cy^1$ is a 5-membered heteroaryl ring having 1-3 heteroatoms independently selected from nitrogen, oxygen, or sulfur.

In certain embodiments, each of $R^1$, $R^x$, $R^y$, $L^1$, $L^2$, $Cy^1$, and $Cy^2$ is selected from those groups depicted in the Schemes and in Tables 1, 2, 3, 4, and 5, infra.

Exemplary compounds of the present invention are set forth in the Examples in the Schemes and in Tables 1 through 5, infra. In certain embodiments, the present invention provides a compound selected from those set forth in Table 1, or a pharmaceutically acceptable salt thereof. In some embodiments, the present invention provides a compound selected from those set forth in Table 2, or a pharmaceutically acceptable salt thereof. In other embodiments, the present invention provides a compound selected from those set forth in Table 3, or a pharmaceutically acceptable salt thereof. In certain embodiments, the present invention provides a compound selected from those set forth in Table 4, or a pharmaceutically acceptable salt thereof. In some embodiments, the present invention provides a compound selected from those set forth in Table 5, or a pharmaceutically acceptable salt thereof.

4. Uses, Formulation and Administration

Pharmaceutically Acceptable Compositions

As discussed above, the present invention provides compounds that are inhibitors of protein kinases (e.g., Raf kinase), and thus the present compounds are useful for the treatment of diseases, disorders, and conditions mediated by Raf kinase. In certain embodiments, the present invention provides a method for treating a Raf-mediated disorder. As used herein, the term "Raf-mediated disorder" includes diseases, disorders, and conditions mediated by Raf kinase. Such Raf-mediated disorders include melanoma, leukemia, or cancers such as colon, breast, gastric, ovarian, lung, brain, larynx, cervical, renal, lymphatic system, genitourinary tract (including bladder and prostate), stomach, bone, lymphoma, melanoma, glioma, papillary thyroid, neuroblastoma, and pancreatic cancer.

Raf-mediated disorders further include diseases afflicting mammals which are characterized by cellular proliferation. Such diseases include, for example, blood vessel proliferative disorders, fibrotic disorders, mesangial cell proliferative disorders, and metabolic diseases. Blood vessel proliferative disorders include, for example, arthritis and restenosis. Fibrotic disorders include, for example, hepatic cirrhosis and atherosclerosis. Mesangial cell proliferative disorders include, for example, glomerulonephritis, diabetic nephropathy, malignant nephrosclerosis, thrombotic microangiopathy syndromes, organ transplant rejection, and glomerulopathies. Metabolic disorders include, for example, psoriasis, diabetes mellitus, chronic wound healing, inflammation, and neurodegenerative diseases.

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, pharmaceutically acceptable derivatives include, but are not limited to, pharmaceutically acceptable salts, esters, salts of such esters, or any other adducts or derivatives that, upon administration to a patient in need, are capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans or animals without undue toxicity, irritation, allergic response, or the like, and are offer with a reasonable benefit/risk ratio. A "pharmaceutically acceptable salt" means any at least substantially non-toxic salt or salt of an ester of a compound of this invention that, upon administration to a recipient, is capable of providing, either directly or indirectly, a compound of this invention or an inhibitorily active metabolite or residue thereof. As used herein, the term "inhibitory metabolite or residue thereof" means that a metabolite or residue thereof is also an inhibitor of a Raf kinase.

Pharmaceutically acceptable salts are well known in the art. For example, S. M. Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

According to the present invention, provided compounds may be assayed in any of the available assays known in the art for identifying compounds having kinase inhibitory activity. For example, the assay may be cellular or non-cellular, in vivo or in vitro, high- or low-throughput format, etc.

In certain exemplary embodiments, compounds of this invention were assayed for their ability to inhibit protein kinases, more specifically Raf.

Thus, in one aspect, compounds of this invention which are of particular interest include those which:
 are inhibitors of protein kinases;
 exhibit the ability to inhibit Raf kinase;
 are useful for treating mammals (e.g., humans) or animals suffering from an Raf-mediated disease or condition, and for helping to prevent or delay the onset of such a disease or condition;
 exhibit a favorable therapeutic profile (e.g., safety, efficacy, and stability).

In certain embodiments, compounds of the invention are Raf kinase inhibitors. In certain exemplary embodiments, compounds of the invention are Raf inhibitors. In certain exemplary embodiments, compounds of the invention have $^{Cell}IC_{50}$ values≦100 µM. In certain other embodiments, compounds of the invention have $^{Cell}IC_{50}$ values≦75 µM. In certain other embodiments, compounds of the invention have $^{Cell}IC_{50}$ values≦50 µM. In certain other embodiments, compounds of the invention have $^{Cell}IC_{50}$ values≦25 µM. In certain other embodiments, compounds of the invention have $^{Cell}IC_{50}$ values≦10 µM. In certain other embodiments, compounds of the invention have $^{Cell}IC_{50}$ values≦7.5 µM. In certain other embodiments, of the invention compounds have $^{Cell}IC_{50}$ values≦5 µM. In certain other embodiments, of the invention compounds have $^{Cell}IC_{50}$ values≦2.5 µM. In certain other embodiments, of the invention compounds have $^{Cell}IC_{50}$ values≦1 µM. In certain other embodiments, of the invention compounds have $^{Cell}IC_{50}$ values≦800 nM. In certain other embodiments, of the invention compounds have $^{Cell}IC_{50}$ values≦600 nM. In certain other embodiments, inventive compounds have $^{Cell}IC_{50}$ values≦500 nM. In certain other embodiments, compounds of the invention have $^{Cell}IC_{50}$ values≦300 nM. In certain other embodiments, compounds of the invention have $^{Cell}IC_{50}$ values≦200 nM. In certain other embodiments, of the invention compounds have $^{Cell}IC_{50}$ values≦100 nM.

In yet another aspect, a method for the treatment or lessening the severity of an Raf-mediated disease or condition is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a Raf-mediated disease or condition. The compounds and compositions, according to the method of the present invention, may be administered using any amount and any route of administration effective for treating or lessening the severity of a Raf-mediated disease or condition. The exact amount required will vary from subject to subject, depending on the species, age, and general condition of the subject, the severity of the infection, the particular agent, its mode of administration, and the like. In certain embodiments, compounds of the invention are formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds of the invention are Raf kinase inhibitors, and thus, without wishing to be bound by any particular theory, the compounds and compositions are particularly useful for treating or lessening the severity of a disease, condition, or disorder where activation of Raf kinase is implicated in the disease, condition, or disorder. When activation of Raf kinase is implicated in a particular disease, condition, or disorder, the disease, condition, or disorder may also be referred to as a "Raf-mediated disease". Accordingly, in another aspect, the present invention provides a method for treating or lessening the severity of a disease, condition, or disorder where activation of Raf kinase is implicated in the disease state.

The activity of a compound utilized in this invention as an Raf kinase inhibitor, may be assayed in vitro, in vivo, ex vivo, or in a cell line. In vitro assays include assays that determine inhibition of either the phosphorylation activity or ATPase activity of activated Raf. Alternate in vitro assays quantitate the ability of the inhibitor to bind to Raf. Inhibitor binding may be measured by radiolabelling the inhibitor (e.g., synthesizing the inhibitor to include a radioisotope) prior to binding, isolating the inhibitor/Raf, complex and determining the amount of radiolabel bound. Alternatively, inhibitor binding may be determined by running a competition experiment where new inhibitors are incubated with Raf bound to known radioligands.

The term "measurably inhibit", as used herein means a measurable change in Raf activity between a sample comprising said composition and a Raf kinase and an equivalent sample comprising Raf kinase in the absence of said composition.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, compound of the invention may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents, or other anti-proliferative agents may be combined with the compounds of this invention to treat proliferative diseases and cancer. Examples of therapies or anticancer agents that may be used in combination with the inventive anticancer agents of the present invention include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs.

Examples of chemotherapeutic anticancer agents that may be used as second active agents in combination with compounds of the invention include, but are not limited to, alkylating agents (e.g. mechlorethamine, chlorambucil, cyclophosphamide, melphalan, ifosfamide), antimetabolites (e.g., methotrexate), purine antagonists and pyrimidine antagonists (e.g. 6-mercaptopurine, 5-fluorouracil, cytarabine, gemcitabine), spindle poisons (e.g., vinblastine, vincristine, vinorelbine, paclitaxel), podophyllotoxins (e.g., etoposide, irinotecan, topotecan), antibiotics (e.g., doxorubicin, daunorubicin, bleomycin, mitomycin), nitrosoureas (e.g., carmustine, lomustine), inorganic ions (e.g., platinum complexes such as cisplatin, carboplatin), enzymes (e.g., asparaginase), hormones (e.g., tamoxifen, leuprolide, flutamide, and megestrol), topoisomerase II inhibitors or poisons, EGFR (Her1, ErbB-1) inhibitors (e.g., gefitinib), antibodies (e.g., rituximab), IMIDs (e.g., thalidomide, lenalidomide), various targeted agents (e.g., HDAC inhibitors such as vorinostat, Bcl-2 inhibitors, VEGF inhibitors); proteasome inhibitors (e.g., bortezomib), cyclin-dependent kinase inhibitors, and dexamethasone.

For a more comprehensive discussion of updated cancer therapies see, The *Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory agents, including immunosuppressive agents, such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinson's agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from composition containing a compound of the invention, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Raf activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Raf kinase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Examples

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Synthesis of Fused Pyrimidine ("Left-Hand Side") Groups

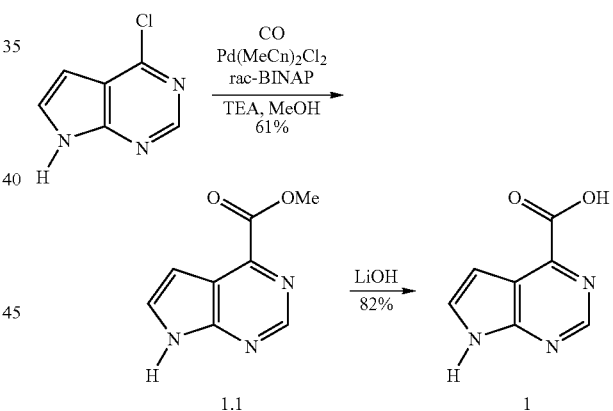

Synthesis of Compound 1.1. A mixture of 4-chloro-7H-pyrrolo[2,3-d]pyrimidine (3 g, 1.96 mmol), [2,2'-bis(diphenylphospheno)-1,1-binaphthyl]palladium(II) chloride (156 mg, 0.192 mmol) and triethylamine (2.56 g, 26 mmol) in methanol (60 ml) was heated (100° C.) under CO (75 psi) for 16 hours (hr). Half of the solvent was removed in vacuo and the mixture filtered to afford compound 1.1 (2.5 g, 44%) as a brown solid. $^1$H NMR (200 MHz, DMSO-$d_6$) δ 12.50 (bs, 1H), 8.88 (s, 1H), 7.79 (d, J=3.4 Hz, 1H), 6.87 (d, J=3.4 Hz, 1H), 3.95 (s, 3H). MS m/z 178 [M+1]$^+$.

Synthesis of Compound 1. A solution of LiOH (0.236 g, 10.2 mmol) in water (4 ml) was added to a solution of compound 1.1 (1.4 g, 7.9 mmol) in THF (20 ml) at 0° C. After 2 hr, the reaction mixture was acidified to pH 2 with conc. HCl. The THF was removed in vacuo and the resulting solution was cooled 0° C. The precipitate was collected by filtration and dried to afford compound 1 (1.1 g, 85%) as a white solid.

¹H NMR (200 MHz, DMSO-d₆): δ=12.80 (bs, 1H), 8.95 (s, 1H), 7.87 (d, J=2.8 Hz, 1H), 6.96 (d, J=2.8 Hz, 1H). MS m/z 164 [M+1]⁺.

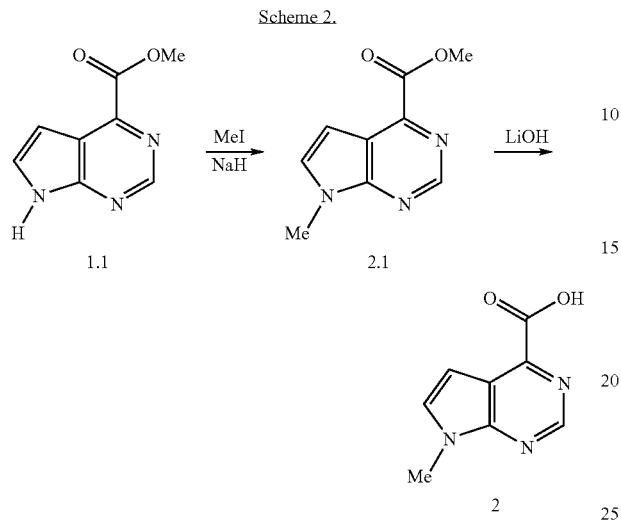

Synthesis of Compound 2.1. Sodium hydride (60% in mineral oil, 75 mg) was added to a solution of compound 1.1 (193 mg, 1.09 mmol) in THF (5 mL) and DMF (5 mL) at 0° C. After 1.5 hr, MeI (88 μL, 1.42 mmol) was added to the reaction at 0° C. After 30 minutes (min), the reaction was added to NH₄Cl (sat.). The aqueous layer was diluted with water and then extracted dichloromethane. The organic layer was dried (Na₂SO₄) and evaporated to afford compound 2.1 (120 mg) as brown solid. ¹H NMR (400.13 MHz, DMSO-d₆) δ=8.95 (s, 1H), 7.86 (d, J=3.5 Hz, 1H), 6.92 (d, J=3.5 Hz, 1H), 3.98 (s, 3H), 3.88 (s, 3H).

Synthesis of compound 2. A solution of 1M LiOH (0.63 mL) was added to a solution of compound 2.1 (120 mg, 0.63 mmol) in THF (8 mL, 0.1 mol) at 0° C. The reaction was then warmed to room temperature (RT). After 30 minutes a white precipitate was observed. The reaction mixture was neutralized by addition of 1N HCl and then the solvent was removed in vacuo to afford compound 2. ¹H NMR (400.13 MHz, DMSO-d₆) δ 8.99 (s, 1H), 7.89 (d, J=3.5 Hz, 1H), 6.97 (d, J=3.5 Hz, 1H), 3.9 (s, 3H).

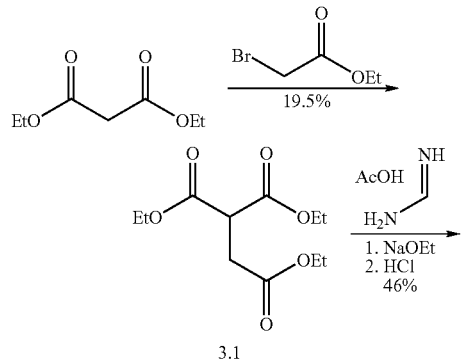

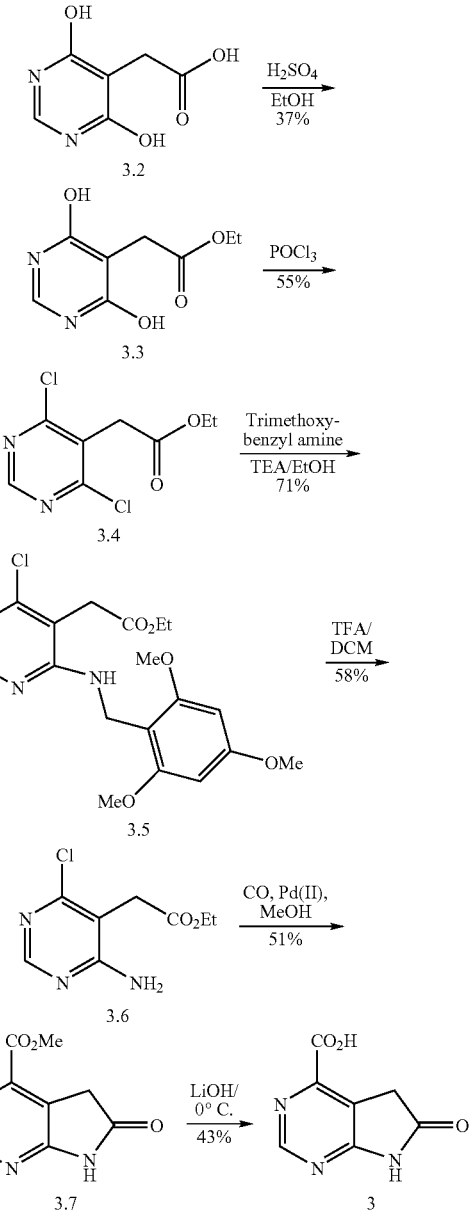

Synthesis of compound 3.1. To a suspension of sodium hydride (60% in mineral oil, 5 g, 0.125 mol) in THF (200 ml) at 0° C. was added diethyl malonate (20 g, 0.125 mol) dropwise. To the reaction mixture was added ethyl bromoacetate (16.4 g, 0.097 mol) maintaining the temperature at 0° C. for 20 minutes. The reaction mixture was allowed to stir at RT for 16 hr and then quenched with saturated ammonium chloride solution (100 ml) at 0° C. The reaction mixture was extracted with ethyl acetate (3×100 ml). The combined organic extracts were dried (Na₂SO₄), concentrated under vacuum and purified with fractional distillation to afford compound 2 (6 g, 20%) as a white liquid. ¹H NMR (200 MHz, CDCl₃) δ 4.3-4.2 (m, 6H), 3.83 (t, J=7.2 Hz, 1H) 2.95 (d, J=7.2 Hz, 2H), 1.2-1.4 (m, 9). MS m/z 247 [M+1]⁺.

Synthesis of compound 3.2. To an ice-cold solution of sodium ethoxide (36 g, 0.529 mol) in ethanol (430 ml) was added compound 3.1 (43.5 g, 0.177 mol) drop-wise over 25 minutes. Formamidine acetate (18.3 g, 0.176 mol) was added portion-wise to the reaction mixture. After 30 min, the reaction mixture was refluxed for 16 hr. The reaction mixture was cooled and then evaporated in vacuo. To the residue was added water (50 mL), cooled to 0° C., and acidified to pH=2 with 5N HCl. The precipitate was filtered to afford compound 3.2 (14 g, 46%) as a yellow solid. $^1$H NMR (200 MHz, DMSO-$d_6$) δ 12.00 (bs, 1H), 8.0 (s, 1H), 3.2 (s, 2H). MS m/z 171 [M+1]$^+$.

Synthesis of compound 3.3. To a suspension of compound 3.2 (14 g, 0.082 mol) in ethanol (140 ml) was added sulfuric acid (0.3 ml) and heated at 85° C. for 24 hr. The hot reaction mixture was filtered; the filtrate was cooled to 0° C. during which yellow solid crashed out which was filtered and dried to afford compound 3.3 (6 g, 37%). $^1$H NMR (200 MHz, DMSO-$d_6$) δ 12.00 (bs, 2H), 8.0 (s, 1H) 4.0 (q, J=6.8 Hz, 2H), 3.2 (s, 2H), 1.19 (t, J=6.8 Hz, 3H). MS m/z 199 [M+1]$^+$.

Synthesis of Compound 3.4. To compound 3.3 (7.5 g, 37.8 mmol) in toluene (100 ml) was added triethylamine (5.2 ml, 37.3 mmol) and the mixture was heated to 105° C. To the reaction mixture, was added POCl$_3$ (10.5 ml, 113 mmol) in toluene (20 ml) dropwise. After 2 hr, the reaction mixture was cooled to 0° C., water (50 mL, 4° C.) was added and extracted with EtOAc (3×150 ml). The organic layer was dried (Na$_2$SO$_4$) and evaporated in vacuo. The residue was purified by flash chromatography using hexane/EtOAc (SiO$_2$, 5/95) as eluant to afford compound 3.4 (4.9 g, 55%) as a solid. $^1$H NMR (200 MHz, CDCl$_3$) δ 8.75 (s, 1H), 4.3 (q, J=7 Hz, 2H), 4.00 (2H, s), 1.3 (t, J=7 Hz, 3H). MS m/z 235 [M+1]$^+$.

Synthesis of Compound 3.5. A mixture compound 3.4 (5 g, 0.021 mol), triethylamine (3.7 ml, 0.021 mol) and trimethoxybenzyl amine (4.65 g, 0.023 mol) in ethanol (50 ml) was heated to 80° C. After 4 hr, the reaction mixture was cooled to 0° C. and filtered to afford compound 3.5 (6.0 g, 71%) as a brown solid. $^1$HNMR (200 MHz, DMSO-$d_6$) δ=8.25 (s, 1H), 6.9 (bs, 1H), 6.25 (s, 2H), 4.40 (d, J=4 Hz, 2H), 4.15 (q, J=7.2 Hz, 2H), 3.80 (s, 3H), 3.75 (s, 6H), 3.70 (s, 2H), 1.17 (t, J=7.2 Hz, 3H). MS m/z 396 [M+1]$^+$.

Synthesis of Compound 3.6. To a solution of compound 3.5 (5.0 g, 0.0125 mol) in dichloromethane (25 ml) at 0° C. was added TFA (25 ml) dropwise. The reaction mixture was warmed to RT and then stirred for 16 hr. The solvent were removed in vacuo, and the resulting liquid was cooled 0° C. and neutralized using NaHCO$_3$ (sat.). The reaction mixture was extracted with ethyl acetate (3×75 ml). The organic layer was dried (Na$_2$SO$_4$) and evaporated in vacuo. The residue was purified by flash chromatography using hexane/EtOAc (SiO$_2$, 30/70) as eluant to afford compound 3.6 (1.6 g, 58%) as a white solid. $^1$H-NMR (200 MHz, CDCl$_3$) δ=8.30 (s, 1H), 5.60 (bs, 2H), 4.2 (q, J=7.2 Hz, 2H), 3.70 (s, 2H), 1.30 (t, J=7.2 Hz, 3H), MS m/z 215.9 [M+1]$^+$.

Synthesis of Compound 3.7. A mixture of compound 3.6 (11 g, 51 mmol), [2,2'-bis(diphenylphospino)-1,1'-binaphthyl]palladium (II) chloride (407 mg, 0.5 mmol) and triethylamine (6.7 g, 66 mmol) in methanol (330 ml) was heated (100° C.) under CO (75 psi). After 16 hr, half of the solvent was removed in vacuo and the resulting mixture was filtered to afford compound 3.7 (5 g, 50%). $^1$H NMR (200 MHz, DMSO-$d_6$): δ 11.65 (bs, 1H), 8.72 (s, 1H), 3.90 (s, 3H), 3.78 (s, 2H). MS m/z 194 [M+1]$^+$.

Synthesis of Compound 3. A solution of LiOH (114 mg, 2.7 mmol) in water (5 ml) was added to a solution of compound 3.7 (0.5 g, 2.5 mmol) in THF (20 ml) at 0° C. After 2 hr, the reaction mixture was acidified to pH=2 with conc. HCl. The THF was removed in vacuo and the solution was cooled (0° C.). The brown solid was filtered to afford compound 3 (0.2 g, 43%). $^1$H NMR (200 MHz, DMSO-$d_6$) δ 11.70 (bs, 1H), 8.80 (s, 1H), 3.78 (s, 2H). MS m/z 179 [M+1]$^+$.

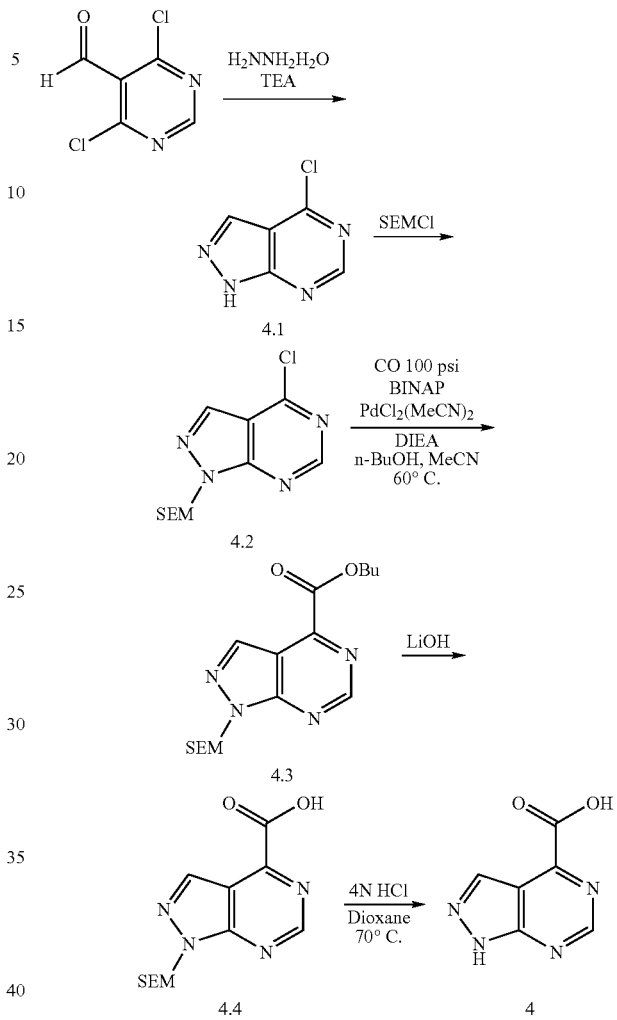

Synthesis of Compound 4.1. Hydrazine hydrate (11.5 mL, 23.7 mmol) was slowly added to a solution of 4,6-dichloropyrimidine-5-carbaldehyde (40.0 g, 22.6 mmol), and triethylamine (30 mL, 22 mmol) in 1,4-dioxane (600 mL), while cooling to maintain an internal temperature below 20° C. After the addition was complete, the reaction was warmed to RT. After 1 hr, the reaction was filtered. The solvent was removed in vacuo to afford compound 4.1 (29 g, 83%) as a light yellow solid. $^1$H NMR (400.13 MHz, DMSO-$d_6$) δ 14.52 (br. s, 1H), 8.83 (s, 1H), 8.45 (s, 1H). MS m/z 155 [M+1]$^+$.

Synthesis of Compound 4.2. Diisopropylethylamine (35 mL, 0.20 mol) was added to a solution of compound 4.1 (25 g, 0.16 mol), [β-(trimethylsilyl)ethoxy]methyl chloride (36 mL, 0.20 mol) in THF (200 mL, 2 mol) and DMF (100 mL, 1 mol) at −20° C. After 1 hr, the reaction mixture was warmed to RT. The reaction mixture was diluted dichloromethane, washed with 0.5 N HCl, and then concentrated. The residue was purified by flash chromatography using hexane/EtOAc (SiO$_2$, 100/0 to 0/100) to afford compound 4.2 (26 g, 56%) as a clear oil. $^1$H NMR (400.13 MHz, CDCl$_3$) 8.84, (s, 1H), 8.24 (s, 1H), 5.86, (s, 2H), 3.68 (m, 2H), 0.95 (m, 2H), 0.03 (s, 9H). MS m/z 285 [M+1]$^+$.

Synthesis of Compound 4.3. A solution of compound 4.2 (6.4 g, 22 mmol), BINAP (2.80 g, 4.49 mmol), Pd(CH₃CN)₂Cl₂ (1.16 g, 4.49 mmol), N,N-diisopropylethylamine (430 uL, 24.7 mmol), acetonitrile (230 mL) and 1-butanol (230 mL) was heated (60° C.) under CO (100 psi). After 3 hr, the reaction mixture was filtered through celite and the solvent was removed. The residue was purified by flash chromatography using dichloromethane/EtOAc (SiO₂, 100/0 to 50/50) as eluant to afford compound 4.3 (5.96 g, 76%) as an oil. ¹H-NMR (400.13 MHz, CDCl₃) 9.25 (s, 1H) 8.59 (s, 1H), 5.91 (s, 2H), 4.57 (t, J=6.6 Hz, 2H), 3.68 (m, 2H), 1.90 (m, 2H), 1.54 (m, 2H), 1.02 (t, J=8.0 Hz, 3H), 0.95 (m, 2H), 0.04 (s, 9H). MS m/z 351 [M+1]⁺.

Synthesis of Compound 4.4. A solution of 1M LiOH (16.8 mL) was added to compound 4.3 (5.88 g, 0.0168 mol) in THF (54 mL). After complete hydrolysis, the solvent was removed in vacuo. The solid was triturated with EtOAc. The solid was dissolved in EtOAc and 1N HCl. The organic layer was dried (MgSO₄) and evaporated to afford compound 4.4 (4 g, 81%) as a white solid. ¹H NMR (400.13 MHz, CDCl₃) 9.33 (s, 1H), 8.80 (s, 1H), 5.95 (s, 1H), 3.91 (m, 1H), 0.96 (m, 1H), −0.03 (s, 9H). MS m/z 195 [M+1]⁺.

Synthesis of Compound 4. A mixture of compound 4.4 (4.0 g, 13.7 mmol) and 4 M of hydrogen chloride in 1,4-dioxane (70 mL) was heated (70° C.). After 3 hr, the reaction was added to dichloromethane (130 ml). The solid was filtered to afford compound 4 (2.54 g) as an off-white solid. ¹H-NMR (400.13 MHz, DMSO-d₆) 9.19 (s, 1H), 8.56 (s, 1H).

Synthesis of Compound 5.2. A solution of compound 5.1 (394 mg, 2.4 mmol), BINAP (290 mg, 0.47 mmol), Pd(CH₃CN)₂Cl₂ (120 mg, 4.7 mmol), N,N-diisopropylethylamine (450 uL, 2.58 mmol), acetonitrile (24 mL) and 1-butanol (24 mL) was heated (60° C.) under CO (100 psi) overnight. The reaction mixture was filtered through celite and the solvent was removed in vacuo. The residue was purified by flash chromatography using hexane/EtOAc (SiO₂, 100/0 to 0/100) as eluant to afford compound 5.2 (640 mg). ¹H NMR (400.13 MHz, DMSO-d₆) δ 9.21 (s, 1H), 8.50 (s, 1H), 4.45 (t, J=6.5 Hz, 2H), 4.11 (s, 3H), 1.80 (m, 2H), 1.45 (m, 2H), 0.95 (t, J=7.3 Hz, 3H). MS m/z 235 [M+1]⁺.

Synthesis of Compound 5. A solution of 1 M LiOH (2.7 mL) was added to a solution of compound 5.2 (549 mg, 2.35 mmol), and MeOH (500 uL) in THF (5 mL). After the reaction was complete, the solvent was removed. The residue was dissolved in water and extracted with dichloromethane. The water layer was acidified with 1 N HCl. The precipitate was filtered to afford compound 5 (92 mg) as an off-white solid. ¹H-NMR (400.13 MHz, DMSO-d₆) 8.95 (s, 1H), 8.51 (s, 1H), 4.05 (s, 3H). MS m/z 179 [M+1]⁺.

Scheme 6.

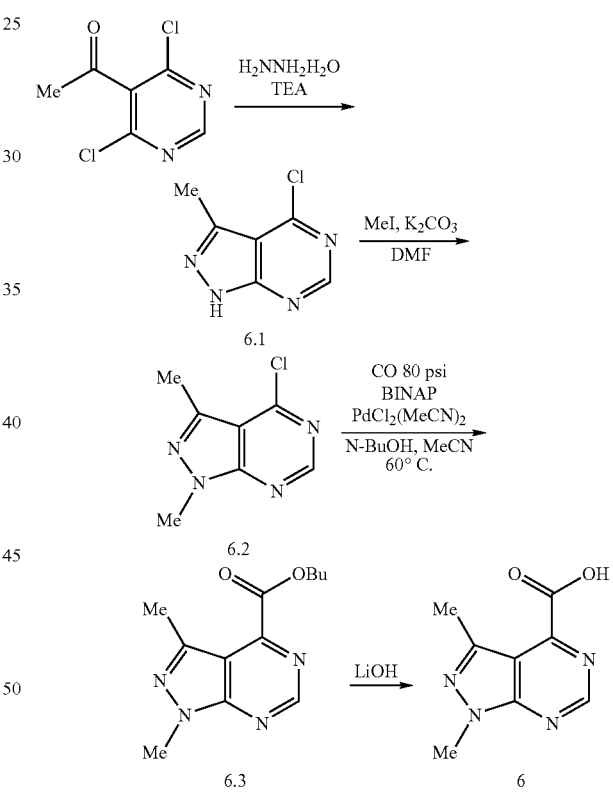

Scheme 5.

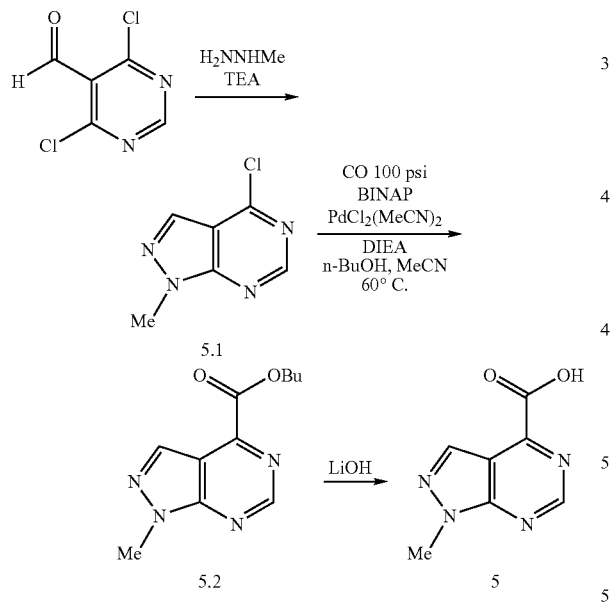

Synthesis of Compound 5.1. N-methylhydrazine (316 uL, 5.9 mmol) was slowly added to a solution of 4,6-dichloropyrimidine-5-carbaldehyde (1.0 g, 5.7 mmol), and triethylamine (0.76 mL, 5.4 mmol) in 1,4-dioxane (17.6 mL) at 8° C. After the addition was complete, the reaction was warmed to RT. After 1 hr, the reaction mixture was filtered and evaporated. The residue was purified by flash chromatography using dichloromethane/EtOAc (SiO₂, 100/0 to 0/100) as eluant to afford compound 5.1 (840 mg) as an off-white solid. ¹H-NMR (400.13 MHz, CDCl₃) δ 8.80 (s, 1H), 8.18 (s, 1H), 4.17 (s, 3H). MS m/z 169 [M+1]⁺.

Synthesis of Compound 6.1. Hydrazine hydrate (107 uL, 2.20 mmol) was slowly added to a solution of 1-(4,6-dichloro-pyrimidin-5-yl)-ethanone (Clark, J. et al J. Chem. Soc. 1976, 9, 1004) (400 mg, 2.09 mmol) and triethylamine (280 uL, 2.0 mmol) in 1,4-dioxane (7 mL) at 8° C. After the addition was complete, the reaction mixture was warmed to RT. After 2.5 hr, the reaction mixture was filtered through celite and then evaporated to afford compound 6.1 (200 mg) as a yellow solid. ¹H-NMR (400.13 MHz, DMSO-d₆) 14.07 (s, 1H), 8.75 (s, 1H), 2.64 (s, 3H). MS m/z 169 [M+1]⁺.

Synthesis of Compound 6.2. A mixture of compound 6.1 (200 mg, 1 mmol), MeI (81 uL, 1.3 mmol), and K₂CO₃ (490 mg, 3.6 mmol) in DMF (2 mL, 30 mmol) was stirred at RT. After 1 hr, the reaction was filtered and evaporated. The residue was purified by flash chromatography using dichloromethane/EtOAc (SiO$_2$, 100/0 to 0/100) as eluant to afford compound 6.2 (74 mg). $^1$H-NMR (400.13 MHz, CDCl$_3$) δ 8.71 (s, 1H), 4.07 (s, 3H), 2.74 (s, 3H). MS m/z 183 [M+1]$^+$.

Synthesis of Compound 6.3. A mixture of compound 6.2 (74 mg, 0.40 mmol), [(R)-(+)-2,2'-bis(diphenylphosphino)-1,1'-binaphthyl]palladium(II) chloride (60 mg, 0.08 mmol), N,N-diisopropylethylamine (140 uL, 0.81 mmol), 1-butanol (6 mL), and acetonitrile (6 mL) was heated (60° C.) under CO (80 psi) overnight. The residue was purified by flash chromatography using hexane/EtOAc (SiO$_2$, 100/0 to 0/100) as eluant to afford compound 6.3 (35 mg) as a colorless oil. $^1$H-NMR (400.13 MHz, CDCl$_3$) δ 9.09 (s, 1H), 4.53 (t, J=7.0 Hz, 2H), 4.11 (s, 1H), 2.75 (s, 3H), 1.87 (m, 2H), 1.51 (m, 2H), 1.00 (t, J=7.3 Hz, 3H). MS m/z 249 [M+1]$^+$.

Synthesis of Compound 6. A solution of compound 6.3 (35 mg, 0.10 mmol), 1 M of lithium hydroxide in water (120 uL) in THF (1 mL) was stirred at RT. After 2 hr, 1M HCl (0.10 mL) was added to the reaction mixture. The solvent was removed in vacuo to afford compound 6 (24 mg) as a white solid. $^1$H-NMR (400.13 MHz, DMSO-d$_6$) δ 9.02 (s, 1H), 4.00 (s, 3H), 2.59 (s, 3H). MS m/z 193 (M+1)$^+$.

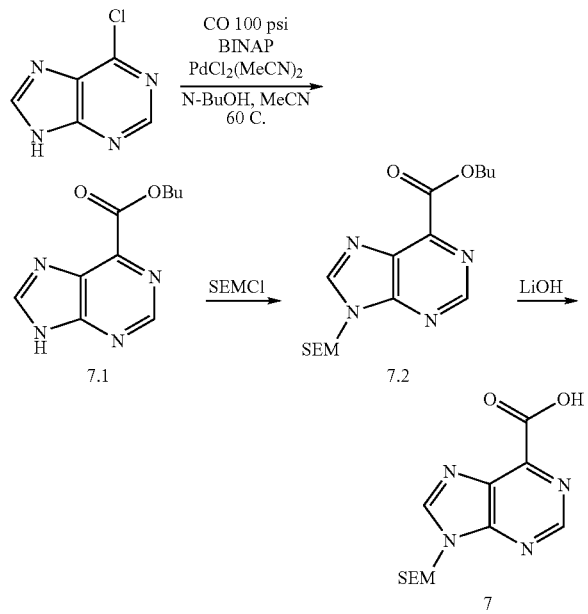

Synthesis of Compound 7.1. A mixture of 6-chloropurine (3 g, 0.02 mol), [(R)-(+)-2,2'-bis(diphenylphosphino)-1,1'-binaphthyl]palladium(II) chloride (100 mg, 0.0001 mol), N,N-diisopropylethylamine (3700 uL, 0.021 mol), acetonitrile (30 mL) and 1-butanol (30 mL) was heated (80° C.) under CO (60 psi). After 2 hr, an additional 100 mg of catalyst was added. The reaction was heated (110° C.) under CO (120 psi). After 2 days, the reaction mixture was filtered and evaporated. The residue was purified by flash chromatography using dichloromethane/EtOAc (SiO$_2$, 100/0 to 0/100) as eluant to afford compound 7.1 (734 mg) as a yellow solid. $^1$H-NMR (400.13 MHz, CDCl$_3$) δ 9.38 (s, 1H), 9.09 (s, 1H), 4.56 (t, J=7.3 Hz, 2H), 1.87 (quint, J=7.0 Hz, 2H), 1.48 (sext, J=7.0 Hz, 2H), 0.97 (t, J=7.0 Hz, 3H). MS m/z 221 [M+1]$^+$.

Synthesis of Compound 7.2. A solution of [β-(trimethylsilyl)ethoxy]methyl chloride (110 uL, 0.64 mmol), compound 7.1 (0.1 g, 0.4 mmol), and N,N-diisopropylethylamine (100 uL, 0.59 mmol) in THF (2 mL) was stirred at RT overnight. The solvent was removed and the residue was purified by flash chromatography using dichloromethane/EtOAc (SiO$_2$, 100/0 to 0/100) as eluant to afford compound 7.2 (68 mg) as colorless oil. MS m/z 351 [M+1]$^+$.

Synthesis of Compound 7. A solution of 1M of LiOH (0.39 mL) was added to a solution of compound 7.2 (68 mg, 0.19 mmol) in THF (2 mL). After 5 min, the reaction was acidified with 4N HCl in 1,4-dioxane and the solvent was removed to afford compound 7 (35 mg) as a white solid.

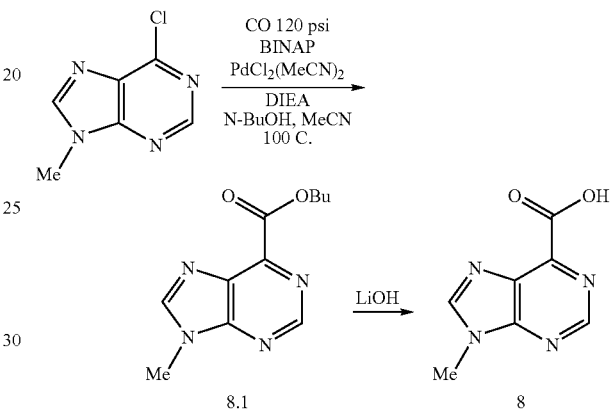

Synthesis of Compound 8.1 A mixture of 6-chloro-9-methyl-9H-purine (950 mg, 5.6 mol), [(R)-(+)-2,2'-bis(diphenylphosphino)-1,1'-binaphthyl]palladium(II) chloride (902 mg, 1.13 mol), N,N-diisopropylethylamine (2 mL, 0.011 mol), 1-butanol (80 mL), and acetonitrile (80 mL) was heated (100° C.) under CO (120 psi) overnight. The reaction was filtered and the solvent was removed in vacuo. The residue was purified by flash chromatography using dichloromethane/EtOAc (SiO$_2$, 100/0 to 0/100) as eluant to afford compound 8.1 (850 mg) as an oil. $^1$H-NMR (400.13 MHz, CDCl$_3$) δ=9.06 (s, 1H), 8.26 (s, 1H), 4.49 (t, J=7.0 Hz, 2H), 3.93 (s, 3H), 1.80 (m, 2H), 1.44 (m, 2H), 0.91 (t, J=7.6 Hz, 3H). MS m/z 235 [M+1]$^+$.

Synthesis of compound 8. A solution of 1M of LiOH (3.6 mL) was added to a solution compound 8.1 (850 mg, 3.6 mmol) in THF (20 mL). After the reaction was complete, the solvent was removed. The residue was taken up in MeOH and 4M hydrogen chloride in 1,4-dioxane (0.646 mL) was added. Concentration of the mixture provided 8. $^1$H-NMR (400.13 MHz, DMSO-d$_6$) δ=8.83 (s, 1H), 8.56 (s, 1H), 3.84 (s, 3H).

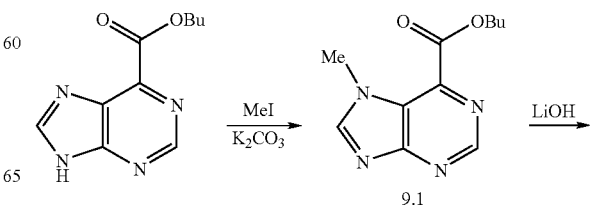

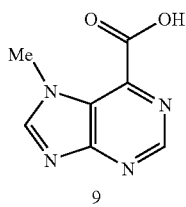

Synthesis of Compound 9.1. A mixture of compound 7.1 (100 mg, 0.454 mmol), MeI (28 uL, 0.00045 mol), and $K_2CO_3$ (310 mg, 0.0023 mol) in DMF (2 mL) was heated (40° C.). After 30 min, the reaction was filtered and the solvent was removed. $^1H$ NMR (400 MHz, $CDCl_3$) δ=9.13 (s, 1H), 8.44 (s, 1H), 4.41 (t, J=7.0 Hz, 2H), 4.06 (s, 3H), 1.80 (m, 2H), 1.44 (m, 2H), 0.87 (t, J=7.6 Hz, 3H). MS m/z 235 [M+1]$^+$.

Synthesis of Compound 9. A solution of 1 M of LiOH (0.45 mL) was added to a solution of compound 9.1 (0.227 mmol) in THF (2 mL). After 1 hr, water was added to the reaction mixture and the pH was adjusted to pH=5. The solvent was removed in vacuo. $^1H$-NMR (400.13 MHz, DMSO-$d_6$) δ=8.76 (s, 1H), 8.53 (s, 1H), 3.98 (s, 3H).

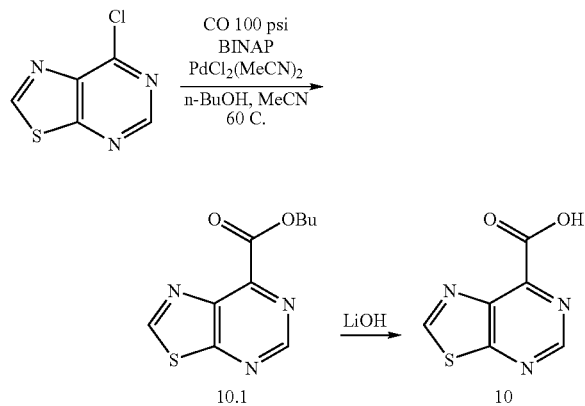

Scheme 10.

Synthesis of Compound 10.1. Thiazolo[5,4-d]pyrimidine-7-chloride (1.00 g, 0.005 mol)(Marchal, L. et al. *Bull. Soc. Chim. Belg.* 1960 69 177-193), BINAP (500 mg, 0.000625 mol), N,N-diisopropylethylamine (1.01 mL, 0.0058 mol), acetonitrile (10 mL) and 1-butanol (10 mL, 0.8 mol) was heated (70° C.) under CO (60 psi). After 24 hr, the reaction mixture was cooled and filtered. The solvent was removed in vacuo. The residue was dissolved in EtOAc (100 mL) and washed with water (3×) and brine (1×). The residue was purified by flash chromatography using hexane/EtOAc ($SiO_2$, 100/0 to 40/60) as eluant to afford compound 10.1 (910 mg) as an off-white solid. $H^1$ NMR (400.13 MHz, $CDCl_3$) δ=9.01 (s 1H), 8.73 (s 1H), 4.67 (t, J=4.0 Hz, 2H), 1.93 (m, 2H), 1.55 (m, 2H), 1.01 (t J=4.0 Hz, 3H). MS m/z 238 [M+1]$^+$.

Synthesis of Compound 10.2. A solution of LiOH (24 mg, 2.5 mmol) in water (5 mL) was added to a solution of compound 10.1 (400 mg 1.6 mmol). The reaction mixture was stirred at RT for 3 hr after which the solvent was removed in vacuo. The resulting white solid was triturated with water and dried to afford compound 10.2 (300 mg) as an off-white solid.

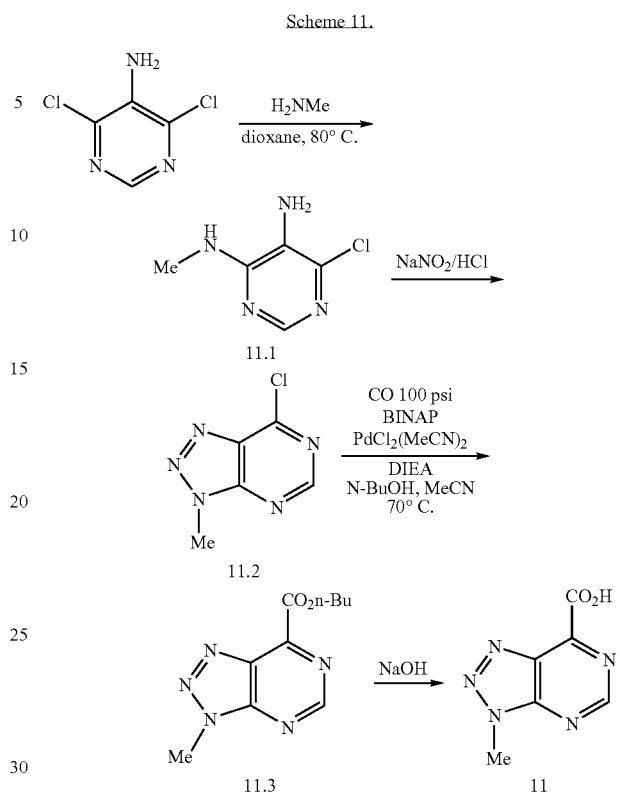

Scheme 11.

Synthesis of Compound 11.1. A mixture of 4,6-dichloropyrimidin-5-amine (10 g, 6.09 mmol) and methyl amine (20 mL, 40% solution in water) in 1,4 dioxane was heated (80° C.). After 16 hr, the reaction mixture was cooled (0° C.), the solid was filtered, washed with water (2×100 mL), and dried to afford compound 11.1 (8 g, 83%) as white solid. $^1H$-NMR (200 MHz, DMSO-$d_6$) δ=7.73 (s, 1H), 6.82 (bs, 1H), 4.92 (bs, 2H), 2.87 (d, J=4.4 Hz, 3H). MS m/z 159 [M+1]$^+$.

Synthesis of Compound 11.2. A solution of conc. HCl (15 mL), ethanol (35 mL) and sodium nitrite (2.4 g 34.7 mmol) was added to a mixture of compound 11.1 (5 g, 31.6 mmol) in 1N HCl (35 mL) at 0° C. After 1 hr, the solid was filtered and dried to afford compound 11.2 (2 g, 37%) as a white solid. $^1H$-NMR (200 MHz, DMSO-$d_6$) δ=9.08 (s, 1H), 4.31 (s, 3H). MS m/z 170 [M+1]$^+$.

Synthesis of Compound 11.3. A mixture of compound 11.2 (1 g, 5.91 mmol), Pd($CH_3CN)_2Cl_2$ (306 mg, 1.18 mmol), BINAP (736 mg, 1.18 mmol) and diisopropylethylamine (992 mg, 7.6 mmol) in n-butanol (15 mL) and acetonitrile (15 mL) was heated (70° C.) under CO (100 psi). After 24 hr, the solvent was removed and the residue was purified by flash chromatography using hexane/EtOAc ($SiO_2$, 74/26) as eluant to afford compound 11.3 (700 mg, 50%) as an off-yellow solid. $^1H$ NMR (200 MHz, DMSO-$d_6$) δ 9.40 (s, 1H), 4.49 (t, J=6.6 Hz, 2H), 4.34 (s, 3H), 1.80-1.71 (m, 2H), 1.54-1.43 (m, 2H), 0.94 (t, 3H). MS m/z 236 [M+1]$^+$.

Synthesis of Compound 11. A solution of 1N NaOH (2.8 mL) was added to a solution of compound 11.3 (0.6 g, 2.55 mmol) in THF (4.2 ml) at 0° C. After 30 min, the THF was removed in vacuo and the mixture was acidified to pH=4 (conc HCl). The precipitate was isolated by filtration to afford compound 11 (0.4 g, 88%) as a white solid. $^1H$ NMR (200 MHz, DMSO-$d_6$): δ=9.20 (bs, 1H), 4.29 (s, 3H). MS 180 [M+1]$^+$.

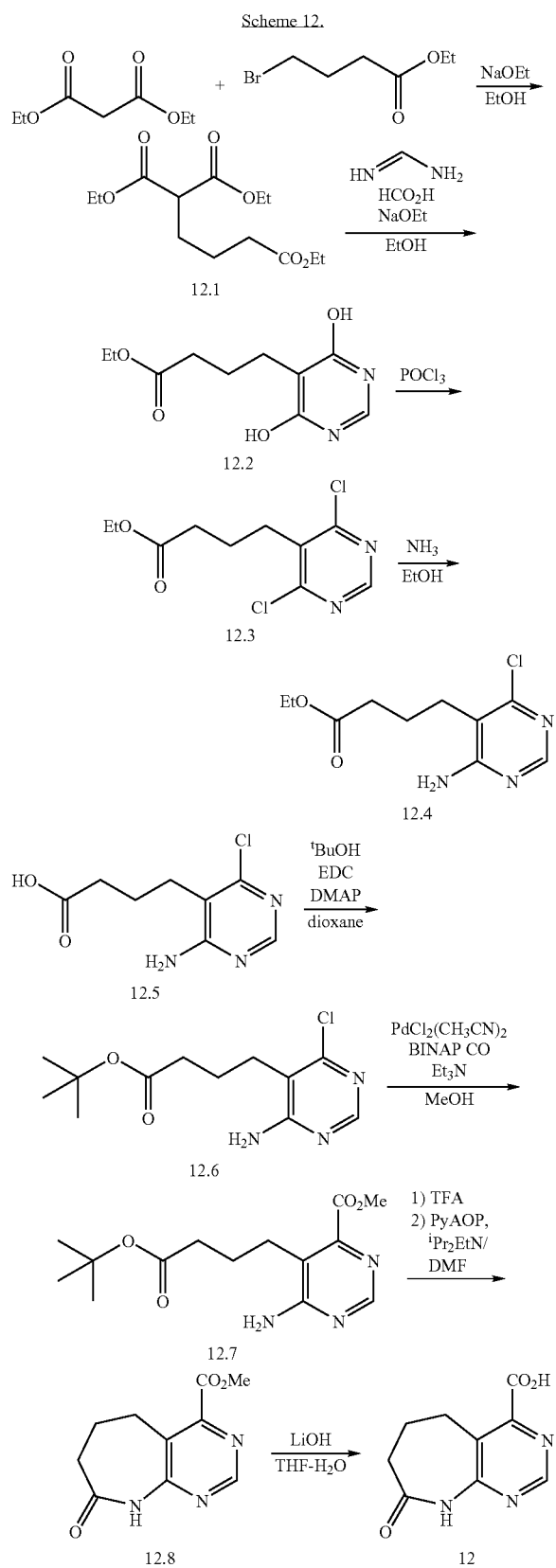

Scheme 12.

tion of sodium ethoxide. Diethyl malonate (10.0 mL, 66 mmol) and ethyl bromobutyrate (9.54 mL, 66 mmol) was added at room temperature and the reaction was stirred for three days. Ethanol was removed under reduced pressure and the reaction mixture was partitioned between water and ether. Product was extracted three times with ether and the combined organic layer was washed with brine and dried over anhydrous sodium sulfate. After removal of ether, compound 12.1 (16 g), which was used without further purification.

Synthesis of Compound 12.2. Sodium metal (2.86 g, 124 mmol) was dissolved in ethanol (120 mL) to prepare a solution of sodium ethoxide. Formamidine acetate (6.72 g, 64.5 mmol) was added at room temperature and the mixture was stirred for one hr. Insoluble salts were allowed to settle and the supernatant was added to compound 12.1 (16 g, 58.5 mmol). The reaction was stirred at RT overnight. The reaction was concentrated to about half the volume, and 3N-HCl (40 mL) was added. The precipitates were collected by filtration. The product was obtained as a mixture of ethyl and methyl esters (6.84 g, 31.9 mmol). $^1$H NMR (DMSO-$d_6$) δ 11.66 (br, 1H), 7.88 (s, 1H), 4.00 (q, 2H, J=6.9 Hz), 2.27 (t, 2H, J=7.3 Hz), 2.21 (t, 2H, J=7.3 Hz), 1.63 (tt, 2H, J=7.3, 7.3 Hz) 1.15 (t, 3H, J=6.9 Hz). MS m/z 227 [M+1]$^+$.

Synthesis of Compound 12.3. Phosphorus oxychloride (20 mL, 216 mmol) was added to compound 12.2 (5.54 g, 24.5 mmol) at room temperature. The reaction was stirred at 125° C. for three hr. After removal of excess phosphorus oxychloride at reduced pressure, ice was added to quench the reaction. The reaction was partitioned between ether and water and the aqueous layer extracted twice more with ether. The combined ether layers were washed with brine and dried over anhydrous sodium sulfate. After removal of solvent under reduced pressure, the crude product was purified using silica gel column chromatography using hexanes and ethyl acetate gradient as eluents to afford compound 12.3 (2.21 g, 34%) $^1$H NMR (CDCl$_3$) δ 8.63 (s, 1H), 4.14 (q, 2H, J=7.3 Hz), 2.95 (t, 2H, J=7.3 Hz), 2.43 (t, 2H, J=7.3 Hz), 1.94 (tt, 2H, J=7.3, 7.3 Hz), 1.26 (t, 3H, J=7.3 Hz). MS m/z 264 [M+1]$^+$.

Synthesis of Compound 12.4. A saturated solution of ammonia in ethanol (5 mL) was added to compound 12.3 (1.33 g, 5.04 mmol) in a sealed tube. The reaction was heated at 85° C. overnight. Excess ammonia and solvent was removed under reduced pressure, and the crude reaction mixture was purified using silica gel column chromatography. Using a gradient of hexanes: ethyl acetate (5:1) to (1:2) to afford compound 12.4 (930 mg, 76%). MS m/z 244 [M+1]$^+$.

Synthesis of Compound 12.5. 4-(4-Amino-6-chloro-pyrimidin-5-yl)-butyric acid ethyl ester (298 mg, 1.22 mmol) was hydrolyzed by dissolving it in THF (4 mL) and adding 1N-lithium hydroxide solution (1.3 mL, 1.3 mmol) and enough methanol (~1.5 mL) to obtain a uniform solution. The reaction was stirred at room temperature for 3 hr and neutralized by adding 3N—HCl solution (435 μL). After removal of most of THF, the acid was filtered and rinsed with water and dried to obtain the product in 88% yield (230 mg, 1.07 mmol). MS m/z 216 [M+1]$^+$.

Synthesis of Compound 12.6. 4-(4-Amino-6-chloro-pyrimidin-5-yl)-butyric acid (230 mg, 1.07 mmol), $^t$BuOH (1 mL), EDC (512 mg, 2.67 mmol) and dimethylamino pyridine (326 mg, 2.67 mmol) were dissolved in dioxane (1 mL) and stirred at RT overnight. Water was added to the reaction mixture and the product was extracted with ethyl acetate. The combined organic layers were dried over anhydrous sodium sulfate. The solvent was removed under reduced pressure and the crude material was purified using silica gel column chromatography. Using a gradient of hexanes: ethyl acetate (3:1)

to (3:2), the product was obtained in 56% yield (163 mg, 0.599 mmol). MS m/z 272 [M+1]⁺.

Synthesis of Compound 12.7. In an autoclave with a pressure gauge, was added 4-(4-amino-6-chloro-pyrimidin-5-yl)-butyric acid tert-butyl ester (320 mg, 1.18 mmol), racemic BINAP (73.3 mg, 0.112 mmol), PdCl₂(CH₃CN)₂ (31.2 mg, 0.120 mmol), triethylamine (247 µL, 1.77 mmol) and methanol (25 mL). The reaction vessel was purged with CO three times and then it was filled with CO to 60 psi. The reaction was heated to 100° C. overnight. The reaction was concentrated after filtering off the insolubles. The crude concentrate was loaded directly onto a silica gel column. Using a gradient of hexanes: ethyl acetate (2:1) to (0:100), the desired product was obtained as a mixture of tert-butyl and methyl esters (178 mg together) which was used without further separation in the next step. The yield of tert-butyl ester was determined to be 36% from NMR. Starting material was recovered in 36% yield. ¹H NMR (CDCl₃) δ 8.47 (s, 1H), 3.95 (s, 3H), 2.64-2.70 (m, 2H), 2.41 (t, 2H, J=5.9 Hz), 1.76-1.81 (m, 2H), 1.47 (s, 9H). MS m/z 296 [M+1]⁺.

Synthesis of Compound 12.8. Trifluoroacetic acid (1 mL) was added to 6-Amino-5-(3-tert-butoxycarbonyl-propyl)-pyrimidine-4-carboxylic acid methyl ester (178 mg, ~0.423 mmol of desired starting material) and stirred at RT for four hr until the tert-butyl ester had been cleaved. The reaction was azeotroped with toluene once to remove trifluoroacetic acid. DMF (4 mL) was added followed by PyAOP (287 mg, 0.550 mmol) and diisopropylethylamine (368 uL, 2.11 mmol). The reaction was stirred at RT overnight. Some DMF was removed under reduced pressure and the reaction was partitioned between water and ethyl acetate. The product was extracted three times from aqueous layer. The combined organic layers were dried over anhydrous sodium sulfate. After removal of the solvent under reduced pressure, the crude material was purified using silica gel column chromatography. Using a gradient of hexanes:ethyl acetate (2:1) to (1:2), the product eluted as a mixture with HOAt. The mixture was dissolved in ethyl acetate and washed with saturated sodium bicarbonate solution. The aqueous phase was back extracted three times with ethyl acetate to obtain compound 12.8 (66 mg 71%). ¹H NMR (CD₃OD) δ 8.81 (s, 1H), 6.97 (s, 3H), 2.95 (dd, 2H, J=6.9, 7.3 Hz), 2.50 (dd, 2H, J=6.9, 7.3 Hz), 2.31 (tt, 3H, J=6.9, 7.3 Hz). MS m/z 222 [M+1]⁺.

Synthesis of Compound 12. Compound 12.8 (66.4 mg, 0.300 mmol) was dissolved in THF (1 mL) at RT. Lithium hydroxide (1M-aqueous, 0.3 mL) was added and the mixture was stirred for 3 hr. 3N-Hydrochloric acid (105 uL) was added and the mixture was toluene azeotroped followed by lyophilization. The crude lyophilized 12 was used without further purification. ¹H NMR (DMSO-d6) δ10.5 (s, 1H), 8.80 (s, 1H), 2.76 (t, 2H, J=6.8 Hz), 2.35 (t, 2H, J=7.3 Hz), 2.14 (tt, 2H, J=6.8, 7.3 Hz). MS m/z 208 [M+1]⁺.

Scheme 13.

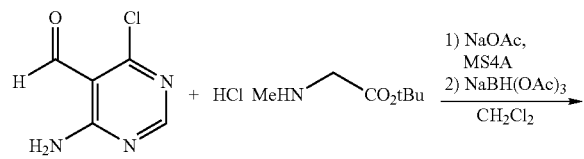

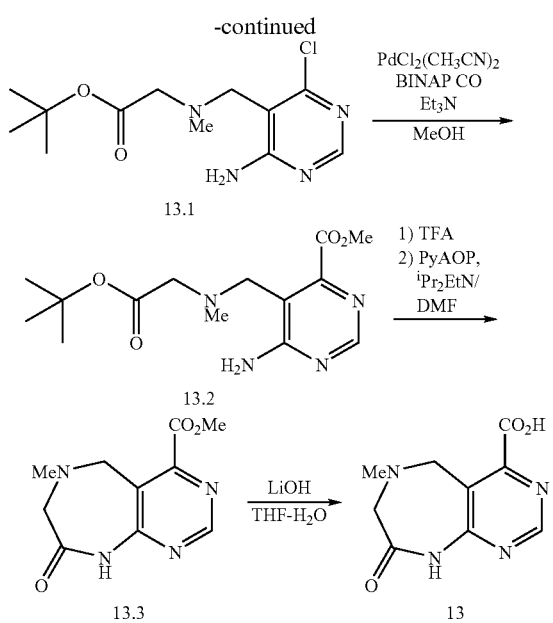

Synthesis of Compound 13.1. Sarcosine tert-butyl ester hydrochloride (898 mg, 4.95 mmol) was dissolved in dichloromethane (10 mL) at RT. Sodium acetate (328 mg, 3.99 mmol) was added and the reaction mixture was sonicated to obtain a uniform suspension. Molecular sieves 4 A (powder, 589 mg) and 4-amino-6-chloro-pyrimidine-5-carbaldehyde (601 mg, 3.81 mmol) were added and the reaction was stirred at RT for 2 hr. Sodium triacetoxyborohydride (1.21 g, 5.69 mmol) was added and the reaction was stirred overnight at RT. Reaction was diluted with dichloromethane and neutralized with saturated sodium bicarbonate solution. After celite filtration to remove molecular sieves, the layers were separated and the aqueous layer was extracted twice more with dichloromethane. The combined organic layers were dried over anhydrous sodium sulfate. After removal of the solvent under reduced pressure, the crude material was purified by silica gel column chromatography using a gradient of hexanes:ethyl acetate (3:1) to (2:1). The product was obtained in 38% yield (417 mg, 1.45 mmol). MS m/z 287 [M+1]⁺.

Synthesis of Compound 13.2. A bomb was pressure gauge was charged with [(4-amino-6-chloro-pyrimidin-5-ylmethyl)-methyl-amino]-acetic acid tert-butyl ester (1.07 g, 3.72 mmol), racemic BINAP (232 mg, 0.373 mmol), PdCl₂(CH₃CN)₂ (96.4 mg, 0.372 mmol), triethylamine (778 uL, 5.58 mmol) and methanol (30 mL). The bomb was purged with CO three times and then filled to 60 psi. The bomb was heated to 100° C. overnight. After filtering off the insolubles, the reaction was concentrated and loaded onto a silica gel column. Using a gradient of hexaes:ethyl acetate (2:1) to (1:2), the product was obtained in 63% yield (722 mg, 2.33 mmol) along with 26% (280 mg, 0.977 mmol) recovered starting material. ¹H NMR (DMSO-d6) δ 8.29 (s, 1H), 3.82 (s, 3H), 3.41 (s, 2H), 3.21 (s, 2H), 2.09 (s, 3H), 1.42 (s, 9H). MS m/z 311 [M+1]⁺.

Synthesis of Compound 13.3. Trifluoroacetic acid (2.5 mL) was added to 6-amino-5-[(tert-butoxycarbonylmethyl-methyl-amino)-methyl]-pyrimidine-4-carboxylic acid methyl ester (722 mg, 2.33 mmol of desired starting material) and stirred at RT for four hr. More TFA (1 mL) was added and stirred further. Cleavage of tert-butyl ester was complete after another addition of TFA (1 mL). The reaction was azeotroped with toluene once to remove trifluoroacetic acid. DMF (20 mL) was added followed by PyAOP (1.46 g, 2.80 mmol) and diisopropylethylamine (2 mL, 11.5 mmol). The reaction was stirred at RT overnight. Some DMF was removed under reduced pressure and the reaction was partitioned between aqueous sodium bicarbonate solution and ethyl acetate. The product was extracted seven times from aqueous layer. The combined organic layers were dried over anhydrous sodium sulfate. After removal of the solvent under reduced pressure, the crude material was purified using silica gel column chromatography. Using a gradient of hexanes:ethyl acetate (1:1) to (0:100), the product was obtained in ca 64% yield (551 mg, 1.53 mmol) containing some DMF and diisopropylethylamine. $^1$H NMR (DMSO-d6) δ 10.87 (s, 1H), 8.80 (s, 1H), 3.93 (s, 2H), 3.90 (s, 2H), 3.63 (s, 2H), 2.32 (s, 3H). MS m/z 237 [M+1]$^+$.

Synthesis of Compound 13. Compound 13.3 (54.8 mg, 0.232 mmol) was stirred in a mixture of THF (626 uL) and 1N-lithium hydroxide solution (208 uL) at RT for 6.5 hr. 3N-Hydrochloric acid (70 uL) was added to the reaction mixture and the reaction was lyophilized. The crude lyophilized 13 was used without further purification. MS m/z 223 [M+1]$^+$.

Scheme 14.

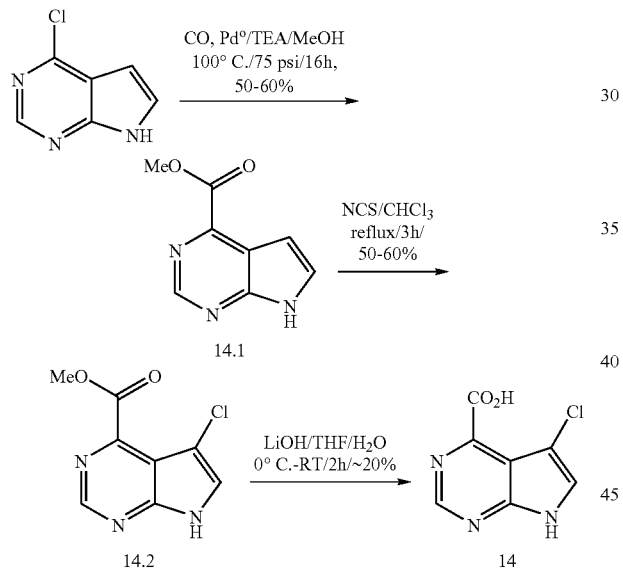

Synthesis of Compound 14.1. A mixture of 4-chloro-7H-pyrrolo[2,3-d]pyrimidine (6 g, 39 mmol), (BINAP) PdCl$_2$ (318 mg, 0.38 mmol), TEA (5.13 g, 50.7 mmol), in MeOH (20 mL) was heated (100° C.) under CO (100 psi). After 16 hr, the MeOH was removed under reduced pressure, the precipitate was filtered off and triturated (EtOAc) to afford compound 14.1 (4.4 g, 65%). $^1$H-NMR (200 MHz, DMSO-d$_6$) δ=12.48 (s, 1H), 8.81 (s, 1H), 7.95 (s, 1H), 687 (s, 1H), 3.95 (s, 3H). MS m/z 178 [M+1]$^+$.

Synthesis of Compound 14.2. A solution of compound 14.1 (1 g, 0.56 mmol), NCS (980 mg, 7.33 mmol) in CHCl$_3$ (50 ml) was refluxed. After 3 hr, the solvent was removed in vacuo. The residue was dissolved (EtOAc), and the organic layer was washed (water), dried (Na$_2$SO$_4$), and evaporated. The residue was triturated (MeOH) to afford compound 14.2 (700 mg, 58%) as a pale yellow solid. $^1$H-NMR (200 MHz, DMSO-D$_6$) δ=12.88 (s, 1H), 8.89 (s, 1H), 7.97 (s, 1H), 3.97 (s, 3H). MS 212 [M+1]$^+$.

Synthesis of Compound 14. A solution of 1 M LiOH (10.6 mmol) was added to a solution of compound 14.2 (1.5 g, 7.10 mmol), in THF/H2O (12 ml of 1:2) at 0° C. The reaction was then warmed to RT. After 2 hr, the reaction mixture was acidified with 1N HCl to pH 2. The THF was removed in vacuo, and the resulting solid was filtered off to afford compound 14 (1.1 g, 78%). $^1$H-NMR (500 MHz, DMSO-d$_6$) δ=12.78 (s, 1H), 8.85 (s, 1H), 9.93 (s, 1H). MS 198 [M+1]$^+$.

Scheme 15.

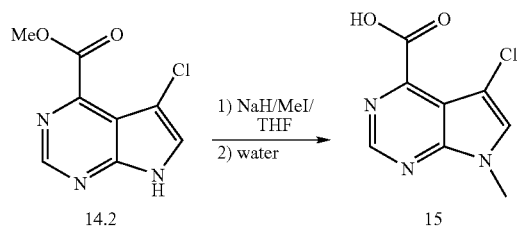

Synthesis of Compound 15.1. Sodium Hydride (60% in oil, 340 mg, 14.2 mmol) was added to a solution of compound 14.2 (1.5 g, 7.1 mmol), in THF (40 mL) at 0° C. The reaction was warmed to RT. After 1 hr, MeI (1.36 ml, 21.2 mmol) was added to the reation. After 16 hr, the reaction mixture was quenched with water. The THF was removed in vacuo. The aqueous layer was acidified with 1 N HCl to pH~2, the resulting solid was filtered off to afford compound 15 (1.1 g 73%). $^1$H-NMR (500 MHz, DMSO-d$_6$) δ=14.28 (s, 1H), 8.86 (s, 1H), 7.88 (s, 1H), 3.80 (s, 3H). MS 212 [M+1]$^+$.

Scheme 16.

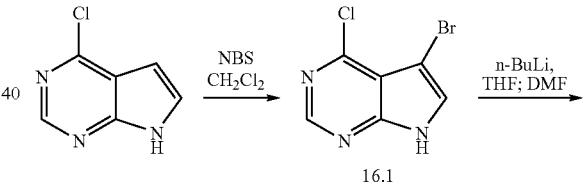

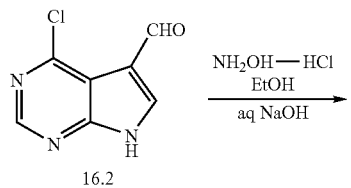

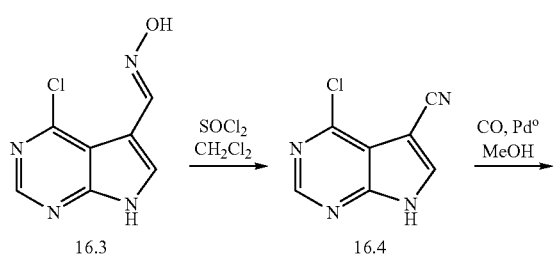

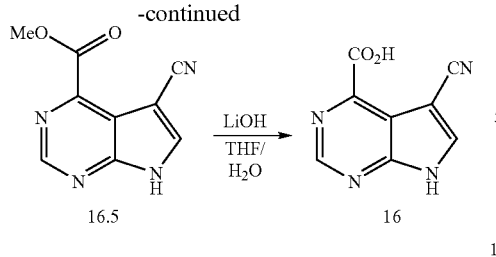

Synthesis of Compound 16.1 To a stirred solution of 4-chloro-7H-pyrrolo[2,3-d]pyrimidine (2 g, 13 mmol) in DCM (80 ml) was added N-Bromosuccinamide (3.2 g, 18 mmol) at RT. After 1 hour, the solvent was removed in vacuo, and then the solid was washed (water) and recrystalized (MeOH) to afford compound 16.1 (2 g, 66%) as an off-white solid. $^1$H-NMR (200 MHz, DMSO-d6) δ 12.96 (bs, 1H), 8.62 (s, 1H), 7.95 (s, 1H). MS m/z 234 [M+1]$^+$.

Synthesis of Compound 16.2 A solution of 1.6 M n-BuLi in hexane (18.8 ml, 40 mmol) was added to a solution of compound 16.1 (5 g, 20 mmol) in THF (200 ml) at –78° C. After 1 hr, DMF (8 ml) was added at –78° C. After 30 min, the reaction was warmed to RT over 1 hr. Water (2 ml) was added to reaction and the solvent was removed in vacuo. The crude material was dissolved (EtOAc), washed (water then NH$_4$Cl sat.) and evaporated. The resulting solid was triturated (EtOAc) to afford compound 16.2 (2.8 g, 74%) as a white solid. $^1$H-NMR (500 MHz, DMSO-d6) δ=13.54 (bs, 1H), 10.22 (s, 1H), 8.73 (s, 1H), 8.58 (s, 1H). MS m/z 181 [M+]$^+$.

Synthesis of Compound 16.3 To a stirred solution of compound 16.2 (3 g, 16 mmol) in Ethanol (30 mL) was added NH$_2$OH.HCl (1.3 g, 19 mmol), and 2M NaOH (5 ml) at RT. After 3 hr, the reaction was heated (50° C.) for 2 h The reaction was cooled, and the solid was filtered and washed (water) to afford compound 16.3 (2.4 g, 75%) as a white solid. $^1$H-NMR (500 MHz, DMSO-d6): δ 12.94 (bs, 1H), 11.72 (s, 1H), 8.64 (s, 1H), 8.55 (s, 1H), 8.07 (s, 1H). MS m/z 197 [M+1]$^+$.

Synthesis of Compound 16.4 To a solution of compound 16.3 (3 g, 15 mmol) in DCM (60 ml) was added SOCl$_2$ (11 ml, 153 mmol) at RT. After 5 hr, SOCl$_2$ (5 ml) was added to the reaction. After 16 hr, the reaction was heated (40° C.) for 1 hr. The solvent was removed in vacuo. The residue was dissolved (EtOAc), washed (NaHCO$_3$ sat.), dried (Na$_2$SO$_4$) and evaporated to afford compound 16.4 (2.1 g, 77%) as an off-white solid. $^1$H-NMR (500 MHz, DMSO-d6) δ 13.64 (bs, 1H), 8.76 (s, 1H), 8.67 (s, 1H). MS m/z 179 [M+1]$^+$.

Synthesis of Compound 16.5. A solution of compound 16.4 (600 mg, 3.4 mol), DIPEA (0.8 ml, 4.4 mmol), and Pd(dppf)$_2$Cl$_2$ (27 mg, 0.04 mmol) in MeOH (12 ml) under CO (100 psi) was heated (100° C.) for 16 hr. The solvent was removed in vacuo, and the residue was triturated (EtOAc) to afford compound 16.5 (400 mg, 58%) as an off-white solid. $^1$H-NMR (500 MHz, DMSO-d6) δ 13.64 (bs, 1H), 9.06 (s, 1H), 8.80 (s, 1H), 3.98 (s, 3H). MS m/z 203 [M+1]$^+$.

Synthesis of Compound 16. Lithium Hydroxide (280 mg, 6.7 mmol) was added to a solution of compound 16.5 (900 mg, 4.4 mmol) in THF/HH$_2$O (10 ml of 5:1) at 0° C. and then the reaction was stirred at RT for 2 hr. The reaction was acidified to pH~2 with 2 N HCl. The solvent was removed in vacuo and the residue was triturated with (EtOAc) to afford compound 16 (780 mg, 93%) as an off white solid. $^1$H-NMR (500 MHz, DMSO-d6): δ 13.64 (bs, 1H), 8.99 (s, 1H), 8.71 (s, 1H). MS m/z 189 [M+1]$^+$.

Scheme 17

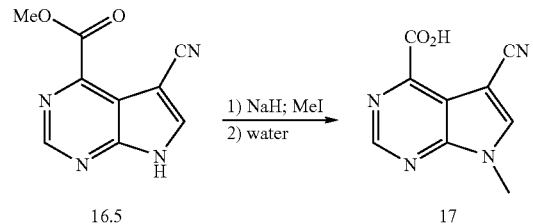

Synthesis of Compound 17. Sodium hydride (60% in mineral oil, 350 mg, 8.9 mmol) was added to a solution of compound 16.5 (1.2 g, 5.9 mmol) in THF (12 ml) 0° C. The reaction mixture was warmed to RT. After 1 hr, methyl iodide (1.1 ml, 17 mmol) was added to the reaction. After 16 hr, the reaction mixture was quenched with water (30 ml) and was then washed with ether (2×50 ml). The aqueous was acidified with 2N HCl, the precipitated material was filtered off to afford compound 17 (1 g, 83%) as an off white solid. 1H-NMR (500 MHz, DMSO-d6): δ 13.14 (bs, 1H), 9.08 (s, 1H), 8.75 (s, 1H), 3.90 (s, 3H). MS m/z 203 [M+1]$^+$.

Scheme 18.

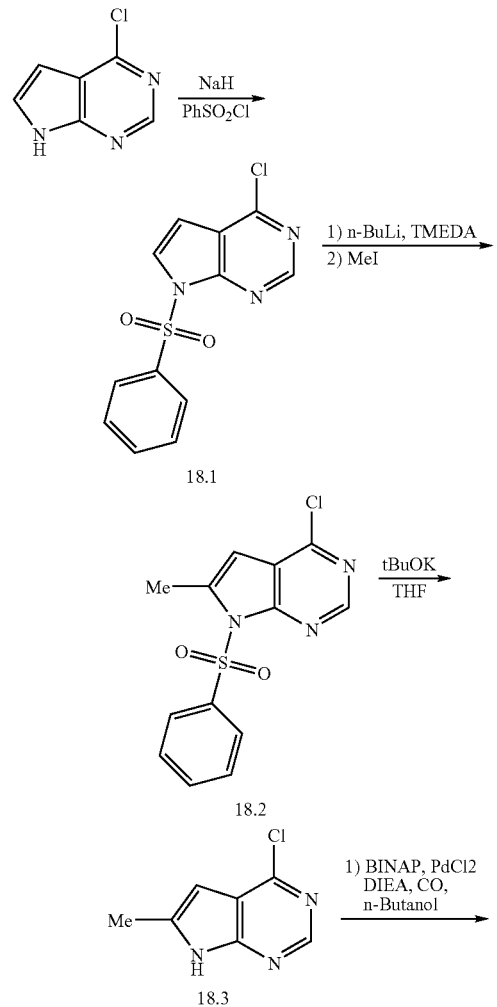

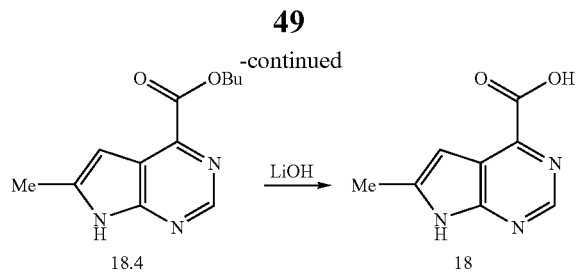

Synthesis of Compound 18.1. Sodium hydride (60% in oil, 0.97 g, 40 mmol) was added to a mixture of 4-chloro-7H-pyrrolo[2,3-d]pyrimidine (2.5 g, 16.2 mmol) in THF (75 ml) at 0° C. After 3 hr, benzene sulfonyl chloride (4.3 g, 24 mmol) was added and the reaction was warmed to RT. After 6 hr, the reaction mixture was poured into saturated NH$_4$Cl and extracted with EtOAc (3×100 ml). The organic layer was washed (brine), dried (Na$_2$SO$_4$) and evaporated. The residue of triturated with hexane (3×100 ml) to afford compound 18.1 (3.5 g, 73%). $^1$H-NMR (200 MHz, DMSO-d6) δ 8.81 (s, 1H), 8.12-8.15 (m, 3H), 7.77 (t, J=4.5 Hz, 1H), 7.66-7.67 (m, 2H), 6.96 (d, J=3.7 Hz, 1H). MS m/z 294 [M+1]$^+$.

Synthesis of Compound 18.2. N,N,N,N-tetramethyl-ethane-1,2-diamine (0.8 ml, 0.057 mol) and 1.6 M n-BuLi in hexane (3.62 ml, 0.057 mol) added at the same time over 5 min to a solution of compound 18.1 (1 g, 34 mmol) in THF (30 ml) at −78° C. After 3 min, methyl iodide (1.1 ml, 0.017 mol) was added to the reaction. After 3 hr, the reaction was warmed to 20° C. over an 1 hr. Reaction mixture was cooled to −78° C. and NH$_4$Cl sat. was added. The reaction was extracted (EtOAc 3×50 ml), dried (Na$_2$SO$_4$) and evaporated. The residue was purified by flash chromatography using hexane/DCM (SiO$_2$, 95/5) as eluant to afford compound 18.2 (450 mg, 43%). 1H-NMR (200 MHz, DMSO-d6) δ 8.73 (s, 1H), 8.16-8.12 (m, 2H), 7.76-7.60 (m, 3H), 6.74 (s, 1H). MS m/z 308 [M+1]$^+$.

Synthesis of Compound 18.3. A mixture of potassium tert-butoxide (450 mg, 4 mmol) and compound 18.2 (250 mg, 0.8 mmol) in THF (7.5 ml) was stirred for 16 hr. Saturated NaHCO$_3$ was added to the reaction. The reaction was extracted (EtOAc 3×100 ml), and then the organic layer was washed (water then brine), dried (Na$_2$SO$_4$), and evaporated. The residue was purified by flash chromatography using hexane/EtOAc (SiO$_2$, 100/0 to 0/100) as eluant to afford compound 18.3 (118 mg, 87%). $^1$H-NMR (200 MHz, DMSO-d6) δ 12.5 (bs, 1H), 8.47 (s, 1H), 6.29 (s, 1H), 2.42 (s, 3H). MS m/z 168 [M+1]$^+$.

Synthesis of Compound 18.4. A mixture of compound 18.3 (0.5 g, 2.9 mmol), PdCl$_2$(BINAP) (486 mg, 0.59 mmol), and DIPEA (0.7 ml, 8 mmol) in n-butanol (7.5 ml) and acetonitrile (7.5 ml) under CO gas (100 psi) was heated (100° C.) for 16 hr. The solvent was removed in vacuo, and the residue was purified by flash chromatography using hexane/EtOAc (SiO$_2$, 100/0 to 0/100) as eluant to afford compound 18.4 (350 mg, 50%). $^1$H-NMR (200 MHz, DMSO-d6) δ 12.35 (bs, 1H), 8.78 (s, 1H), 6.58 (s, 1H), 4.37 (t, J=6.6 Hz, 2H), 2.47 (s, 3H), 1.78-1.71 (m, 2H), 1.49-1.38 (m, 2H), 0.94 (t, J=7.4 Hz, 3H). MS m/z 234 [M+1]$^+$.

Synthesis of Compound 18. A solution 1M LiOH (0.85 ml 0.85 mmol) was added to a solution of compound 18.4 (100 mg, 0.42 mmol) in THF (1.3 ml) at 0° C. The reaction stirred at RT for 2 hr, and then the solvent was removed in vacuo to afford compound 18 (78 mg as lithium salt). $^1$H-NMR (200 MHz, DMSO-d6) δ 8.11 (s, 1H), 6.45 (s, 1H), 2.32 (s, 3H). MS m/z 184 [M+1]$^+$.

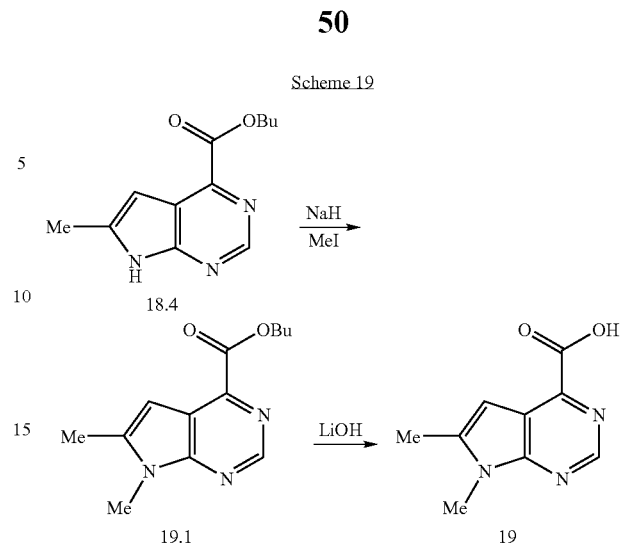

Scheme 19

Synthesis of Compound 19.1. Sodium Hydride (60% in mineral oil, 20 mg, 0.5 mmol) to a solution of compound 18.4 (100 mg, 0.42 mmol) in THF (3 ml) at 0° C. The reaction was then warmed to RT. After 1 hr, MeI (80 uL, 1.3 mmol) was added to the reaction. After 16 hr, the reaction was quenched (water) and extracted (EtOAc 3×25 ml). The organic layer was washed (brine), dried (Na$_2$SO$_4$) and evaporated to afford compound 19.1 (85 mg, 80%). $^1$H-NMR (200 MHz, DMSO-d6) δ=8.83 (s, 1H), 6.68 (s, 1H), 4.37 (t, J=6.6 Hz, 2H), 3.75 (s, 3H), 2.49 (s, 3H), 1.78-1.71 (m, 2H), 1.44-1.40 (m, 2H), 0.93 (t, J=7.4 Hz, 3H). MS m/z 248 [M+1]$^+$.

Synthesis of Compound 19. A solution of 1M LiOH (1 mL, 1 mmol) was added to a solution compound 19.1 (125 mg·0.5 mmol) in THF (1.5 ml) at 0° C. The reaction was warm to RT. After 2 hr, the THF was removed in vacuo. The aqueous solution was acidified with 11N HCl to pH 4. The obtained white solid was filtered and dried to afford compound 19 (40 mg, 42%). $^1$H-NMR (200 MHz, DMSO-d6) δ=8.84 (s, 1H), 7.01 (s, 1H), 3.89 (s, 3H), 2.61 (s, 3H). MS m/z 192 [M+1]$^+$.

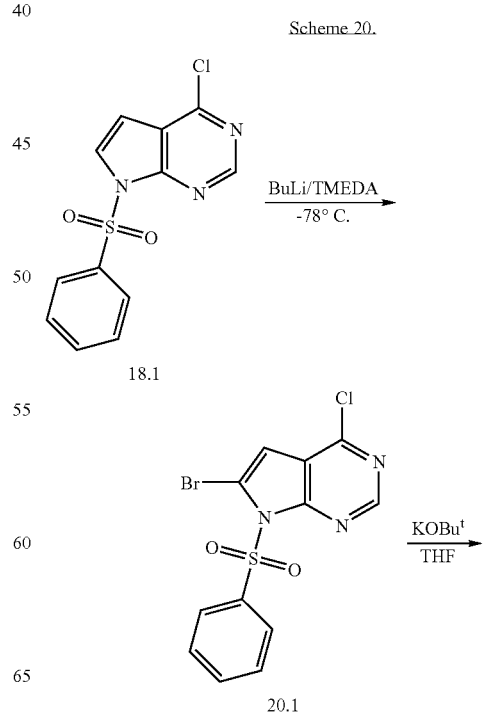

Scheme 20.

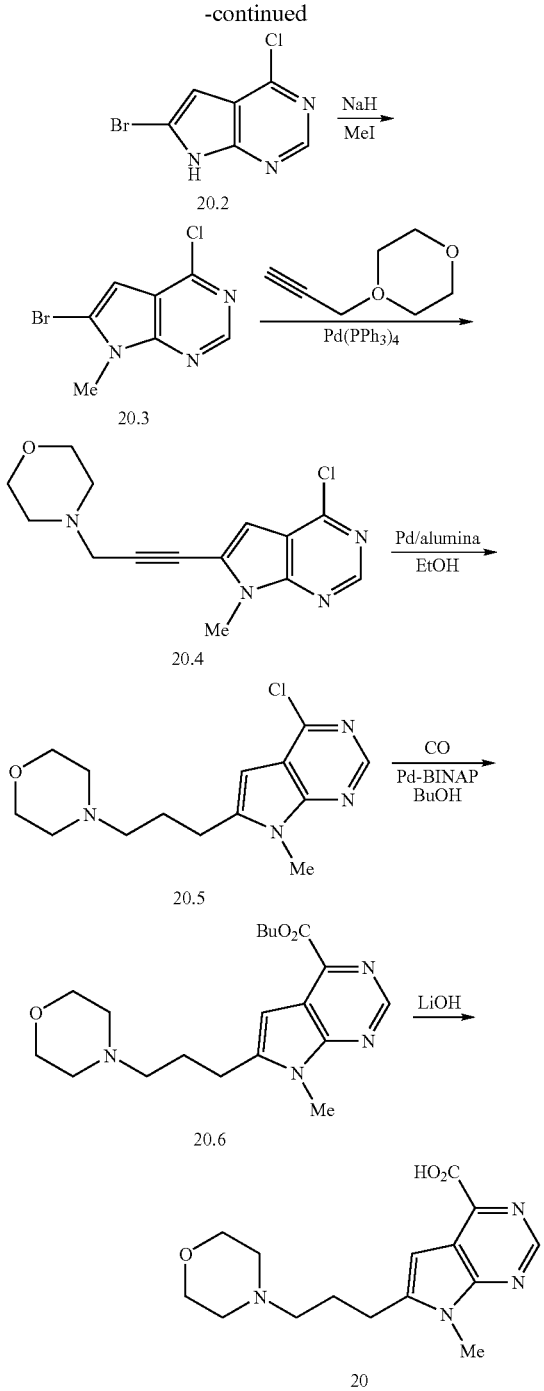

Synthesis of Compound 20.1. N,N,N,N-Tetramethylethylene diamine (0.5 ml, 3.5 mmol) and 1.6 M n-BuLi in hexane (2.13 ml, 3.4 mmol) were added at the same time over 5 min to a solution of compound 18.1 (500 mg, 1.7 mmol) in THF (10 ml) at −78° C. After 3 min, a solution of 1,2-dibromo tetrachloroethane (1.1 g, 3.4 mmol) in THF (5 mL) at −78° C. After 3 hr at −78° C., the reaction was warmed to RT over 1 hr. The reaction was cooled to −78° C., and then quenched with NH$_4$Cl (sat.). The mixture was extracted (EtOAc 3×50 ml), dried (Na$_2$SO$_4$), and evaporated. The residue was purified by flash chromatography using hexane/DCM (SiO$_2$, 100/0 to 0/100) as eluant to afford compound 20.1 (400 mg, 63%). $^1$H-NMR (200 MHz, DMSO-d6) δ=8.83 (s, 1H), 8.17-8.07 (m, 2H), 7.84-7.64 (m, 3H), 7.30 (s, 1H). MS m/z 374 [M+1]$^+$.

Synthesis of Compound 20.2. Potassium tert-butoxide (1.2 g, 10 mmol) was added to a solution of compound 20.1 (800 mg, 2.2 mmol) in THF (24 ml). After 16 hr, NaHCO$_3$ sat. was added to the reaction, and the reaction was extracted (EtOAc 3×100 ml). The organic layer was washed (water then brine), dried (Na$_2$SO$_4$), and evaporated. The residue was purified by flash chromatography using hexane/EtOAc (SiO$_2$, 100/0 to 0/100) as eluant to afford compound 20.2 (400 mg, 80%). $^1$H-NMR (200 MHz, DMSO-d6) δ 13.41 (bs, 1H), 8.57 (s, 1H), 6.79 (s, 1H). MS m/z 232 [M+1]$^+$.

Synthesis of Compound 20.3. Sodium Hydride (60% in mineral oil, 103 mg, 2.5 mmol) was added to a solution of compound 20.2 (400 mg, 1.7 mmol) in THF (16.4 ml) at 0° C. The reaction was warm to RT. After 1 hr, methyl iodide (73 mg, 5.3 mmol) was added to the reaction mixture. After 16 hr, the reaction was quenched (water) and extracted (EtOAc 3×25 ml). The organic layer was washed (brine), dried (Na$_2$SO$_4$), and evaporated. The residue was purified by flash chromatography using hexane/EtOAc (SiO$_2$, 100/0 to 0/100) as eluant to afford compound 20.3 (250 mg, 60%). $^1$H-NMR (200 MHz, DMSO-d6) δ 8.64 (s, 1H), 6.96 (s, 1H), 3.79 (s, 3H). MS m/z 245 [M+1]$^+$.

Synthesis of Compound 20.4. A solution of compound 20.3 (500 mg, 2.02 mol), propargyl morpholine (250 mg, 2.04 mmol), Pd(PPh$_3$)$_4$ (117 mg, 0.10 mmol), CuI (38 mg, 0.2 mmol) and DIEA (394 mg, 3.5 mmol) in water (15 ml) was heated (70° C.). The reaction was cooled (0° C.), and water (50 ml at 0° C.) was added. The mixture was extracted (ethyl ether, 3×100 ml), and then the organic layer was dried (Na$_2$SO$_4$) and evaporated. The residue was purified by flash chromatography using DCM/MeOH (SiO$_2$, 97/3) as eluant to afford compound 20.4 (200 mg, 34%). $^1$H-NMR (200 MHz, DMSO-d6): δ=8.68 (s, 1H), 6.96 (s, 1H), 3.82 (s, 3H), 3.69 (s, 2H), 3.61 (t, J=8.8 Hz, 4H), 2.55 (t, J=8.8 Hz, 4H). MS m/z 291 [M+1]$^+$.

Synthesis of Compound 20.5. A mixture of compound 20.4 (400 mg, 1.4 mmol), 5% Pd on Alumina (100 mg) in EtOH (20 ml) under H$_2$ (balloon) was stirred for 2 hr. The reaction was filtered through Celite®, and the solvent was removed in vacuo. The residue was purified by flash chromatography using DCM/MeOH (SiO$_2$, 97/3) as eluant to afford compound 20.5 (220 mg, 54%). 1H-NMR (200 MHz, MeOD-d4) δ=8.51 (s, 1H), 6.47 (s, 1H) 3.84 (s, 3H), 3.72 (t, J=9.4 Hz, 4H), 2.93 (t, J=7.4 Hz, 2H), 2.58-2.50 (m, 6H), 2.02 (m, 2H). MS m/z 295 [M+1]$^+$.

Synthesis of Compound 20.6. A mixture of compound 20.5 (220 mg, 0.74 mmol), (BINAP) PdCl$_2$ (121 mg, 0.14 mmol) and DIEA (144 mg, 1.1 mmol) in n-butanol (3.3 ml) and acetonitrile (3.3 ml) was heated (80° C.) under CO gas (100 psi). After 16 hr, the solvent was removed in vacuo, and the residue was purified by flash chromatography using hex/EtOAc (SiO$_2$, 100/0 to 0/100) as eluant to afford compound 20.5 (92 mg, 34.4%). $^1$H-NMR (500 MHz, MeOD-d4) δ 8.81 (s, 1H), 6.82 (s, 1H), 4.49 (t, J=13 Hz, 2H), 3.87 (s, 3H), 3.72 (t, J=4 Hz, 4H), 2.98 (t, J=7.5 Hz, 2H), 2.57-2.5 (m, 6H) 2.06-2.03 (m, 2H), 1.88-1.85 (m, 2H), 1.57-1.53 (m, 2H), 1.05 (t, J=14.5 Hz, 3H). MS m/z 361 [M+1]$^+$.

Synthesis of Compound 20. A solution of 1M LiOH (0.2 ml, 0.23 mmol) was added to a solution of compound 20.6 (80 mg, 0.22 mmol) in THF (0.3 ml) at 0° C. After 2 h at RT, the THF removed in vacuo, and the aqueous layer was acidified with 11N HCl to pH 1. The obtained solid was filtered and dried to afford compound 20 (50 mg, 74%). $^1$H-NMR (500

MHz, DMSO-d6) δ 8.76 (s, 1H), 6.78 (s, 1H), 3.76 (s, 3H) 3.72 (bs, 4H), 3.07 (bs, 6H), 2.88 (bs, 2H), 2.07 (bs, 2H). MS m/z 305 [M+1]⁺.

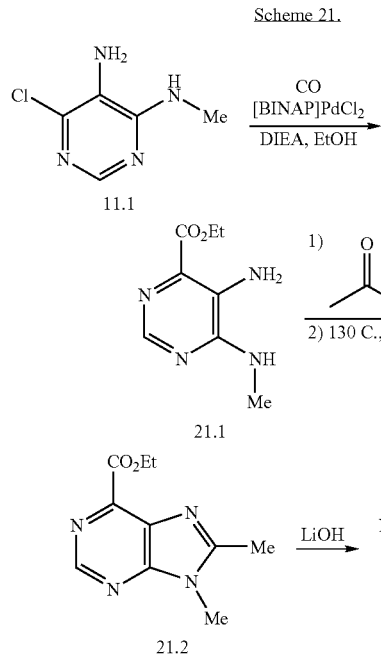

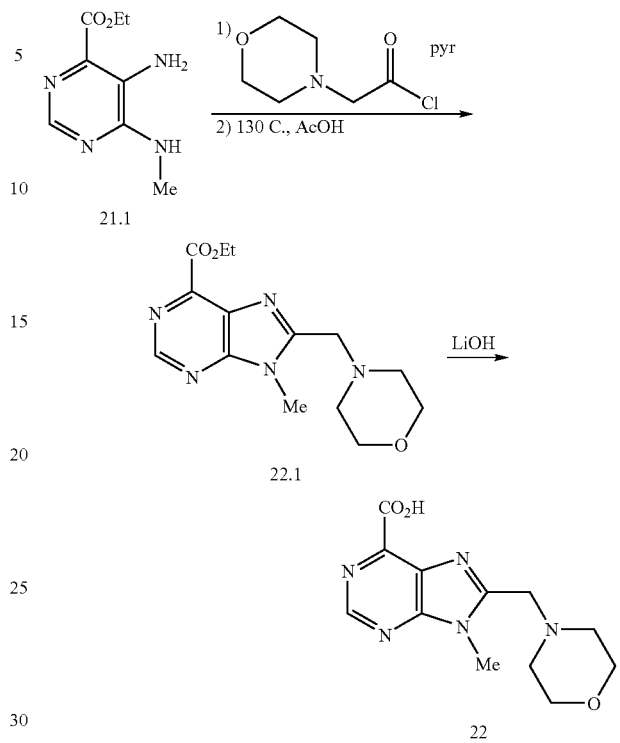

Synthesis of Compound 21.1. A mixture of compound 11.1 (1.5 g, 9.4 mmol), BINAP (1 g, 2 mmol), bis(acetonitrile)palladium(II) chloride (0.450 g, 1.73 mmol), DIEA (1.97 mL, 11.3 mmol) and EtOH (22 mL) in MeCN (22 mL) was heated (130° C.) under CO (120 psi). After 4 hr, the reaction was filtered through celite, and the solvent was removed in vacuo. The residue was purified by flash chromatography using DCM/EtOAc (SiO₂, 100/0 to 0/100) as eluant to afford compound 21.1 (338 mg, 18%) as a yellow solid. ¹H NMR (300 MHz, DMSO-d₆) δ=7.88 (s, 1H), 7.19 (q, J=4.5 Hz, 1H), 6.43 (br. s., 2H), 4.26 (q, J=7.2 Hz, 2H), 2.91 (d, J=4.5 Hz, 3H), 1.29 (t, J=7.2 Hz, 3H)

Synthesis of Compound 21.2. A mixture of compound 21.1 (60 mg, 0.30 mmol), acetyl chloride (54 uL, 0.74 mmol), triethylamine (64 uL, 0.46 mmol), pyridine (100 uL 1 mmol), and methylene chloride (1 mL, 0.02 mol) was stirred at RT. MeOH was added to the reaction and the solvent was removed in vacuo. MS m/z 239 [M+1]⁺. A solution of the residue and acetic acid (2 mL, 0.04 mol) was heated in the microwave at 130° C. for 30 min. The solvent was removed, and the residue was purified by HPLC using water/MeCN with 10 mM NH₄HCO₃ (C18, 90/10 to 10/90) as eluant to afford compound 21.2 (6 mg, 9%). ¹H NMR (400 MHz, DMSO-d₆) δ=8.93 (s, 1H), 4.43 (q, J=7.1 Hz, 2H), 3.78 (s, 3H), 2.66 (s, 3H), 1.36 (t, J=7.1 Hz, 3H) MS m/z 221 [M+1]⁺.

Synthesis of Compound 21. A solution of 1 M of lithium hydroxide (1 mL) was added to a solution of compound 21.2 (6 mg, 0.3 mmol) in tetrahydrofuran (3 mL, 0.04 mol). After 30 min, the solvent was removed in vacuo, and the residue was purified by HPLC using water/MeCN with 0.1 TFA (C18, 90/10 to 10/90) as eluant to afford compound 21 as a brown solid. ¹H NMR (400 MHz, DMSO-d₆) δ=8.93 (s, 1H), 3.78 (s, 3H), 2.67 (s, 3H). MS m/z 193 [M+1]⁺.

Synthesis of Compound 22.1. A mixture of oxalyl chloride (87 uL, 1.0 mmol) was added to a mixture of 2-morpholinoacetic acid hydrochloride (93 mg, 0.51 mmol), TEA (70 uL, 0.5 mmol), and DMF (1 drop) in acetonitrile (1 mL) was stirred. After 1 hr, the solvent was removed in vacuo. The acid chloride was redissolved in acetonitrile (1 mL) and added to a solution of compound 21.1 (80 mg, 0.4 mmol) in pyridine (300 uL, 4 mmol). The solvent was removed in vacuo. MS m/z 324 [M+1]⁺. A solution of residue in acetic acid (1 mL) was heated at 130° C. in a microwave for 10 min. The solvent was removed in vacuo to afford compound 22.1 (20 mg, 20%) MS m/z 306 [M+1]⁺.

Synthesis of Compound 22. A solution of 1 M of lithium hydroxide (98 uL) was added to a solution of compound 22.1 (20 mg, 0.06 mmol) in THF (0.6 mL) with a couple drops of methanol. 4 M of hydrogen chloride in 1,4-dioxane (20 μL) was added to the solution and the solvent was removed. ¹H NMR (400 MHz, MeOD) δ=9.20 (s, 1H), 5.11 (s, 2H), 4.08 (br. s., 4H), 4.04 (s, 3H), 3.74 (m, 4H). MS m/z 278 [M+1]⁺.

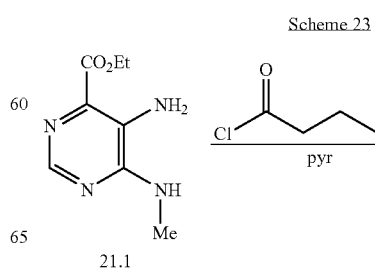

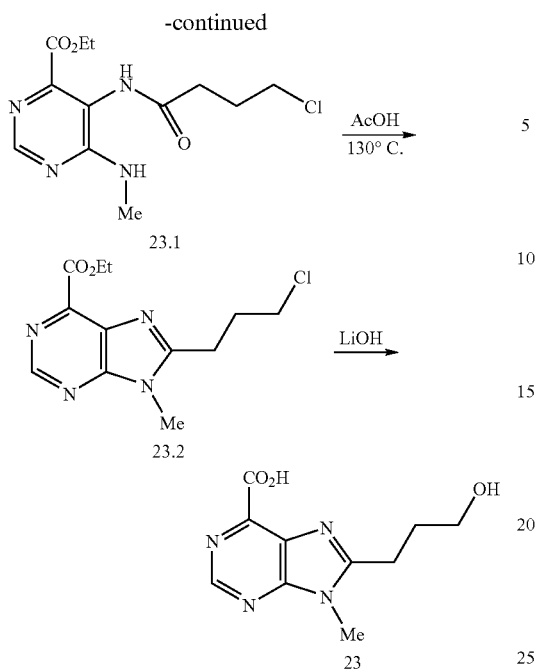

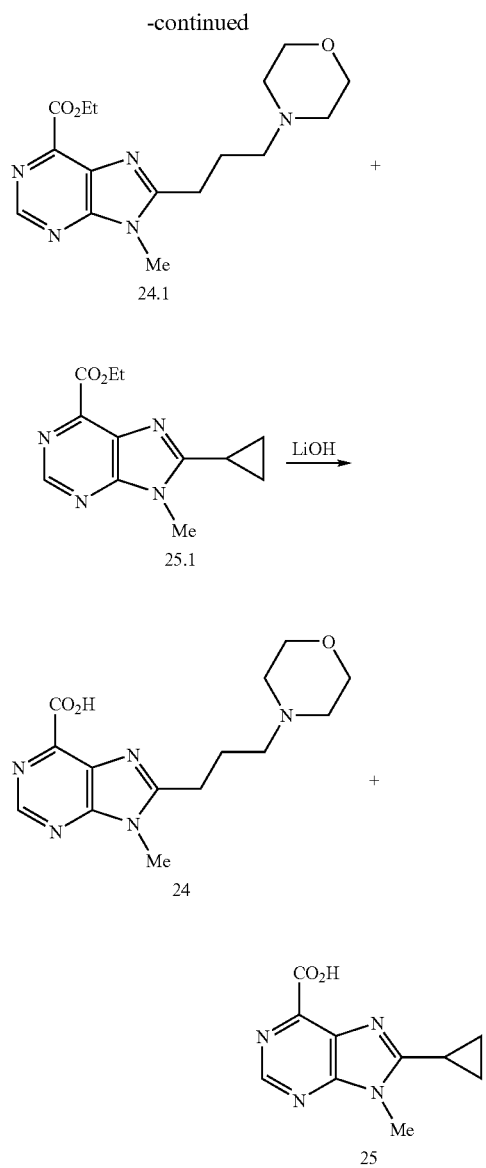

Synthesis of Compound 23.1. 4-Chlorobutyryl chloride (340 μL, 3.0 mmol) was added to a mixture of compound 21.1 (300 mg, 1.53 mmol) and pyridine (1.2 ML, 15.3 mol) in Acetonitrile (5 mL) at 0° C. After 30 min EtOH was added to the reaction, and the solvent was removed in vacuo. The residue was purified by flash chromatography using DCM/EtOAc (SiO$_2$, 100/0 to 0/100) as eluant to afford compound 23.1 (226 mg 49%) as a light yellow solid. $^1$H NMR (400 MHz, CDCl3) δ=9.74 (br. s., 1H), 8.57 (s, 1H), 6.43 (br. s., 1H), 4.45 (q, J=7.2 Hz, 2H), 3.65 (t, J=6.2 Hz, 2H), 3.06 (d, J=4.8 Hz, 3H), 2.69 (t, J=7.2 Hz, 2H), 2.20 (quin, J=6.7 Hz, 2H), 1.44 (t, J=7.1 Hz, 3H).

Synthesis of Compound 23.2. A solution of compound 23.1 (228 mg, 0.76 mmol) in acetic acid (3 mL) was heated (110 C) in a microwave for 10 min. The solvent was removed, and the residue was purified by flash chromatography using DCM/EtOAc (SiO$_2$, 100/0 to 0/100) as eluant to afford compound 23.2 (83 mg, 38%) of clear oil was recovered. $^1$H NMR (400 MHz, CDCl$_3$) δ=9.04 (s, 1H), 4.58 (q, J=7.1 Hz, 2H), 3.89 (s, 3H), 3.75 (t, J=6.0 Hz, 2H), 3.23-3.15 (m, 2H), 2.47 (dt, J=6.7, 13.5 Hz, 2H), 1.49 (t, J=7.1 Hz, 3H). MS m/z 283 [M+1]$^+$.

Synthesis of Compound 23. A solution of 1 M lithium hydroxide (70 μL) was added to a mixture of compound 23.2 (10 mg, 0.035 mmol) in tetrahydrofuran (1 mL) with a couple drops of MeOH. After 30 min, 4 M of hydrogen chloride in 1,4-dioxane (20 μL) was added to the reaction and the solvent was removed in vacuo to afford compound 23. MS m/z 237 [M+1]$^+$.

Scheme 24

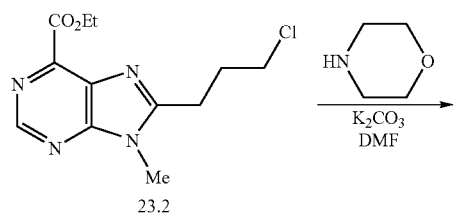

Synthesis of Compound 24.1 and 25.1. A mixture of compound 23.2 (15 mg, 0.05 mmol), morpholine (6.9 μL, 0.08 mmol), and K$_2$CO$_3$ (40 mg, 0.3 mmol) in DMF (2 mL) was stirred. The reaction was filtered and the solvent was removed. Proton NMR indicates a 1:3 ratio of compound 24.1 to compound 25.1. Compound 24.1 $^1$H-NMR $^1$H NMR (400 MHz, CDCl3) δ=9.03 (s, 1H), 4.59 (q, J=7.2 Hz, 2H), 3.88 (s, 3H), 3.65-3.60 (m, 4H), 3.10-3.04 (m, 2H), 2.49 (t, J=6.8 Hz, 2H), 2.44 (d, J=4.5 Hz, 4H), 2.12-2.09 (m, 2H), 1.49 (t, J=7.1 Hz, 3H). Compound 24.1 $^1$HNMR (400 MHz, CDCl$_3$) δ=8.99 (s, 1H), 4.57 (q, J=7.1 Hz, 2H), 3.95 (s, 3H), 1.52-1.43 (m, 3H), 1.48 (t, J=7.2 Hz, 3H), 1.29-1.22 (m, 2H)

Synthesis of Compound 24 and 25. A solution 1 M of lithium hydroxide (0.10 mL) was added to a solution of compound 24.1 and compound 25.1 (0.053 mmol) in tetrahydrofuran (2 mL) and ethanol (couple drops). After 2.5 hr, 4 M of hydrogen chloride in 1,4-dioxane (50 μL) was added to the reaction, and the solvent was removed in vacuo to afford compound 24 and compound 25. Compound 24 MS m/z 304 [M+1]$^-$. Compound 25 MS m/z 217 [M+1]$^-$.

Scheme 26.

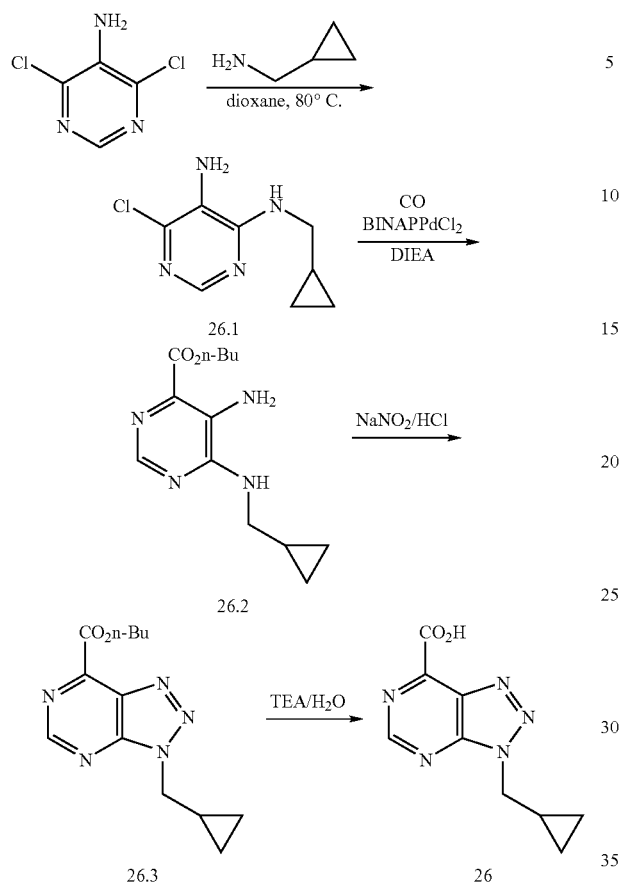

Synthesis of Compound 26.1 A solution of 4,6-dichloro-5-amino pyrimidine (4 g, 24.3 mmol), cyclopropylmethylamine (3.3 g, 29.7 mmol), DIEA (7.5 g, 61 mol) in 1,4-dioxane (9 ml) was refluxed for 16 hr. The solvent was removed in vacuo, and the residue was purified by column chromatography to afford compound 26.1 (2.5 g, 53%) $^1$H-NMR (200 MHz, DMSO-d$_6$): δ 7.70 (s, 1H), 6.92 (t, J=5.4 Hz, 1H), 5.04 (s, 1H), 3.24 (t, J=5.4 Hz, 2H), 1.06-1.02 (m, 1H), 0.47-0.40 (m, 2H), 0.25-0.20 (m, 2H). MS 199 [M+1]$^+$.

Synthesis of Compound 26.2. A mixture of compound 26.1 (700 mg, 3.5 mmol), (BINAP) PdCl$_2$ (600 mg, 0.70 mmol), DIEA (600 mg, 4.5 mmol), in MeCN (7.5 mL) and n-butanol (7.5 mL) was heated (150° C.) under CO (100 psi). After 5 hr, the solvent was removed in vacuo, and the residue was purified by column chromatography to afford compound 26.2 (250 mg, 27%). $^1$H-NMR (200 MHz, DMSO-d$_6$) δ=7.82 (s, 1H), 7.20 (t), 6.54 (s, 2H), 4.22-4.16 (m, 2H), 3.25-3.21 (m, 2H), 1.71-1.57 (m, 2H), 1.41-1.30 (m, 2H), 1.15-1.05 (m, 1H), 0.90 (t, J=7.2 Hz, 3H), 0.50-0.44 (m, 2H), 0.25-0.20 (m, 2H). MS m/z 265 [M+1]$^+$.

Synthesis of Compound 26.3. To a stirred solution of compound 26.2 (250 mg, 0.94 mmol) in ethanol (3 mL) and DCM (7 mL) was added 1N HCl (1.4 ml), 11N HCl (0.6 ml), followed by addition of NaNO$_2$ (71 mg) and stirred at 0° C. After 2 hr, the reaction was extracted (DCM). The organic layer was dried (Na$_2$SO$_4$) and evaporated, and the residue was purified by column chromatography to afford compound 26.3 (70 mg, 26%). $^1$H-NMR (200 MHz, DMSO-D$_6$) δ=9.41 (s, 1H), 4.65 (d, J=7.4 Hz, 2H), 4.49 (t, J=6.2 Hz, 2H), 1.80-1.73 (m, 2H), 1.55-1.44 (m, 3H), 0.96 (t, J=14.2 Hz, 3H), 0.58-0.52 (m, 4H). MS m/z 276 [M+1]$^+$.

Synthesis of Compound 26. Triethyl amine (30 ul, 0.21 mmol) was added to a solution of compound 26.3 (60 mg, 0.22 mmol), in THF/H2O (2 ml of 1:1) was at 0° C. The reaction was then warmed to RT. After 2 hr, the solvent was removed in vacuo to afford compound 26 (60 mg). $^1$H-NMR (200 MHz, DMSO-D6) δ=8.98 (s, 1H), 4.53 (d, J=7.4 Hz, 2H), 1.17-0.48 (m, 5H).

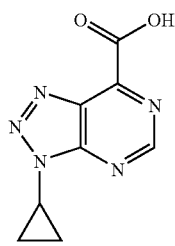

27

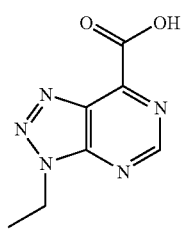

28

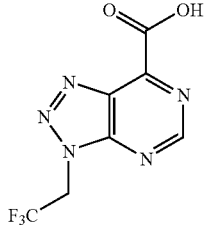

29

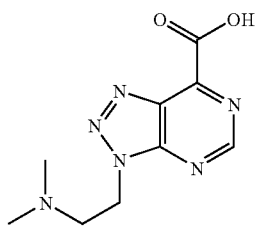

30

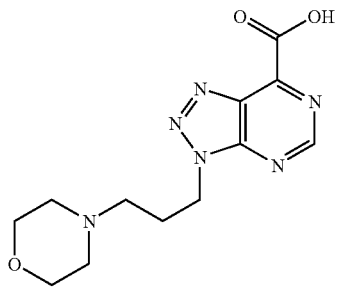

31

Synthesis of Compound 27, 28, 29, 30, and 31. The synthesis of compounds 27, 28, 29, 30, and 31 were accomplished following Scheme 26 substituting the appropriate amine for cyclopropylmethylamine.

Scheme 32.

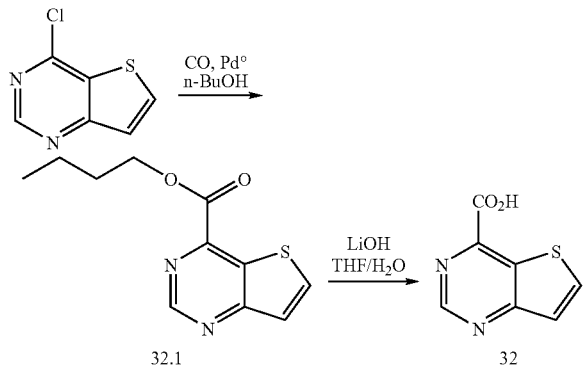

Synthesis of Compound 32. The synthesis of compounds 23 was accomplished following the synthesis of compound 4.4 substituting 4-chlorothieno[3,2-d]pyrimidine for compound 4.2.

Synthesis of -$L^1$-$Cy^1$-$L^2$-$Cy^2$ Moieties (1) Thiazole Condensation

Synthesis of Compound A.1. To an ice cold solution of 2-amino-acetamide (100 g, 0.90 mol) in water/dioxane (1200 mL, 1:1), CbzCl (130 mL, 0.90 mol) was added slowly. The reaction was brought to room temperature and stirred at RT for 12 hr. Dioxane was removed under reduced pressure and the reaction mixture was filtered and air-dried to obtain compound A.1 as a white solid (167.0 g, 88%). $^1$H NMR: (CDCl$_3$-DMSO-d$_6$, 200 MHz) δ: 7.4 (s, 5H), 6.8 (1H, D$_2$O exchangeable), 6.2 (1H, D$_2$O exchangeable), 6.1 (1H, D$_2$O exchangeable), 5.1 (s, 2H), 3.8 (d, 2H, J=5 Hz); MS: m/z 209.3 [M+1]$^+$.

Synthesis of Compound A.2. To a solution of compound A.1 (0.5 g, 0.0024 mol) in dioxane (7 mL) was added Lawesson's reagent (0.5 g, 0.0013 mol). The reaction was heated at 60° C. for 30-45 min. The reaction was brought to RT and stirred for an additional 4 hr. Dioxane was removed under reduced pressure. The reaction mixture was diluted with EtOAc (3 mL) and the organic layer was washed with sat. NaHCO$_3$ (2 mL). The aqueous layer was again extracted with EtOAc (2×5 mL). The combined organic extracts were again washed with sat. NaHCO$_3$ (3×5 mL), dried (Na$_2$SO$_4$) and concentrated under reduced pressure to furnish compound A.2 as a light yellow solid (0.42 g, 79%). $^1$H NMR: (CDCl$_3$-DMSO-d$_6$, 200 MHz) δ: 7.4 (s, 5H), 6.4 (1H, D$_2$O exchangeable), 5.2 (s, 2H), 4.2 (d, 2H, J=5 Hz); MS: m/z 224.9 [M+1]$^+$.

Synthesis of Compound A.3. Ethyl chloroacetate (50 g, 0.409 mol) and ethyl formate (30.3 g, 0.409 mol) were taken in anhydrous toluene (500 mL) and cooled to 0° C. NaOEt (33 g, 0.485 mol) was added portion wise. The reaction mixture was stirred at 0° C. for 5 hr and then at RT for 12 hr. The reaction mixture was quenched with water (250 mL) and washed with Et$_2$O (2×250 mL). The aqueous layer was cooled to 0° C. and acidified to pH 4 using 5N HCl. The aqueous layer was extracted with Et$_2$O (3×300 mL). The combined organic layers were dried (Na$_2$SO$_4$) and concentrated under reduced pressure to obtain compound A.3 as light brown oil (54 g, 88%), which was used without further purification.

Synthesis of Compound A.4. To a solution of aldehyde A.3 (54 g, 0.36 mol) in anhydrous DMF (42 mL), was added a solution of compound A.2 (40.3 g, 0.18 mol) in anhydrous DMF (320 mL). The reaction was heated at 50° C. for 3 days. The mixture was cooled to 0° C., and Et$_2$O (390 mL) followed Scheme A-1.

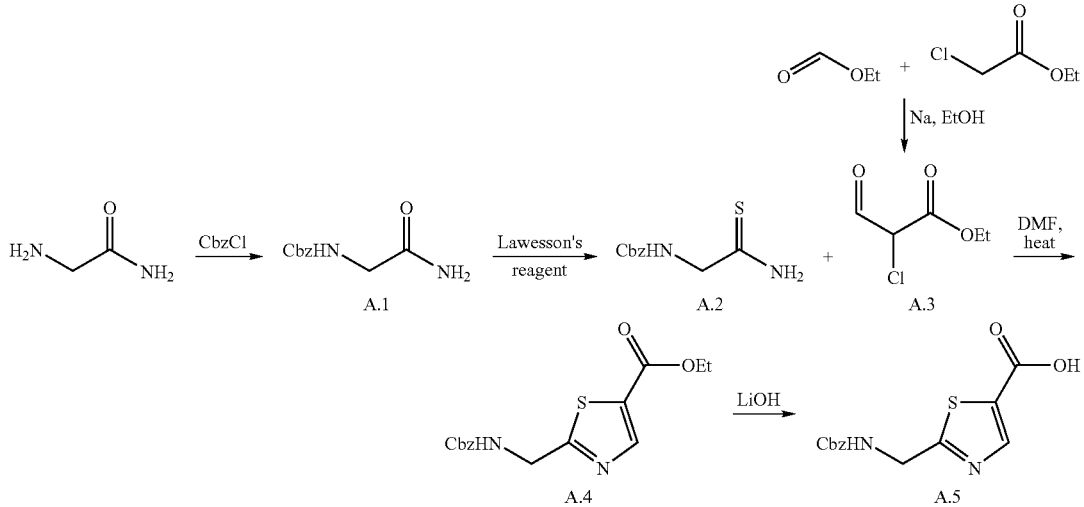

by sat. NaHCO$_3$ solution (200 mL) were added slowly. After separation of the phases, the aqueous layer was extracted with Et$_2$O (2×300 mL). The combined organic extracts were washed with sat. NaHCO$_3$ (3×500 mL), dried (Na$_2$SO$_4$) and concentrated under reduced pressure to give crude material as thick brown oil, which was purified by column chromatography (EtOAc/hexanes) to give compound A.4 as a brown solid (22 g, 19%). $^1$H NMR: (CDCl$_3$, 200 MHz) δ: 8.3 (s, 1H), 7.4 (s, 5H), 5.6 (brs, 1H), 5.2 (s, 2H), 4.7 (d, 2H, J=5 Hz), 4.4 (m, 2H), 1.4 (m, 3H); MS: m/z 320.9 [M+1]$^+$.

Synthesis of Compound A.5. To an ice-cold solution of compound A.4 (10 g, 0.0311 mol) in THF/H$_2$O (80 mL, 1:1) was added LiOH (2.6 g, 0.062 mol). The reaction was stirred for 3 hr, whereupon THF was removed under reduced pressure and the aqueous layer was extracted with Et$_2$O (2×50 mL). The aqueous layer was cooled to 0° C. and acidified with 3N HCl (20 mL) during which solid precipitated out. The solid was filtered, washed with water (2×100 mL) and dried to give compound A.5 as a white solid (7 g, 77%). $^1$H NMR: (CDCl$_3$-DMSO-d$_6$) δ 8.2 (s, 1H), 7.4 (s, 5H), (brs, 1H), 5.2 (s, 2H), 4.8 (d, 2H, J=4 Hz); $^{13}$C NMR: (DMSO-d$_6$, 60 MHz): 176.33, 162.04, 156.39, 147.62, 136.78, 130.25, 128.3, 127.7, 65.9, 42.71, 40.34; MS: m/z 292.8 [M+1]$^+$.

(2) Oxalyl Chloride Coupling

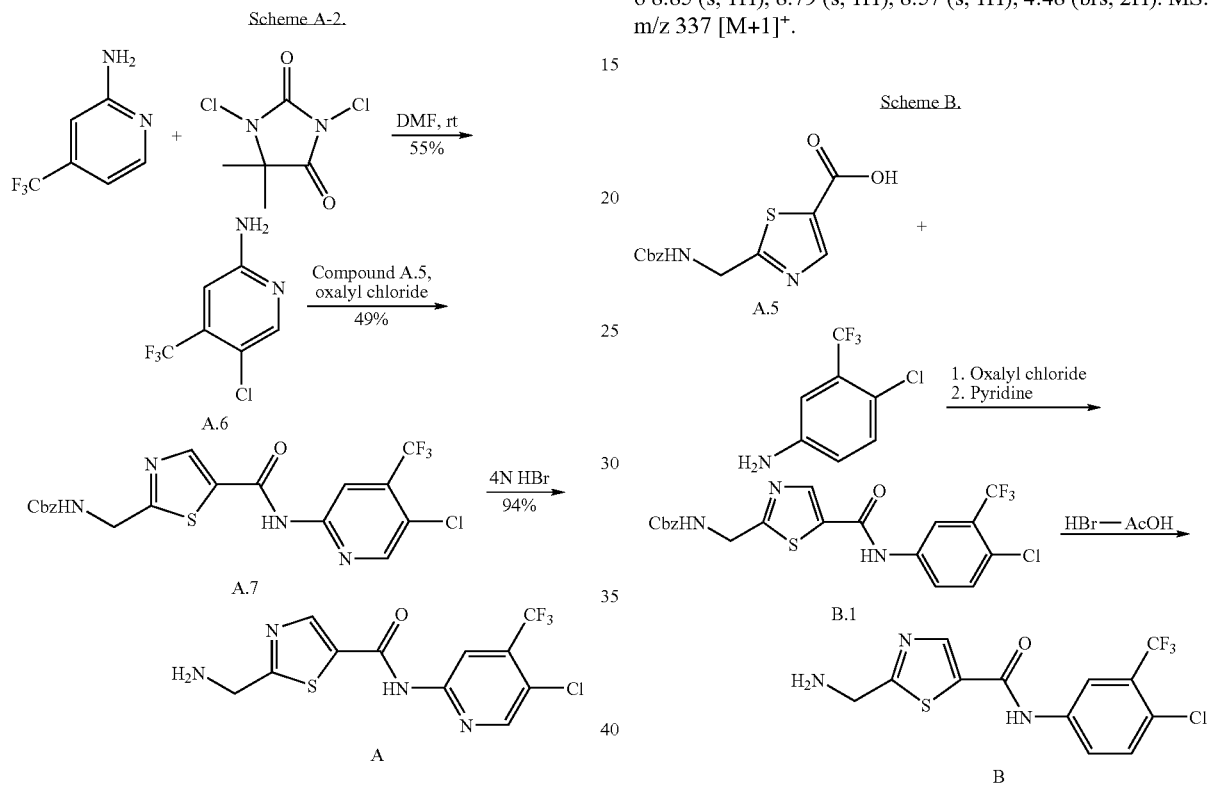

Synthesis of Compound A.6. To a solution of 2-amino-4-trifluoropyridine (2.00 g, 0.0123 mol) in DMF (4 mL, 0.05 mol) was added a solution of 1,3-dichloro-5,5-dimethylhydantoin (1.4 g, 0.0074 mol) in DMF (4 mL) dropwise. The reaction was stirred at RT for 2 hr, whereupon the reaction mixture was diluted with ether (80 mL) and washed with water (10 mL). The organic phase was dried and concentrated to give the crude product, which was purified on combiflash (0-20% EtOAc/Hexanes) to give compound A.6 as light yellow oil. (65% yield); $^1$H NMR: (DMSO-d$_6$) δ 8.16 (s, 1H), 6.87 (s, 1H), 6.76 (brs, 1H); MS: m/z 197 [M+1]$^+$.

Synthesis of Compound A.7. A 20 mL vial was charged with compound A.5 (191.8 mg, 0.0006561 mol), methylene chloride (3.0 mL), a 2.0 M solution of oxalyl chloride in methylene chloride (390 μL) and DMF (10.0 μL, 0.000129 mol). The reaction mixture was stirred for 15 minutes at RT, then concentrated in vacuo and the resultant residue was taken up in acetonitrile (3.0 mL). To this solution was added a solution of compound A.6 (129 mg, 0.000656 mol) and pyridine (0.5 mL, 0.006 mol) in acetonitrile (1.5 mL). The reaction mixture was stirred at RT overnight. The solvent was removed under reduced pressure, and the residue was purified by combiflash (0-30% EtOAc/CH$_2$Cl$_2$) to give compound A.7 in 49% yield. MS: m/z 471 [M+1]$^+$.

Synthesis of Compound A. A vial was charged with compound A.7 (1.0E2 mg, 0.00021 mol), acetic acid (1.0 mL, 0.018 mol) and hydrogen bromide (300 μL, 4 M/acetic acid). The reaction mixture was stirred at RT for 2 hr. The reaction mixture was diluted with methanol and concentrated under reduced pressure. The residue was diluted with aqueous NaHCO$_3$ and ethyl acetate. After separation of the phases, the organic layer was washed with aqueous NaHCO$_3$ and brine, dried over sodium sulfate, and concentrated to give compound A as a light brown solid (73% yield), which was used without further purification. $^1$H NMR (300 MHz, DMSO-d$_6$): δ 8.85 (s, 1H), 8.79 (s, 1H), 8.57 (s, 1H), 4.48 (brs, 2H). MS: m/z 337 [M+1]$^+$.

Synthesis of Compound B. Compound A.5 was coupled to 4-chloro-3-trifluoromethyl-phenylamine and deprotected according to procedures described in the preparation of compound A. $^1$H NMR (400 MHz, CDCl$_3$): δ 8.40 (s, 1H), 8.21 (d, J=2.6 Hz, 1 H), 7.96 (dd, J$^1$=8.7 Hz, J$^2$=2.6, 1H), 7.60 (d, J=8.7 Hz, 1H), 4.48 (brs, 2H); MS: m/z 336 [M+1]$^+$.

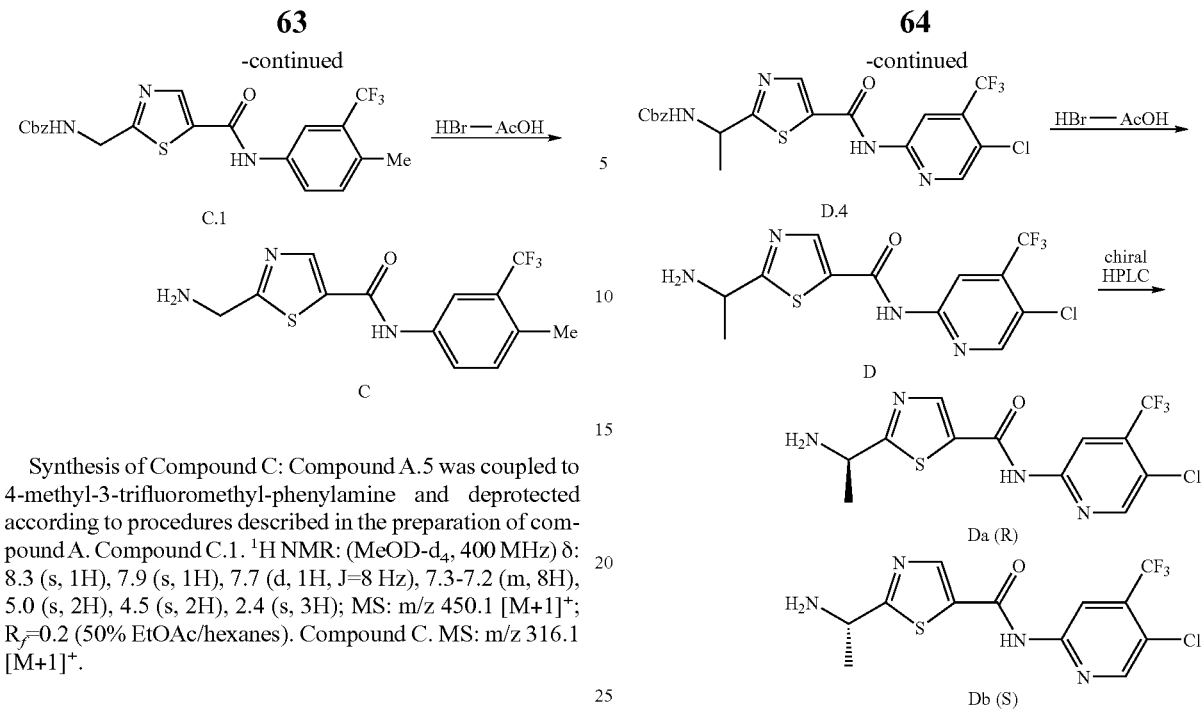

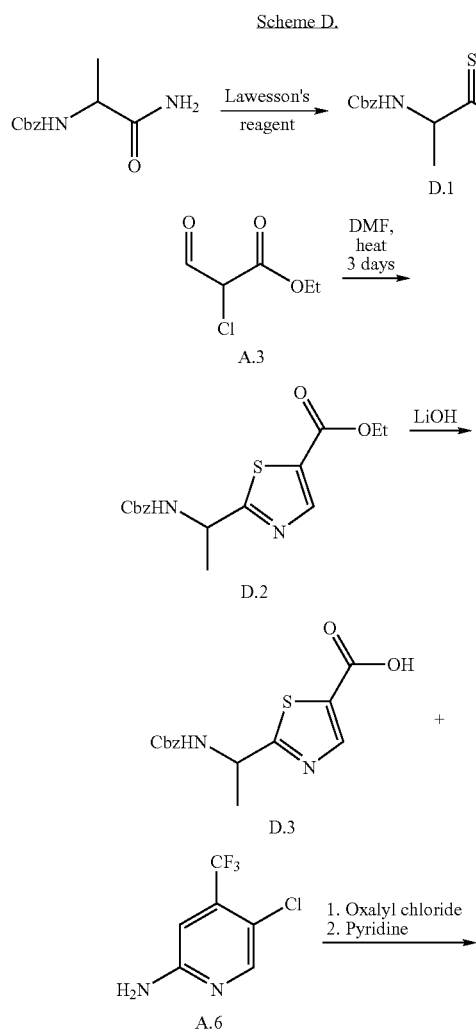

Synthesis of Compound C: Compound A.5 was coupled to 4-methyl-3-trifluoromethyl-phenylamine and deprotected according to procedures described in the preparation of compound A. Compound C.1. $^1$H NMR: (MeOD-d$_4$, 400 MHz) δ: 8.3 (s, 1H), 7.9 (s, 1H), 7.7 (d, 1H, J=8 Hz), 7.3-7.2 (m, 8H), 5.0 (s, 2H), 4.5 (s, 2H), 2.4 (s, 3H); MS: m/z 450.1 [M+1]$^+$; R$_f$=0.2 (50% EtOAc/hexanes). Compound C. MS: m/z 316.1 [M+1]$^+$.

As shown in Scheme D, using Z-alanine-NH$_2$ as starting material, compound D was synthesized following the same procedures as previously detailed in Schemes A-1 and A-2.

Synthesis of Compound D.1. To a solution of Z-alanine-NH$_2$ (5 g, 22.5 mmol) in dioxane (100 mL) was added Lawesson's reagent (5.4 g, 13.5 mmol). The reaction was heated at 60° C. overnight. The solvent was removed under reduced pressure, the resulting residue was diluted with a 1:1 mixture of saturated aqueous NaHCO$_3$: H$_2$O (100 mL), and extracted with ethyl acetate (3×100 mL). The combined extracts were washed with brine (100 mL), dried over anhydrous sodium sulfate, and concentrated in vacuo. Purification by flash column chromatography (10-60% EtOAc/hexanes) afforded compound D.1 (4.7 g, 90%) as a white solid. MS: m/z: 239 [M+1]$^+$.

Synthesis of Compound D.2. Compound D.1 was condensed with compound A.3 according to the procedure described previously (Scheme A-1) to afford compound D.2 (50% yield) as a light yellow solid. $^1$H NMR (CDCl$_3$, 200 MHz): δ 8.3 (s, 1H), 7.3-7.5 (m, 5H), 5.4-5.5 (m, 1H), 5.1 (m, 2H), 4.3-4.4 (m, 2H), 1.6-1.7 (d, 2H), 1.3-1.4 (t, 3H); MS: m/z 335 [M+1]$^+$.

Synthesis of Compound D.3. Hydrolysis of compound D.2 according to the procedure described previously (Scheme A-1) afford compound D.3 (83.5% yield) as a white solid. $^1$H NMR (CDCl$_3$, 200 MHz): δ 8.2 (s, 1H), 7.2-7.4 (m, 5H), 5.1 (m, 2H), 4.8-4.9 (m, 1H), 1.3-1.5 (d, 2H); $^{13}$C NMR (75 MHz, DMSO-d6): δ 181.12, 162.22, 155.81, 147.85, 136.89, 130.05, 128.46, 128.0, 127.89, 65.86, 20.47; MS: m/z 307 [M+1]$^+$.

Synthesis of Compound D.4. Compound D.3 was coupled to compound A.6 according to the procedure described previously (Scheme A-2) to afford compound D.4 (60% yield). $^1$H NMR (CDCl$_3$, 200 MHz): δ 8.6 (s, 1H), 8.4 (s, 2H, 1H D$_2$O exchangeable), 8.2 (s, 1H), 7.2 (s, 5H), 5.4-5.5 (m, 1H), 5.1 (s, 2H), 5.1 (s, 2H), 1.7 (d, J=7 Hz, 3H); MS: m/z 484.9 [M+1]$^+$.

Synthesis of Compound D. Compound D.4 was deprotected according to the procedure described previously (Scheme A-2) to afford compound D (85% yield). $^1$H NMR (400 MHz, DMSO-d$_6$): δ 8.77 (s, 1H), 8.70 (s, 1H), 8.59 (s, 1H), 4.22 (q, J=7.0 Hz, 1H), 1.39 (d, J=7.0 Hz, 2H); MS: m/z 351 [M+1]$^+$.

Synthesis of Compound Da and Compound Db. Compound D was separated by preparative chiral HPLC, using CHIRALCEL OJ column and hexane/IPA/EtOH (80:15:5) as the mobile phase to afford compound Da and compound Db.

Scheme D'.

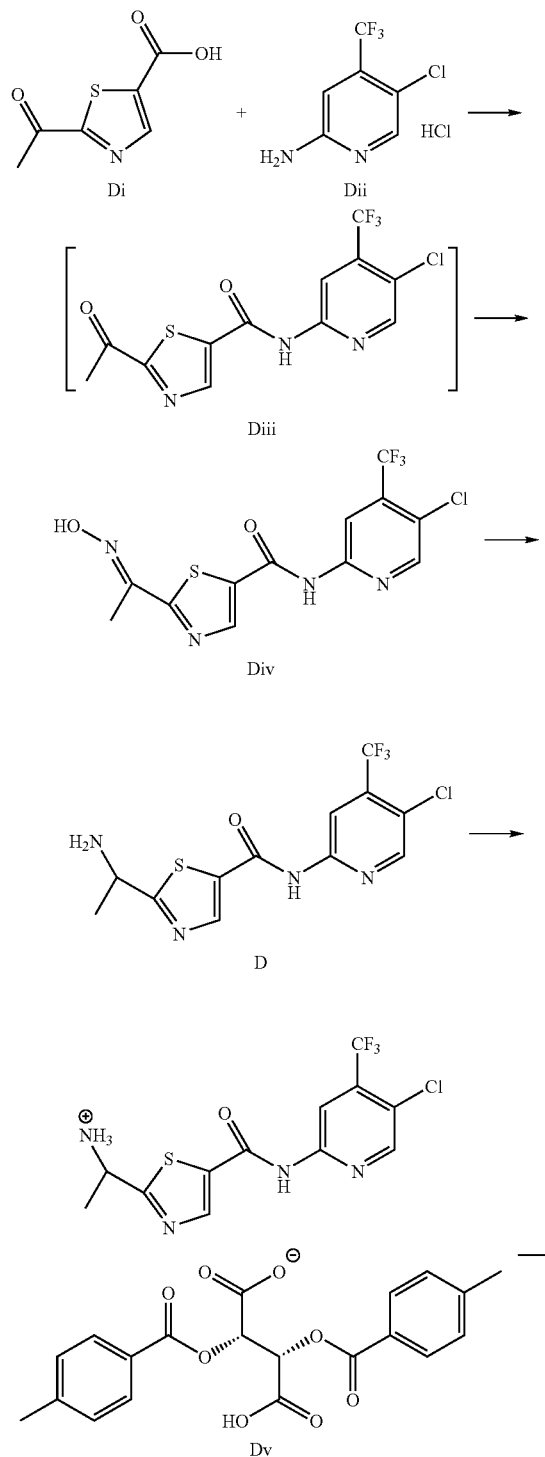

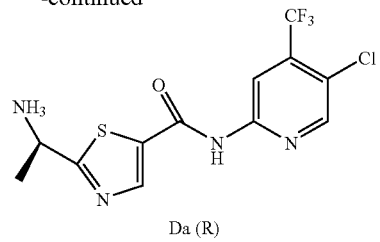

Alternatively, compound Da (R) was prepared as shown in Scheme D', above.

Synthesis of Compound Diii. To a clean dry flask was charged 21.83 g (127.5 mmols, 1.06 eq) of 2-acetylthiazole-5-carboxylic acid (Compound Di), 40.5 mL of 1,2-dimethoxyethane, and 42.8 mg (5 mol %) of N,N-dimethylformamide under a nitrogen atmosphere. The resulting mixture was allowed to stir at 20-30° C. while 15.85 g (123.8 mmoles, 1.03 eq) of oxalyl chloride was charged dropwise over 30 minutes. The resulting reaction solution was allowed to stir for at least 3 hr at 25° C. In a separate flask was charged 28.07 g mmoles, 1 eq) of 5-chloro-4-(trifluoromethyl)pyridine-2-amine hydrochloride (Compound Dii), 87 mL of acetonitrile, and 29.1 mL of (360.3 mmoles, 2.99 eq) pyridine under a nitrogen atmosphere. The resulting solution was cooled to 10° C. with stirring. To the cooled Dii solution was added the activated Di solution dropwise over 30 minutes. The final combined solution was allowed to warm to RT, and the stirring was continued for an additional 2 hours. This solution may be used in the next step without isolation. However, Compound Diii can be isolated from the solution at this point by adding water dropwise until a thick slurry is obtained.

Synthesis of Compound Div. The solution of Diii, from the procedure described above, was heated to 45° C. while maintaining stirring and a nitrogen atmosphere. To the heated solution was added 9.30 g of NH$_2$OH dropwise over 5 minutes. After the addition was complete, stirring was continued at 45° C. for an additional 4 hr. The reaction solution was then heated to 60° C. and 215 mL of water was added over the course of 1 hr. The resulting slurry was cooled to room temperature and filtered to collect the solids. The filter cake was washed with 25% v/v acetonitrile/water, then water, and dried to constant weight at RT. A total of 44.26 g of compound Div was produced in 98% yield. Mass spectra showed a molecular ion [M+1]$^+$ of 365.01.

Synthesis of Compound D. To a clean dry flask was charged 11.5 g (31.5 mmoles, 1 eq) of compound Div, 4.6 g (70.3 mmoles, 2.23 eq) of zinc dust, 35 mL of water, and 57 mL of 1-butanol under a nitrogen atmosphere. While stirring vigorously, the resulting mixture was cooled to 0-5° C. To the cold mixture was charged 10.8 mL (188.7 mmoles, 6 eq) of acetic acid dropwise, while maintaining the internal reaction temperature of <10° C. Once the addition is complete, the reaction was allowed to warm to 30° C., and the stirring was continued for an additional 3-4 hr. After aging the reaction solution, the contents of the flask were cooled to ~5° C., and 56 mL of NH$_4$OH was added dropwise while maintaining an internal temperature <10° C. The biphasic mixture was warmed to 35° C. and the aqueous phase was removed. The organic layer was washed once more with a mixture of 24 mL of NH$_4$OH and 24 mL of water at 35° C. The aqueous phase was removed and the 16 mL of heptane was added to the organic layer. The organic solution was then washed with a solution of 1.15 g of EDTA in 50 mL of water at 35° C. The aqueous phase was removed, and the organic phase, at 35° C., was filtered through a 4-5.5 micron filter funnel into a separate clean dry flask. To the filtered solution was added 215 mL of heptane at ambient temperature with stirring over the course of 1 hr. The slurry was cooled to 0-5° C. and held with stirring for an additional 3 hr. The solids were collected by filtration and washed with 35 mL of heptane in 2 portions. The wet solids were dried at 50° C. under high vacuum for 30 hr. Compound D, 8.52 g, was isolated as a pale pink solid in a 77% yield. The mass spectrum showed a molecular ion [M+1]$^+$ of 351.35.

Synthesis of Compound Dv. To a clean dry flask was charged 80 g (228 mmoles, 1 eq) of Compound D, 263 g of 2-propanol, and 263 mL of water under a nitrogen atmosphere. The resulting mixture was heated to 53° C. and stirred until all the solids dissolved. In a separate clean dry flask was charged 59.2 g (153 mmoles, 0.67 eq) of D-ditoluoyl tartaric acid, 481 g of 2-propanol, and 206 g of water under a nitrogen atmosphere. The tartaric acid solution was stirred until all the solids dissolved at RT, and then added to the Compound D solution through a coarse filter funnel at such a rate to maintain the internal temperature of the Compound D solution at 45-53° C. The coarse filter funnel was washed with an additional 40 mL of a 3:12-propanol:water solution. Immediately following the funnel wash, the stirring of combined solutions was stopped, and the contents of the flask were held at 45° C. for 9 hr. After aging, the reaction mixture was cooled to 20° C., and the stirring was resumed. The contents of the flask were held at 20° C. with stirring for approximately 12 hr. The solids were then collected by filtration, and the wet solids were washed with 80 mL of a cold 2-propanol:water (3:1) solution in 2 portions. The wet solids were then dried at 50° C. under vacuum to constant weight. A total of 74.2 g of Compound Dv was obtained in a 88% yield.

The stereochemical purity of Compound Dv was further enhanced by the following procedure. To a clean dry flask was charged 66.5 g (90 mmoles, 1 eq) of Compound Dv, 335 g of water, and 1330 g of 2-propanol under a nitrogen atmosphere. With stirring, the contents of the flask were heated to 60° C., and held at that temperature for 1 hr. After aging, the stirring was stopped, and the contents of the flask were cooled to 0° C. over 4 hr. During this cooling period, the stirring was started and stopped after approximately 20 seconds 5 times over evenly spaced intervals. The contents of the flask were held at 0° C. for 2 hr without stirring. After aging, the solids were collected by filtration. The wet solids were dried at 50° C. under vacuum to constant weight. A total of 53.8 g of Compound Dv was obtained in a 81% yield. Mass spectral analysis (positive mode) showed a molecular ion of 351.43 [M+1]$^+$.

Synthesis of Compound Da (R). To a clean dry flask was charged 156 g (217 mmoles, 1 eq) of Compound Dv, 1560 mL of methyl tert-butyl ether, and 780 mL of methanol under a nitrogen atmosphere. The contents of the flask were then stirred at RT, and a solution of 250 g (1110 mmoles, 5.26 eq) of sodium bicarbonate in 2340 mL of water was added slowly to maintain the internal temperature of ≦30° C. The resulting mixture was stirred for an additional hour at 30° C. After aging, the stirring was stopped and the organic and aqueous layers were allowed to separate. The aqueous layer was removed, and the organic layer was concentrated under vacuum to obtain a thick slurry. To the slurry was added 1000 mL of heptane, and the resulting mixture was cooled to 0-5° C. The solids were collected from the cold solution by filtration. The wet solids were then dried at 50° C. under vacuum to constant weight. A total of 68.7 g of Compound Da was obtained in a 92% yield. Mass spectral analysis showed a molecular ion [M+1]$^+$ of 351.35.

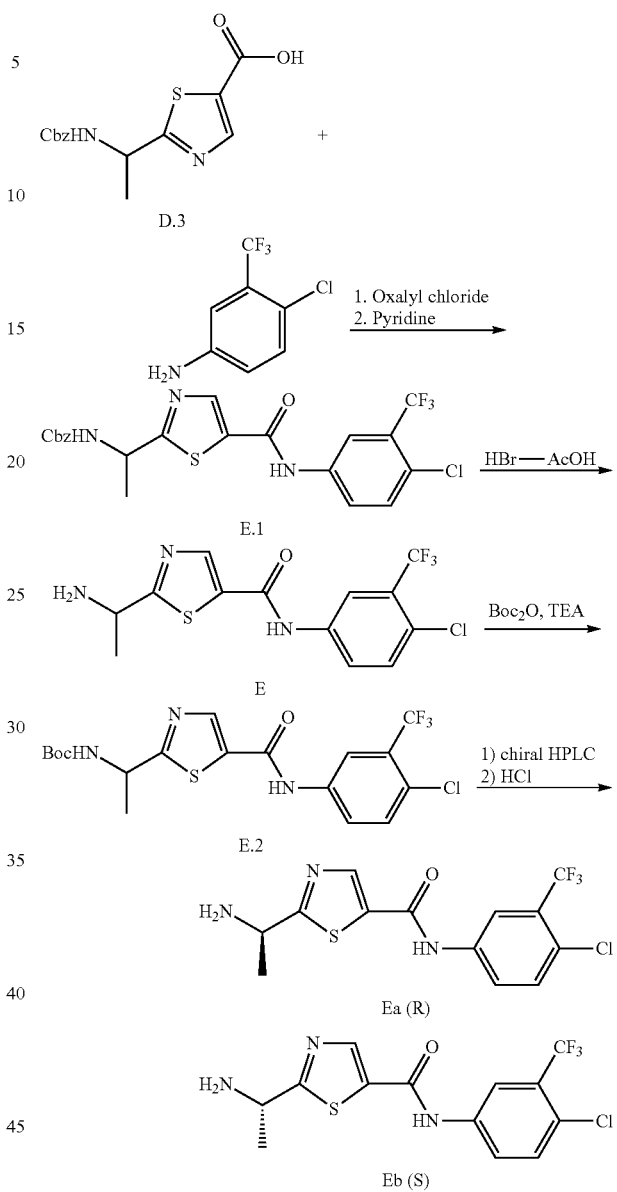

Synthesis of Compound E. Compound D.3 was coupled to 4-chloro-3-trifluoromethyl-phenylamine and deprotected according to procedures described in the preparation of compound A. $^1$H NMR (400 MHz, DMSO-d$_6$): δ 11.54 (s, 1H), 9.06 (s, 1H), 8.92 (br. s, 3H), 8.30 (d, J=Hz, 1H), 8.05 (dd, J=8.8, 2 Hz, 1H), 7.86 (d, J=8.8 Hz, 1H), 4.91 (quintet, J=6 Hz, 1H), 1.65 (d, J=6.8 Hz, 3H). MS: m/z 350 [M+1]$^+$.

Synthesis of Compound E.2. To a flask containing compound E (10.3 mg, 0.0294 mmol) was added a solution of carbonic acid di-tert-butyl ester (17.6 mg, 0.0799 mmol) in CH$_2$Cl$_2$ (0.6 mL) at RT. Triethylamine (8 μL) was added and the reaction was stirred at RT overnight. Water and ethyl acetate were added to the reaction mixtures and the layers were separated. The aqueous layer was extracted once more with ethyl acetate. The combined organic layers were dried over anhydrous sodium sulfate and concentrated in vacuo. Purification by column chromatography (EtOAc/Hexanes) afforded compound E.2 as a white solid (8.2 mg, 62%). Rf=0.1 (100% EtOAc); MS: m/z: 450 [M+1]$^+$.

Synthesis of Compound Ea and Eb. Compound E.2 was separated by preparative chiral HPLC, using CHIRALPAK AD column and hexanes/EtOH (85:15) as the mobile phase. The compounds were deprotected by treatment with 4M-hydrochloric acid in dioxane at RT to afford compound Ea and compound Eb. MS: m/z: 350 [M+1]$^+$.

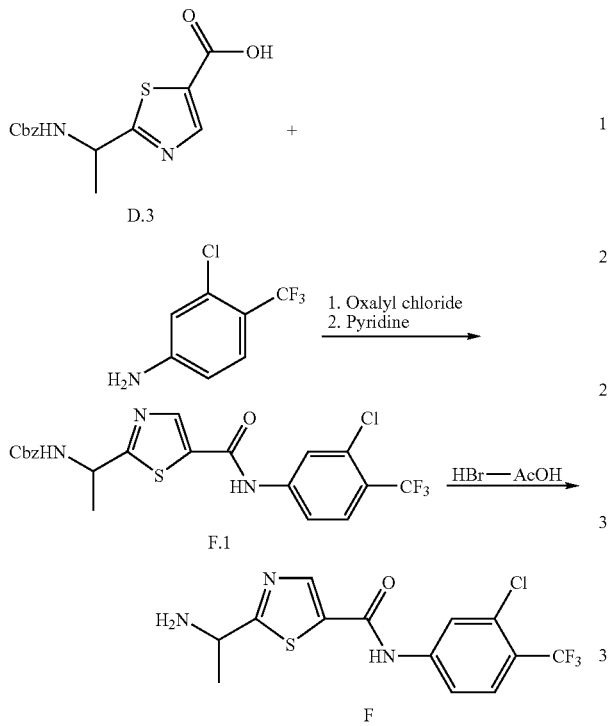

Synthesis of Compound F. Compound D.3 was coupled to 3-chloro-4-trifluoromethyl-phenylamine and deprotected according to the procedures described in the preparation of compound A. $^1$H NMR (400 MHz, DMSO-d$_6$): δ 11.38 (s, 1H), 8.96 (s, 1H), 8.87 (br. s, 3H), 8.42 (d, J=2.4 Hz, 1H), 8.18 (dd, J=9, 2.6 Hz, 1H), 7.73 (d, J=9 Hz, 1H), 4.91 (br. s, 1H), 1.65 (d, J=6.8 Hz, 3H); MS: m/z 350 [M+1]$^+$.

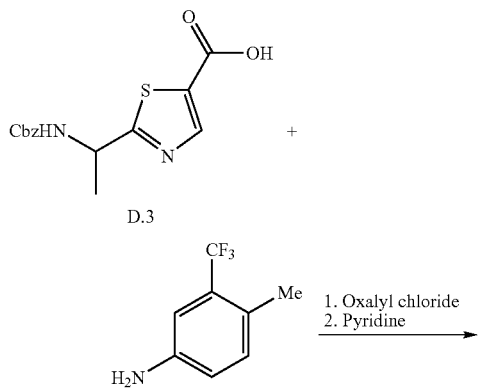

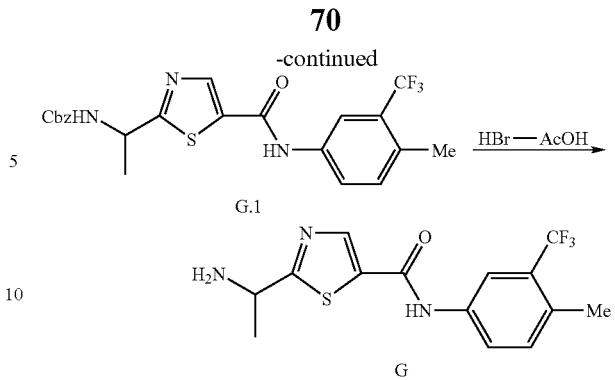

Synthesis of Compound G: Compound D.3 was coupled to 3-methyl-4-trifluoromethyl-phenylamine and deprotected according to the procedures described in the preparation of compound A. Compound G.1. $^1$H NMR: (MeOD-d$_4$, 400 MHz) δ: 8.3 (s, 1H), 7.9 (s, 1H), 7.7 (d, 1H, J=8 Hz), 7.3-7.2 (m, 8H), 5.0 (s, 2H), 5.0-4.9 (m, 1H), 2.4 (s, 3H), 1.49 (d, 1H, J=4 Hz); MS: m/z 464.1 [M+1]$^+$; R$_f$=0.5 (50% EtOAc/hexanes). Compound G. MS: m/z 330.1 [M+1]$^+$.

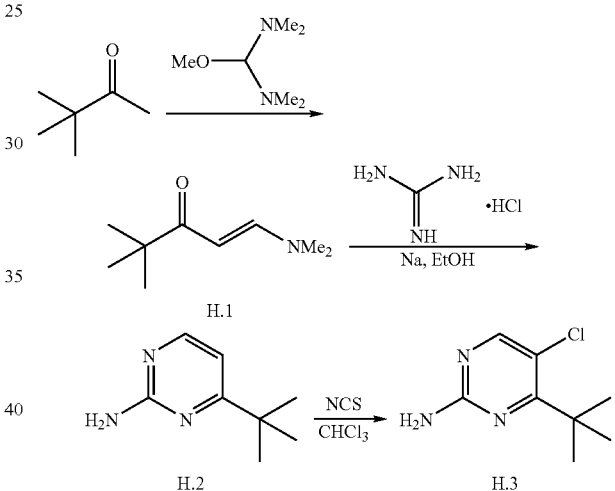

Synthesis of Compound H.1. In a 50 mL round-bottomed flask, pinacolone (6.2 mL, 50.0 mmol) and methoxy-bis(dimethylamino)methane (10 mL) were heated at 110° C. under nitrogen. After 18 hr, the solvent was removed under reduced pressure. The crude product was purified by flash chromatography (hexanes/EtOAc 50/50 to 33/66) to afford compound H.1 (5.94 g, 77%) as a yellow oil which solidified upon standing. $^1$H NMR (400 MHz, CDCl$_3$): δ7.56 (d, J=12.7 Hz, 1H), 5.20 (d, J=12.7 Hz, 1H), 2.92 (br s, 6H), 1.11 (s, 9H); MS: m/z 156 [M+1]$^+$.

Synthesis of Compound H.2. To a solution of Na (74 mg, 3.22 mmol) in EtOH (21 mL) was added guanidine hydrochloride (308 mg, 3.22 mmol). The resultant suspension was stirred at RT, and after 30 min, a solution of compound H.1 (500 mg, 3.22 mmol) in EtOH (2.1 mL) was added. The reaction was refluxed overnight under nitrogen. After 20 hr, the solvent was removed under reduced pressure. To the residue was added Et$_2$O and H$_2$O. The aqueous layer was extracted three times with Et$_2$O. The combined organic layers were washed with brine, dried over anhydrous sodium sulfate, filtered, and concentrated. The crude product was purified by flash chromatography (hexanes/EtOAc=1:1→1:3) to afford 379 mg (78%) of compound H.2. Rf=0.3 (50% EtOAc/hexanes); $^1$H NMR (400 MHz, MeOD-d$_4$): δ8.11 (d, J=5.38 Hz, 1H), 6.69 (d, J=5.38 Hz, 1H), 1.27 (s, 9H); MS: m/z 152 [M+1]$^+$.

Synthesis of Compound H.3. A solution of compound H.2 (200 mg, 1.32 mmol) and N-chlorosuccinimide (185 mg, 1.39 mmol) in chloroform (3.4 mL) was refluxed. After 1.5 hr, sat. aq. NaHCO₃ and EtOAc were added. The aqueous layer was extracted three times with EtOAc. The combined organic layers were washed with brine, dried over anhydrous sodium sulfate, filtered, and concentrated. The crude product was purified by flash chromatography (hexanes/EtOAc=5:1→3:1) to afford 200 mg (81%) of compound H.3 as a white solid. ¹H NMR (400 MHz, MeOD-d₄): δ8.02 (s, 1H), 1.40 (s, 9H); MS: m/z 186 [M+1]⁺.

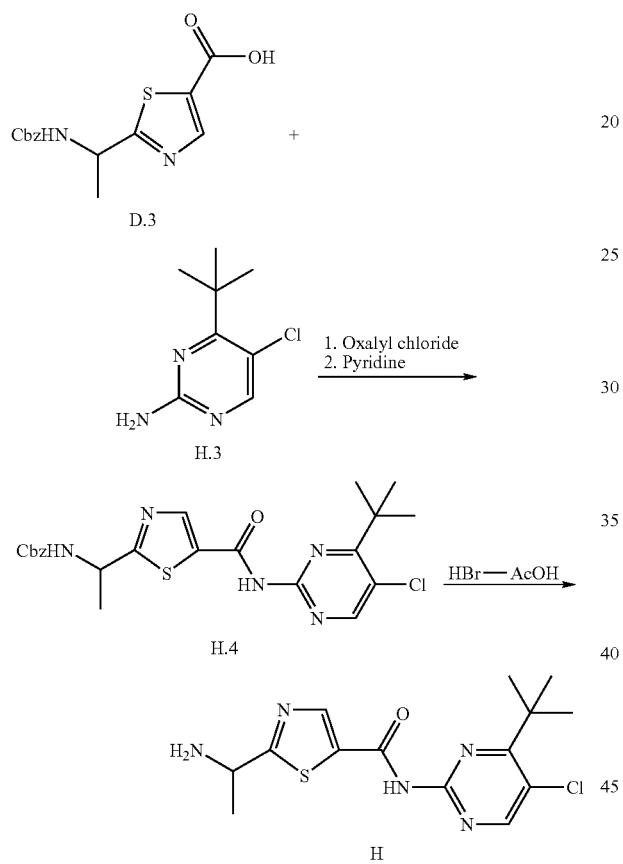

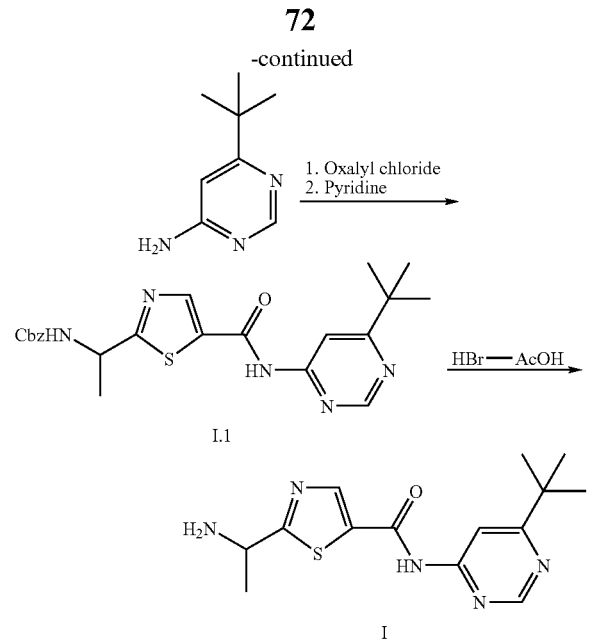

Synthesis of Compound H. Compound D.3 was coupled to 4-tert-butyl-5-chloro-pyrimidin-2-ylamine and deprotected according to procedures described in Method 4. Rf=0.2 (5% MeOH/EtOAc); MS: m/z 340 [M+1]⁺.

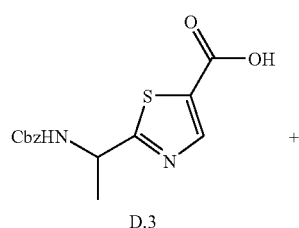

Synthesis of Compound I. Compound D.3 was coupled to 6-tert-butyl-pyrimidin-4-ylamine and deprotected according to procedures described in the preparation of compound A. Rf=0.1 (5% MeOH/EtOAc); MS: m/z 306 [M+1]⁺.

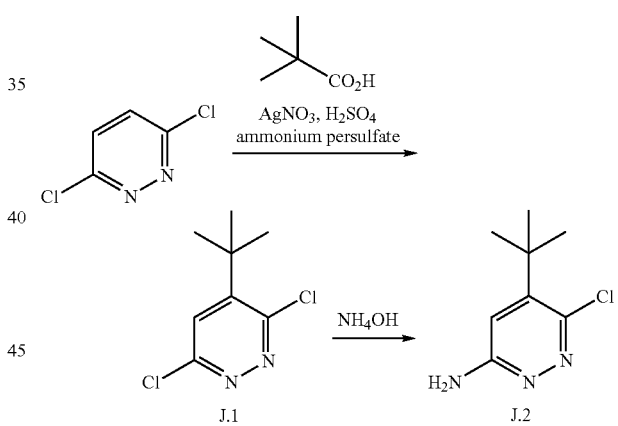

Synthesis of Compound J.1. A flask was charged with 3,6-dichloropyridazine (1.49 g, 0.01 mol, 1.0 equiv), silver nitrate (0.17 g, 0.001 mol, 0.1 equiv), water (30 mL), pivalic acid (3.57 g, 0.035 mol, 3.5 equiv), and sulfuric acid (1.6 mL, 0.03 mol, 3.0 equiv). The mixture was heated to 70° C. and a solution of ammonium persulfate (2.28 g, 0.01 mol, 1.0 equiv) in water (10 mL) was added dropwise over ten minutes. The reaction was stirred at 70° C. for one hour and then cooled to RT. The reaction mixture was poured into ice water and then adjusted to pH 8 with aqueous ammonium hydroxide. The aqueous mixture was extracted with CH₂Cl₂ (2×250 mL). The combined organic extracts were filtered through a cotton plug, washed with aqueous 1 N NaOH (70 mL), dried over anhydrous MgSO₄ and concentrated under reduced pressure. Purification by flash column chromatography (20% EtOAc/hexanes) afforded the title compound (1.32 g, 64%) as a white solid. ¹H NMR: (CDCl₃, 400 MHz) δ: 7.5 (s, 1H), 1.5 (s, 9H); Rf=0.5 (80% EtOAc/hexanes).

Synthesis of Compound J.2. To a solution of compound J.1 (1.32 g, 0.006 mol) in EtOH (1 mL) was added 50% aqueous ammonium hydroxide (10 mL). The reaction mixture was stirred at 140° C. for 19 hr, then additional aqueous ammonium hydroxide (10 mL) was added and the mixture was stirred at 130° C. for one hour. After cooling to RT, the reaction mixture was concentrated under reduced pressure and the resultant residue was suspended in water. The solid was filtered, washed with water and Et$_2$O, and dried to afford compound J.2 as a peach solid (0.27 g, 23%). $^1$H NMR: (CDCl$_3$) δ 7.01 (s, 1H), 1.5 (s, 9H); MS: m/z 186.1 [M+1]$^+$.

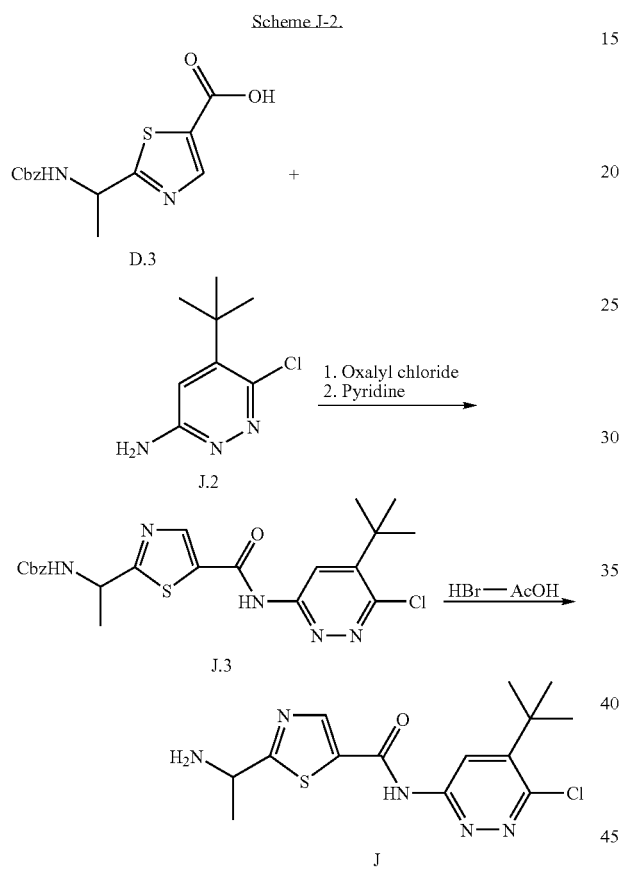

Synthesis of Compound J: Compound D.3 was coupled to compound J.2, 5-tert-butyl-6-chloro-pyridazin-3-ylamine, and deprotected according to procedures described in the preparation of compound A. Compound J.3. MS: m/z 474.1 [M+1]$^+$; R$_f$=0.4 (50% EtOAc/hexanes). Compound J. MS: m/z 340.1 [M+1]$^+$.

Scheme K.

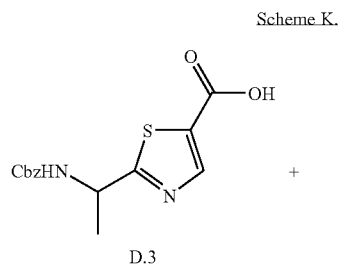

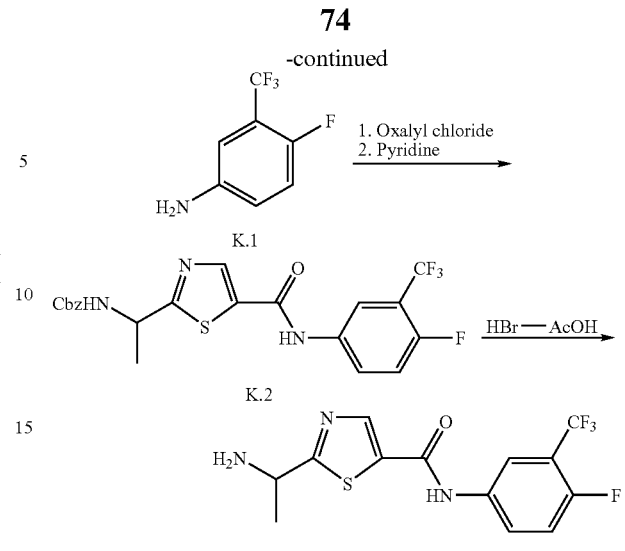

Synthesis of Compound K: Compound D.3 was coupled to compound K.1, 4-fluoro-3-trifluoromethyl-phenylamine, and deprotected according to procedures described in the preparation of compound A. Compound K.2. Rf=0.2 (50% EtOAc/hexanes); MS: m/z 468 [M+1]$^+$. Compound K. Rf=0.1 (100% EtOAc); MS: m/z 334 [M+1]$^+$.

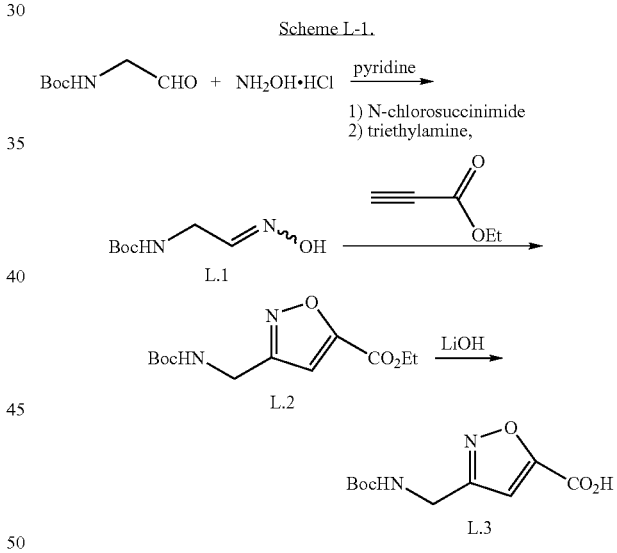

Synthesis of Compound L.1. (2-Oxo-ethyl)-carbamic acid tert-butyl ester (1.0 g, 6.28 mmol), hydroxylamine hydrochloride (647 mg, 9.31 mmol) and pyridine (5 mL) were dissolved in methanol (40 mL) and the reaction was stirred at RT overnight. Solvent was removed at reduced pressure and the reaction was partitioned between chloroform and water. The aqueous layer was extracted with chloroform (2×). The combined organic layers were dried over anhydrous sodium sulfate. Removal of solvent under reduced pressure afforded crude L.1 which was used without further purification.

Synthesis of Compound L.2. To a solution of L.1 (~1.2 g, ~6.28 mmol) in DMF (35 mL) was added N-chlorosuccinimide (1.05 g, 7.86 mmol) at RT. The reaction mixture was heated at 60° C. for one hour. The reaction mixture was cooled to 0° C. and propynoic acid ethyl ester (1.8 mL, 17.8 mmol) was added. Triethylamine (1.06 mL, 7.61 mmol) in DMF (8 mL) was added dropwise over 30 minutes. The reaction mixture was slowly allowed to warm to RT. The reaction mixture was diluted with ethyl acetate and water. The layers were separated and the aqueous layer was extracted with ethyl acetate (2×). The combined organic layers were washed with water followed by brine and dried over anhydrous sodium sulfate. After removal of the solvent under reduced pressure the crude material was purified by silica gel column chromatography (ethyl acetate/hexane) to afford L.2 (1.68 g, 86%). $^1$H NMR (400 MHz, CDCl$_3$): δ 6.93 (s, 1H), 5.02 (br, 1H), 4.42 (s, 2H), 4.41 (q, 2H, J=6.9 Hz), 1.45 (s, 9H), 1.39 (t, 3H, J=6.9 Hz); MS: m/z 271 [M+1]$^+$.

Synthesis of Compound L.3. Compound L.2 (1.68 g, 6.22 mmol) was dissolved in THF (20 mL) at 0° C. Aqueous lithium hydroxide (1M-solution, 6.5 mL, 6.5 mmol) was added and the reaction was stirred for one hour. THF was removed under reduced pressure and the reaction mixture was washed with hexanes. The reaction mixture was acidified using 3N-hydrochloric acid and extracted with chloroform (3×). The combined organic layers were dried over anhydrous sodium sulfate. Upon removal of solvent under reduced pressure, crude L.3 was obtained (743 mg, 49%) which was used without further purification. MS: m/z 243 [M+1]$^+$.

Scheme L-2.

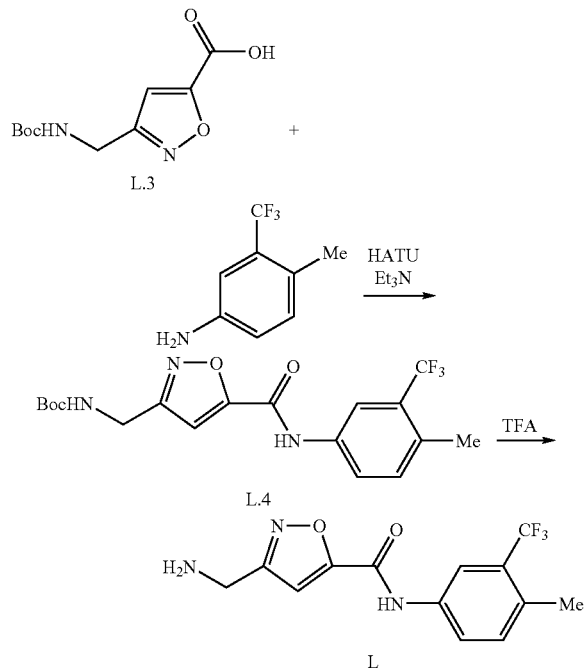

Synthesis of Compound L.4. Compound L.3 (51.0 mg, 0.211 mmol) and 4-methyl-3-trifluoromethyl-phenylamine (33 μL, 0.230 mmol) were dissolved in DMF (1 mL) at RT. HATU (98.0 mg, 0.258 mmol) and triethylamine (74 μL, 0.531 mmol) were added and the reaction mixture was stirred at RT overnight. Ethyl acetate and water were added to the reaction mixture and the layers were separated. The aqueous layer was extracted with ethyl acetate (2×) and the combined layers were dried over anhydrous sodium sulfate. Upon removal of the solvent under reduced pressure, the crude L.4 was obtained as a white solid, which was used without further purification. MS: m/z 400 [M+1]$^+$.

Synthesis of Compound L. Compound L.4 (<0.211 mmol) was dissolved in 20% TFA in dichloromethane (1 mL) at 0° C. The reaction was allowed to warm to RT over one hour. Benzene was added and the solvents were removed under reduced pressure. The reaction mixture was dissolved in dichloromethane and saturated sodium bicarbonate solution was added. After separation of the phases, the aqueous layer was extracted with dichloromethane (2×). The combined organic layers were dried over anhydrous sodium sulfate. The solvent was removed under reduced pressure and the crude L obtained was used without further purification. MS: m/z 300 [M+1]$^+$.

Scheme M-1.

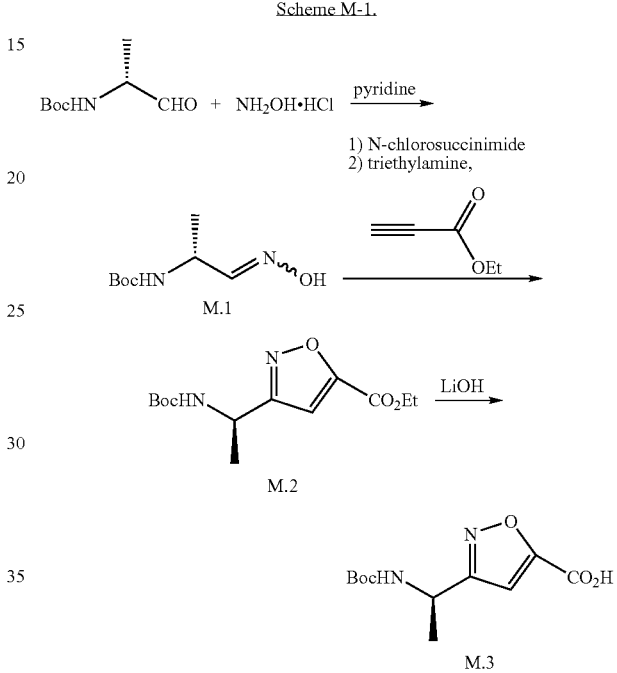

Synthesis of Compound M.2 and Compound M.3: As shown in Scheme M-1, using (1R)-(1-methyl-2-oxo-ethyl)-carbamic acid tert-butyl ester starting material, compounds M.2 and M.3 were synthesized following the same procedures as previously detailed in Schemes L-1 and L-2. Compound M.2. This compound was prepared using a procedure described for compound L.2. $^1$H NMR (400 MHz, CDCl$_3$): δ 6.88 (s, 1H), 4.97 (br, 1H), 4.41 (q, 2H, J=7.4 Hz), 1.53 (d, 3H, J=4.9 Hz), 1.44 (s, 9H), 1.39 (t, 3H, J=7.4 Hz); MS: m/z 285 [M+1]$^+$. Compound M.3. This compound was prepared using a procedure described for compound L.3 in scheme L-1 and the product was used without further purification. MS: m/z 225 [M+1]$^+$.

Scheme M-2.

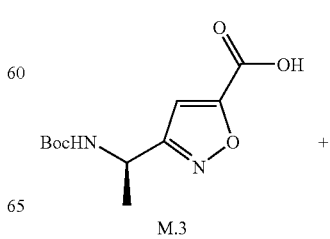

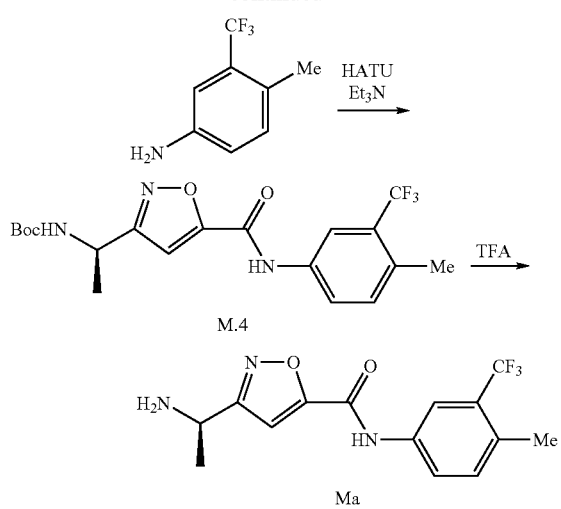

Synthesis of Compound Ma. Compound M.3 was coupled to 4-methyl-3-trifluoromethyl-phenylamine and deprotected according to procedures described in the synthesis of compound L. MS: m/z 314 [M+1]$^+$.

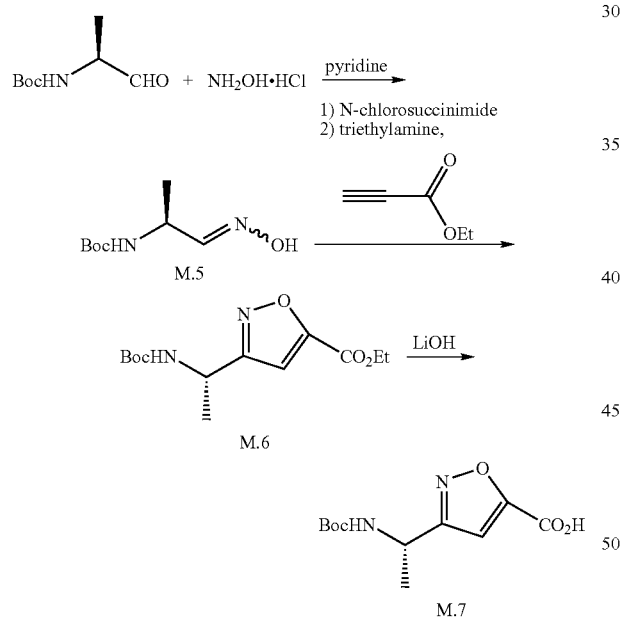

Synthesis of Compound M.6 and M.7: As shown in Scheme M-3, using (1S)-(1-methyl-2-oxo-ethyl)-carbamic acid tert-butyl ester as starting material, compound Mb was synthesized following the same procedures as previously detailed in Schemes L-1 and L-2. Compound M.6. This compound was prepared using the procedure described for compound L.2. $^1$H NMR (400 MHz, CDCl$_3$): δ 6.88 (s, 1H), 4.97 (br, 1H), 4.41 (q, 2H, J=7.4 Hz), 1.53 (d, 3H, J=4.9 Hz), 1.44 (s, 9H), 1.39 (t, 3H, J=7.4 Hz); MS: m/z 285 [M+1]$^+$. Compound M.7. This compound was prepared using the procedure described for compound L.3 in scheme L-1 and the product was used without further purification. MS: m/z 225 [M+1]$^+$.

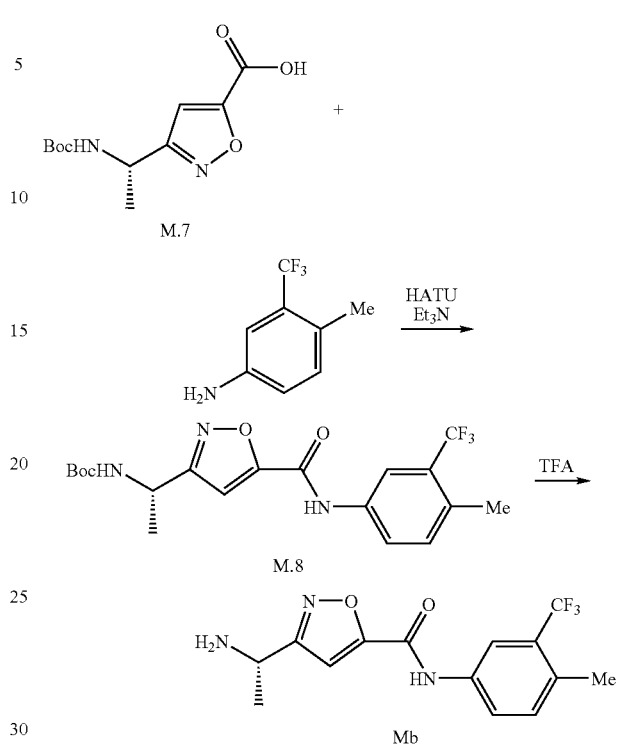

Synthesis of Compound Mb. Compound M.7 was coupled to 4-methyl-3-trifluoromethyl-phenylamine and deprotected according to procedures described in synthesis of compound L. MS: m/z 314 [M+1]$^+$.

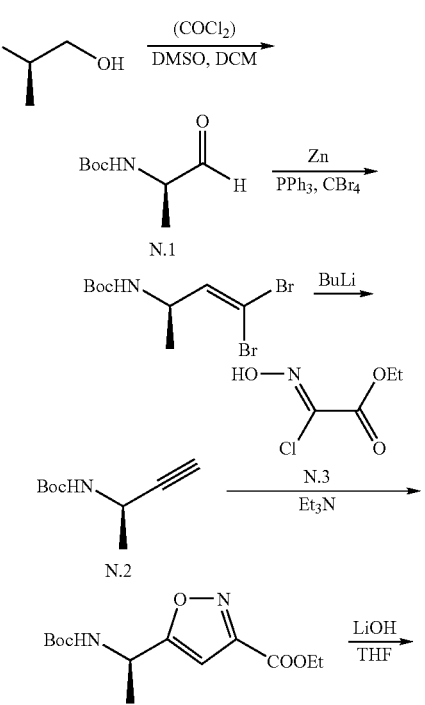

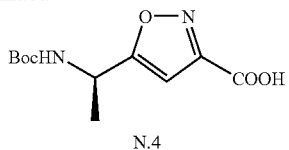

N.4

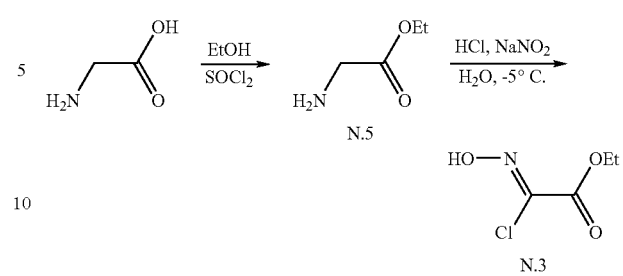

Synthesis of Compound N.1. To a cooled (−78° C.) solution of oxalyl chloride (90 mL, 1.03 mol) in CH₂Cl₂ was added dropwise a solution of DMSO (100 mL, 1.41 mol) in CH₂Cl₂. The mixture was stirred at −78° C. for 1 hr, and a solution of (R)-tert-butyl 1-hydroxypropan-2-ylcarbamate (90 g, 0.51 mol) in CH₂Cl₂ was added. After stirring for 3 hr, 500 mL of triethylamine was added and the reaction mixture was stirred for another 3 hr at −78° C. The reaction was quenched with 1% HCl and the reaction mixture was warmed to RT. The organic layer was separated and the aqueous layer was extracted with CH₂Cl₂. The organic layer was washed with water, dried over MgSO₄, and evaporated to provide the compound N.1 (76.0 g, 85.4%). ¹H NMR (CDCl3) δ 9.56 (s, 1H), 4.23 (br s, 1H), 1.45 (s, 9H), 1.32 (s, 3H).

Synthesis of Compound N.2. A solution of zinc (135 g, 2.08 mol), PPh₃ (545 g, 2.08 mol) and CBr₄ (682 g, 4.08 mol) in CH₂Cl₂ (2 L) was stirred at 0° C. for 1.5 hr. A solution of compound N.1 (114 g, 0.66 mol) in DCM was added in one portion, and the reaction mixture was stirred at 0° C. for another 3 hr. The mixture was quickly passed though a silica gel, and the solvent was evaporated to give the crude (R)-tert-butyl 4,4-dibromobut-3-en-2-ylcarbamate. To a cooled (−78° C.) solution of the crude compound (R)-tert-butyl 4,4-dibromobut-3-en-2-ylcarbamate in THF (2 L) was added dropwise 2.5 M BuLi (0.75 L, 1.88 mol) under nitrogen. The reaction was quenched with water and the organic layer was separated. The aqueous layer was extracted with ethyl acetate. The organic layers were combined, washed with water, dried over MgSO₄, filtered and concentrated to afford compound N.2, which was used without further purification. ¹H NMR (CDCl₃) δ=4.47 (br s, 1H), 2.24 (s, 1H), 1.49 (s, 9H), 1.27 (s, 3H).

Synthesis of Compound N.4. To a stirred solution of compound N.2 (262.5 g, 1.56 mol) and compound N.3 (78.2 g, 0.52 mol) in DMF (1 L) was added dropwise Et₃N (216 mL, 1.56 mol) at 90° C. The mixture was stirred for 5 hr, and then concentrated in vacuo. The residue was re-dissolved in ethyl acetate. The ethyl acetate solution was washed with water, dried over Na₂SO₄, and evaporated to provide the crude compound (R)-ethyl 5-(1-(tert-butoxycarbonylamino)ethyl)isoxazole-3-carboxylate. To a solution of (R)-ethyl 5-(1-(tert-butoxycarbonylamino)ethyl)isoxazole-3-carboxylate in THF (2 L) was added aqueous 2.5 N LiOH (1 L) at RT. The mixture was stirred for 1 hr, and then evaporated under reduced pressure to remove THF. The residue was partitioned between water (1 L) and ethyl acetate (0.5 L). The organic layer was separated and the aqueous layer was extracted with ethyl acetate twice. The aqueous layer was adjusted to pH 2 with 10% HCl and extracted with ethyl acetate (2×1 L). All the organic layers were combined, washed with water, dried over Na₂SO₄, filtered and concentrated under reduced pressure. The residue was dried under vacuum to afford compound N.4 (55 g, 45%), which was used without further purification. ¹H NMR (CDCl₃) δ=6.57 (s, 1H), 4.12 (q, 1H), 1.56 (d, 3H), 1.37 (s, 9H).

Synthesis of Compound N.5. To a suspension of glycine (300 g, 4 mol) in ethanol (1500 mL) was added dropwise SOCl₂ at −5° C. After the addition was complete, the mixture was heated to reflux and stirred for 3 hr. The reaction mixture was cooled to 0° C., and methyl t-butyl ether (500 mL) was added. The resultant suspension was filtered and the filter cake was washed with methyl t-butyl ether and dried under vacuum to provide the pure compound N.5, ethyl 2-aminoacetate (482 g, 86.7%) as a white solid. ¹H NMR (D₂O) δ 4.21 (q, 2H), 3.84 (s, 2H), 1.21 (t, 3H).

Synthesis of Compound N.3. To a solution of compound ethyl 2-aminoacetate (30.0 g, 0.24 mol) in water (50 mL) and 36% HCl (36 mL) was added dropwise a solution of NaNO₂ in water (100 mL) at −5° C. The reaction mixture was extracted with ethyl acetate. The organic layer was dried over MgSO4, filtered and concentrated to give compound N.3, (Z)-ethyl 2-chloro-2-(hydroxyimino)acetate (17.4 g, 42.1%). ¹H NMR (DMSO-d₆) δ 13.41 (s, 1H), 4.25 (q, 2H), 1.24 (t, 3H).

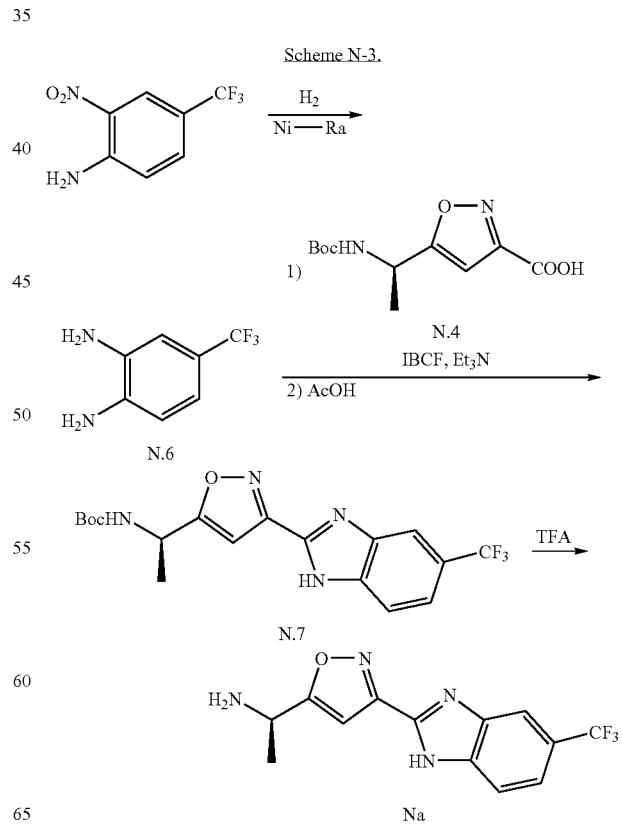

Synthesis of Compound N.6. A mixture of 2-nitro-4-trifluoromethyl-phenylamine (240 g, 1.16 mol) and Raney Ni (10 g) in methanol (2400 mL) was stirred at RT under hydrogen (50 psi) overnight. The reaction mixture was filtered and concentrated to provide the compound N.6 (197.7 g, 96.4%). $^1$H NMR (CDCl$_3$) δ 6.98 (d, 1H), 6.93 (s, 1H), 6.71 (d, 2H).

Synthesis of Compound N.7. To a solution of compound N.4 (55 g, 0.215 mol) and Et$_3$N (36 mL, 0.26 mol) in THF (2 L) was added dropwise isobutyl chloroformate (33 mL, 0.26 mol) at −20° C. The reaction mixture was stirred for 1 hr, and a solution of compound N.6 (45.4 g, 0.26 mol) in THF was added. After stirring for 2 hr at −20° C., the mixture was allowed to warm up to RT and stirred for another 2 hr. Water was added to quench the reaction and the reaction mixture was evaporated under reduced pressure to remove THF. The aqueous layer was extracted with ethyl acetate (2×). The combined organic layers were washed with water, dried over Na$_2$SO$_4$, filtered and concentrated. The residue was re-dissolved in acetic acid (250 mL) and stirred for 2 hr at 90° C. The solution was concentrated under vacuum and partitioned with ethyl acetate and water. The organic layer was separated, washed with water, Na$_2$CO$_3$ solution and brine, dried over Na$_2$SO$_4$, filtered and concentrated. The crude product was purified by column chromatography to afford compound N.7 (75.7 g, 88.8%). $^1$H NMR (DMSO-d$_6$) δ 7.8 (m, 4H), 6.9 (s, 1H), 4.91 (m, 1H), 1.46 (d, 3H), 1.39 (s, 9H).

Synthesis of Compound Na. A mixture of compound N.7 (86.5 g, 0.22 mol) in TFA (300 mL) was stirred at RT for 2 hr. The reaction mixture was concentrated in vacuo and re-dissolved in ethyl acetate. The ethyl acetate solution was washed with K$_2$CO$_3$ and water, dried over Na$_2$SO$_4$, and concentrated. The crude product was purified by column chromatography to afford compound Na (30.2 g, 46.7%). $^1$H NMR (DMSO-d$_6$) δ 7.98 (s, 1H), 7.78 (d, 1H), 7.56 (d, 1H), 6.94 (s, 1H), 4.16 (q, 1H), 1.36 (d, 3H).

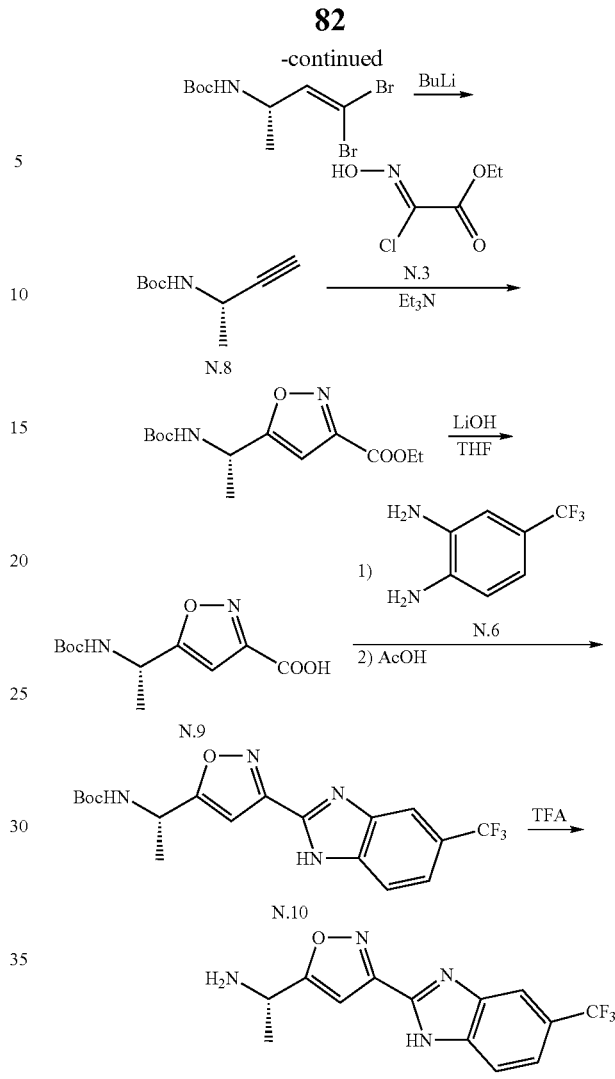

Synthesis of Compound Nb. This compound was synthesized in the same manner as described for compound Na in schemes N-1~N-3 starting from (1S)-(1-methyl-2-oxo-ethyl)-carbamic acid tert-butyl ester.

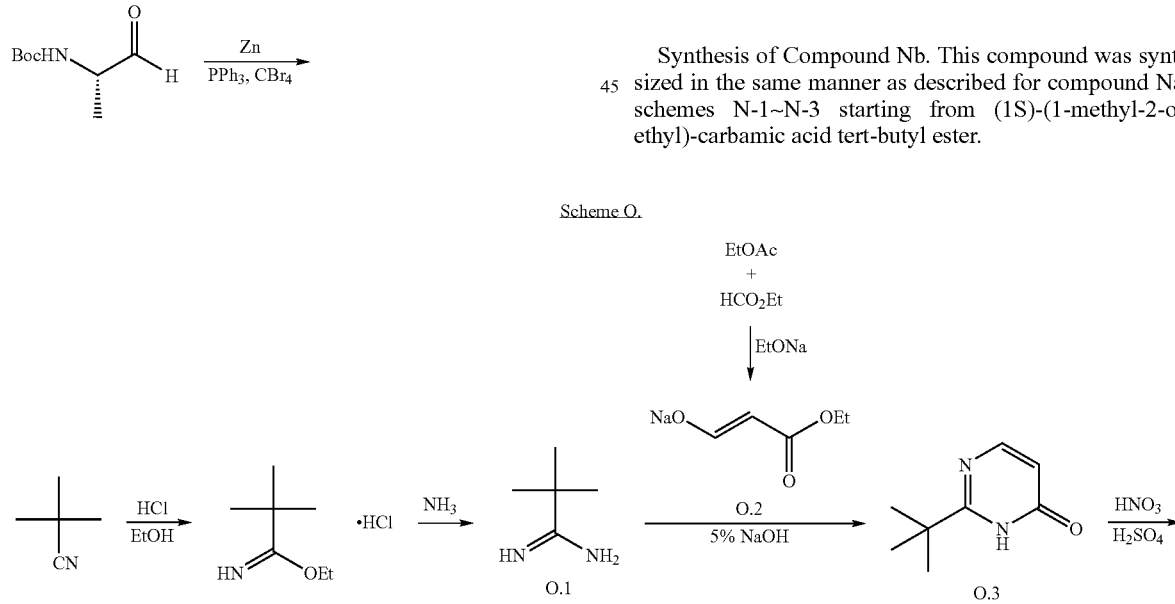

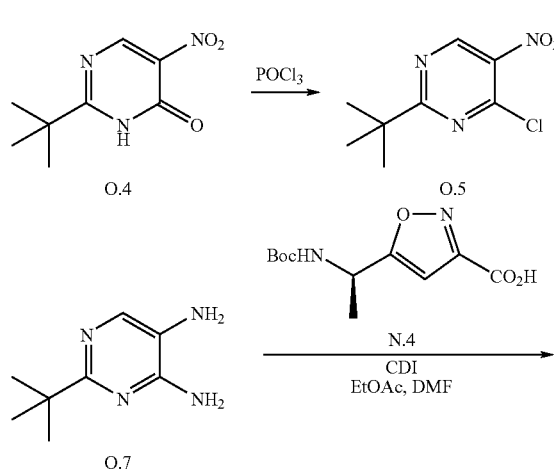
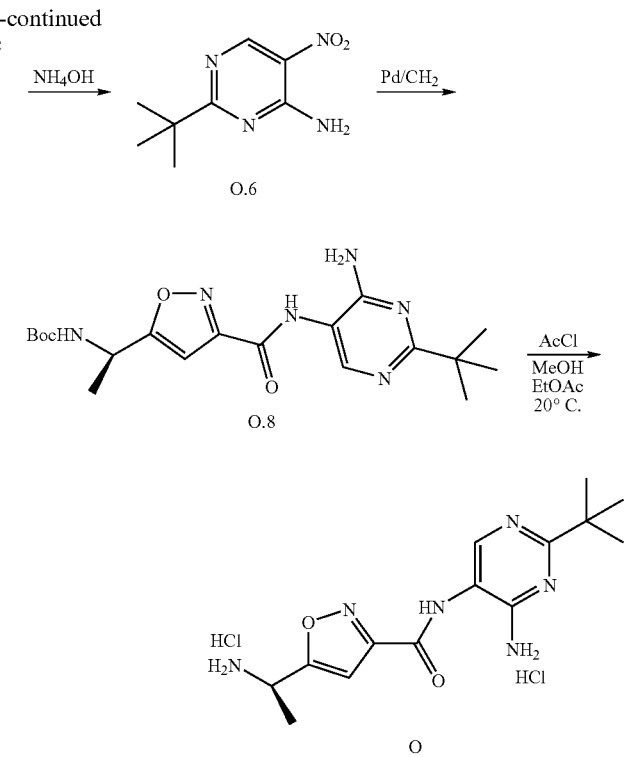

Synthesis of Compound O.1. Pivalonitrile (13 g, 157 mmol) was dissolved in absolute ethanol (50 mL) and cooled in a salt-ice bath. HCl gas was bubbled through this solution for 1 hr to saturate the solution. The reaction was warmed to RT. After 3 hr, the solvent was removed in vacuo to afford ethyl pivalimidate (16 g, 62%) as white solid. The crude ethyl pivalimidate (16 g, 97 mmol) was taken up in absolute ethanol (20 mL) and absolute ethanol saturated with ammonia (30 mL) was added. The reaction mixture was stirred at RT for 3 hr, whereupon ammonium chloride was filtered off and the salt washed with ethanol. The filtrate was concentrated in vacuo and the solid obtained was dried under vacuum to afford compound O.1, pivalimidamide (10 g, 76%). $^1$H NMR (DMSO-$d_6$, 200 MHz): δ 8.6 (br s, 1H), 1.2 (s, 9H); MS m/z 101 [M+1]$^+$.

Synthesis of Compound O.2. Sodium metal (15 g, 0.65 moles) was added to dry toluene and the mixture was heated to 120° C. Ethanol (38 mL, 0.847 g) was added dropwise through an addition funnel, and the mixture was refluxed for 3 hr after the addition. The reaction was cooled to RT and dry ether (400 mL) was added. To the resultant suspension, a mixture of ethyl formate (45 mL, 75 mmol) and ethyl acetate (54.7 mL, 88 mmol) were added dropwise. The reaction was stirred at RT for 3 days. Solvent was evaporated and the obtained solid O.2, sodium (E)-3-ethoxy-3-oxoprop-1-en-1-olate (60 g, 67%), was used without further purification.

Synthesis of Compound O.3. A mixture of 0.1 (25 g, 182 mmol), O.2 (50 g, 363 mmol) and 5% aqueous sodium hydroxide (320 mL) was stirred at RT overnight. The reaction mixture was brought to pH ~5.0 with conc. HCl and the product was extracted with DCM (3×). The combined organic layers were dried ($Na_2SO_4$) and concentrated in vacuo. The resultant crude residue was purified by column chromatography to obtain compound O.3, 2-tert-butylpyrimidin-4(3H)-one, as a yellow solid (15 g, 54%). $^1$H NMR (CDCl$_3$, 200 MHz) δ: 12.2 (brs, $D_2O$ exchangeable, 1H), 8.0 (d, J=6.9 Hz, 1H), 6.3 (d, J=6.9 Hz, 1H), 1.4 (s, 9H); MS: m/z 153 [M+1]$^+$.

Synthesis of Compound O.4. Compound O.3 (10 g, 66 mmol) was taken up in concentrated sulfuric acid (64 mL) and heated to 110° C. To the reaction mixture at 110° C., concentrated nitric acid (64 mL) was added dropwise in four equal portions. After 70% conversion, the reaction mixture was poured into ice water and extracted (DCM). The organic layer was dried ($Na_2SO_4$) and concentrated in vacuo to afford compound O.4, 2-tert-butyl-5-nitropyrimidin-4(3H)-one, as a white solid (5.0 g, 39%). $^1$H NMR (CDCl$_3$, 200 MHz) δ: 12.0 (br s, 1H), 9.0 (s, 1H), 1.4 (s, 9H); MS m/z 198 [M+1]$^+$.

Synthesis of Compound O.5. A solution of compound O.4 (12 g, 60.9 mmol) in phosphorus oxychloride (96 mL) was stirred at reflux for 5 hr. The reaction mixture was cooled to RT and the excess phosphorus oxychloride was concentrated in vacuo. The residue was added to ice-water and extracted into DCM. The organic layer was dried ($Na_2SO_4$) and removed in vacuo to afford compound O.5, 2-tert-butyl-4-chloro-5-nitropyrimidine, as a brown liquid (12 g, 92%) which was used without further purification.

Synthesis of Compound O.6. To a stirred solution of compound O.5 (12 g, 55.7 mmol) in methanol (96 mL) was added ammonium hydroxide solution (156 mL) at 0-5° C. The reaction was warmed to RT and stirred overnight. The mixture was concentrated in vacuo, and the residue was dissolved in water and extracted with DCM. The organic layer was dried ($Na_2SO_4$) and concentrated in vacuo to afford compound O.6, 2-tert-butyl-5-nitropyrimidin-4-amine, as a light green solid (8.4 g, 77%). $^1$H NMR (CDCl$_3$, 200 MHz) δ 9.2 (s, 1H), 7.8 (br. s, 1 H), 6.0 (br. s, 1H), 1.38 (s, 9H); MS: m/z 197.0 [M+1]$^+$.

Synthesis of Compound O.7. To a stirred solution of compound O.6 (8.0 g, 40 mmol) in methanol (200 mL) was added 10% palladium carbon (1.0 g). The reaction was stirred under an atmospheric pressure of hydrogen for 6 hr at RT. The mixture was filtered through celite and the solution was concentrated in vacuo to afford compound O.7, 2-tert-butylpyrimidine-4,5-diamine, as an off-white solid (6.7 g, 98.96%). $^1$H NMR: (CDCl$_3$, 200 MHz) δ 7.8 (s, 1H), 4.7 (br. s, 2H), 3.0 (br. s, 2H), 1.35 (s, 9H); $^{13}$C NMR: (CDCl$_3$, 60 MHz) δ 167.9, 155.9, 138.4, 125.2, 38.9, 30.2; MS: m/z 167.1 [M+1]$^+$.

Synthesis of Compound O.8. To a three-neck round-bottom flask equipped with a thermometer, a magnetic stirrer and a nitrogen inlet was added ethyl acetate (50.0 mL), and CDI (9.7 g, 59.9 mmol) at RT. To the resultant slurry was added a solution of compound N.4, 5-(1-tert-Butoxycarbonylaminoethyl)-isoxazole-3-carboxylic acid (15.7 g, 60 mmol) in ethyl acetate (80 mL) at RT over 1 hr. The clear solution was heated to 40° C. for additional 10 min. The reaction was cooled to RT and to it was added a solution of compound O.7 (10.0 g, 59.9 mmol) in DMF (20 mL) over 30 min. The reaction mixture was stirred at RT for an additional 5 hr, whereupon ethyl acetate (150 mL) was added. The mixture was washed with water (3×110 mL) and the organic layer was concentrated under reduced pressure to give compound O.8, (R)-tert-butyl 1-(3-(4-amino-2-tert-butylpyrimidin-5-ylcarbamoyl)isoxazol-5-yl)ethylcarbamate, as a glassy solid (25.7 g, 91.2%). $^1$H NMR (CDCl$_3$, 200 MHz) δ: 8.3 (s, 1H), 8.2 (s, 1H), 6.65 (s, 1H), 5.1-5.2 (m, 1H), 1.6 (d, 3H), 1.4 (s, 9H), 1.3 (s, 9H); MS: m/z 405.2 [M+1]$^+$.

Synthesis of Compound O. To a three-neck round-bottom flask equipped with a thermometer, a magnetic stirrer and a nitrogen inlet was added compound O.8 (17.6 g, 37.4 mmol) and methanol (60.0 mL) at RT. To the resultant clear solution was then added acetyl chloride (16.5 mL, 232 mmol) while maintaining the reaction temperature below 40° C. The solution was stirred at RT for an additional 1 to 2 hr, whereupon ethyl acetate (95 mL) was added. The product started to crystallize from the reaction mixture and additional ethyl acetate (265 mL) was added over 1 hr. The resultant slurry was stirred for additional 1 hr and filtered. The wet cake was washed with ethyl acetate (3×50 mL) and dried under vacuum to give compound O, (R)—N-(4-amino-2-tert-butylpyrimidin-5-yl)-5-(1-aminoethyl)isoxazole-3-carboxamide dihydrochloride (13.11 g, 91.9%) as a white solid. $^1$H NMR (DMSO-d$_6$, 400 MHz) δ 10.64 (s, 1H), 9.19 (br s, 3H), 8.83 (s, 1H), 7.17 (s, 1H), 4.83 (br. s, 1H), 1.64 (d, J=7 Hz, 3H), 1.41 (s, 9H); MS: m/z 305.3 [M+1]$^+$.

Synthesis of Compound P.1. 1-(1-Methylcyclopropyl)ethanone (8 g, 81.5 mmol) and methoxybis(N,N-dimethyl)methane (14 g, 16.2 ml, 106.0 mmol) were heated at 110° C. for 18 hr. Excess methoxybis(N,N-dimethyl)methane was removed by concentration in vacuo to obtain compound P.1 as yellow crystals (11.1 g, 88.2%). $^1$H NMR (CDCl$_3$, 200 MHz) δ: 7.60 (d, J=11.3 Hz, 1H), 5.20 (d, J=11.3 Hz, 1H), 1.4 (s, 3H), 1.1-1.2 (m, 2H), 0.7-0.8 (m, 2H); MS: m/z 154.2 [M+1]$^+$.

Synthesis of Compound P.2. In a 350 mL sealed flask (2-nitroethene-1,1-diyl)bis(methylsulfane) (15 g, 90 mmol) was dissolved in 7M ammonia in methanol (150 mL) and stirred at 50° C. overnight. After 18 hr, solvent was removed in vacuo and the solid obtained was washed with DCM to afford P.2 as an orange solid (7.2 g, 76.9%). $^1$H NMR (DMSO-D6, 200 MHz) δ: 6.6 (s, 1H).

Synthesis of Compound P.3. Compound P.1 (8.0 g, 52.3 mmol) and compound P.2 (5.38 g, 52.3 mmol) were dissolved in AcOH:EtOH (1:4). The reaction mixture was heated at 100° C. for 16 hr, then cooled to RT and concentrated in vacuo. The resultant residue was dissolved in 1 M NaOH and extracted with ethyl acetate (3×). The combined organic layers were washed with brine, dried over anhydrous sodium sulfate and concentrated in vacuo. The crude product was purified by column chromatography (50-100% DCM/hexane) to afford compound P.3 (4.8 g, 47.6%). $^1$H NMR (CDCl$_3$, 200 MHz): δ 8.25 (d, J=8.5 Hz, 1H), 6.6-6.7 (d, J=8.5 Hz, 1H), 1.5 (s, 3H), 1.2-1.3 (m, 1H), 0.8-0.9 (m, 1H); MS: m/z 194.1 [M+1]$^+$.

Synthesis of Compound P.4. Compound P.3 (5.0 g, 25.9 mmol) was dissolved in methanol (200 mL) and palladium/C (1.0 g) was added. The reaction mixture was stirred under an atmospheric pressure of hydrogen for 4 hr and filtered through celite. The filtrate was concentrated in vacuo to provide a residue which was purified by column chromatography (2% methanol/DCM) to obtain compound P.4 (2 g, 47.4%). $^1$H NMR: (CDCl$_3$, 200 MHz) δ 6.85 (d, J=8.5 Hz, 1H), 6.7-6.8 (brs, J=8.5 Hz, 1H), 4.1-4.3 (br s, 2H, NH), 3.1-3.3 (brs, 2H, NH), 1.4 (s, 3H), 1.0-1.1 (m, 2H), 0.6-0.8 (m, 2H);

Scheme P-1.

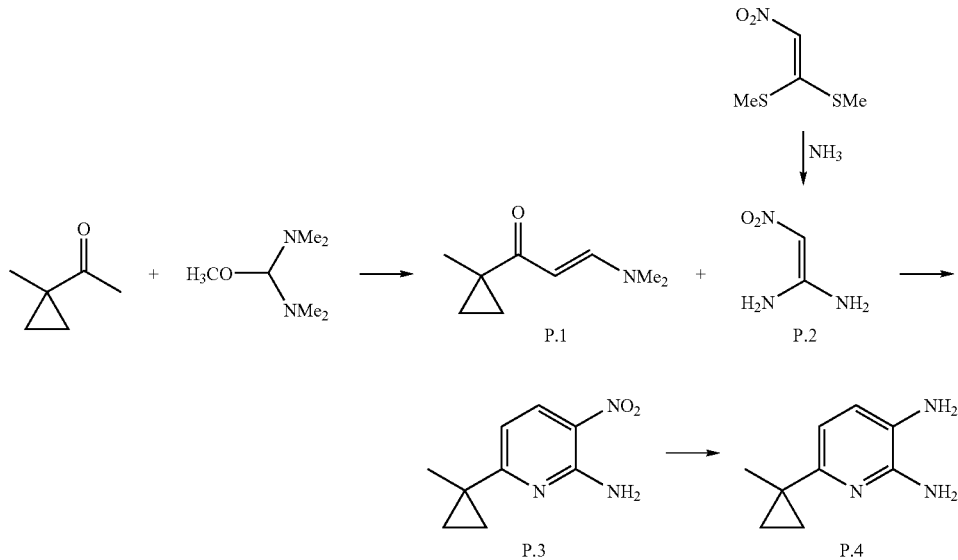

$^{13}$C NMR (CDCl3, 60 MHz): δ 154.03, 148.50, 125.75, 123.08, 111.17, 23.24, 19.65, 15.80; MS: m/z 164.2 [M+1]+.

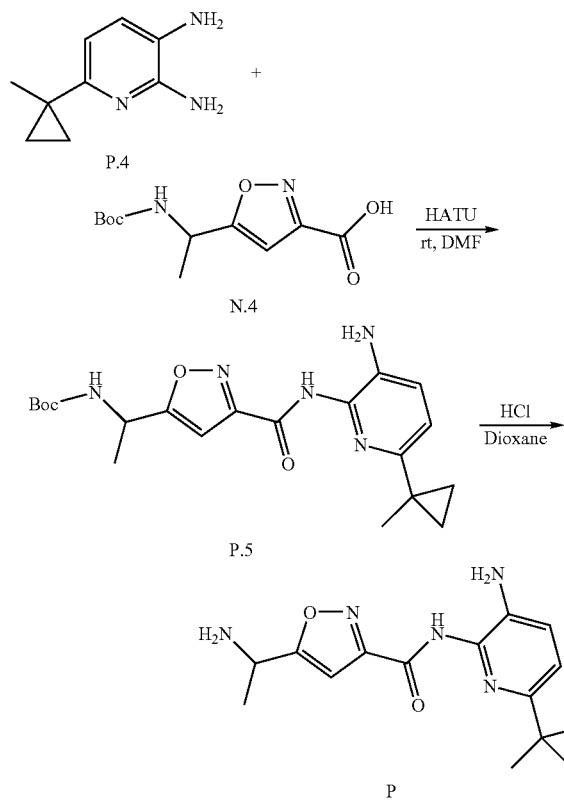

Synthesis of Compound P.5. Compound N.4 (1 g, 0.004 mol) was dissolved in DMF (30 mL). Compound P.4 (0.64 g, 0.004 mol), HATU (2.4 g, 0.006 mol), and diisopropylethylamine (3.0 mL, 0.02 mol) were added and the reaction mixture was stirred at RT for 1 hr. Solvent was removed in vacuo and the crude reaction mixture was dissolved in EtOAc and washed with saturated aqueous NaHCO3 (3×) and brine (1×). The organic layer was dried over anhydrous sodium sulfate and concentrated in vacuo. The crude product was purified by column chromatography (0-5% MeOH/DCM) to afford compound P.5 (1.28 g, 80%). $^1$H NMR (DMSO-d6, 200 MHz): δ 9.89 (s, 1H, NH), 7.64 (d, J=7.6 Hz, 1H, NH), 7.39 (d, J=6.6 Hz, 1H) 6.62 (s, 1H), 6.59 (d, J=7.6 Hz, 1H), 5.64 (br s, 1H), 4.91-4.84 (m, 1H), 1.44 (s, 3H), 1.49-1.39 (m, 12H), 1.08 (dd, J=3.4 Hz, J=2.6 Hz, 2H), 0.68 (dd, J=3.4 Hz, J=2.6 Hz, 2H); MS: m/z 402.5 [M+1]+.

Synthesis of Compound P. A solution of compound P.5 (1.0 g, 0.0025 mol) in 4 N HCl/Dioxane (5 mL) was stirred for 3 hr and concentrated in vacuo. The resultant residue (0.65 g, 86%) was used without further purification. MS: m/z 302.5 [M+1]+.

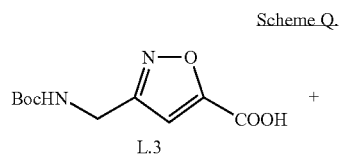

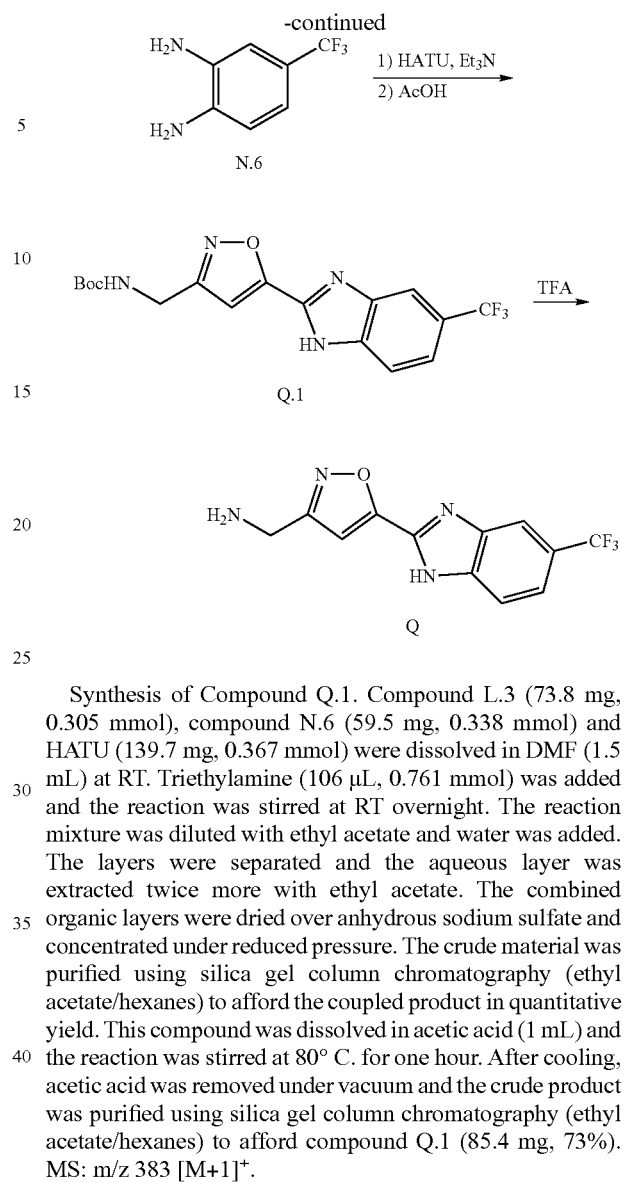

Synthesis of Compound Q.1. Compound L.3 (73.8 mg, 0.305 mmol), compound N.6 (59.5 mg, 0.338 mmol) and HATU (139.7 mg, 0.367 mmol) were dissolved in DMF (1.5 mL) at RT. Triethylamine (106 μL, 0.761 mmol) was added and the reaction was stirred at RT overnight. The reaction mixture was diluted with ethyl acetate and water was added. The layers were separated and the aqueous layer was extracted twice more with ethyl acetate. The combined organic layers were dried over anhydrous sodium sulfate and concentrated under reduced pressure. The crude material was purified using silica gel column chromatography (ethyl acetate/hexanes) to afford the coupled product in quantitative yield. This compound was dissolved in acetic acid (1 mL) and the reaction was stirred at 80° C. for one hour. After cooling, acetic acid was removed under vacuum and the crude product was purified using silica gel column chromatography (ethyl acetate/hexanes) to afford compound Q.1 (85.4 mg, 73%). MS: m/z 383 [M+1]+.

Synthesis of Compound Q. Compound Q.1 (85.4 mg, 0.223 mmol) was dissolved in 20% TFA in dichloromethane (1 mL) at 0° C. and the reaction mixture was gradually warmed to RT over one hour. Benzene was added and the solvents were removed under reduced pressure. The resultant residue was dissolved in dichloromethane and saturated sodium bicarbonate solution was added. The layers were separated and the aqueous layer was extracted twice more with dichloromethane. The combined organic layers were dried over anhydrous sodium sulfate and concentrated under reduced pressure to afford compound Q which was used without further purification. MS: m/z 283 [M+1]+.

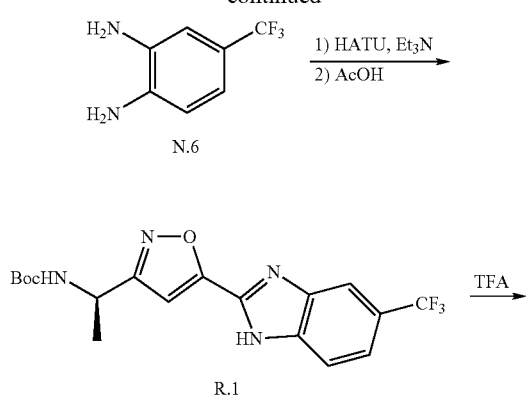

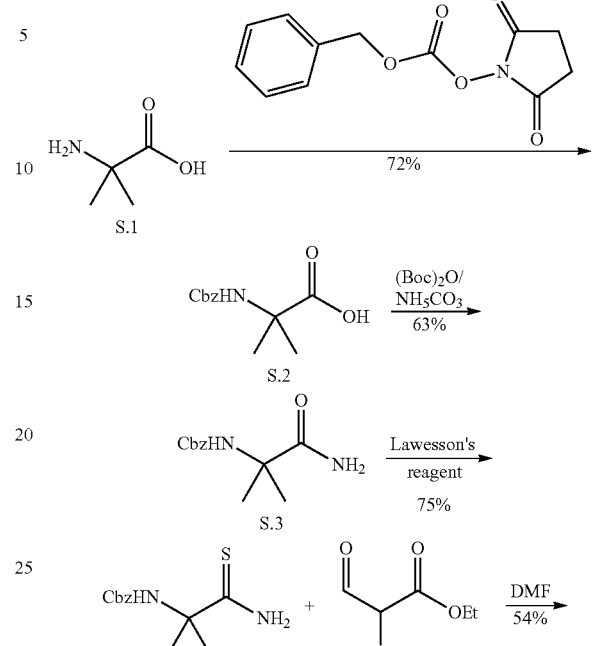

Synthesis of Compound R. This compound was synthesized in a similar manner as compound Q following scheme Q-1 using compound M.3 instead of L.3. MS: m/z 297 [M+1]$^+$.

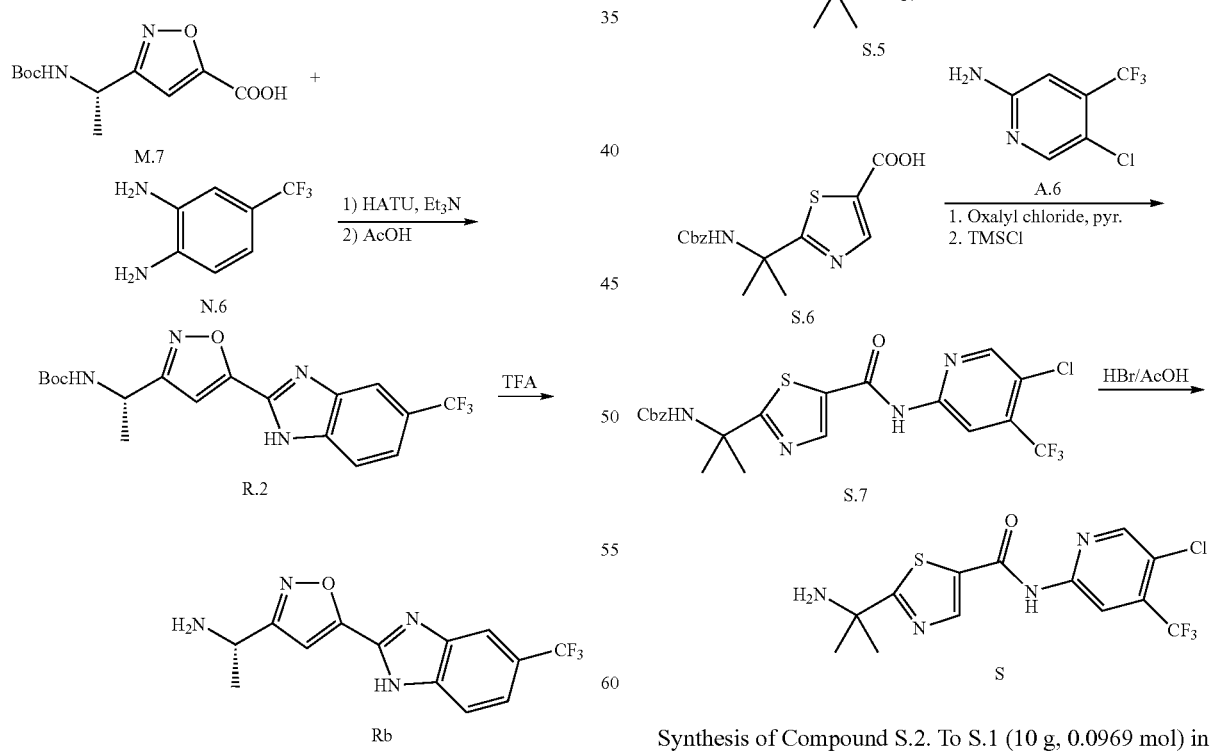

Synthesis of Compound Rb. This compound was synthesized in a similar manner as compound Q following scheme Q using compound M.7 instead of L.3. MS: m/z 297[M+1]$^+$.

Synthesis of Compound S.2. To S.1 (10 g, 0.0969 mol) in THF (60 ml) and water (60 mL) at 0° C. was added sodium bicarbonate (16.27 g, 0.193 mole) followed by N-(benzyloxy carbonyloxy) succinimide (60.37 g, 0.242 mol). The reaction mixture was stirred at RT for 12 hr. The THF was removed under vacuum and the aqueous phase was washed with ether (2×100 mL). The aqueous phase was cooled to 0° C. and acidified to pH=2 with 5N HCL (50 mL). The reaction mixture was extracted with ethyl acetate (2×100 mL); the combined organic layer was dried over sodium sulfate and concentrated under reduced pressure. The crude material was purified by column chromatography (1% MeOH in dichloromethane) to give S.2 (16 g, 72%). $^1$H NMR (CDCl$_3$, 200 MHz) δ 7.45-7.32 (m, 5H), 5.40 (bs, 1H,) 5.12 (s, 2H), 1.82 (s, 6H); MS: m/z 238 [M+1]$^+$.

Synthesis of Compound S.3. To a suspension of S.2 (20 g, 0.0843 mol) in acetonitrile were added (400 mL), di-tert-butyl-dicarbonate (24 mL, 0.107 mol), ammonium bicarbonate (8 g, 0.101 mol) and pyridine (5.2 ml). The reaction mixture was stirred at RT for 3 hr and then the acetonitrile was removed under reduced pressure. The reaction mixture was diluted with water (50 mL) and the resulting solid was removed by filtration. The solid was washed with water ad dried to afford S.3 (12 g, 63%) as a off-white solid. This material was used for the next reaction with out any further purification. $^1$H NMR (CDCl$_3$, 200 MHz) δ 7.41-7.38 (m, 5H), 6.30 (bs, 1H), 5.40 (bs, 2H), 5.15 (s, 2H), 1.78 (s, 6H); MS: m/z 236 [M+1]$^+$.

Synthesis of Compound S.4. Lawessons reagent (10.28 g, 0.0254 mol) was added to a suspension of S.3 (10 g, 0.04237 mol) in dioxane (58 mL) at RT. The reaction mixture was heated at 60° C. for 30 minutes, cooled to RT and stirred for additional 1.5 hr. The resulting solution was concentrated under reduced pressure and the residue was diluted with saturated sodium bicarbonate (50 mL). The solid obtained was filtered, washed with water and dried under vacuum to afford an off-white solid S.4 (8.0 g, 75%) which was for the next step without further purification. $^1$H NMR (CDCl$_3$, 200 MHz) δ 7.90 (bs, 1H) 7.72 (bs, 1H) 7.41-7.38 (m, 5H), 5.58 (bs, 1H), 5.12 (s, 2H), 1.72 (s, 6H). MS: m/z 253 [M+1]$^+$.

Synthesis of Compound S.5. A solution of A.3 (9.5 g, 0.0635 mol) in DMF (64 mL) was added to thioamide S.4 (8 g, 0.031 mol). The reaction mixture was stirred at 50° C. under nitrogen atmosphere overnight. After cooling to RT, ether (70 mL) was added. The solution was cooled to 0° C. and saturated sodium bicarbonate (30 mL) was added slowly. The reaction mixture was extracted with ether (2×50 mL); the combined organic layer was washed with saturated sodium bicarbonate (1×50 mL), dried over sodium sulfate and concentrated under vacuum to give a brown oil. Purification by column chromatography (20% ethyl acetate/hexane) provided compound S.5 (6 g, 54%) as a brown solid. $^1$H NMR (CDCl$_3$ 200 MHz) δ 8.13 (s, 1H) 7.40-7.35 (m, 5H) 5.70 (bs, 1H), 5.10 (s, 2H), 4.35 (q, J=7.2 Hz, 2H) 1.80 (s, 6H), 1.37 (t, J=7.2 Hz, 3H). MS m/z: 349 [M+1]$^+$.

Synthesis of Compound S.6. To a 0° C. solution of S.5 (300 mg, 0.86 mmol) in THF (4 mL) and water (4 mL) was added lithium hydroxide (200 mg, 0.0258 mol) in water (1 mL). The reaction mixture was stirred at RT for 2.5 h and then the solvent was removed under reduced pressure. The aq. layer was washed with ether (2×15 ml), cooled to 0° C. and acidified to pH=2 with 5N HCl. The obtained precipitate was filtered and dried to give S.6 (180 mg, 66%). $^1$H NMR (200 MHz, DMSO-d6) δ 13.45 (bs, 1H), 8.20 (bs, 1H), 8.18 (s, 1H), 7.40-7.38 (m, 5H), 5.02 (s, 2H), 1.60 (s, 6H). MS m/z: 320.9 [M+1]$^+$.

Synthesis of Compound S.7. To a solution of S.6 (205 mg, 0.64 mmol) in methylene chloride (4 mL) at rt was added oxalyl chloride (160 μL, 0.0019 mol) followed by the addition of DMF (50 μL) and stirred at RT for 1 hr. Separately a solution of A.6 (132 mg, 0.000672 mol), acetonitrile (2 ml) and pyridine (520 μL, 0.0065 mol) was stirred at RT followed by the addition of chlorotrimethylsilane (100 μL, 0.0008 mol). The acid chloride was concentrated under reduced pressure to a tan solid and redissolved in acetonitrile (2 mL). To the acid chloride solution was added the activated aniline. After 3 hr, the reaction mixture was diluted with ethyl acetate (75 mL) and washed with dilute citric acid (50 mL), aqueous sodium bicarbonate (50 mL) and water. The organic layer was dried over sodium sulfate and concentrated to a residue which was purified by to give compound S.7. MS m/z: 498.95 [M+1]$^+$.

Synthesis of Compound S. To a solution of S.7 (80 mg, 0.16 mmol) in acetic acid (3 mL) was added 4M hydrogen bromide in acetic acid (1 mL, 0.004 mol) and stirred at RT for 4 hr. The reaction mixture was concentrated to a residue which was triturated with saturated sodium bicarbonate The residue was dissolved in ethyl acetate and washed with saturated sodium bicarbonate. The organic layer was dried over sodium sulfate and concentrated to provide S. MS m/z: 364.97 [M+1]$^+$.

Scheme T

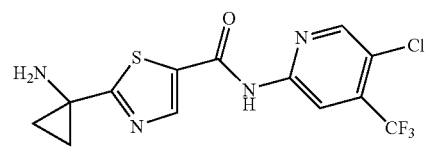

T

Synthesis of Compound T. The synthesis of T was accomplished following Scheme S substituting 1-amino-cyclopropanecarboxylic acid for 2-amino-2-methyl-propionic acid (S.1).

Schemse U.

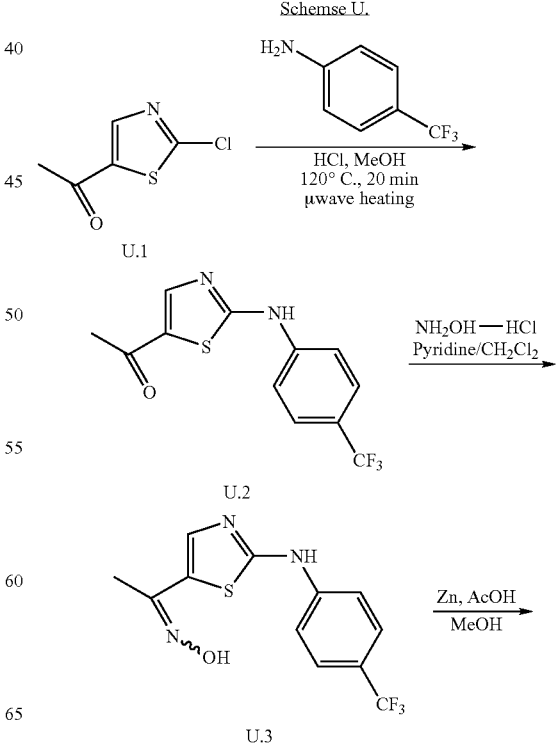

-continued

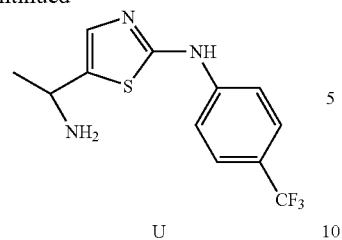

U

Synthesis of Compound U.2. To a 2 mL reaction vial was charged with U.1 (50 mg, 0.2 mmol), 4-trifluoromethylbenzenamine (30 μL, 0.24 mmol), MeOH (500 μL) and 4 M of HCl in 1,4-dioxane (5 μL, 0.02 mmol). The mixture was heated in microwave oven for 20 min at 120° C. This crude mixture was purified via prep-HPLC, affording U.2 (30 mg, 50%). $^1$H NMR (DMSO-d6, 400 MHz) δ: 11.2 (br s. 1H), 8.2 (s, 1H), 7.8-7.9 (d, 2H), 7.7-7.8 (d, 2H), 2.4 (s, 3H); m/z 287 [M+1]$^+$.

Synthesis of Compound U.3. To a solution of U.2 (1.0 g, 3.49 mmol) in methanol (20 mL) at 0° C., were added pyridine (1.17 mL, 13.98 mmol) and hydroxylamine hydrochloride (485 mg, 6.99 mmol). After stirring at RT overnight, methanol was removed and the residue was diluted with water. The formed solid was collected via filtration, affording compound U.3 (800 mg, 80%). $^1$H NMR (mixture of cis, trans isomers, DMSO-d6 200 MHz) δ: 11.4 and 11.1 (1H, —OH), 10.7-10.8 (br s, 1H), 7.8-7.9 (d, 2H), 7.8 and 7.6 (s, 1H), 7.6-7.7 (d, 2H), 2.1 and 2.2 (s, 3H); m/z 302 [M+1]$^+$.

Synthesis of Compound U. To a mixture of U.3 (800 mg, 2.65 mmol) in 1:1 ethanol and acetic acid (30 mL) was added Zn powder (1 g, 15.9 mmol). After stirring overnight at RT, solvents were distilled off and residue was taken in water. The solution was basified with NH$_4$OH, extracted into EtOAc and concentrated. Crude compound was purified by column chromatography using DCM to 2-4% MeOH in DCM as elute to afford U as a brown color solid (500 mg, 65.61%). $^1$H NMR (200 MHz, DMSO-d6) δ: 10.4-10.6 (br s, 1H), 7.8-7.9 (d, 2H), 7.6-7.7 (d, 2H), 7.1 (s, 1H), 4.2-4.3 (m, 1H), 1.3-1.4 (d, 3H); m/z 288 [M+1]$^+$.

Synthesis of Compound Ua and Ub. Preparatory chiral SFC of compound U (440 mg) on a Chiralpak AS-H (2×25 cm) with an eluant of 30% isopropanol (0.1% Et$_2$NH)/CO$_2$ at 100 bar at 60 mL/min and monitoring at 220 nM afforded and 206 mg of Ub (ee>99%) as the first eluting peak and 186 mg of Ua (ee>99%) as the second eluting peak.

Scheme V.

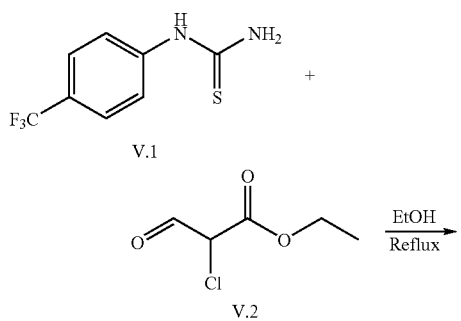

-continued

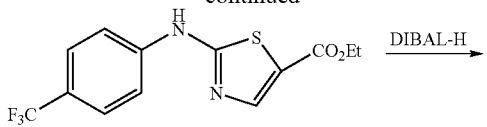

V.3

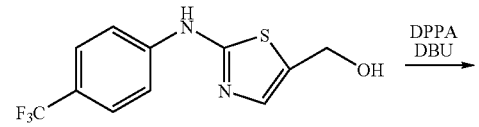

V.4

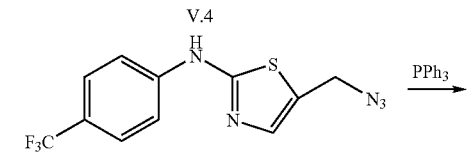

V.5

V

Synthesis of Compound V.3. A RT solution of V.1 (10 g, 45.45 mmol) in ethanol (100 mL) was treated with V.2 (10.26 g, 68.18 mmol, Plouvier, B.; Bailly, C.; Houssin, R.; Henichart, J. P. Heterocycles 1991, 32, 693-701), and the reaction mixture was heated at reflux for 16 hr. The ethanol solvent was distilled off and the residue was dissolved in EtOAc. The organic layer was washed with sodium bicarbonate solution, water, and brine, dried over anhydrous Na$_2$SO$_4$, filtered, and concentrated under vacuum. Purification by flash column chromatography (SiO$_2$, 100% hexane to 12% EtOAc-Hexane) afforded V.3 as a yellow solid (10 g, 69.63%). $^1$HNMR (CDCl$_3$, 200 MHz) δ 9.3-9.4 (br s, 1H, DH$_2$O exchangeable), 8.0 (s, 1H), 7.6-7.7 (d, 2H), 7.3-7.4 (d, 2H), 4.2-4.4 (q, 2H), 1.3-1.4 (t, 3H); m/z: 317 [M+1]$^+$.

Synthesis of Compound V.4. A solution of V.3 (4 g, 12.65 mmol) in dry DCM (60 mL) was cooled to −78° C. under a N$_2$ atmosphere, and treated with DIBAL-H (38 mL, 1M solution in toluene, 38 mmol). The reaction was stirred at −78° C. for 2 hr, then quenched by addition of saturated NH$_4$Cl solution, and slowly warmed to RT. The reaction mixture was filtered through celite, and the filter cake was washed with DCM. The organic layer was separated and dried over anhydrous Na$_2$SO$_4$, filtered, and concentrated under vacuum. Purification by flash column chromatography (SiO$_2$, 100% hexanes to 25% ethyl acetate-Hexane) afforded V.4 as white solid (1.8 g, 52%). $^1$HNMR (200 MHz, DMSO-d6) δ: 10.5 (s, 1H, D$_2$O exchangeable), 7.7-7.8 (d, 2H), 7.5-7.6 (d, 2H), 7.1 (s, 1H), 5.3 (t, 1H, D$_2$O exchangeable), 4.5 (s, 2H); m/z: 274.9 [M+1]$^+$.

Synthesis of Compound V.5. A solution of V.4 (1.8 g, 6.57 mmol) in toluene (30 mL) and THF (10 mL) was cooled in an ice bath at 0° C., and treated with diphenylphosphonic azide (2.835 g, 13.139 mmol) and DBU (2 g, 13.139 mmol). The reaction mixture was stirred overnight at RT. The mixture was concentrated under vacuum, and the residue was purified by flash column chromatography to obtain V.5 (1 g, 51%) as yellow solid. $^1$HNMR (1H, CDCl$_3$, 200 MHz) δ: 7.6-7.7 (d, 2H), 7.5-7.6 (d, 2H), 7.3 (s, 1H), 4.4 (s, 2H); m/z: 300 [M+1]$^+$.

Synthesis of Compound V. A solution of SBN-69-5 (500 mg, 1.672 mmol) in THF (20 mL) and water (1 mL) was treated with triphenylphosphine (657 mg, 2.508 mmol). The mixture was stirred overnight at RT. Solvents were evaporated and the residue was purified by column chromatography (SiO$_2$, 100% DCM to 2.5% MeOH/DCM) to obtain the product as brown colour solid. (300 mg, 65.78%). $^1$HNMR: (1H, DMSO-D6, 200 MHz) δ: 10.4-10.6 (br s, 1H), 7.7-7.9 (d, 2H), 7.6-7.7 (d, 2H), 7.1 (s, 1H), 3.9 (s, 2H); m/z: 274 [M+1]$^+$.

Scheme W.

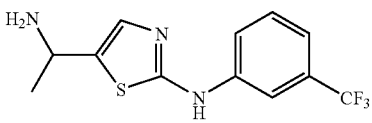

W

Synthesis of Compound W. The synthesis of W was accomplished following Scheme U substituting 3-trifluoromethylaniline for 4-trifluoromethylaniline. MS m/z 288 [M+1]$^+$.

Scheme X.

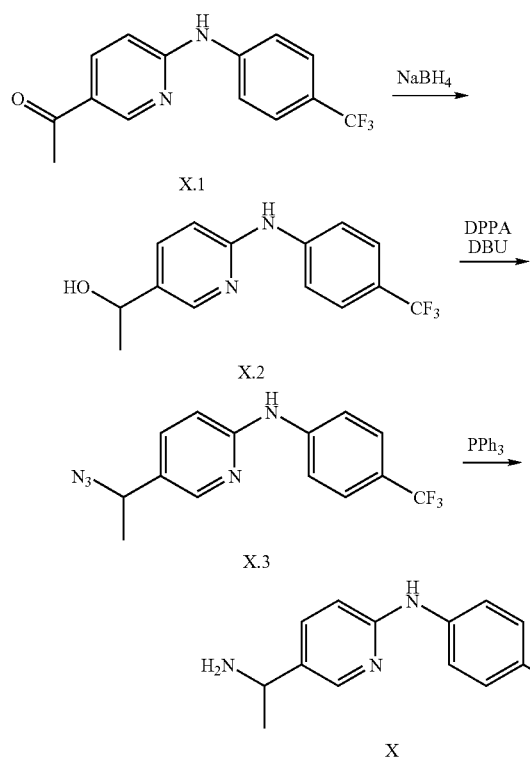

Synthesis of Compound X.1. The synthesis of X.1 was accomplished following Scheme U substituting 1-(6-chloro-3-pyridinyl)-1-ethanone for 1-(2-chlorothiazol-5-yl)ethanone (U.1).

Synthesis of Compound X.2. A suspension of X.1 (804 mg, 2.87 mmole) in 30 mL of ethanol was treated with sodium borohydride (0.217 g, 5.74 mmol), and the reaction mixture was stirred at RT for 16 hr. The mixture was concentrated to dryness and the residue was dissolved in EtOAc and H$_2$O. The organic layer was separated, dried over MgSO$_4$, filtered, and concentrated, absorbing onto 10 g SiO$_2$. Purification by flash column chromatography (40 g SiO2, 10% EtOAc/hexane for 5 min then gradient to 60% EtOAc/hexanes over 15 min) afforded 738 mg (91%) of X.2 as a clear oil that slowly solidified the a white solid. MS, m/z=284 [M+1]$^+$.

Synthesis of Compound X.3. A solution of X.2 (738 mg, 2.61 mmol) in anhydrous DCM (10 mL) was and cooled in an ice bath, treated with diphenylphosphonic azide (0.817 mL, 3.79 mmol) in a dropwise fashion, and stirred for 15 min. 1,8-Diazabicyclo[5.4.0]undec-7-ene (0.567 mL, 3.79 mmol) was added in a dropwise fashion. The reaction mixture was stirred in the ice bath for 1 hr, warmed to RT and stirred for 16 hr. The reaction mixture was partitioned between EtOAc and H2O. The organic layer was dried over MgSO$_4$, filtered, and concentrated, absorbing onto 5 g SiO$_2$. Purification by flash column chromatography (40 g SiO$_2$, 5% EtOAc/hexane then gradient to 40% EtOAc/hexanes) yielded X.3 (464 mg, 58%) as a yellow viscous oil. MS m/z 292 [M+1]$^+$.

Synthesis of Compound X. A solution of X.3 (463 mg, 1.51 mmol) in THF (10 mL) and H$_2$O (3 mL) was treated with triphenylphosphine (0.593 g, 2.26 mmol) and was heated at 60° C. for 16 hr. The reaction mixture was cooled to RT, diluted with EtOAc and extracted with 1 N HCl (2×10 mL). The aqueous layer was made basic by addition of 10% NaOH and extracted with EtOAc (2×). The combined organic layers were dried over MgSO$_4$, filtered, and concentrated to obtain X (316 mg, 75%) as a viscous oil that solidified to a white solid upon standing. MS m/z 282 [M+1]$^+$.

Scheme Y.

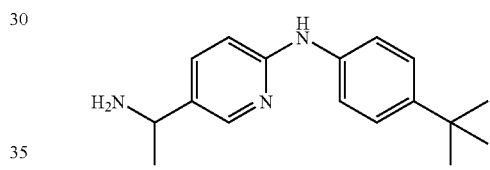

Y

Synthesis of Compound Y. The synthesis of Y was accomplished following Scheme X substituting 4-t-butyl-aniline for 4-trifluoromethylaniline.

Scheme Z.

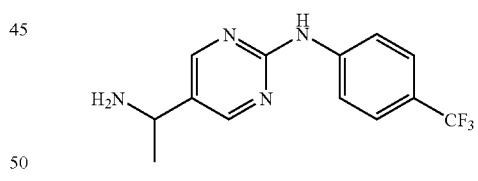

Z

Synthesis of Compound Z. The synthesis of Z was accomplished following Scheme U and X substituting 1-(2-chloropyrimidin-5-yl)ethanone (*Bioorg. Med. Chem.* 2005, 13, 3707) for 1-(2-chlorothiazol-5-yl)ethanone (U.1).

Scheme AA.

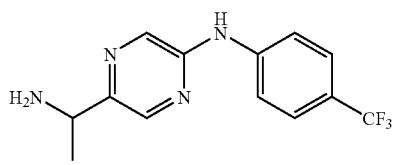

AA

Synthesis of Compound AA. The synthesis of AA was accomplished following Scheme U and X substituting 1-(2-chloropyrazin-5-yl)ethanone (*Bioorg. Med. Chem.* 2005, 13, 3707) for 1-(2-chlorothiazol-5-yl)ethanone (U.1).

Scheme BB.

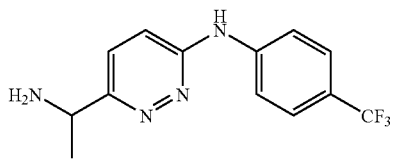

BB

Synthesis of Compound BB. The synthesis of BB was accomplished following Scheme U substituting 1-(2-chloropyridazin-5-yl)ethanone (*Bioorg. Med. Chem.* 2005, 13, 3707) for 1-(2-chlorothiazol-5-yl)ethanone (U.1).

Scheme CC.

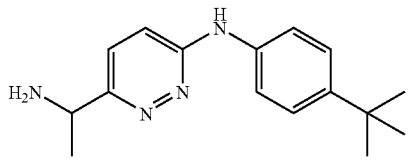

CC

Synthesis of Compound CC. The synthesis of CC was accomplished following Scheme U substituting 1-(2-chloropyridazin-5-yl)ethanone (*Bioorg. Med. Chem.* 2005, 13, 3707) for 1-(2-chlorothiazol-5-yl)ethanone (U.1) and 4-t-butylaniline for 4-trifluoromethylaniline.

Scheme DD.

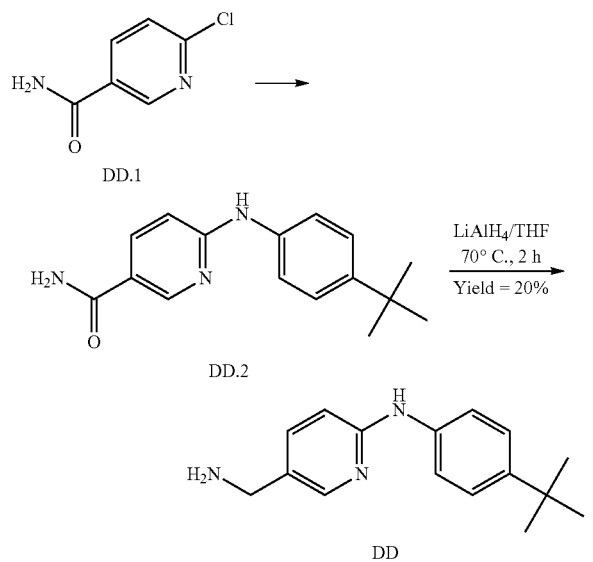

Synthesis of Compound DD.2. Compound DD.2 was synthesized as described in the sythesis of compound U.2. m/z 270 [M+1]$^+$.

Synthesis of Compound DD. To a mixture of DD.2 (200 mg, 0.7 mmol) in THF (5 mL) was added lithium tetrahydroaluminate (90 mg, 2.0 mmol) and heated it at 70° C. for 2 hr. After cooling down to 25° C., the mixture was quenched with ice water, followed by added 1 N NaOH. The formed solid was removed via filtration, and the filtrate was concentrated and further purified via prep-HPLC, affording DD (40 mg, 20%). m/z 256 [M+1]$^+$.

Scheme EE.

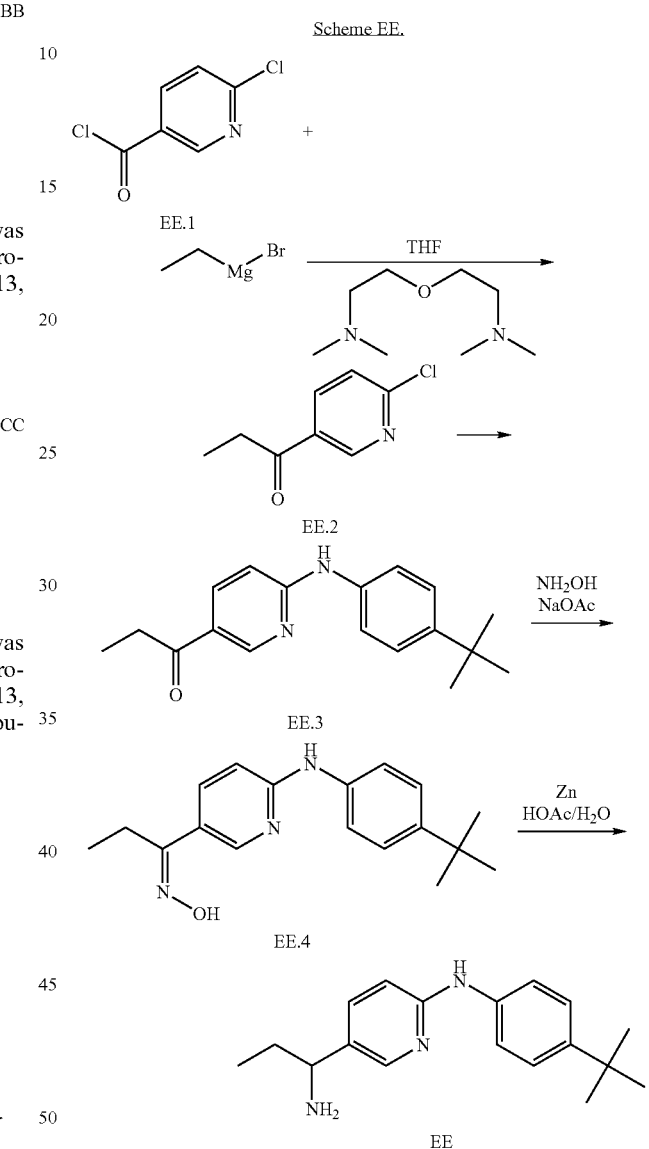

Synthesis of Compound EE.2. To a solution (in a flame dried vial) of ethanamine, 2,2'-oxybis[N,N-dimethyl- (0.50 mL, 2.6 mmol) in tetrahydrofuran (7.0 mL) at 0° C., was added 1.0 M of ethylmagnesium bromide in tetrahydrofuran (2.6 mL, 2.6 mmol). After stirring at 0-5° C. for 15 min, this mixture was slowly added to a solution (in a flame dried vial) of EE.1 (350 mg, 2.0 mmol) in tetrahydrofuran (4.0 mL) at −60° C. over 10 min and the resulted mixture was further stirred at −60° C. for 8 min. The mixture was then quenched with aqueous ammonium chloride. The aqueous layer was extracted with EtOAc. The organic layer was concentrated to afford EE.2 as a white solid (250 mg, 74%). m/z 170 [M+1]$^+$.

Synthesis of Compound EE. Compound EE was synthesized as described in Scheme U. m/z 284 [M+1]$^+$.

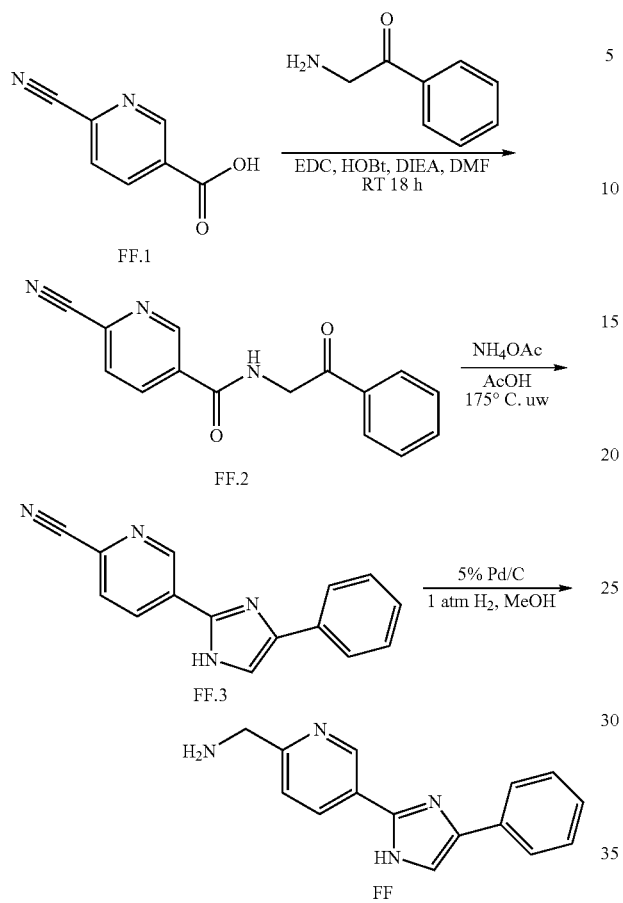

Synthesis of Compound FF.2. In a 50 mL round-bottom flask, FF.1 (0.949 g, 0.641 mmole), 2-amino-1-phenyletha-none (1.10 g, 0.00641 mole), and 1-hydroxybenzotriazole (0.866 g, 0.641 mmole) were dissolved in DMF (20 mL). The mixture was treated with N-(3-dimethylaminopropyl)-N′-ethylcarbodiimide hydrochloride (1.474 g, 0.7691 mmole) and N,N-diisopropylethylamine (1.12 mL, 0.641 mmole). The yellow reaction mixture was allowed to stir at RT for 18 hr and then diluted with 200 mL of EtOAc. The organic layer was washed 2×50 mL of water. FF.2 precipitated as a white solid which was collected by filtration. The filtrate was washed with 50 mL brine, dried over $Na_2SO_4$, and concentrated. The combined solids were titurated with $Et_2O$ to yield 1.55 g (0.0064 mol, 91%) of FF.2.

Synthesis of Compound FF.3. In a 20 mL microwave reaction vial FF.2 (1.5 g, 0.0565 mole) and ammonium acetate (0.262 g, 0.023 mole) were suspended in acetic acid (10.0 mL). The mixture was then stirred at RT for 1 hr before then heated at 175° C. for 15 min under microwave irradiation. The acetic acid was then removed in vacuo and the resulting residue was neutralized to pH 7 with solid and 100 ml of sat $NaHCO_3$ (aq) and solid in the presence of 200 mL of EtOAc. The aqueous layer was washed 2×75 mL EtOAc. The combined organic layers were dried over $Na_2SO_4$, filtered, and concentrated to yield an orange tar. Purification by flash column chromatography ($SiO_2$, 50% EtOAc/Hexanes gradiant to 100% EtOAc) yielded 250 mg (18%) of FF.3.

Synthesis of Compound FF. In a 5 mL microwave reaction vial FF.3 (0.250 g, 1.02 mmole) and 5% Pd/C (0.2 g) were taken up in methanol (4 mL). The reaction was stirred under a $H_2$ balloon at RT for 24 hr. The mixture was filtered through celite and concentration to yield 250 mg of FF.

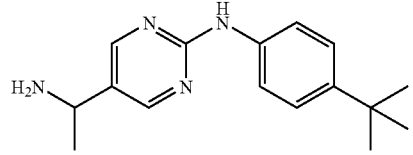

Synthesis of Compound GG. The synthesis of GG was accomplished following Scheme U and Scheme X substituting 1-(2-chloropyrimidin-5-yl)ethanone (Bioorg. Med. Chem. 2005, 13, 3707) for 1-(2-chlorothiazol-5-yl)ethanone (U.1) and 4-t-butylaniline for 4-trifluoromethylaniline.

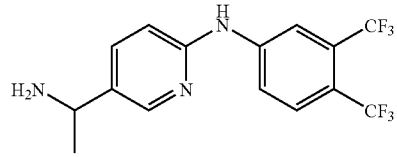

Synthesis of Compound HH. The synthesis of HH was accomplished following Scheme X substituting 4-chloro-3-trifluoromethylaniline for 4-trifluoromethylaniline. MS m/z=316 [M+1]⁺.

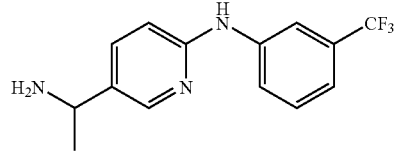

Synthesis of Compound II. The synthesis of II was accomplished following Scheme X substituting 3-trifluoromethylaniline for 4-trifluoromethylaniline.

Synthesis of Compounds JJ-TT. Compounds JJ-TT could be synthesized following Scheme D using the appropriately substituted aniline for compound A.6.

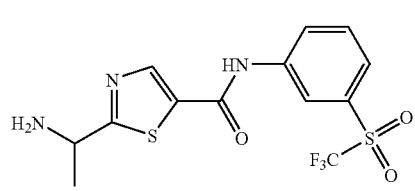

KK
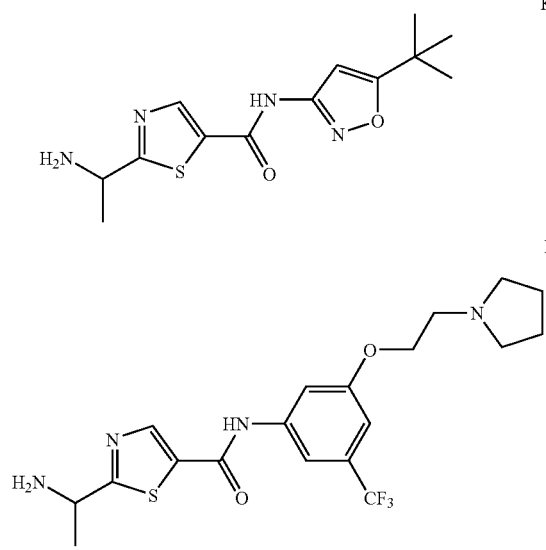
LL
MM
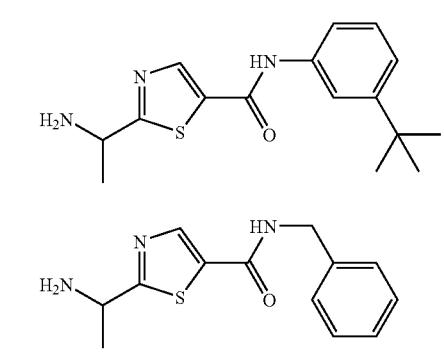
NN
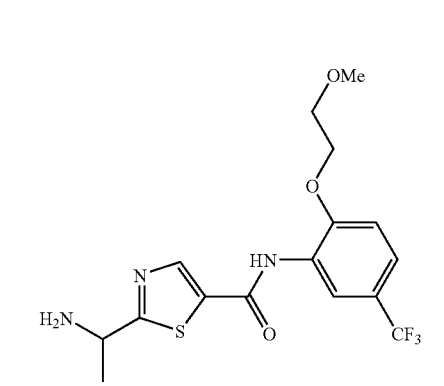
OO
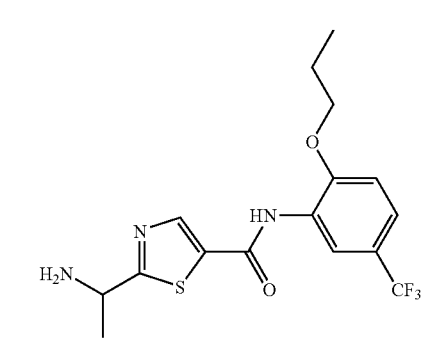
PP
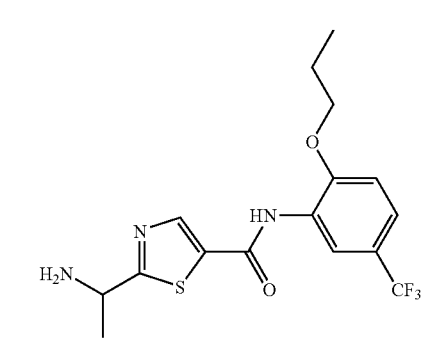
QQ
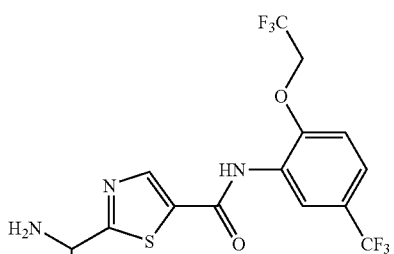
RR
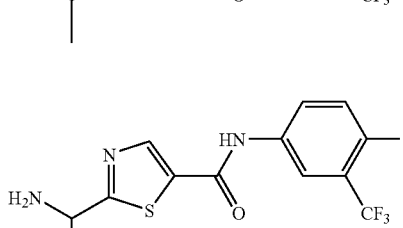
SS
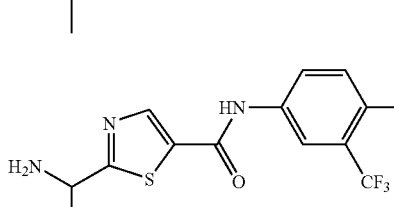
TT
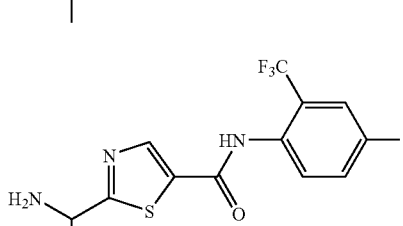
Scheme UUa. Compound UUa can be synthesized following Scheme M substituting 3-trifluoromethylaniline for 4-methyl-3-trifluoromethyl-phenylamine.
UUa
Scheme VV.
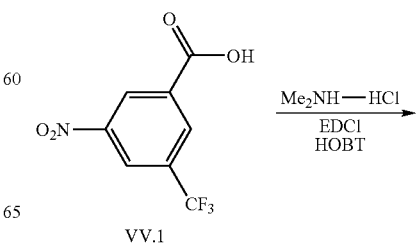
VV.1

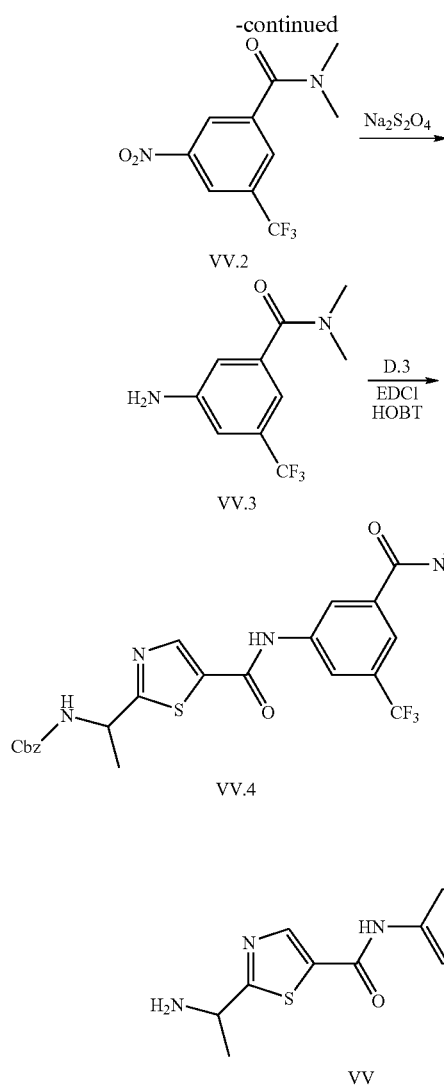

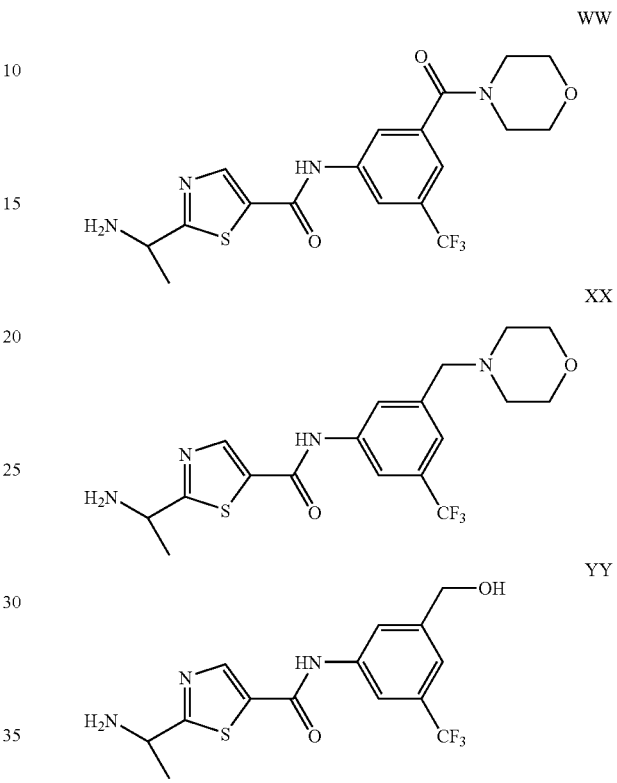

Synthesis of VV. Compound VV was synthesized as described in Scheme D for compound D. $^1$H-NMR (CD$_3$OD, 200 MHz): δ 8.58 (s, 1H), 8.21 (s, 1H), 8.0 (s, 1H), 7.56 (s, 1H), 5.40-5.38 (m, 1H), 3.23 (s, 3H), 3.13 (s, 3H), 1.80 (d, J=7.0 Hz, 2H); m/z: 387 [M+1]$^+$.

Compounds WW-YY. Using the appropriate amine, the following amines could be synthesized as exemplified in Scheme VV.

Synthesis of VV.2. A solution of VV.1 (2 g, 0.0085 mol), dimethylamine hydrochloride (1 g, 0.0127 mol), EDCI (4.0 g, 0.0212 mol), HOBT (574 mg, 0.0042 mol) and DIPEA (1.4 g, 0.0110 mol) in DMF (20 ml) was stirred at 80° C. for 16 hr. The reaction mixture was diluted with water (50 ml) and extracted with ethyl acetate (3×100 ml). The combined organic layers was washed with water (3×50 ml), dried over Na$_2$SO$_4$ and concentrated under reduced pressure. The resulting crude material was purified by column chromatography to give VV.2 as a brown liquid (1.4 g, 63%): $^1$H-NMR (CDCl$_3$, 200 MHz): d 8.61 (s, 1H), 8.58 (s, 1H); 8.11 (s, 1H), 3.23 (s, 3H), 3.13 (s, 3H); m/z: 263 [M+1]$^+$.

Synthesis of VV.3 A solution of VV.2 (1.3 g, 0.0049 mol), sodium dithionite (3.4 g, 0.0198 mol), sodium carbonate (1 g, 0.0099 mol) in MeOH (13 ml) and water (13 ml) was stirred at RT for 2 hr. The volatiles were removed under reduced pressure and extracted with ethyl acetate (3×100 ml). The combined organic layers was dried over Na$_2$SO$_4$ and concentrated under reduced pressure to obtain VV.3 as a light yellow solid (600 mg, 54.5%). $^1$H-NMR (CDCl$_3$, 200 MHz) δ 7.0 (s, 1H), 6.90 (s, 1H), 6.80 (s, 1H), 3.23 (s, 3H), 3.13 (s, 3H); m/z: 233 [M+1]$^+$.

Synthesis of VV.4 Compound VV.4 was synthesized as described in Scheme D for compound D.4. m/z: 521 [M+1]$^+$.

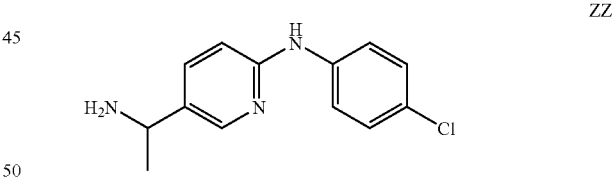

Synthesis of Compound ZZ. The synthesis of compound ZZ was accomplished following Scheme X substituting 4-chloroaniline for 4-trifluoromethylaniline. MS m/z 248.1 [M+1]$^+$.

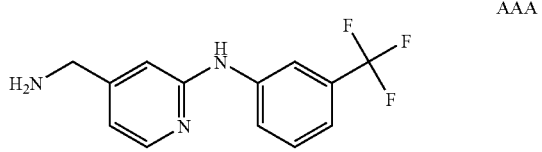

Sythesis of Compound AAA. The synthesis of compound AAA was accomplished following Scheme DD substituting 2-chloroisonicotinamide for compound DD.1 and 3-trifluoromethylaniline for 4-t-butylaniline. MS m/z 268 [M+1]+.

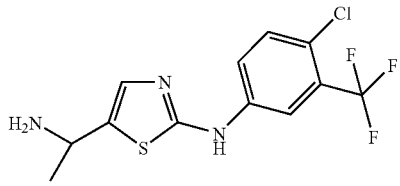

Sythesis of Compound BBB. The synthesis of compound BBB was accomplished following Scheme U substituting 4-chloro-3-(trifluoromethyl)aniline for 4-trifluoromethylaniline. MS m/z 322 [M+1]+.

General Coupling of the Fused Pyrimidine ("Left-Hand Side") and -L$^1$-Cy$^1$-L$^2$-Cy$^2$ Moieties Scheme X.

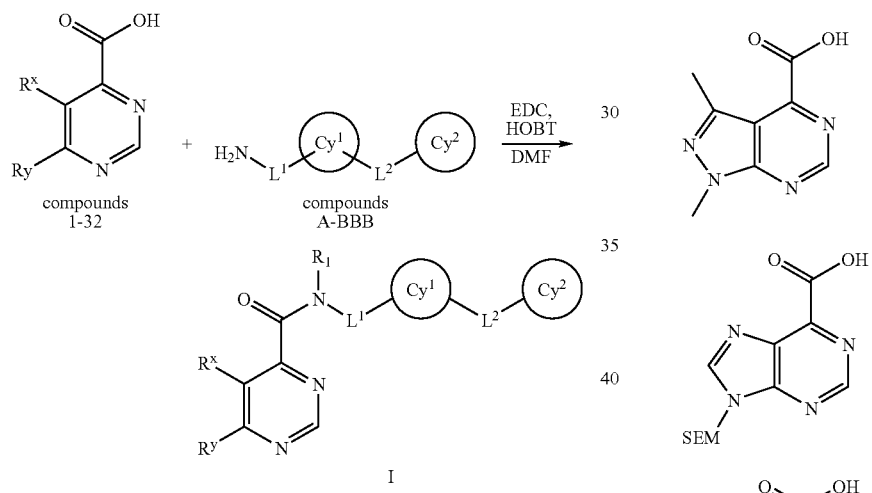

Compounds 1-32

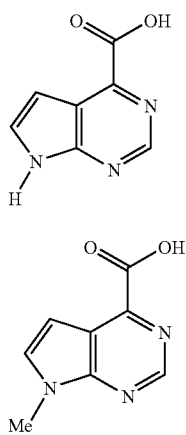

1

2

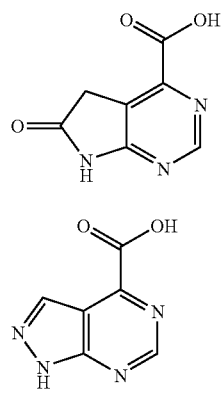 3

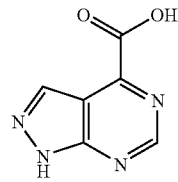 4

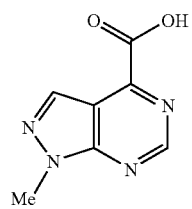 5

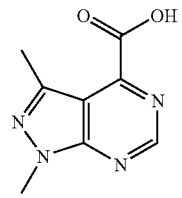 6

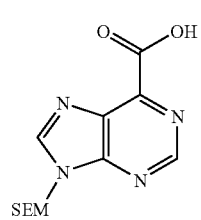 7

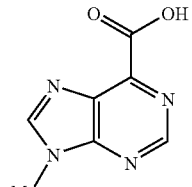 8

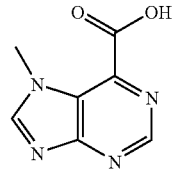 9

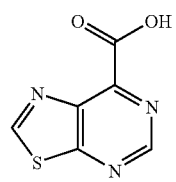 10

107
-continued
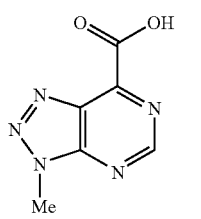
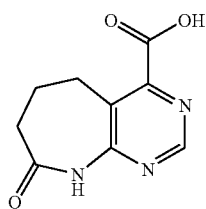
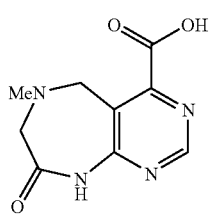
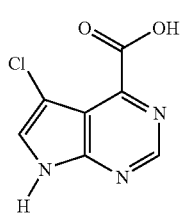
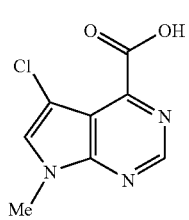
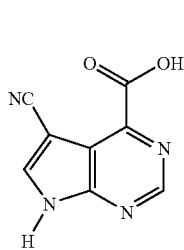
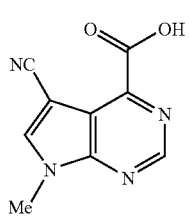
108
-continued
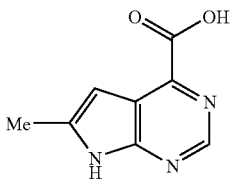
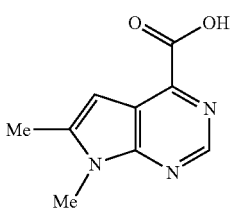
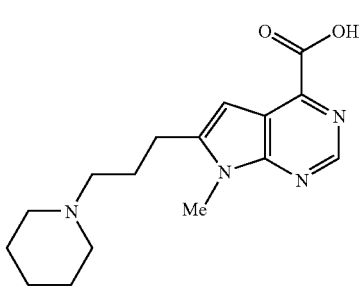
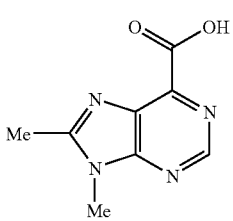
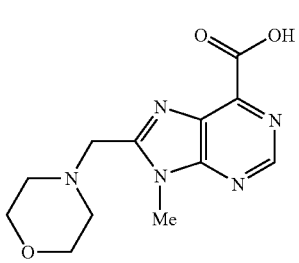
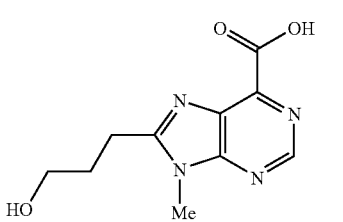
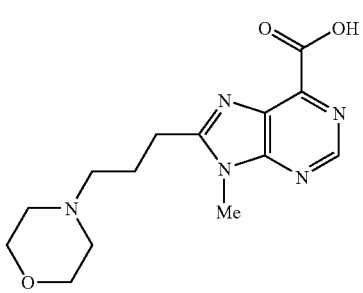

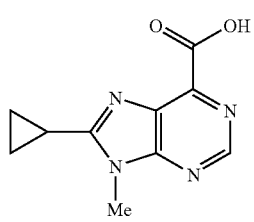
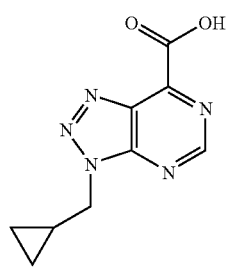
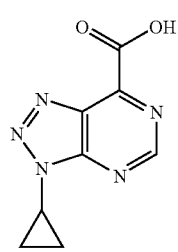
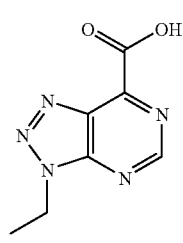
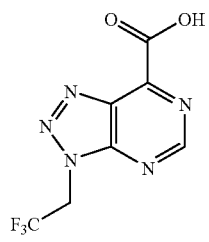
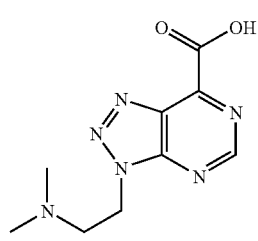
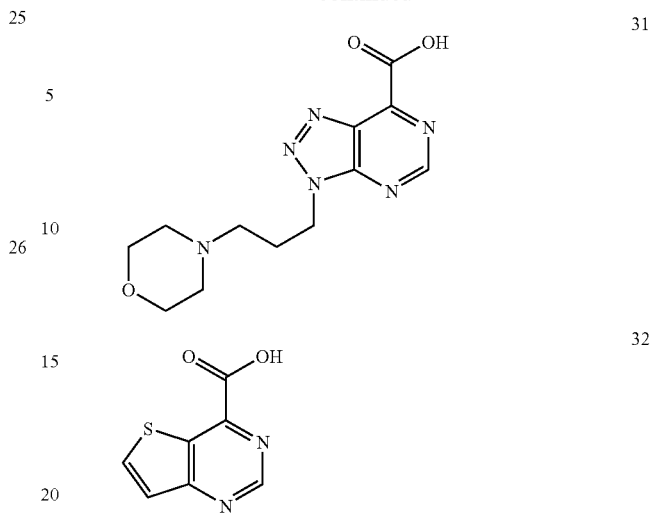
Compounds A-BBB
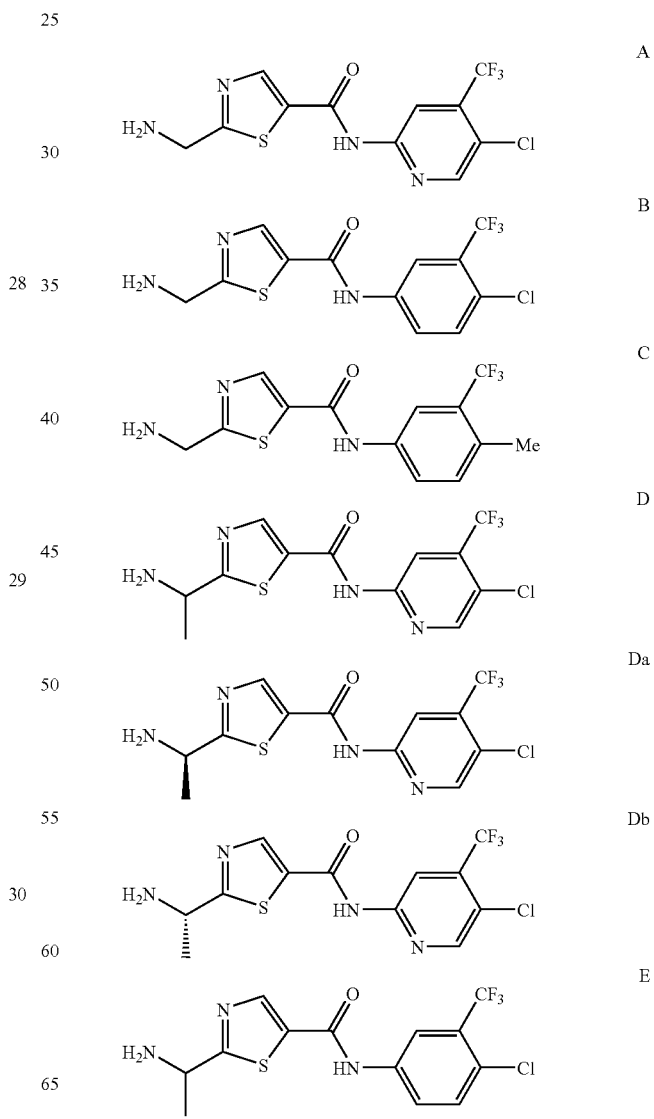

| | | | | |
|---|---|---|---|---|
| Ea | 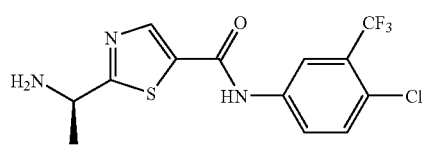 | 5 | 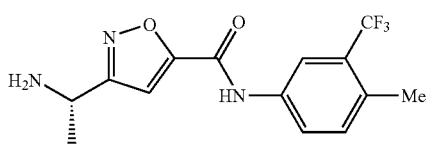 | Mb |
| Eb | 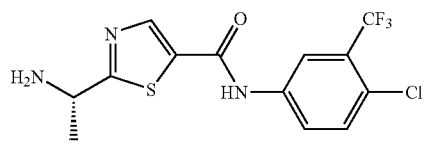 | 10 | 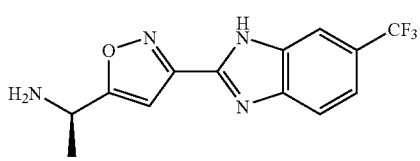 | Na |
| F | 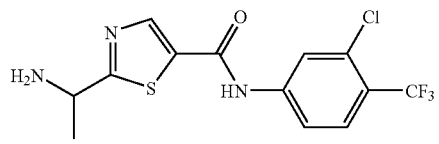 | 15 | 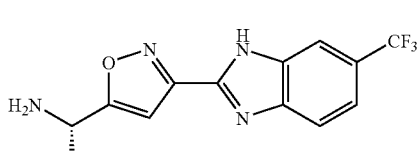 | Nb |
| G | 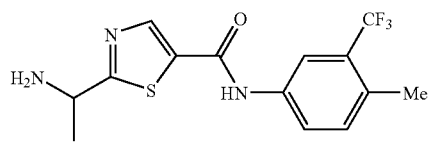 | 20 | | |
| | | 25 | 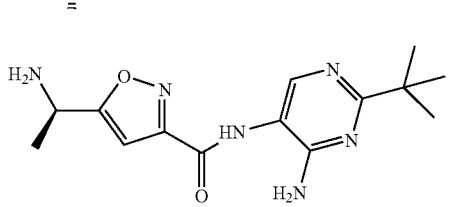 | O |
| H | 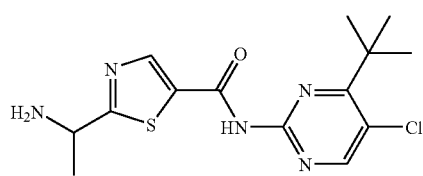 | 30 | 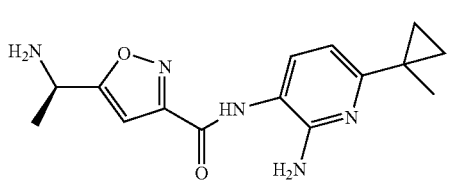 | P |
| I | 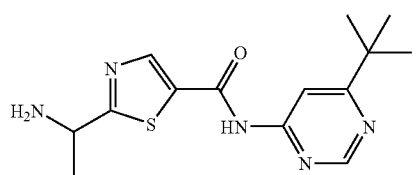 | 35 | | |
| | | 40 | 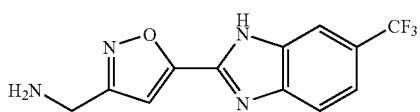 | Q |
| J | 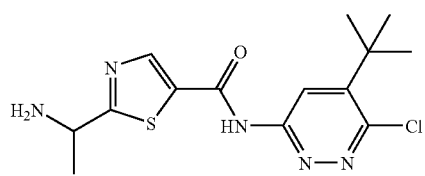 | 45 | 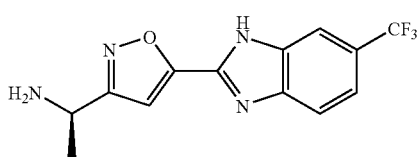 | Ra |
| K | 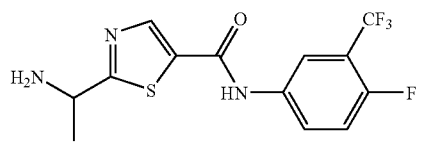 | 50 | 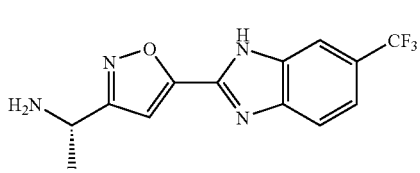 | Rb |
| L | 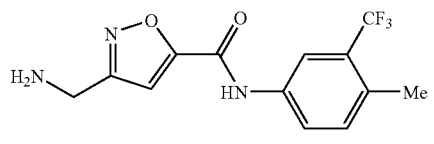 | 55 | 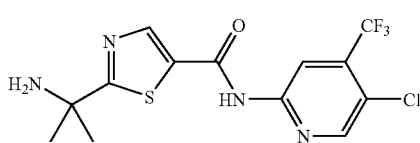 | S |
| Ma | 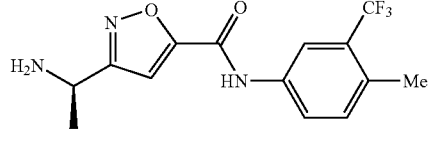 | 60 | 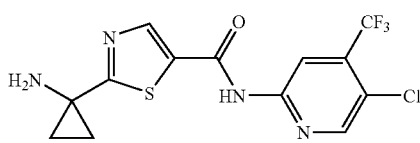 | T |
| | | 65 | | |

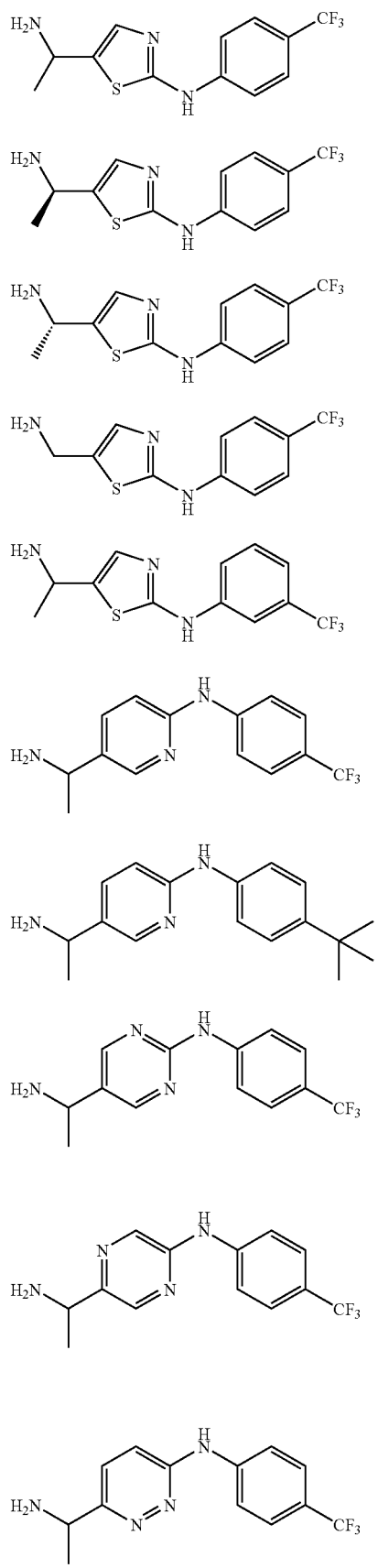
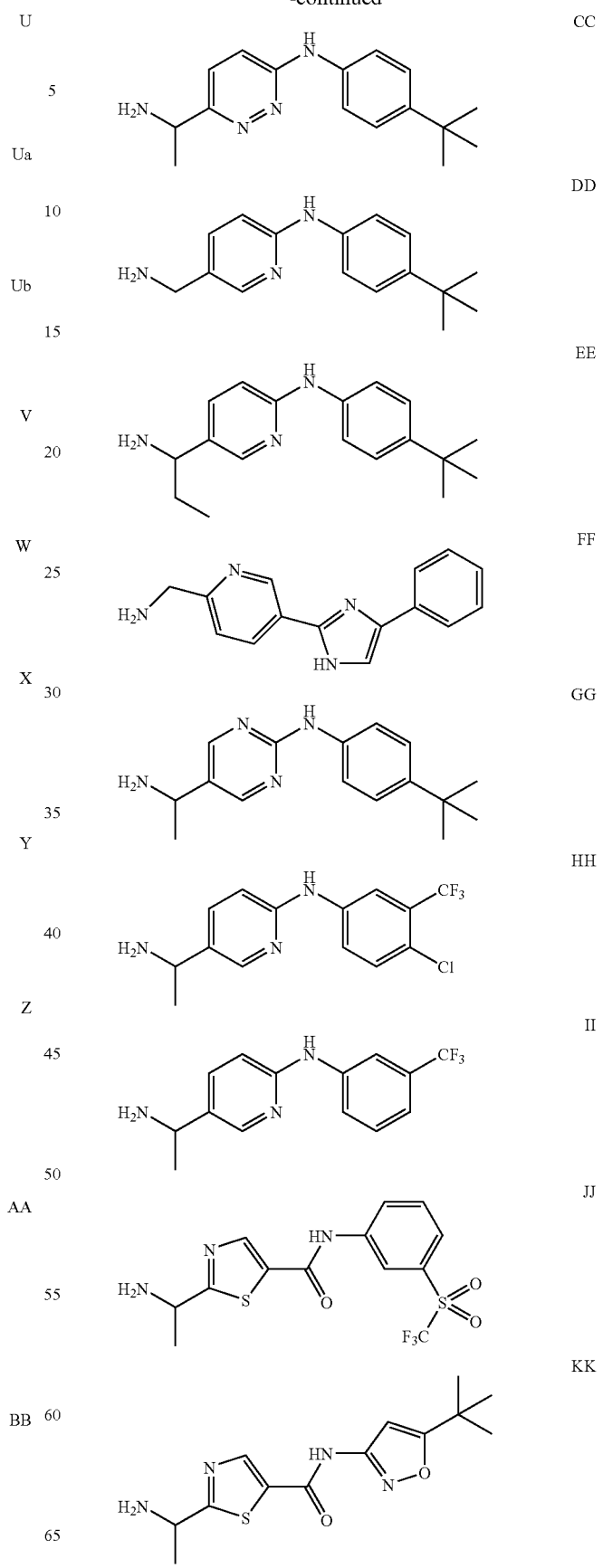

LL
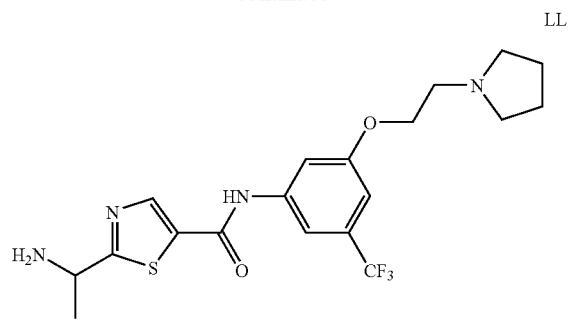
RR
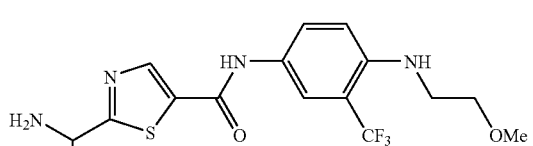
MM
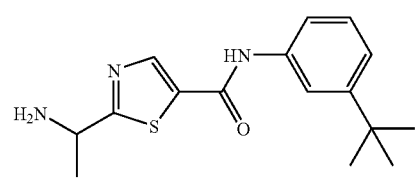
SS
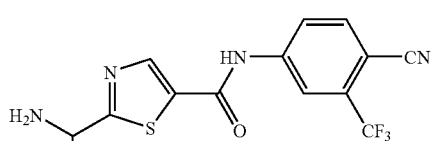
NN
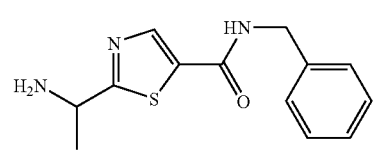
TT
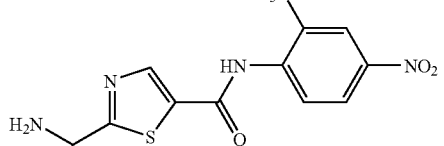
OO
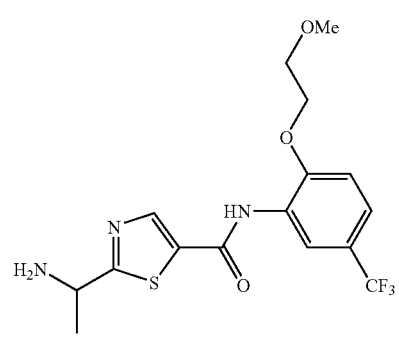
UUa
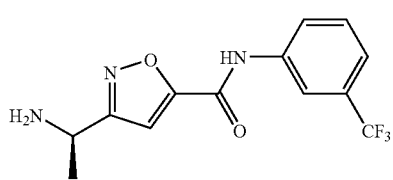
VV
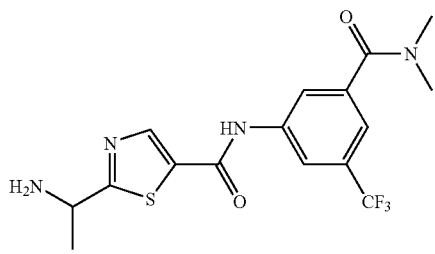
PP
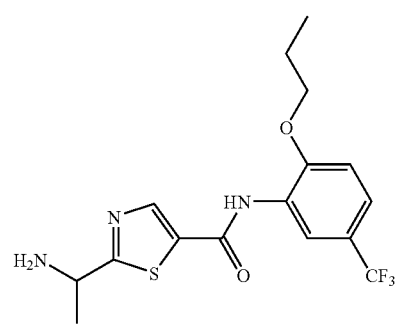
WW
QQ
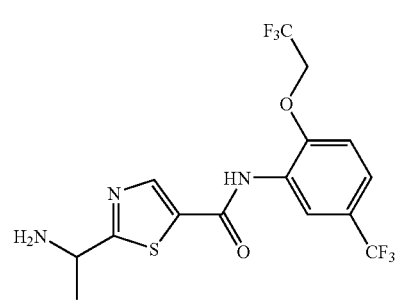
XX
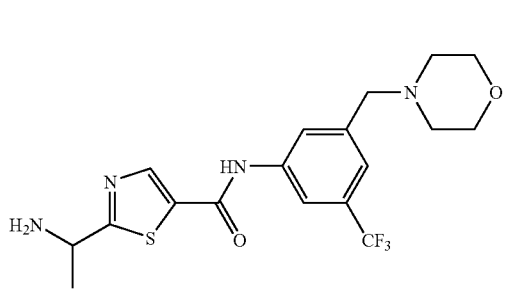

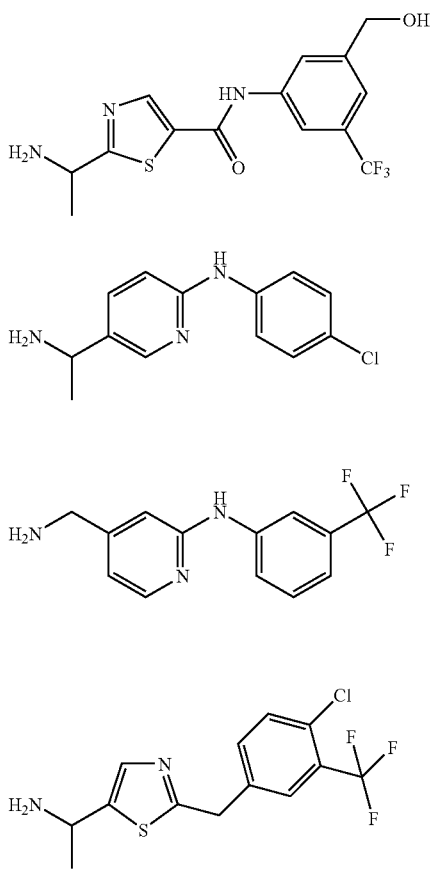
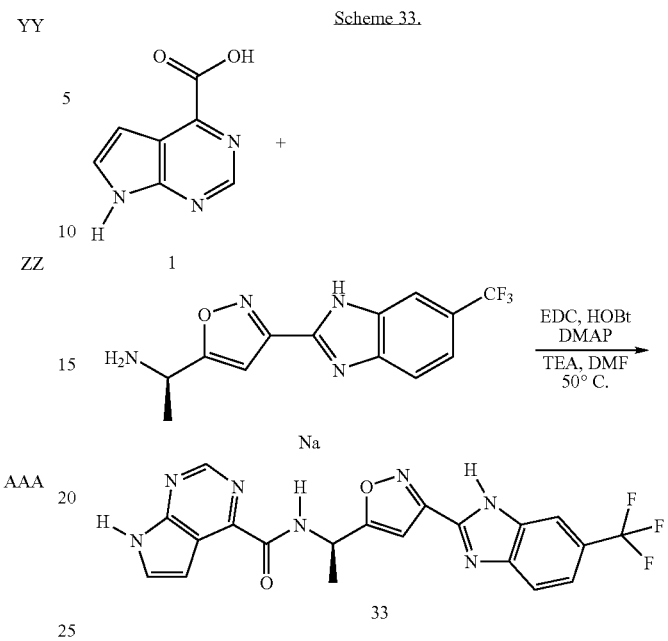

Synthesis of Compound 33. To a mixture of compound 1 (60 mg, 0.4 mmol), EDC (100 mg, 0.55 mmol), HOBt (74 mg, 0.55 mmol), DMAP (2 mg, 0.02 mmol) and triethylamine (200 μL, 1 mmol) in DMF was added compound Na (120 mg, 0.40 mmol). The reaction mixture was stirred at 50° C. for 3 hr. The reaction mixture was diluted with dichloromethane and washed with sat. NaHCO$_3$ and then 1N HCl. The solvent was removed and the residue was purified by HPLC to afford compound 33 (22 mg) as a light yellow solid. $^1$H NMR (400.13 MHz, MeOD-d$_4$) δ 8.68 (s, 1H), 7.80 (br. s, 1H), 7.63 (d, J=8.6 Hz, 1H), 7.46 (br. d, J=8.6 Hz, 1H), 7.45 (d, J=3.6 Hz, 1H), 6.97 (d, J=3.6 Hz, 1H), 6.85 (d, J=0.9 Hz, 1H), 5.46 (q, J=7.4, 1H), 1.63 (d, J=7.1, 3H). MS m/z 442 [M+1]$^+$.

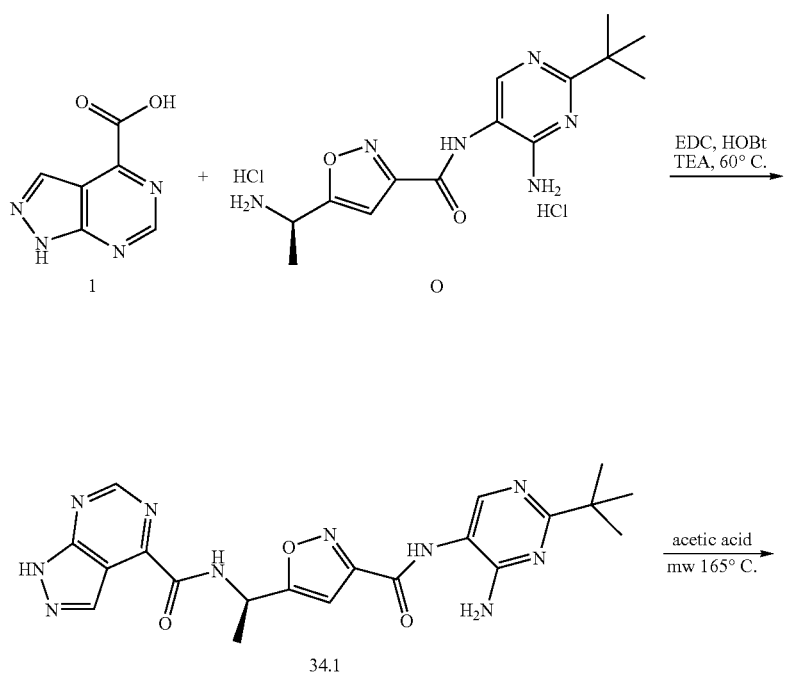

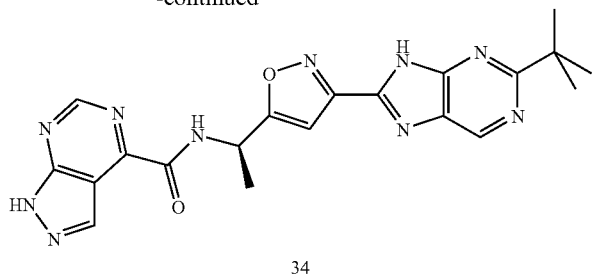

34

Synthesis of compound 34.1. A mixture of compound 1 (60 mg, 0.37 mmol), EDC (106 mg, 0.55 mmol), HOBt (74 mg, 0.55 mmol), DMF (1 mL, 0.01 mol), and triethylamine (200 μL, 1 mmol) in DMF was heated to 60° C. After 10 min, compound O (120 mg, 0.40 mmol) was added and the reaction mixture was stirred at 50° C. After 2 hr, the reaction mixture was diluted with dichloromethane, washed sat. NaHCO₃ and brine, dried (Na₂SO₄) and concentrated to afford compound 34.1. MS m/z 450 [M+1]⁺.

Synthesis of compound 34. The compound 34 was dissolved in acetic acid (2.5 mL, 0.044 mol) and heated for 30 min at 165° C. in the microwave. The solvent was removed in vacuo. The crude solid was pre-absorbed onto SiO₂ and eluted (dichloromethane to EtOAc) through a small plug of silica to afford compound 34 (58 mg) as a yellow solid. ¹HNMR (DMSO-d₆, 400 MHz) δ 14.27 (br. s, 1H), 12.43 (s, 1H), 9.65 (d, J=8.5 Hz), 9.15 (br. s, 1H), 8.90 (s, 1H), 7.77 (dd, J=3.3, 2.4 Hz, 1H), 7.06 (s, 1H), 7.05 (dd, J=3.6, 1.8 Hz, 1H), 5.54 (quint., J=7.6 Hz, 1H), 1.71 (d, J=6.9 Hz, 1H), 1.42 (s, 1H). MS m/z 432 [M+1]⁺.

Scheme 35.

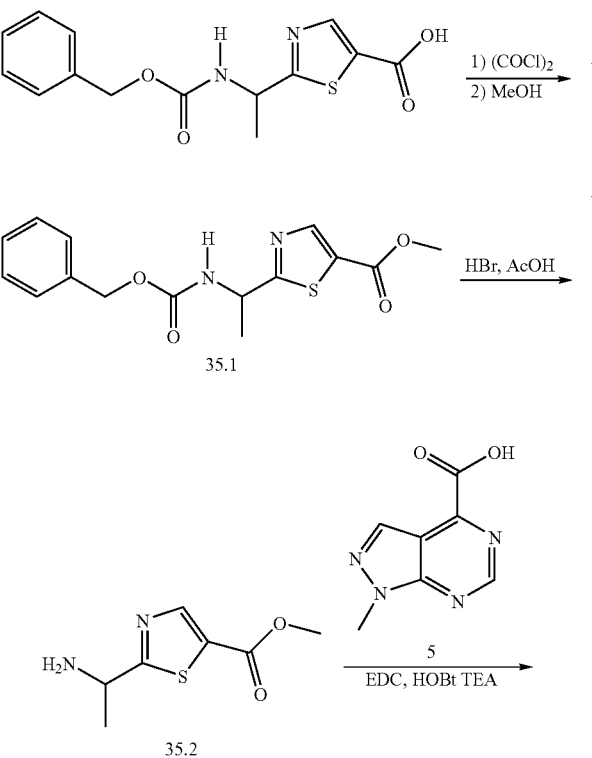

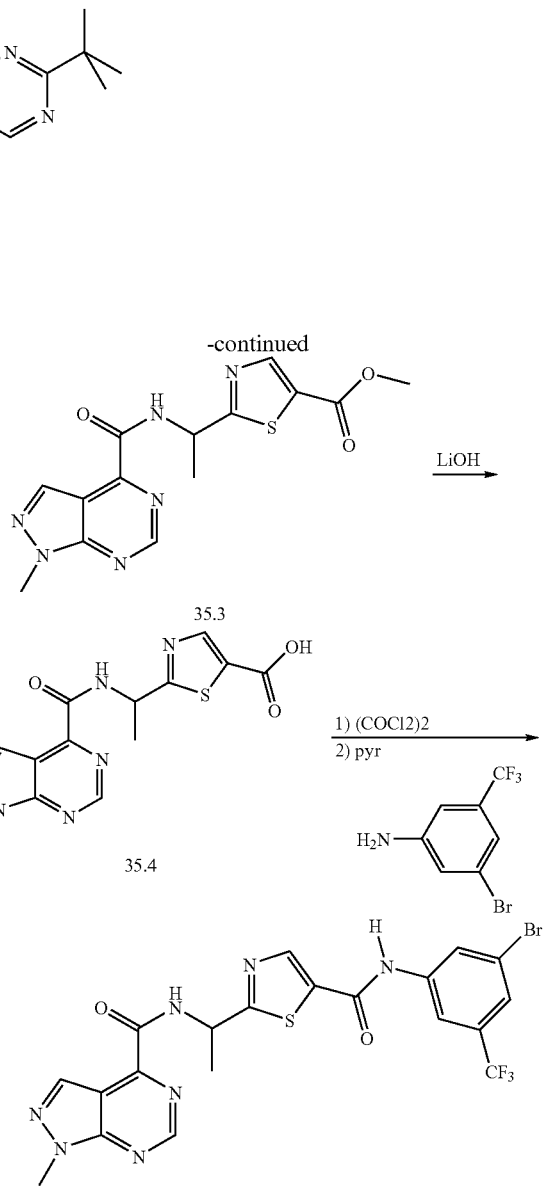

Synthesis of Compound 35.1. A solution of compound D.3 (10 g, 33 mmol), Oxalyl chloride (5.52 mL, 65.3 mmol) and DMF (200 μL) in acetonitrile (100 mL) was stirred at RT. After 1 hr MeOH (100 mL) was added and the reaction. After 1.5 hr, the solvent was removed in vacuo. The residue was taken-up in DCM, which was then washed (NaHCO₃ sat.), dried (Na₂SO₄), and evaporated to afford compound 35.1 (10.4 g, 99%) as a yellow oil. ¹HNMR (CDCl₃, 200 MHz) δ: 8.28 (s, 1H), 7.38 (s, 5H), 5.4-5.5 (m, 1H), 5.15 (s, 2H), 3.9 (s, 3H), 1.7-1.6 (d, 3H). MS m/z 321 [M+1]⁺.

Synthesis of Compound 35.2. A mixture of compound 35.1 (8.89 g, 27.7 mmol) and 4 M of Hydrogen bromide in acetic acid (100 mL) was stirred at 40° C. for 4 hr. The orange solution was dried under reduced pressure. The mixture was dissolved in 130 mL water and washed three times with 55 mL portions of ethyl acetate. The aqueous phase was cooled to 0° C. in an ice-water bath and basified with 7.5 mL of 50% NaOH, which was then extracted with chloroform 3 times (approx. 80 mL each). The organic layer was dried (Na$_2$SO$_4$) and evaporated to afford compound 35.2 (2.75 g, 53%) as an off-white solid. $^1$H NMR (400 MHz, DMSO-d$_6$) δ=8.30 (s, 1H), 4.21 (q, J=6.7 Hz, 1H), 3.82 (s, 3H), 1.38 (d, J=6.8 Hz, 3H). MS m/z 187 [M+1]$^+$.

Synthesis of Compound 35.3. A mixture of compound 5 (3.2 g, 18 mmol), HOBt (1 g, 8 mmol), compound 35.2 (3.36 g, 18 mmol) in acetonitrile (49 mL) was stirred. N-(3-dimethylaminopropyl)-N'-ethylcarbodiimide hydrochloride (4.9 g, 26 mmol) was then added to the reaction. After 5 hr, the reaction was diluted (DCM 80 mL), washed (NaHCO$_3$ then 0.5 N HCl), dried (Na$_2$SO$_4$), and evaporated to afford compound 35.3 (5.69 g) as a off-white solid. $^1$H NMR (400 MHz, DMSO-d$_6$) δ=10.01 (d, J=8.1 Hz, 1H), 9.20 (s, 1H), 8.62 (s, 1H), 8.38 (s, 1H), 5.58-5.48 (m, 1H), 4.12 (s, 3H), 3.81 (s, 3H), 1.72 (d, J=7.1 Hz, 3H). MS m/z 347 [M+1]$^+$.

Synthesis of Compound 35.4. A mixture of compound 35.3 (1.4 g, 4.1 mmol), THF (41 mL), and 1 M of LiOH (4 mL) and MeOH (2 mL) was stirred for 16 hr. Another half equivalent of LiOH (2 ml) was added and the reaction was stirred an additional 16 hr. The solvent was removed in vacuo, and the residue was taken up in water. The solution acidified (1N HCl) and extracted (EtOAc). The organic layer was removed in vacuo to afford (1.43 g) as a pale yellow solid. $^1$H NMR (400 MHz, CDCl3-d) δ=9.05 (s, 1H), 8.79 (d, J=8.1 Hz, 1H), 8.75 (s, 1H), 8.41 (s, 1H), 5.72-5.62 (m, 1H), 4.19 (s, 3H), 1.84 (d, J=7.1 Hz, 3H). MS m/z 333 [M+1]$^+$.

Synthesis of Compound 35. A solution of compound 35 (100 mg, 0.3 mmol), (COCl)$_2$ (51 μL, 0.6 mmol), and DMF (a drop) in MeCN (0.9 mL) was stirred at RT. After 1 hr, the solvent was removed in vacuo. The residue was azeotroped with MeCN. The solution of the residue in MeCN was added to a solution of 3-bromo-5-(trifluoromethyl)aniline (43 μL, 0.3 mmol) in pyridine (243 μL). After 1 hr, the solvent was removed in vacuo. The residue was then dissolved (DCM), and then the organic layer was washed (NaHCO$_3$ then 30% HCl), dried (Na2SO4) and evaporated to afford compound 35 (89 mg, 54%) as a yellow oil. $^1$H NMR (400 MHz, CDCl$_3$) =9.04 (s, 1H), 8.77 (d, J=8.1 Hz, 1H), 8.70 (s, 1H), 8.40 (s, 1H), 8.31 (br. s., 1H), 8.08 (s, 1H), 7.84 (s, 1H), 7.53 (s, 1H), 5.66 (quin, J=7.3 Hz, 1H), 4.19 (s, 3H), 1.86 (d, J=6.8 Hz, 3H). MS m/z 554 [M+1]$^+$.

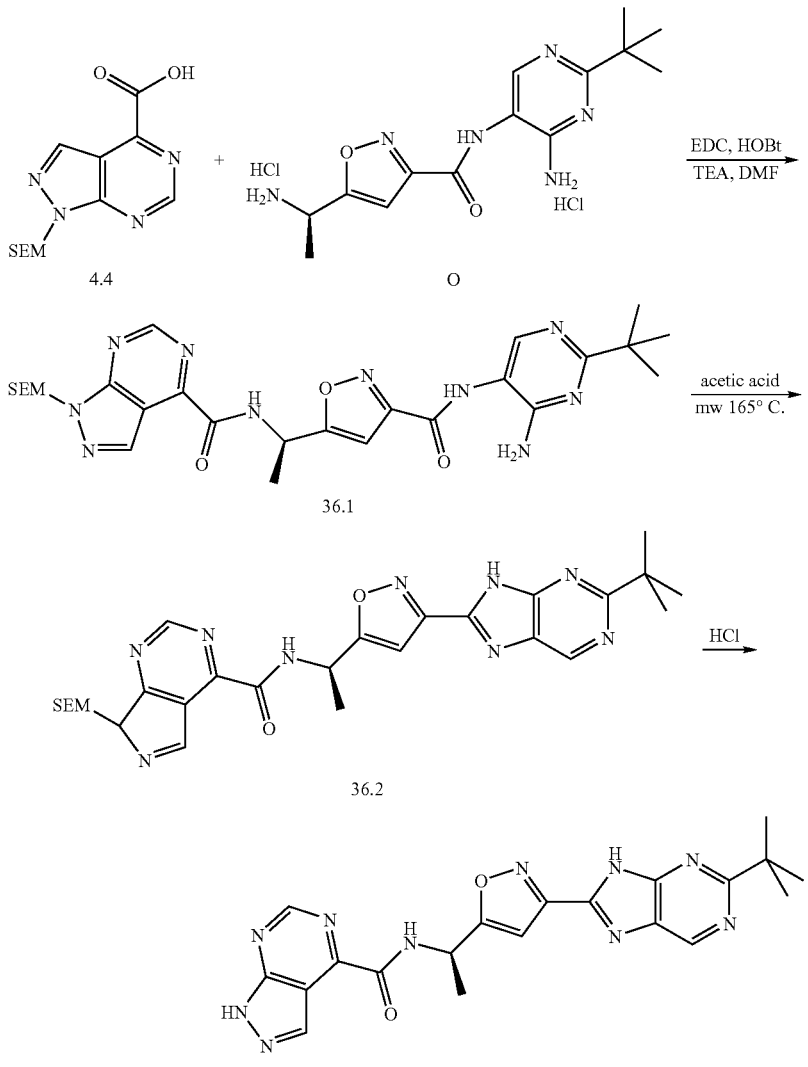

Scheme 36.

36

Synthesis of Compound 36.1 A mixture of compound 4.4 (300 mg, 1 mmol), N-(3-dimethylaminopropyl)-N'-ethylcarbodiimide hydrochloride (280 mg, 1.4 mmol), 1-hydroxybenzotriazole (40 mg, 0.3 mmol), compound O (293 mg, 0.961 mmol), and N,N-diisopropylethylamine (335 μL, 1.92 mmol) in acetonitrile (2 mL) was stirred at RT. After 1 hr, the reaction mixture was diluted with dichloromethane, washed with sat. NaHCO₃, dried (Na₂SO₄), and concentrated. The residue was taken up in acetic acid (5 mL, 0.09 mol) and the solution was heated in a microwave for 25 min at 160° C. The solvent was removed to afford crude compound 36.1, which was used without additional purification.

Synthesis of compound 36. A solution of crude compound 36.1 (0.96 mmol) and 4M of hydrogen chloride in 1,4-dioxane (3 mL) was heated at 70° C. After 1 hr, the solvent was removed and the residue was purified by HPLC to afford compound 36 (34 mg) as a off-white solid. ¹H NMR (DMSO-d₆, 400 MHz) 9.89 (d, J=8.5 Hz, 1H), 9.16 (s, 1H), 9.15 (s, 1H), 8.64 (s, 1H), 7.09 (s, 1H), 5.56 (m, 1H), 1.72 (d, J=7.2 Hz, 3H), 1.42 (s, 19H). MS m/z 433 [M+1]⁺.

Synthesis of Compound 37. A solution of compound 4Da (20 mg, 0.04 mmol) and N-chlorosuccinimide (40 mg, 0.3 mmol) in acetonitrile (500 μL) was heated at 140° C. in the microwave for 60 min. The reaction mixture was diluted with MeOH and purified by HPLC to afford the compound 37 (3.1 mg). ¹H NMR (400.13 MHz, CDCl₃) δ 10.79 (brs, 1H), 9.10 (s, 1H), 8.69 (s, 1H), 8.68 (d, J=8.0 Hz, 1H), 8.61 (brs, 1H), 8.46 (s, 1H), 8.35 (s, 1H), 5.72 (dq, J=8.0, 7.0 Hz, 1H), 1.87 (d, J=7.0 Hz, 3H). MS m/z 531 [M+1]⁺.

Scheme 38.

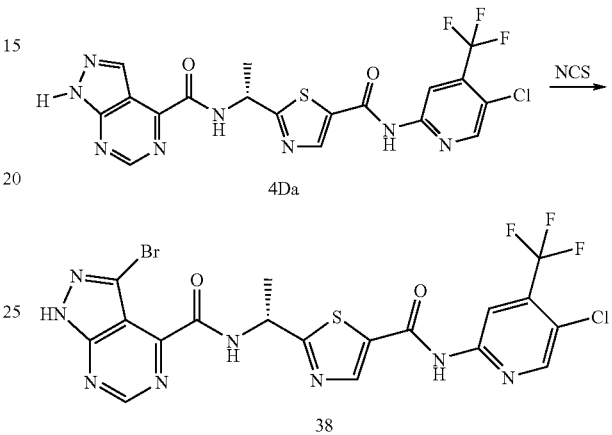

Scheme 37.

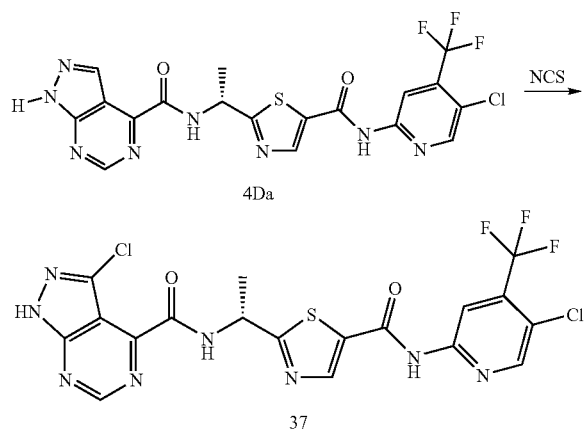

Synthesis of compound 38. A mixture of compound 4Da (20 mg, 0.04 mmol) and N-bromosuccinimide (20 mg, 0.1 mmol) in acetonitrile (1 mL, 0.02 mol) was heated at 100° C. for 10 min in the microwave. The reaction mixture was purified by HPLC to afford the compound 38 (8.4 mg) as a white solid. ¹H NMR (400.13 MHz, DMSO-d₆) 14.77 (s, 1H), 11.78 (s, 1H), 9.83 (d, J=8.0 Hz, 1H), 9.15 (s, 1H), 8.79 (s, 1H), 8.78 (s, 1H), 8.58 (s, 1H), 5.52 (dq, J=8.0, 7.0 Hz, 1H), 1.69 (d, J=7.0 Hz, 1H). MS m/z 575 [M+1]⁺.

Scheme 39.

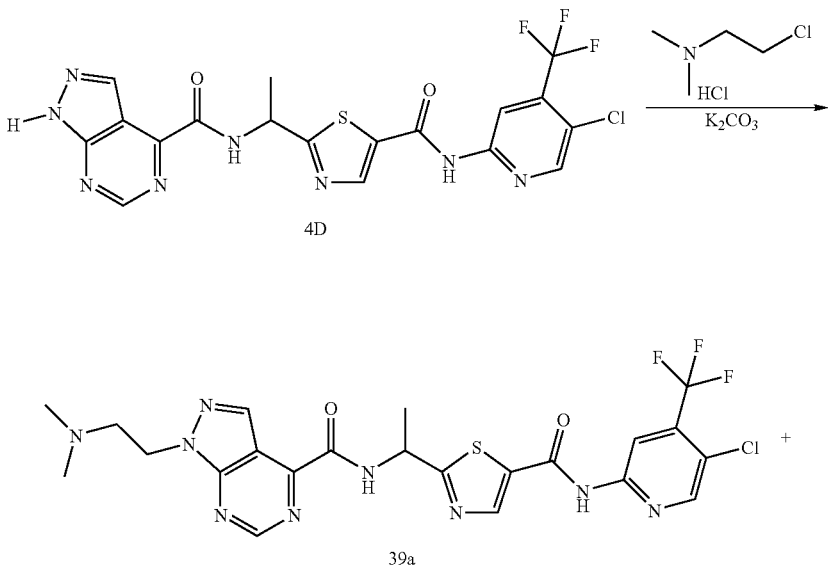

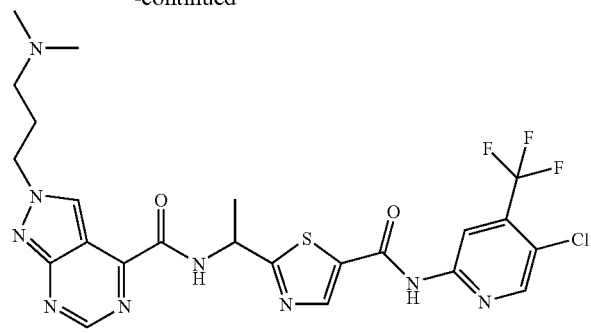

39b

Synthesis of Compound 39a and 39b. A mixture of 2-chloro-N,N-dimethylethanamine hydrochloride (210 mg, 1.4 mol), compound 4D (600 mg, 1.0 mol), and $K_2CO_3$ (834 mg, 6.04 mmol) in DMF (9 mL) was heated (60° C.) overnight. The reaction was filtered and purified by HPLC to afford the compound 39a and 39b. Compound 39a $^1$H NMR (400.13 MHz, DMSO-$d_6$) 11.77 (s, 1H), 10.55 (brs, 1H), 10.06 (d, J=7.7 Hz, 1H), 9.26 (s, 1H), 8.77 (s, 2H), 8.72 (s, 1H), 8.54 (s, 1H), 5.54 (dq, J=8.4, 7.4 Hz, 1H), 4.96 (t, J=6.4, 2H), 3.67 (m, 2H), 3.57 (s, 6H), 1.73 (d, J=7.4 Hz, 3H). MS m/z 568 [M+1]$^+$. Compound 39b $^1$H NMR (400 MHz, DMSO-$d_6$) d=11.77 (s, 1H), 10.45 (br. s., 1H), 10.01 (d, J=8.1 Hz, 1H), 9.23 (s, 1H), 9.21 (s, 1H), 8.77 (s, 1H), 8.53 (s, 1H), 5.52 (dq, J=7.0, 8.0 Hz, 1H), 5.07 (t, J=6.1 Hz, 2H), 3.78 (q, J=6.0 Hz, 2H), 2.82 (d, J=4.5 Hz, 6H), 1.72 (d, J=6.9 Hz, 3H). MS m/z 568 [M+1]$^+$.

Scheme 40.

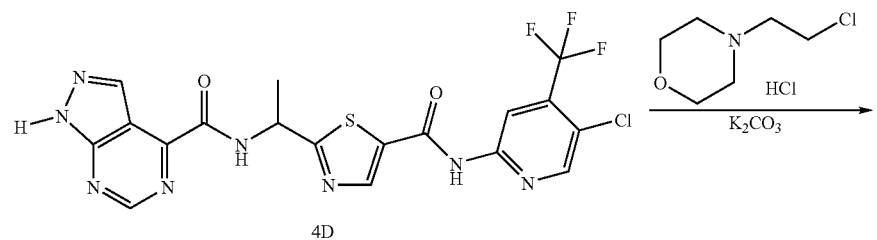

4D

40a

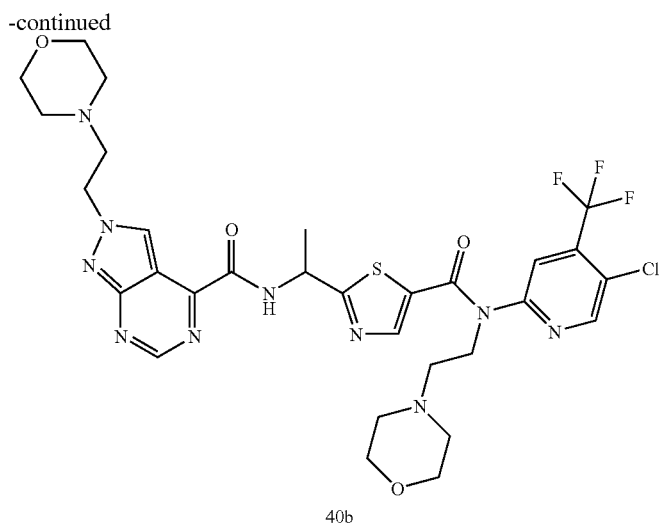

40b

Synthesis of Compound 40a and 40b. A mixture of 4-(2-chloroethyl)morpholin-4-ium chloride (112 mg, 0.604 mmol), compound 4D (100 mg, 0.20 mmol), and $K_2CO_3$ (139 mg, 1.01 mmol) in DMF (2 mL) was heated (60° C.) overnight. The reaction mixture was filtered and purified by HPLC to afford compound 40a (58 mg) and compound 40b (22 mg). Compound 40a $^1$H NMR: (400.13 MHz, $CDCl_3$) δ 9.06 (s, 1H), 8.88 (s, 1H), 8.81 (d, J=8.1 Hz, 1H), 8.79 (s, 1H), 8.36 (s, 1H), 7.93 (s, 1H), 5.65 (dq, J=8.1, 7.0 Hz, 1H), 4.84 (t, J=6.2 Hz, 2H), 4.56 (t, J=7.1 Hz, 2H), 3.79 (m, 8H), 3.24 (t, J=6.5 Hz, 2H), 3.04 (t, J=6.5 Hz, 2H), 2.83 (m, 4H), 2.76 (m, 4H), 1.84 (d, J=7.0 Hz, 3H). MS m/z 723 [M+1]$^+$. Compound 40b $^1$H NMR (400 MHz, CDCl3) d=9.17 (s, 1H), 8.93 (s, 1H), 8.88 (s, 1H), 8.75 (d, J=8.08, 1H), 8.36 (s, 1H), 8.00 (s, 1H), 5.66-5.57 (m, 1H), 4.95-4.83 (m, 2H), 4.69-4.58 (m, 2H), 3.89-3.73 (m, 8H), 3.38 (t, J=6.2 Hz, 2H), 3.11 (t, J=6.6 Hz, 2H), 2.88-2.83 (m, 4H), 2.81-2.76 (m, 4H), 1.84 (d, J=6.9 Hz, 3H). MS m/z 723 [M+1]$^+$.

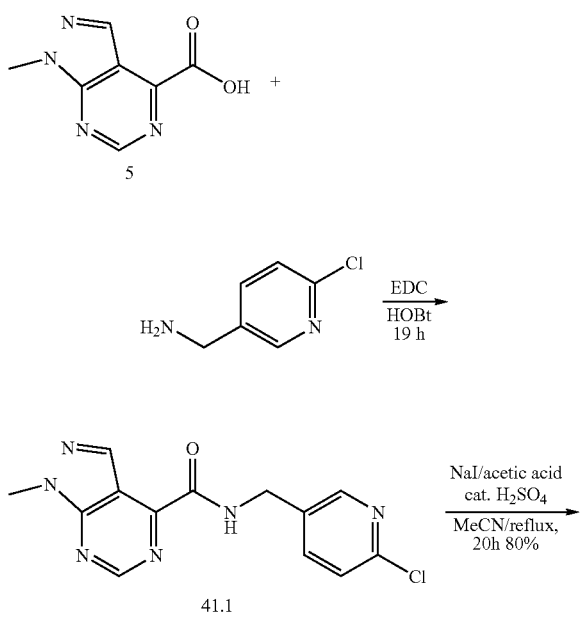

Scheme 41.

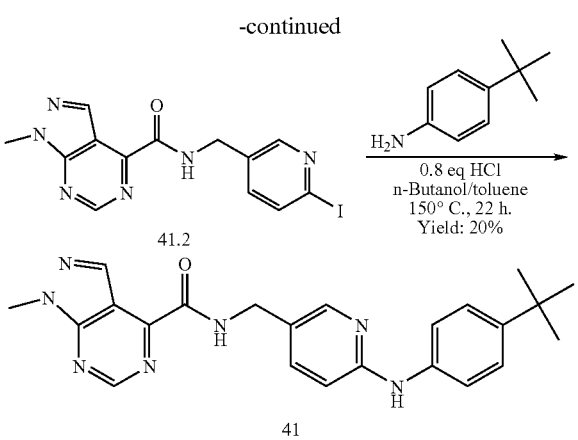

Synthesis of Compound 41.1. To a solution of compound 5 (1.33 g, 7.5 mmol) in N,N-dimethylformamide (6 mL) were added 1-hydroxybenzotriazole (0.760 g, 5.6 mmol), N-(3-dimethylaminopropyl)-'-ethylcarbodiimide hydrochloride (1.79 g, 9.4 mmol), and 4-methylmorpholine (0.99 mL, 9.0 mmol). To this formed brown solution was then added 6-chloro-pyridin-3-yl)-methylamine (1.30 g, 9.0 mmol). After 19 hr stirring, the reaction mixture was concentrated, and this solution became solid at RT. To this solid was added 30 mL isopropanol to get a light yellow solid suspension, which was collected via filtration, affording compound 41.1. m/z 303 [M+1]$^+$.

Synthesis of compound 41.2. To a suspension of compound 41.1 (0.60 g, 2.0 mmol), acetic acid (0.450 mL, 7.91 mmol) and sodium iodide (1.33 mg, 8.91 mmol) in acetonitrile (24 mL) was added sulfuric acid (0.042 mL, 0.792 mmol). The reaction mixture was refluxed at 90° C. for 70 hr, and the crude was purified via pre-HPLC, affording compound 41.2 (620 mg, 80%). m/z 395 [M+1]$^+$.

Synthesis of compound 41. To a reaction vial was charged with compound 41.2 (20 mg, 0.04 mmol), 4-tert-butyl-phenylamine (0.026 mL, 0.166 mmol), 1-butanol (2.0 mL), toluene (1.0 mL) and 4 M of HCl in 1,4-dioxane (0.0083 mL, 0.03 mmol). After stirring at 150° C. for 22 hr, the crude was purified via prep-HPLC, affording compound 41 (3 mg, 20%). $^1$H NMR (400 MHz, DMSO-$d_6$) δ=9.70 (t, J=6.3 Hz, 1H), 9.08 (s, 1H), 8.56 (s, 1H), 8.14-7.91 (m, 2H), 7.77-7.64 (m, 1H), 7.37 (d, J=8.8 Hz, 2H), 7.28 (d, J=8.8 Hz, 2H), 6.85 (d, J=8.8 Hz, 1H), 4.38 (d, J=6.3 Hz, 2H), 4.04 (s, 3H), 1.19 (s, 9H); m/z 416 [M+1]+.

Scheme 42.

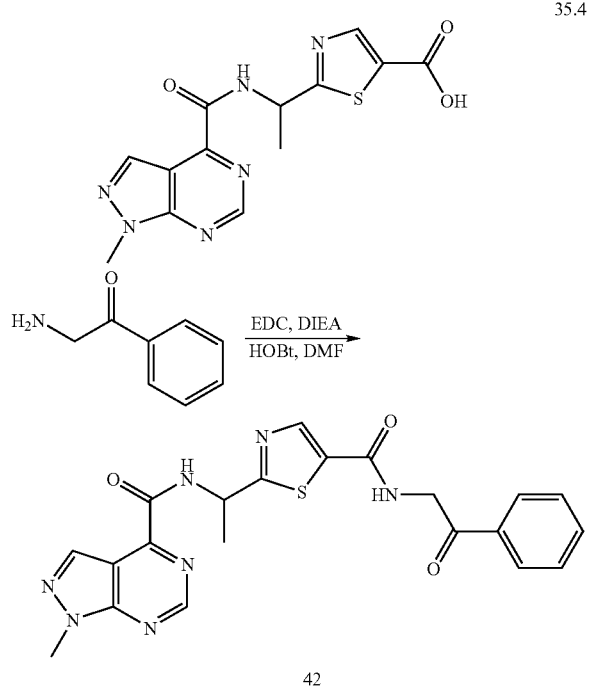

42

Synthesis of Compound 42. Into the reaction was added compound 35.4 (40 mg, 0.120 mmol), 2-amino-1-phenylethanone HCl (22.7 mg, 0.13 mmol), 1-hydroxybenzotriazole (16 mg, 0.1204 mmol) into N,N-dimethylformamide (2 mL). The resulting solution was stirred at RT for 5 min after which N-(3-dimethylaminopropyl)-N'-ethylcarbodiimide hydrochloride (28 mg, 0.14 mmol) and then N,N-diisopropylethylamine (16 mg, 0.12 mmol). The resulting reaction mixture was allowed to stir at RT for 16 hr. The reaction mixture was the diluted with 50 mL of EtOAc and washed 3× water 1× brine and then dried over Na2SO4. Removed solvent in vacuo. Took residue up in EtOAc and filtered through a plug of SiO2 eluting with EtOAc to yield 50 mg of compound 42. 1H NMR (400 MHz, MeOD) δ=9.02 (s, 1H), 8.53 (s, 1H), 8.24-8.19 (m, 1H), 7.93 (d, J=7.1 Hz, 2H), 7.59-7.50 (m, 1H), 7.48-7.38 (m, 2H), 5.53 (q, J=7.1 Hz, 1H), 4.75 (s, 2H), 4.06 (s, 3H), 1.71 (d, J=7.1 Hz, 3H).

Scheme 43.

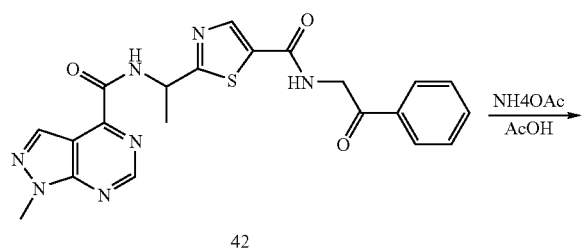

42

-continued

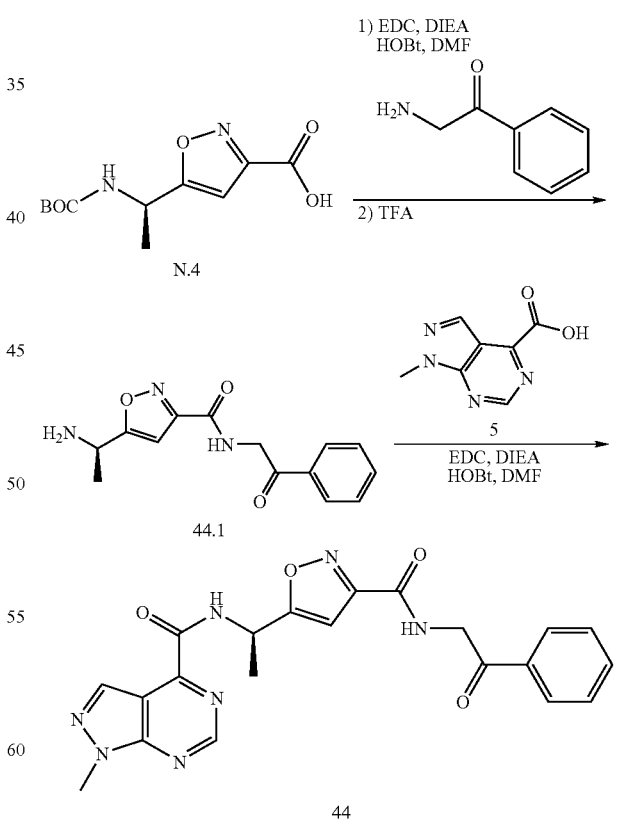

Synthesis of Compound 43. In a 5 mL microwave reaction vial compound 42 (50 mg, 0.11 mmol) and ammonium acetate (43 mg, 0.56 mmol) were taken up in acetic acid (2.0 mL). The reaction was sealed and then the reaction was microwaved on 200 watts, 175° C. for 15 minutes. After cooling the reaction mixture was quenched with 50 mL of sat Na2CO3 and 75 mL of EtOAc. The reaction mixture was then washed 2× Na2CO3 1× brine and dried over Na2SO4. The solvent was rotovaped to yield a yellow oil. The yellow oil was then purified by prep reverse phase HPLC (10%-90% CH3CN/water 0.1% TFA) to yield 15 mg of compound 43. 1H NMR (400 MHz, MeOD) δ=9.05-9.01 (m, 1H), 8.55-8.51 (m, 1H), 8.33-8.28 (m, 1H), 7.77 (s, 1H), 7.66 (d, J=7.1 Hz, 2H), 7.44-7.37 (m, 2H), 7.37-7.30 (m, 1H), 5.59 (q, J=7.1 Hz, 1H), 4.06 (s, 3H), 1.76 (d, J=7.1 Hz, 3H) MS m/z 431 [M+1]+.

Scheme 44.

Synthesis of Compound 44.1. In a 10 mL vial compound N.4 (136 mg, 0.530 mmol), 2-amino-1-phenylethanone HCl (100 mg, 0.58 mmol), 1-hydroxybenzotriazole (72 mg, 0.53 mmol), and N,N-diisopropylethylamine (92 μL, 0.530 mmol) were taken up in N,N-dimethylformamide (5 mL) followed by N-(3-dimethylaminopropyl)-N'-ethylcarbodiimide hydrochloride (122 mg, 0.636 mmol). The resulting reaction mixture was then allowed to stir at RT for 16 hr. After 16 h the reaction mixture was diluted with 100 mL EtOAc and washed 2×75 mL sat NaHCO₃ 1×75 mL brine and the EtOAc layer was dried over Na₂SO₄. The EtOAc was then removed in vacuo. MS m/z 317 (M-56)⁺ The residue (40 mg, 0.107 mmol) was taken up in trifluoroacetic acid (1 mL, 10 mmol) and was allowed to stir at RT. After 3 hr, the TFA was removed in vacuo to afford compound 44.1 (21 mg) as an oil.

Synthesis of compound 44. N-(3-Dimethylaminopropyl)-N'-ethylcarbodiimide hydrochloride (0.0246 g, 0.128 mmol) was added to a solution of compound 44.1 (0.0210 g, 0.118 mmol), 1-hydroxybenzotriazole (0.0144 g, 0.107 mmol) and N,N-diisopropylethylamine (0.0276 g, 0.214 mmol) in N,N-dimethylformamide (1 mL, 10 mmol). After 18 hr the reaction mixture was diluted with EtOAc washed 1× sat Na₂CO₃ 1× water 1× brine and the organic layer was dried over Na₂SO₄. The EtOAc was removed in vacuo and the resulting residue was triturated with MeOH to afford compound 44 (22 mg). ¹H NMR (400 MHz, DMSO-d6) δ=9.84 (d, J=8.6 Hz, 1H), 9.18 (s, 1H), 8.97 (t, J=5.8 Hz, 1H), 8.64 (s, 1H), 8.02 (d, J=7.1 Hz, 2H), 7.72-7.65 (m, 1H), 7.60-7.52 (m, 2H), 6.78 (s, 1H), 5.50 (t, 1H), 4.77 (d, J=5.6 Hz, 2H), 4.12 (s, 3H), 1.67 (d, 3H) MS m/z 434 [M+1]⁺.

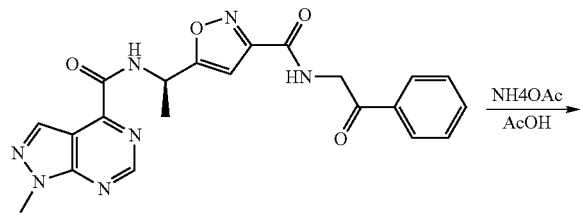

Scheme 45.

44

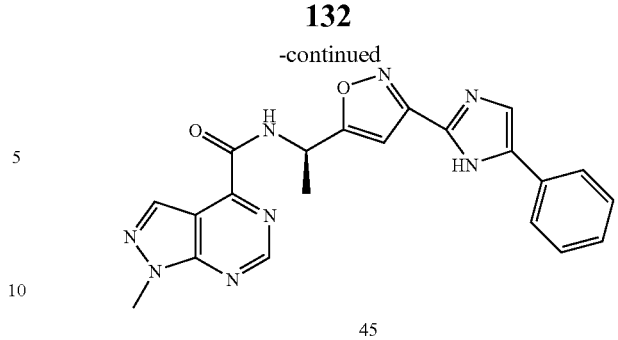

45

Synthesis of Compound 45. In a 5 mL microwave reaction vial compound 44 (15 mg, 0.035 mmol) and ammonium acetate (13 mg, 0.173 mmol) were taken up in acetic acid (1.0 mL). The reaction was sealed and stirred at RT for 5 min. The reaction was then microwaved on 200 watts, 175° C. for 15 minutes. The reaction was then diluted with 75 mL of EtOAc and quenched with 50 mL of sat. Na₂CO₃. The organic layer was then washed 1×35 mL sat. Na₂CO₃ 1×35 mL water and 1×20 mL brine. The organic layer was then dried over Na₂SO₄ and the EtOAc was removed in vacuo. The resulting brown residue was then purified by prep HPLC (10%-90% CH3CN/water 0.1% TFA acidic method) to afford compound 45 (3.5 mg 19%). ¹H NMR (400 MHz, DMSO-d6) δ=9.87 (d, J=8.6 Hz, 1H), 9.19 (s, 1H), 8.64 (s, 1H), 7.84 (d, J=5.6 Hz, 3H), 7.39 (t, J=7.6 Hz, 2H), 7.29-7.23 (m, 1H), 6.89 (s, 1H), 5.57-5.47 (m, 1H), 4.12 (s, 3H), 1.70 (d, 3H) MS m/z 415 [M+1]⁺.

The compounds of the present invention provided in Table 1 were prepared by similar procedures as described in the synthesis of compound 33 using the corresponding acid (Compound 1-32) and amine (Compound A-BBB).

TABLE 1

| # | Structure | Characterization Data |
|---|-----------|----------------------|
| 1B | 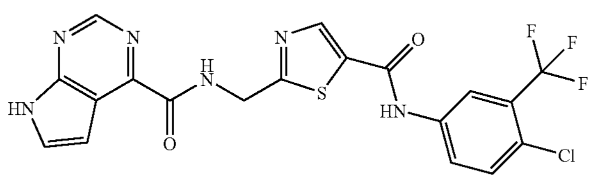 | 1HNMR: (400.13 MHz, DMSO-d6) δ 12.45 (s, 1H), 10.72 (s, 1H), 9.96 (t, J = 5.9 Hz, 1H), 8.92 (s, 1H), 8.51 (s, 1H), 8.23 (d, J = 2.9 Hz, 1H), 8.02 (dd, J = 8.9, 2.7 Hz, 1H), 7.78 (dd, J = 3.5, 2.3 Hz, 1H), 7.72 (d, J = 9.0 Hz), 7.05 (dd, J = 3.5, 1.5 Hz, 1H), 4.85 (d, J = 6.3 Hz, 2H), MS: m/z 481 [M + 1]⁺. |
| 1D | 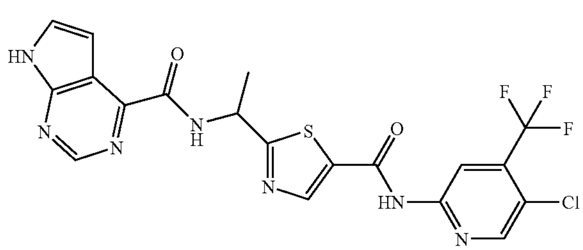 | 1H NMR (400 MHz, DMSO-d6) δ = 12.45 (br. s., 1H), 11.74 (s, 1H), 9.74 (br. s., 1H), 8.92 (s, 1H), 8.76 (br. s., 1H), 8.75 (br. s., 1H), 8.55 (s, 1H), 7.76 (br.s., 1H), 5.56-5.45 (m, 1H), 1.71 (d, J = 6.8 Hz, 3H). MS m/z 496 [M + 1]⁺. |

TABLE 1-continued

| # | Structure | Characterization Data |
|---|---|---|
| 1U | 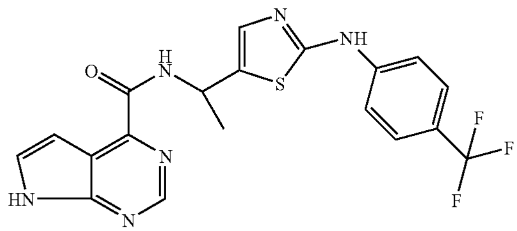 | 1H-NMR (500 MHz, DMSO-d6): δ 12.38 (bs, 1H), 10.47 (s, 1H), 9.31 (d, J = 8.5 Hz, 1H), 8.83 (s, 1H), 7.77 (d, J = 8.5 Hz, 2H), 7.62 (d, J = 8.5 Hz, 2H), 7.21 (s, 1H), 7.03 (s, 1H), 5.39-5.36 (m, 1H), 1.64 (d, J = 7 Hz, 3H); m/z 433 [M + 1]+. |
| 1NA | 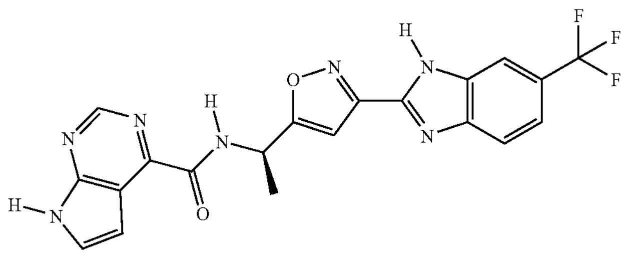 | 1H NMR (400.13 MHz, MeOD-d4) δ 8.68 (s, 1H), 7.80 (br. s, 1H), 7.63 (d, J = 8.6 Hz, 1H), 7.45 (br, d, J = 8.6 Hz, 1H), 4.448 (d, J = 3.6 Hz, 1H), 6.97 (d, J = 3.6 Hz, 1H), 5.46 (q, J = 7.4, 1H), 1.63 (d, J = 7.1, 3H). MS m/z 442 [M + 1]+. |
| 2Da | 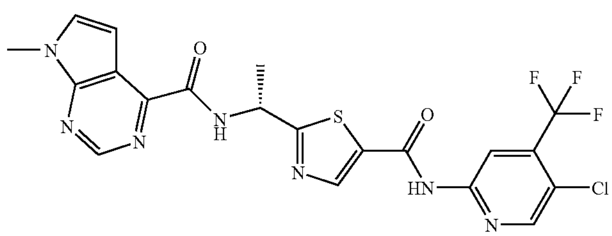 | 1HNMR: (400.13 MHz, DMSO-d6) δ 11.75 (S, 1H), 9.78 (d, J = 8.1 Hz, 1H), 8.96 (s, 1H), 8.78 (s, 1H), 8.76(m, 2H), 8.55 (s, 1H), 7.81 (d, J = 3.4 Hz, 1H), 7.05 (d, J = 3.4 Hz, 1H), 5.50 (dq, J = 8.1, 7.1 Hz, 1H), 3.89 (s, 3H), 1.72 (d, J = 7.1 Hz, 3H) MS: m/z 510 [M + 1]+. |
| 3Na | 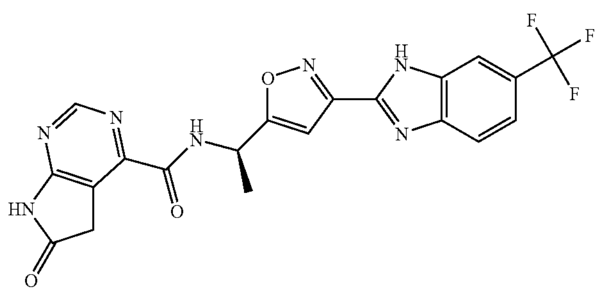 | 1H NMR (400.13 MHz, MeOD-d6) δ 8.77 (s, 1H), 8.08 (s, 1H), 7.93 (d, J = 9 Hz, 1H), 7.78 (d, J = 8.5 Hz, 1H), 7.06 (s, 1H), 5.57 (q, J = 7.3 Hz, 1H), 1.78 (d, J = 7.3 Hz, 3H) m/z 458 [M + 1]+. |
| 4A | 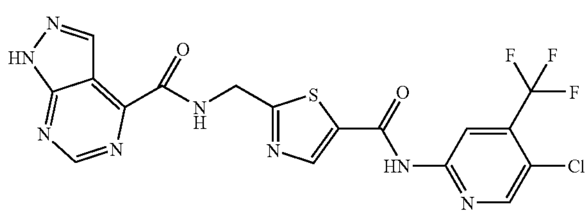 | MS m/z 483 [M + 1]+. |
| 4D | 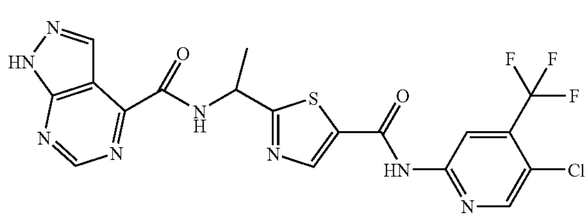 | 1H NMR (400 MHz, MeOD) δ = 9.12 (s, 1H), 8.68 (s, 1H), 86.2 (s, 1H), 8.58 (s, 1H), 8.55 (s, 1H), 5.70-5.62 (m, 1H), 1.84 (d, J = 7.1 Hz, 3H). MS m/z 497 [M + 1]+. |

TABLE 1-continued

| # | Structure | Characterization Data |
|---|---|---|
| 4Da | 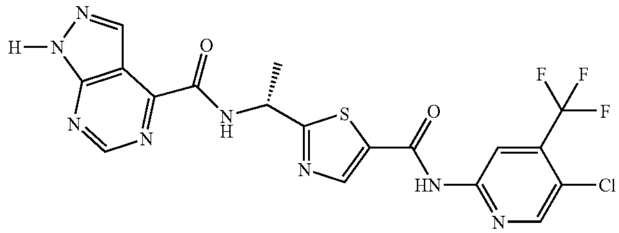 | 1HNMR: (400.13 MHz, DMSO-d6) δ 14.41 (s, 1H), 11.75 (s, 1H), 9.99 (d, J = 8.2 Hz, 1H), 9.17 (s, 1H), 8.77 (s, 1H), 8.76 (s, 1H), 8.62 (d, J = 1.2 Hz, 1H), 8.55 (s, 1H), 5.53 (dq, J = 8.2, 7.1 Hz, 1H), 1.73 (d, J = 7.1 Hz, 3H), MS m/z 497 [M + 1]$^+$. |
| 4Db | 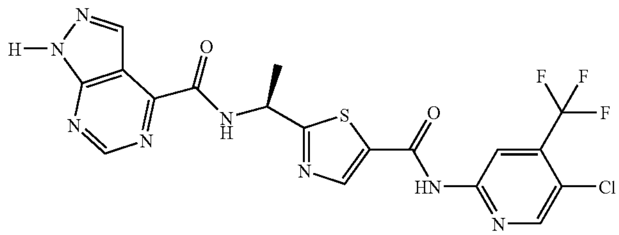 | 1H NMR (400 MHz, DMSO-d6) δ 9.97 (d, J = 8.2 Hz, 1H), 9.17 (s, 1H), 8.77 (s, 1H), 8.75 (s, 1H), 8.62 (s, 1H), 8.55 (s, 1H), 5.58-5.48 (m, 1H), 1.73 (d, J = 7.1 Hz, 3H). MS m/z 497 [M + 1]$^+$. |
| 4E | 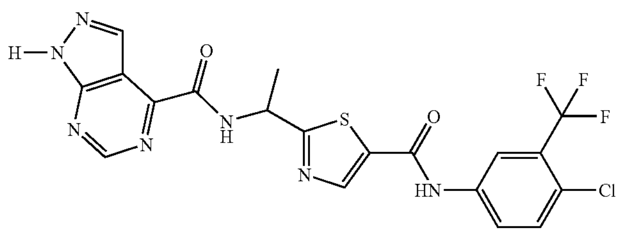 | 1H NMR (400.13 MHz, DMSO-d6) δ 14.43 (s, 1H), 10.34 (s, 1H), 10.01 (d, J = 8.1 Hz, 1H), 9.18 (s, 1H), 8.63 (s, 1H), 8.53 (s, 1H), 8.23 (d, J = 8.2 Hz, 1H), 8.03 (dd, J = 8.7, 2.6 Hz, 1H), 7.72 (d, J = 8.7 Hz, 1H), 5.55 (dq, J = 8.0, 7.2 Hz, 1H), 1.73 (d, J = 7.0 Hz, 3H). MS m/z 496 [M + 1]$^+$. |
| 4F | 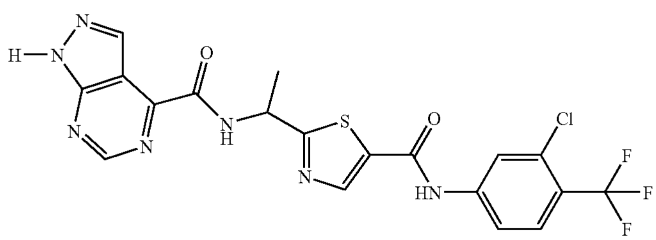 | 1H NMR (400.13 MHz, DMSO-d6) δ 14.04 (br. s, 1H), 10.80 (s, 1H), 10.01 (d, J = 8.5 Hz, 2H), 9.18 (s, 1H), 8.63 (s, 1H), 8.56 (s, 1H), 8.1 (br. s, 1H), 7.86 (s, 1H), 7.85 (d, J = 1.6 Hz, 1H), 5.55 (dq, J = 8.1, 6.5, 1H), 1.74 (d, J = 7.1 Hz, 3H). MS: m/z 496 [M + 1]$^+$. |
| 4Na | 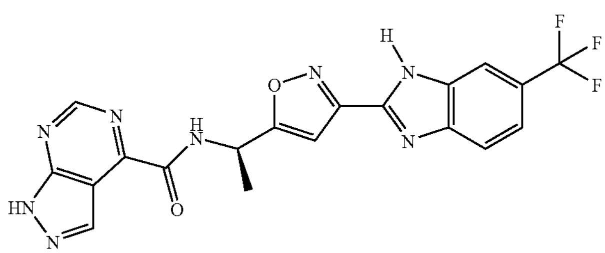 | 1H NMR (400.13 MHz, MeOH-d4) 9.09 (s, 1H), 8.67 (s, 1H), 7.98 (s, 1H), 7.81 (d, J = 8.8Hz), 7.62 (d, J = 8.8 Hz, 1H), 7.04 (s, 1H), 5.66 (q, J = 6.8 Hz, 1H), 1.82 (d, J = 7.1 Hz, 3H). MS m/z 443 [M + 1]$^+$. |
| 4U | 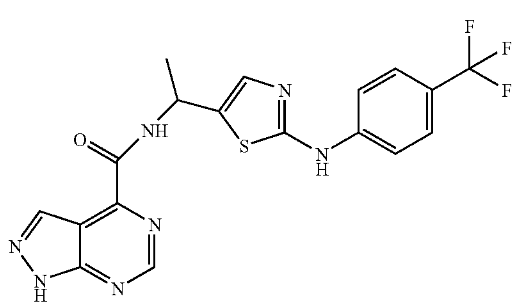 | 1H-NMR (500 MHz, DMSO-d6): δ 14.30 (bs, 1H), 10.46 (s, 1H), 9.51 (s, 1H), 9.12 (s, 1H), 8.61 (s, 1H), 7.77 (d, J = 8.5 Hz, 2H), 7.62 (d, J = 8.5 Hz, 2H), 7.21 (s, 1H), 5.39-5.36 (m, 1H), 1.64 (d, J = 7 Hz, 3H); m/z 434 [M + 1]$^+$. |

TABLE 1-continued

| # | Structure | Characterization Data |
|---|---|---|
| 5D | 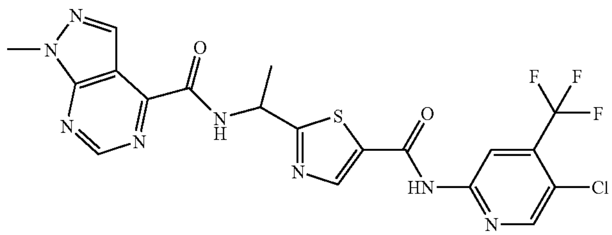 | 1H NMR (400 MHz, DMSO-d6) δ = 11.75 (s, 1H), 10.01 (d, J = 8.2 Hz, 1H), 9.21 (s, 1H), 8.77 (s, 1H), 8.76 (d, J = 2.3 Hz, 1H), 8.62 (s, 1H), 8.54 (s, 1H), 5.58-5.49 (m, 1H), 4.12 (s, 3H), 1.73 (d, J = 7.1 Hz, 3H) MS m/z 511 [M ++0H]+. |
| 5Da | 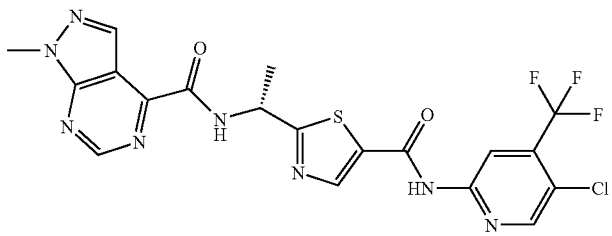 | 1HNMR: (400.13 MHz, CDCl3) δ 9.08 (s, 1H), 8.76 (s, 1H), 8.75 (d, J = 8.0 Hz, 1H), 8.67 (s, 1H), 8.52 (s, 1H), 8.45 (s, 1H), 8.33 (s, 1H), 5.70 (dq, J = 8.0, 7.0 Hz, 1H), 4.21 (s, 3H), 1.87 (d, J = 7.0 Hz, 3H). MS m/z 511 [M + 1]+. |
| 5E | 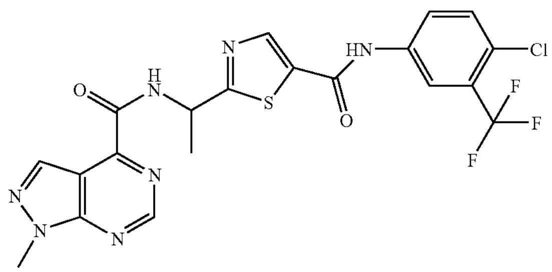 | 1H-NMR (500 MHz, DMSO-d6): δ 10.73 (s, 1H), 10.03 (d, J = 10.0 Hz, 1H), 9.20 (s, 1H), 8.61 (s, 1H), 8.51 (s, 1H), 8.21 (s, 1H), 8.01 (d, J = 5.0 Hz, 1H), 7.72 (d, J = 10.0 Hz, 1H), 5.54-5.51 (m, 1H), 4.11 (s, 3H), 1.72 (d, J = 5.0 Hz, 3H); m/z 510 [M + 1]+. |
| 5Na | 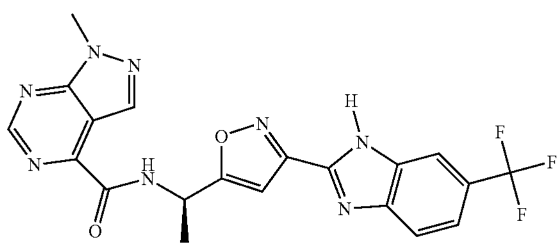 | 1H NMR (400 MHz, CDCl3) δ = 8.96 (s, 1H), 8.67 (s, 1H), 8.44 (s, 1H), 7.94 (br. s., 1H), 7.69 (br. s., 1H), 7.51 (d, J = 8.6 Hz, 1H), 6.99 (s, 1H), 5.66-5.55 (m, 1H), 4.12 (s, 3H), 1.75 (d, J = 7.1 Hz, 3H). MS m/z 457 [M + 1]+. |
| 5U | 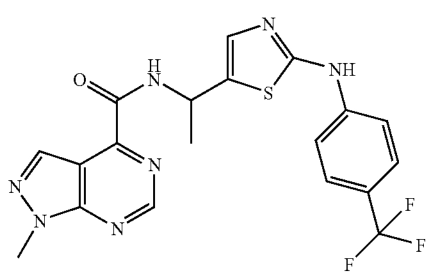 | 1H-NMR (500 MHz, DMSO-d6): δ 10.48 (s, 1H), 9.60 (d, J = 8.5 Hz, 1H), 9.13 (s, 1H), 8.61 (s, 1H), 7.76 (d, J = 8.5 Hz, 2H), 7.62 (d, J = 8.5 Hz, 2H), 7.22 (s, 1H), 5.40-5.36 (m, 1H), 4.09 (s, 3H), 1.65 (d, J = 7 Hz, 3H) |
| 5V | 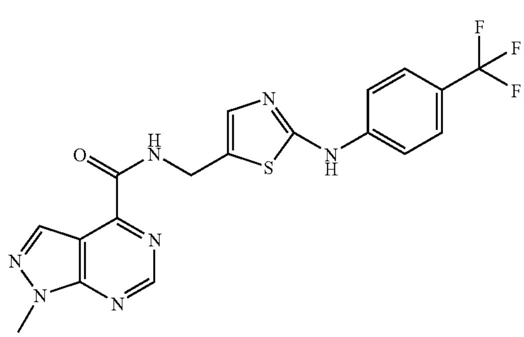 | 1H-NMR (500 MHz, DMSO-d6): δ 10.48 (s, 1H), 9.78 (s, 1H), 9.13 (s, 1H), 8.62 (s, 1H), 7.77 (d, J = 8.5 Hz, 2H), 7.62 (d, J = 8.5 Hz, 2H), 7.22 (s, 1H), 4.59 (d, J = 6 Hz, 2H), 4.09 (s, 3H); m/z 434 [M + 1]+. |

TABLE 1-continued

| # | Structure | Characterization Data |
|---|---|---|
| 5W | 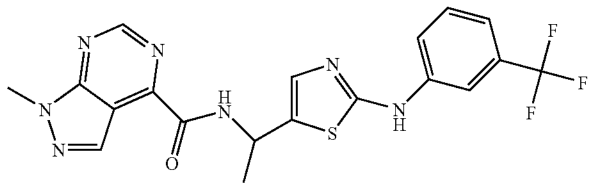 | m/z 448 [M + 1]+. |
| 5X | 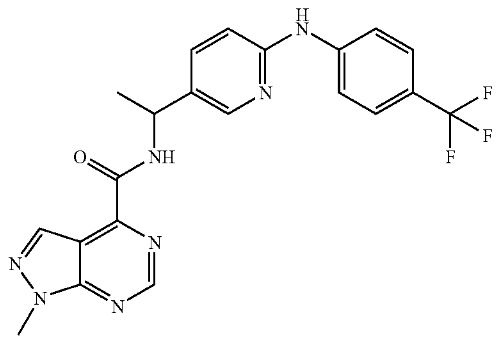 | 1H NMR (400 MHz, DMSO-d6) d = 9.53 (d, J = 8.6 Hz, 1H), 9.49 (s, 1H), 9.15 (s, 1H), 8.60 (s, 1H), 8.30 (d, J = 2.5 Hz, 1H), 7.87 (d, J = 8.6 Hz, 2H), 7.78 (dd, J = 2.5, 8.6 Hz, 1H), 7.57 (d, J = 8.6 Hz, 2H), 6.89 (d, J = 8.6 Hz, 1H), 5.22 (quin, J = 7.3 Hz, 1H), 4.10 (s, 3H), 1.59 (d, J = 6.6 Hz, 3H); m/z 442 [M + 1]+. |
| 5Y | 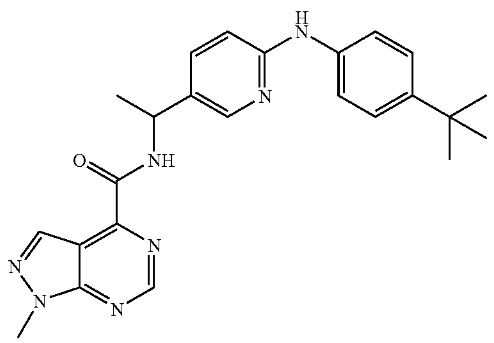 | 1H NMR (300 MHz, DMSO-d6) d = 9.45 (d, J = 8.3 Hz, 1H), 9.14 (s, 1H), 8.87 (s, 1H), 8.60 (s, 1H), 8.21-8.17 (m, 1H), 7.67 (dd, J = 2.5, 8.5 Hz, 1H), 7.57-7.47 (m, J = 8.7 Hz, 2H), 7.29-7.20 (m, J = 8.7 Hz, 2H), 6.78 (d, J = 8.3 Hz, 1H), 5.18 (quin, J = 7.3 Hz, 1H), 4.09 (s, 3H), 1.57 (d, J = 7.2 Hz, 3H), 1.25 (s, 9H); m/z 430 [M + 1]+. |
| 5Z | 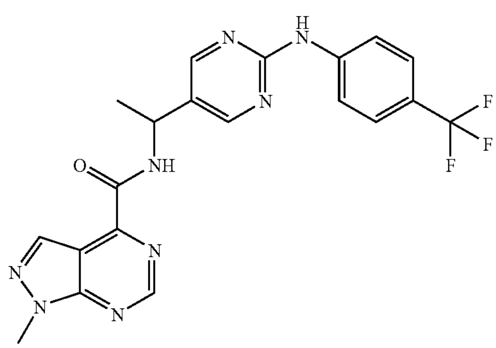 | 1H NMR (300 MHz, DMSO-d6) d = 10.10 (s, 1H), 9.63 (d, J = 8.3 Hz, 1H), 9.16 (s, 1H), 8.66 (s, 2H), 8.60 (s, 1H), 8.01-7.92 (m, J = 8.7 Hz, 2H), 7.66-7.56 (m, J = 8.7 Hz, 2H), 5.23 (quin, J = 7.4 Hz, 1H), 4.10 (s, 3H), 1.62 (d, J = 7.2 Hz, 3H); m/z 443 [M + 1]+. |
| 5AA | 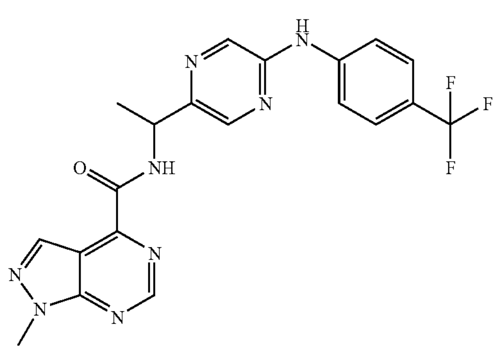 | 1H-NMR (500 MHz, DMSO-d6) δ 9.90 (s, 1H), 9.31 (d, J = 4 Hz, 1H), 9.15 (s, 1H), 8.60 (s, 1H), 8.32 (d, J = 15 Hz, 2H), 7.88 (d, J = 10 Hz, 2H), 7.62 (d, J = 5 Hz, 2H), 5.30 (m, 1H), 4.09 (s, 3H), 1.58 (d, J = 5 Hz, 3H); m/z 443 [M + 1]+. |

TABLE 1-continued

| # | Structure | Characterization Data |
|---|---|---|
| 5BB | 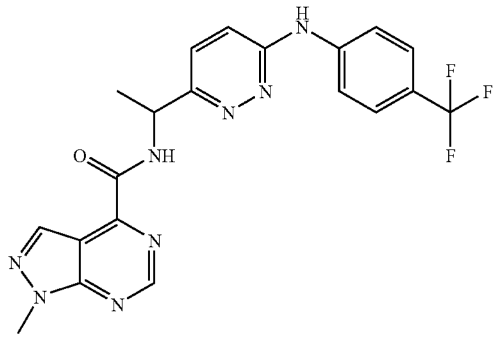 | 1HNMR (DMSO-dD6, 500 MHz) δ 9.1 (s, 1H), 8.6 (s, 1H), 7.9 (d, J = 10 Hz, 2H), 7.6 (d, J = 10 Hz, 3H), 7.2 (d, J = 10 Hz, 1H), 5.3 (m, 1H), 4.1 (s, 3H), 1.6 (s, 3H); m/z 443 [M + ]+. |
| 5CC | 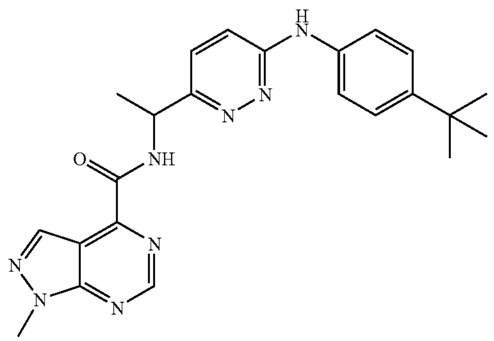 | 1H-NMR (CDCl3, 500 MHz): δ 9.19 (d, 1H), 9.02 (s, 1H), 8.73 (s, 1H), 7.39-7.28 (m, 5H), 7.07 (d, J = 9 Hz, 1H), 6.88 (s, 1H), 5.43-5.40 (m, 1H), 4.17 (s, 3H), 1.74 (d, J = 7 Hz, 3H), 1.32 (s, 9H); m/z 431 [M + 1]+. |
| 5EE | 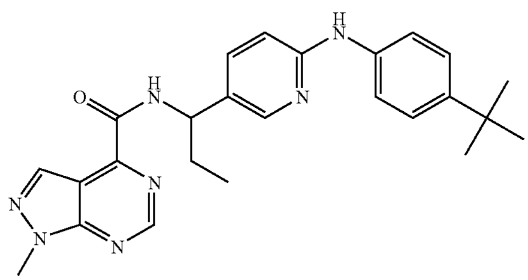 | 1H NMR (400 MHz, DMSO-d6) d = 9.49-9.43 (d, J = 8.8 Hz, 1H), 9.16 (s, 1H), 8.87 (s, 1H), 8.59 (s, 1H), 8.17 (d, J = 2.0 Hz, 1H), 7.68 (dd, J = 2.5, 8.7 Hz, 1H), 7.52 (d, J = 8.8 Hz, 2H), 7.25 (d, J = 8.9 Hz, 2H), 7.25 (d, J = 4.5 Hz, 1H), 4.98-4.77 (m, 1H), 4.10 (s, 3H), 2.12-1.95 (m, 1H), 1.94-1.78 (m, 1H), 1.25(s, 9H), 0.89 (t, J = 7.3 Hz, 3H); m/z 444 [M + 1]+. |
| 5FF | 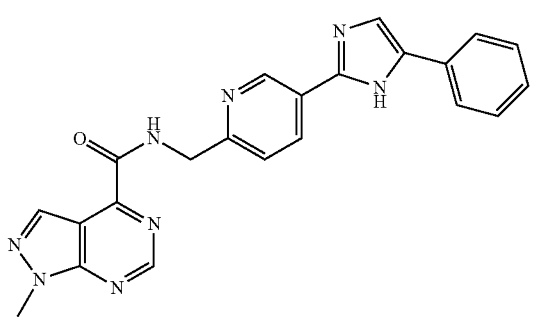 | 1H NMR (400 MHz, DMSO-d6) δ 9.85 (t, J = 6.1 Hz, 1H), 9.21 (s, 1H), 9.19-9.12 (m, 1H), 8.67-8.59 (m, 1H), 8.43-8.30 (m, 1H), 8.02 (br. s., 1H), 7.87 (d, J = 7.6 Hz, 2H), 7.58 (d, J = 8.1 Hz, 1H), 7.47 (t, J =7.6 Hz, 2H), 7.39-7.30 (m, 1H), 4.76 (d,J = 6.1 Hz, 2H), 4.20-4.05 (m, 3H) MS411 [M + 1]+. |
| 5JJ | 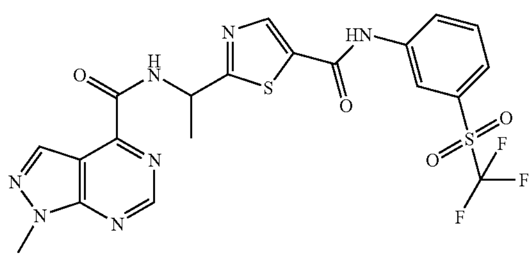 | 1H-NMR (500 MHz, DMSO-d6): δ = 10.89 (s, 1H), 10.02 (d, J = 5.0 Hz, 1H), 9.20 (s, 1H), 8.61 (s, 1H), 8.56 (d, J = 7.5 Hz, 2H), 8.26 (d, J = 5.0 Hz, 1H), 7.92 (s, 2H), 5.54-5.51 (m, 1H), 4.11 (s, 3H), 1.73 (d, J = 5.0 Hz, 3H); m/z 540 [M + 1]+. |

TABLE 1-continued

| # | Structure | Characterization Data |
|---|---|---|
| 5KK | 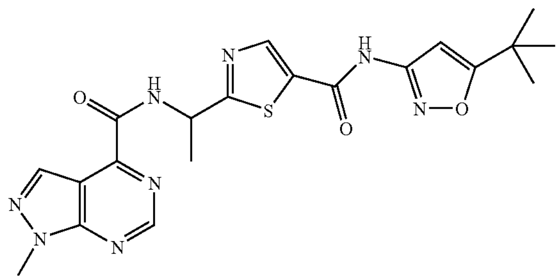 | 1H-NMR (500 MHz, DMSO-d6): δ 11.62 (s, 1H), 9.99 (d, J = 8.0 Hz, 1H), 9.22 (s, 1H), 8.62 (s, 2H), 6.66 (s, 1H), 5.48-5.45 (m, 1H), 4.11 (s, 3H), 1.69 (d, J = 5.0 Hz, 3H), 1.45 (s, 9H); m/z 455 [M + 1]+. |
| 5LL | 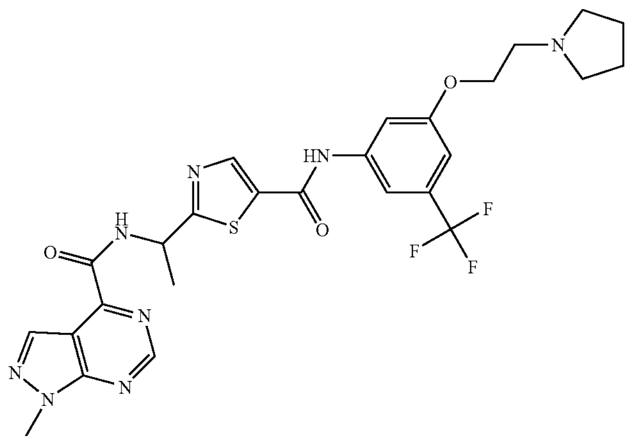 | m/z 589 [M + 1]+. |
| 5MM | 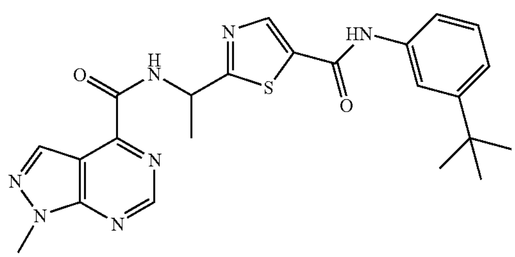 | 1H NMR (300 MHz, DMSO-d6) d = 10.29 (s, 1H), 9.98 (d, J = 8.3 Hz, 1H), 9.21 (s, 1H), 8.63 (s, 1H), 8.51 (s, 1H), 7.68-7.62 (m, 1H), 7.58 (d, J = 7.9 Hz, 1H), 7.27 (t, J = 7.9 Hz, 1H), 7.18-7.09 (m, 1H), 5.62-5.45 (m, 1H), 4.12 (s, 3H), 1.73 (d, J = 7.2 Hz, 3H), 1.28 (s, 9H); m/z 464 [M + 1]+. |
| 5NN | 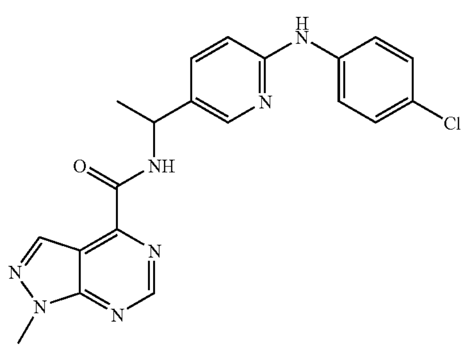 | 1H NMR (400 MHz, DMSO-d6) d = 9.56 (d, J = 8.3 Hz, 2H), 9.18-9.12 (m, 1H), 8.61-8.56 (m, 1H), 8.18 (d, J = 2.3 Hz, 1H), 7.87 (dd, J = 2.3, 8.8 Hz, 1H), 7.65-7.58 (m, 2H), 7.37-7.29 (m, 2H), 6.93 (d, J = 8.8 Hz, 1H), 5.21 (quin, J = 7.3 Hz, 1H), 4.11 (s, 3H), 1.57 (d, J = 7.0 Hz, 3H). |
| 5OO | 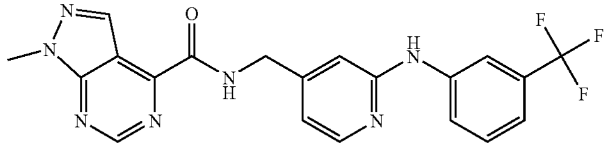 | 1H NMR (400 MHz, DMSO-d6) d = 9.87 (t, 1H), 9.53 (br. s., 1H), 9.20 (s, 1H), 8.63 (s, 1H), 8.16 (br. s., 1H), 7.83 (d, J = 7.8 Hz, 1H), 7.56-7.36 (m, 1H), 7.20 (d, J = 7.7 Hz, 1H), 6.93-6.75 (m, 2H), 4.53 (d, J = 6.4 Hz, 2H), 4.12 (s, 3H); m/z 428 [M + 1]+. |

TABLE 1-continued

| # | Structure | Characterization Data |
|---|---|---|
| 5PP | 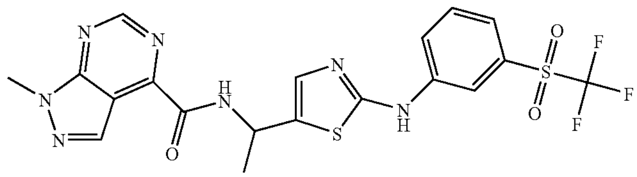 | m/z 512 [M + 1]+.− |
| 5BBB | 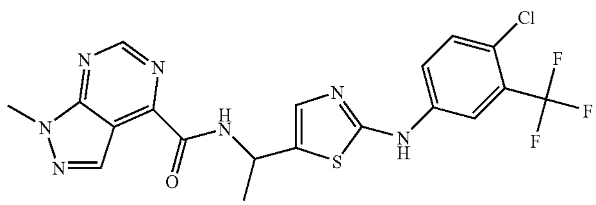 | m/z 482 [M + 1]+. |
| 6D | 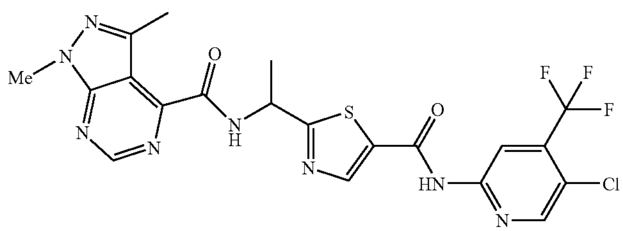 | 1H NMR (400.13 MHz, DMSO-d6) δ 11.77 (s, 1H), 9.89 (d, J = 8.2 Hz, 1H), 9.11 (s, 1H), 8.78(s, 1H), 8.77 (s, 1H), 8.56 (s, 1H), 5.52 (dq, 8.0 7.0 Hz, 1H), 4.03 (s, 3H), 2.65 (s, 3H), 1.70 (d, J = 7.0 Hz, 3H) MS m/z 525 [M + 1]+. |
| 6U | 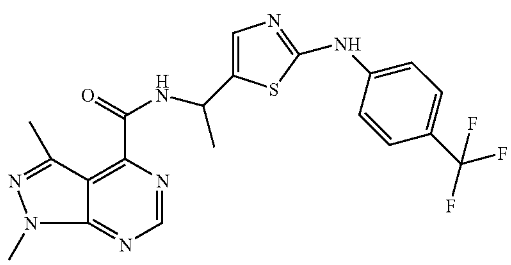 | 1H-NMR (500 MHz, DMSO-d6): δ 10.49 (s, 1H), 9.44 (d, J = 8 Hz, 1H), 9.02 (s, 1H), 7.78 (d, J = 8.5 Hz, 2H), 7.62 (d, J = 8.5 Hz, 2H), 7.23 (s, 1H), 5.39-5.36 (m, 1H), 3.99 (s, 3H), 2.64 (s, 3H), 1.63 (d, J = 7 Hz, 3H); m/z 462 [M + 1]+. |
| 7D | 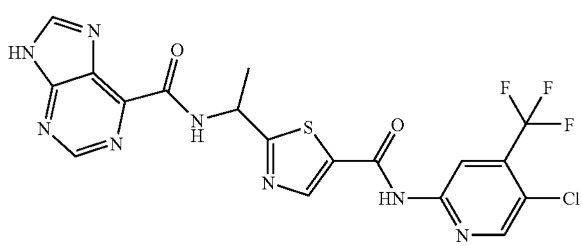 | MS m/z 497 [M + 1]+. |
| 8D | 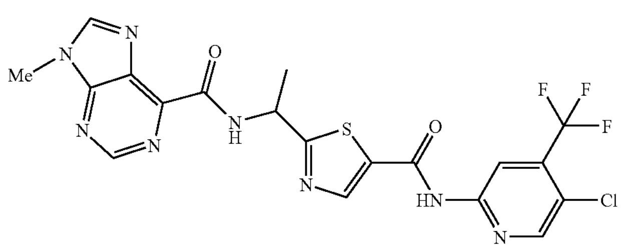 | 1HNMR (400.13 MHz, DMSOd6) δ 11.77 (s, 1H), 9.79 (d, J = 7.7 Hz, 1H), 9.09 (s, 1H), 8.78 (s, 1H), 8.77 (s, 2H), 8.56 (s, 1H), 5.53 (dq, J = 7.7, 7.1 Hz, 1H), 3.91 (s, 3H), 1.70 (d, J = 7.1 Hz, 3H). MS m/z 511 [M + 1]+. |

TABLE 1-continued

| # | Structure | Characterization Data |
|---|---|---|
| 9D | 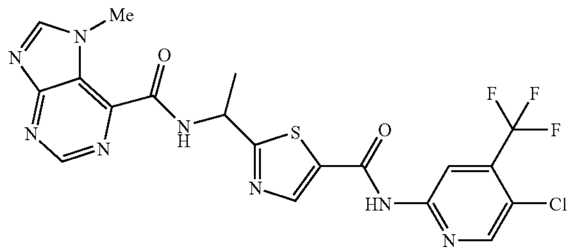 | 1HNMR (400.13 MHz, DMSO-d6) δ 11.76 (s, 1H), 9.94 (d, J = 8.0 Hz, 1H), 9.10 (s, 1H), 8.81 (s, 1H), 8.78 (s, 1H), 8.77 (s, 1H), 8.57 (s, 1H), 4.41 (dq, J = 8.0 7.1 Hz, 1H). 4.06 (s, 1H), 1.71 (d, J = 7.1 Hz, 3H). MS m/z 511 [M + 1]+. |
| 10D | 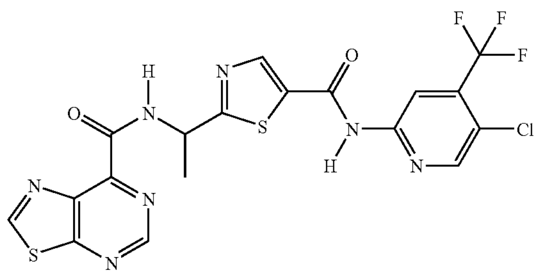 | 1HNMR (400.13 MHz, CDCl3) δ 9.47 (m 1H), 9.39 (s, 1H) 9.35 (s, 1H), 8.65 (s, 1H), 8.42 (s 1H) 8.36 (s 1H) 5.79 (m, 1H), 1.87 (ad, 3H), 1.55 (m, 2H), 1.01 (tj = 4.0 Hz, 3H). MS m/z 514 [M + 1]+. |
| 11D | 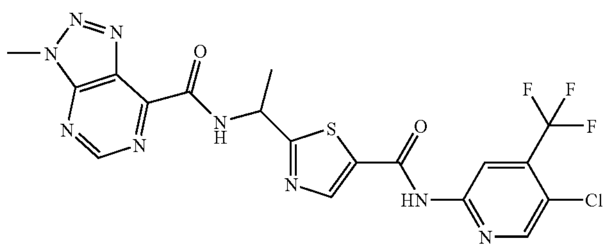 | (DMSO-D6-200 MHz): δ 11.80 (bs, 1H), 9.99 (d, J = 8.2 Hz, 1H), 9.39 (s, 1H), 8.74 (s, 1H), 8.72 (s, 1H), 8.54 (s, 1H), 5.58-5.50 (m, 1H), 4.34 (s, 3H), 1.69 (d, J = 7 Hz, 3H); m/z 512 [M + 1]+. |
| 11Da | 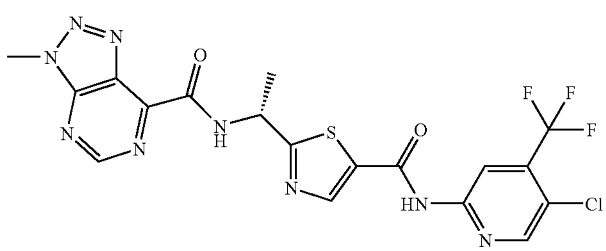 | 1HNMR: (400.13 MHz, DMSO-d6) δ 11.76 (s, 1H), 10.01 (d, J = 8.2 Hz, 1H), 9.21 (s, 1H), 8.77 (s, 1H), 8.62 (s, 1H), 8.55 (s, 1H), 5.52 (dq, J = 8.2, 7.1 Hz, 1H), 4.13 (s, 3H), 1.73 (d, J = 7.1 Hz, 3H). MS m/z 512 [M + 1]+. |
| 11V | 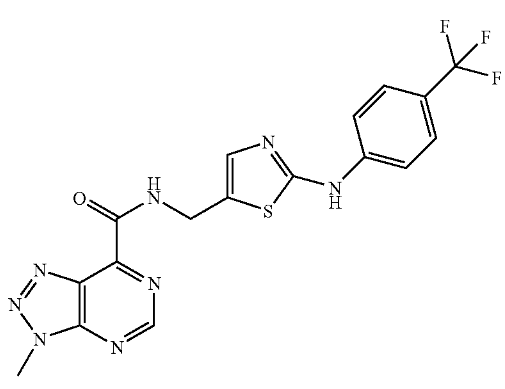 | 1H-NMR (500 MHz, DMSO-d6): δ 10.51 (s, 1H), 9.74 (s, 1H), 9.33 (s, 1H), 7.78 (d, J = 8.5 Hz, 2H), 7.62 (d, J = 8.5 Hz, 2H), 7.25 (s, 1H), 4.63 (d, J = 6 Hz, 2H), 4.33 (s, 3H); m/z 435 [M + 1]+. |

TABLE 1-continued

| # | Structure | Characterization Data |
|---|---|---|
| 12Da | 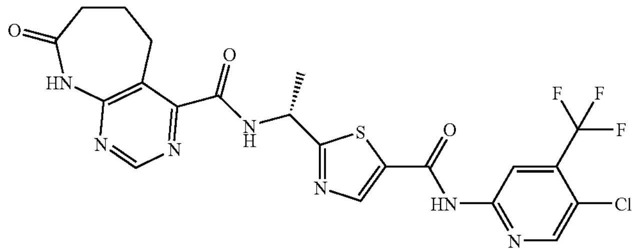 | MS m/z 540 [M + 1]+. |
| 13Da | 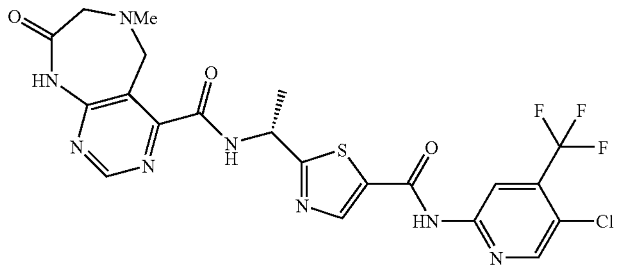 | MS m/z 555 [M + 1]+. |
| 14U | 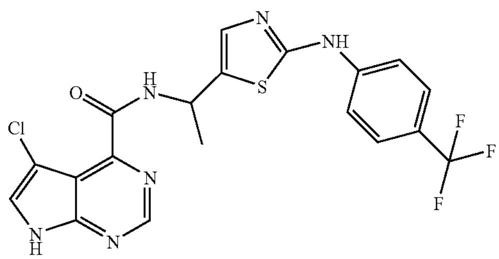 | 1H-NMR (500 MHz, DMSO-d6): δ 12.68 (bs, 1H), 10.50 (s, 1H), 9.21 (d, J = 8 Hz, 1H), 8.82 (s, 1H), 7.87 (s, 1H), 7.79 (d, J = 8.5 Hz, 2H), 7.63 (d, J = 8.5 Hz, 2H), 7.22 (s, 1H), 5.36-5.34 (m, 1H), 1.59 (d, J = 7 Hz, 3H); m/z 467 [M + 1]+. |
| 15U | 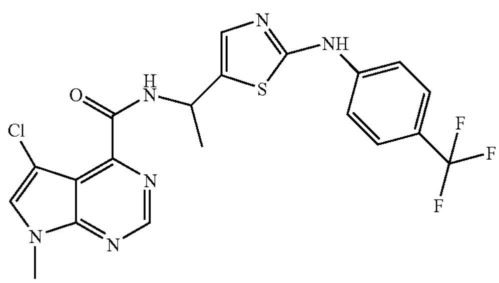 | 1H-NMR (500 MHz, DMSO-d6): δ 10.48 (bs, 1H), 9.12 (bs, 1H), 8.82 (s, 1H), 7.98 (s, 1H), 7.79 (d, J = 8.5 Hz, 2H), 7.63 (d, J = 8.5 Hz, 2H), 7.22 (s, 1H), 5.36-5.34 (m, 1H), 3.90 (s, 3H), 1.72 (d, J = 7 Hz, 3H); m/z 481 [M + 1]+. |
| 16U | 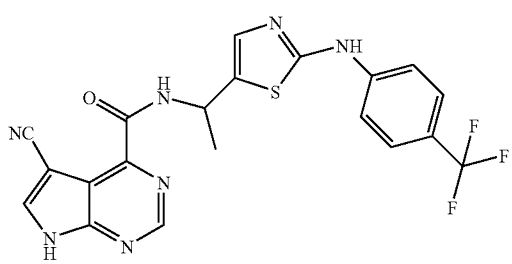 | 1H-NMR (DMSO-D6 + D2O, 500 Mhz): δ 8.95 (s, 1H), 8.58 (s, 1H), 7.73 (d, J = 8.5 Hz, 2H), 7.60 (d, J = 8.5 Hz, 2H), 7.21 (s, 1H), 5.37-5.35 (m, 1H), 1.62 (d, J = 7 Hz, 3H); m/z 458 [M + 1]+. |
| 17U | 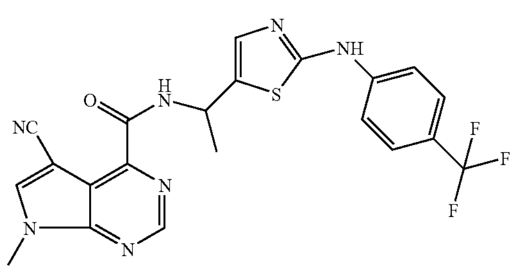 | 1H-NMR (500 MHz, DMSO-d6): δ 10.49 (s, 1H), 9.44 (d, J = 8 Hz, 1H), 9.06 (s, 1H), 8.74 (s, 1H), 7.78 (d, J = 8 Hz, 2H), 7.62 (d, J = 8.5 Hz, 2H), 7.23 (s, 1H), 5.41-5.39(m, 1H), 3.90(s, 3H), 1.64(d, J = 7 Hz, 3H); m/z 472 [M + 1]+. |

TABLE 1-continued

| # | Structure | Characterization Data |
|---|---|---|
| 17Ua | 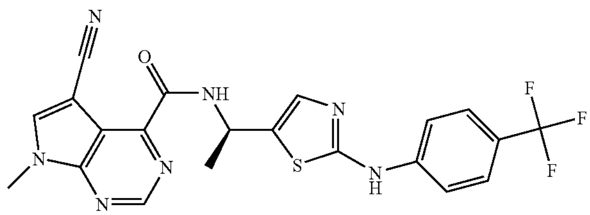 | 1H NMR (300 MHz, DMSO-d6) d = 10.51 (br. s., 1H), 9.45 (d, J = 8.7 Hz, 1H), 9.07 (s, 1H), 8.76 (s, 1H), 7.78 (d, J = 8.7 Hz, 2H), 7.63 (d, J = 9.1 Hz, 2H), 7.25 (s, 1H), 5.69-5.26 (m, 1H), 3.91 (s, 3H), 1.65 (d, J = 8.7 Hz, 3H) MS m/z 472 [M + 1]+. |
| 18D | 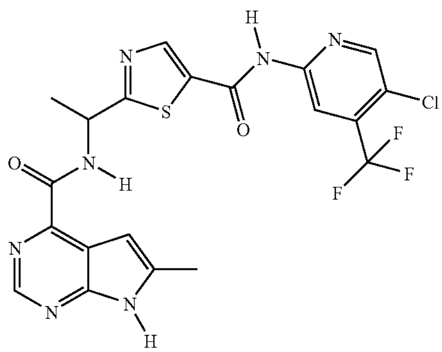 | 1H-NMR (500 MHz, DMSO-d6): d 12.23 (bs, 1H), 11.76 (bs, 1H), 9.60 (bs, 1H) 8.78 (s, 1H), 8.75 (s, 1H), 8.73 (s, 1H), 8.53 (s, 1H), 6.74 (s, 1H), 5.49-5.46 (m, 1H), 2.49 (s, 3H), 1.70 (d, J = 7.5 Hz, 3H); m/z 510 [M + 1]+. |
| 19D | 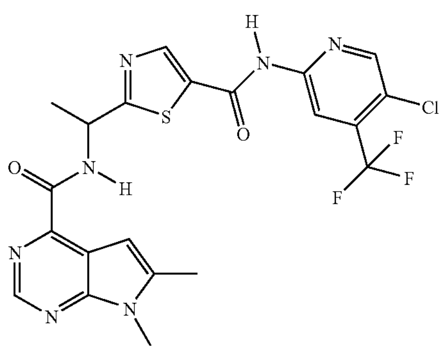 | 1H-NMR (500 Mhz, DMSO-d6): d 11.72 (bs, 1H), 9.68 (d, J = 8.5 Hz, 1H), 8.84 (s, 1H), 8.76 (s, 1H), 8.73 (s, 1H), 8.53 (s, 1H), 6.84 (s, 1H), 5.49-5.46 (m, 1H), 3.77 (s, 3H), 2.52 (s, 3H), 1.70 (d, J = 7.5 Hz, 3H); m/z 524 [M + 1]+. |
| 20Da | 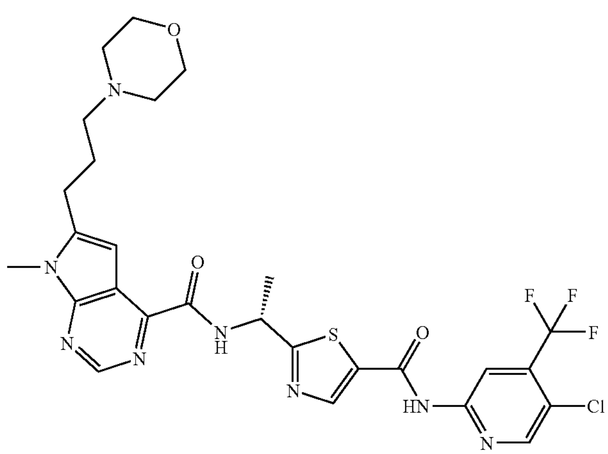 | 1H-NMR (300 MHz, MeOD-d4) δ = 8.86 (s, 1H), 8.59 (s, 1H), 8.56 (s, 1H), 8.53 (s, 1H), 7.00 (s, 1H), 5.59 (q, J = 7.1 Hz, 1H), 4.07 (d, J = 11.7 Hz, 2H), 3.86 (s, 3H), 3.76 (t, J = 12.3 Hz, 2H), 3.55 (d, J = 12.8 Hz, 2H), 3.36-3.31 (m, 2H), 3.25-3.12 (m, 2H), 3.03 (t, J = 7.4 Hz, 2H), 2.35-2.21 (m, 2H), 1.81 (d, J = 6.8 Hz, 3H) MS m/z 637 [M + 1]+. |

TABLE 1-continued

| # | Structure | Characterization Data |
|---|---|---|
| 21Da | 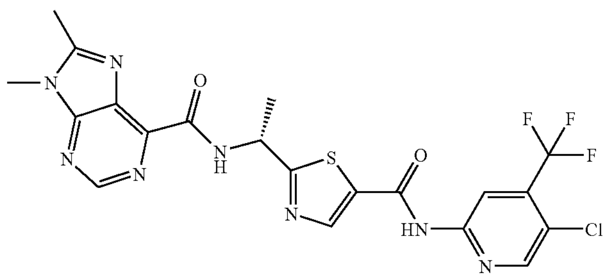 | 1H-NMR (400 MHz, MeOD-d$_4$) δ 9.11 (s, 1H), 8.59 (s, 1H), 8.56 (s, 1H), 8.53 (s, 1H), 5.70-5.62 (m, 1H), 3.95 (s, 3H), 2.86 (s, 3H), 1.82 (d, J = 6.9 Hz, 3H) MS m/z 525 [M + 1]$^+$. |
| 22Da | 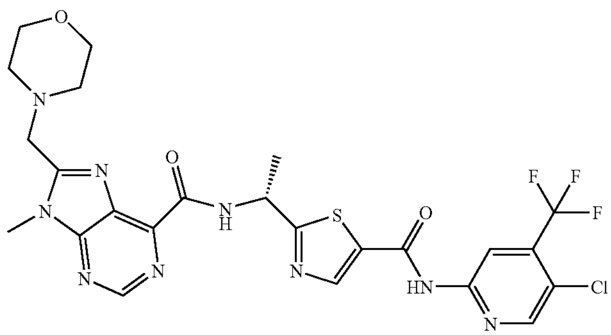 | 1H NMR (400 MHz, MeOD-d$_4$) δ = 9.10 (s, 1H), 8.60 (s, 1H), 8.57 (s, 1H), 8.54 (s, 1H), 5.66 (q, J = 7.1 Hz, 1H), 4.92 (s, 2H), 4.03 (t, J = 4.7 Hz, 4H), 3.94 (s, 3H), 3.60 (br. s., 4H), 1.83 (d, J = 7.1 Hz, 3H) MS m/z 610 [M + 1]$^+$. |
| 23Da | 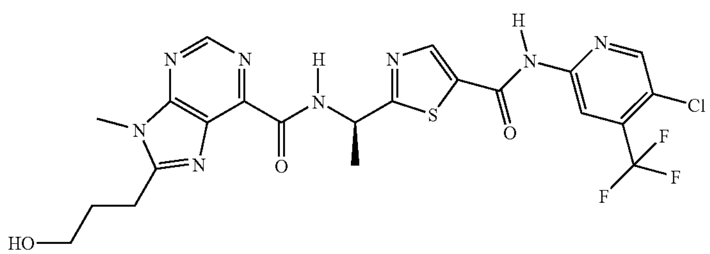 | 1H NMR (400 MHz, CDCl$_3$) δ = 8.60 (s, 1H), 8.49 (s, 1H), 8.35 (s, 1H), 8.24 (s, 1H), 5.40 (m, 1H), 3.71 (br. s., 2H), 3.61-3.46 (m, 2H), 2.99 (br. s., 3H), 2.24 (br. s., 2H), 1.68 (d, J = 6.9 Hz, 3H) MS m/z 569 [M + 1]$^+$. |
| 24Da | 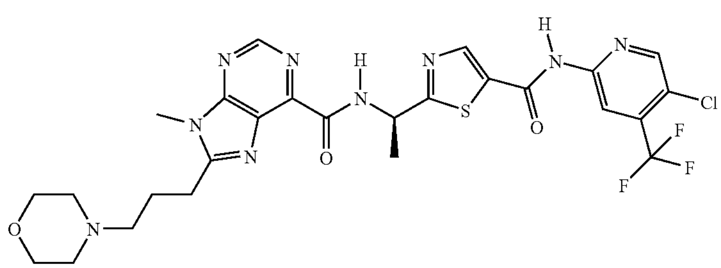 | 1H NMR (300 MHz, MeOD-d$_4$) δ 9.07 (s, 1H), 8.63 (s, 1H), 8.61 (s, 1H), 8.57 (s, 1H), 5.65 (m, 1H), 4.01 (br. s., 4H), 3.92 (s, 3H), 3.68 (br. s., 4H), 3.52-3.45 (m, 2H), 3.29-3.05 (m, 2H), 2.53-2.40 (m, 2H), 1.87 (d, J = 7.1 Hz, 3H). MS m/z 638 [M + 1]$^+$. |
| 25Da | 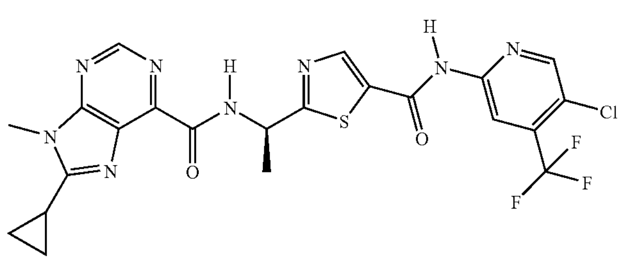 | 1H NMR (300 MHz, MeOD-d$_4$) δ = 9.07 (br. s., 1H), 8.63 (s, 1H), 8.59 (s, 1H), 8.57 (s, 1H), 5.67 (q, J = 6.9 Hz, 1H), 4.07 (s, 3H), 2.49 (s, 1H), 1.84 (d, J = 7.0 Hz, 3H), 1.55-1.35 (m, 4H) |

TABLE 1-continued
| # | Structure | Characterization Data |
|---|---|---|
| 26D | 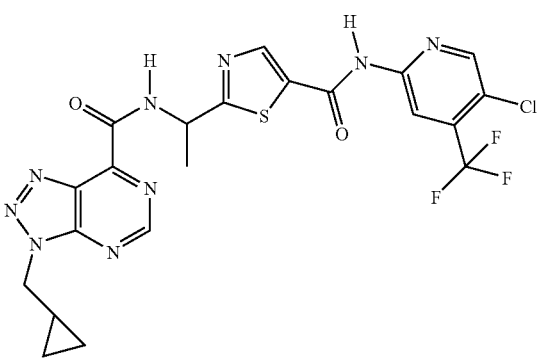 | 1+1H-NMR (500 MHz, DMSO-d$_6$): δ 11.78 (s, 1H), 9.98 (d, J = 7 Hz, 1H), 9.39 (s, 1H), 8.78 (s, 2H), 8.58 (s, 1H), 5.45 (m, 1H), 4.64 (d, J = 7 Hz, 2H), 1.72 (d, J = 7 Hz, 3H), 1.43-1.40 (m, 1H), 0.60-0.48 (m, 4H), MS m/z 552 [M + 1]$^+$. |
| 27D | 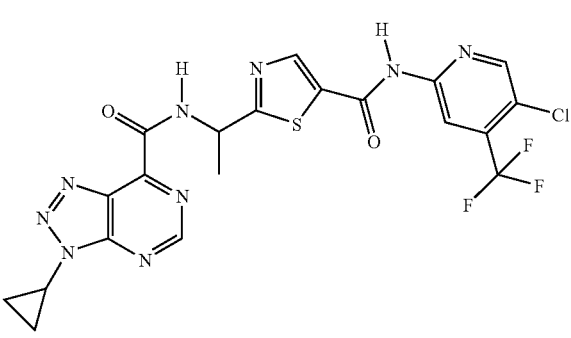 | 1H-NMR (200 MHz, DMSO-d$_6$): δ 11.77 (s, 1H), 10.01 (d, NH), 9.38 (s, 1H), 8.77 (s, 2H), 8.55 (s, 1H), 5.58-5.50 (m, 1H), 4.14-4.11 (m, 1H), 1.72 (d, J = 8 Hz, 3H), 1.40-1.23 (m, 4H); m/z 538 [M + 1]$^+$. |
| 28D | 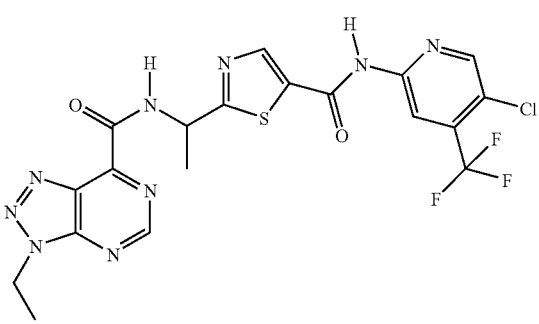 | 1H-NMR (500 MHz, MeOD-d$_4$): δ 9.34 (s, 1H), 8.62 (s, 1H), 8.58 (s, 1H), 8.54 (s, 1H), 5.72-4.71 (m, 1H), 4.91-4.83 (m, 2H), 1.85 (d, J = 7 Hz, 3H), 1.70 (d, J = 7.5 Hz, 3H); m/z 525 [M + 1]$^+$. |
| 29D | 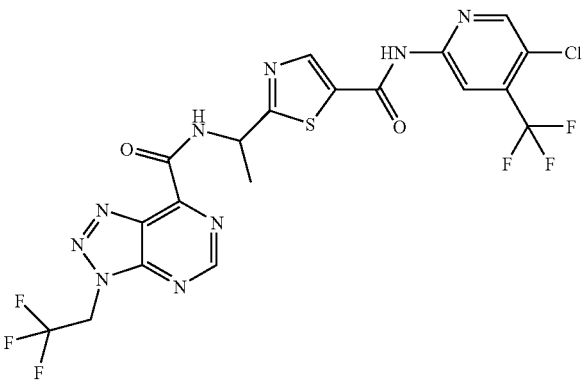 | 1H-NMR (200 MHz, DMSO-d$_6$): δ 11.75 (s, 1H), 9.97 (d, NH), 9.49 (s, 1H), 8.77 (s, 2H), 8.55 (s, 1H), 6.00-5.86 (m, 2H), 5.59-5.52 (m, 1H), 1.72 (d, J = 6.6 Hz, 3H); m/z 580 [M + 1]$^+$. |

TABLE 1-continued

| # | Structure | Characterization Data |
|---|---|---|
| 30D | 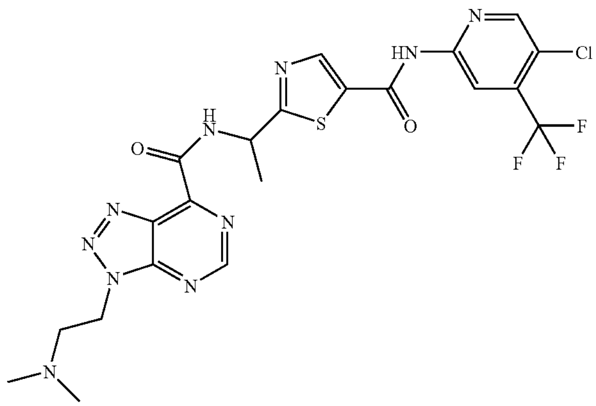 | 1H-NMR (200 MHz, DMSO-$d_6$): δ 11.77 (s, 1H), 10.01 (d, NH), 9.39 (s, 1H), 8.77 (s, 2H), 8.56 (s, 1H), 5.56-5.54 (m, 1H), 4.88 (t, J = 6.0 Hz, 2H), 2.89 (t, J = 6.0 Hz, 2H), 2.16 (s, 6H), 1.70 (d, J = 7.4 Hz, 3H); m/z 569 [M + 1]$^+$. |
| 31D | 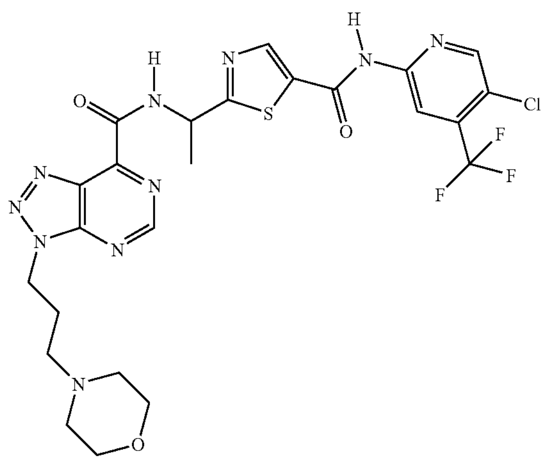 | 1H-NMR (200 MHz, DMSO-$d_6$): δ 11.76 (s, 1H), 10.01 (d, NH), 9.39 (s, 1H), 8.77 (s, 2H), 8.56 (s, 1H), 5.59-5.52 (m, 1H), 4.82 (t, J = 6.6 Hz, 2H), 3.37-3.24 (m, 10H), 2.15-2.11 (m, 2H), 1.72 (d, J = 7 Hz, 3H); m/z 624 [M]$^+$. |
| 32U | 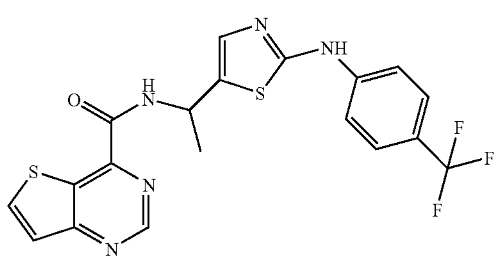 | 1H-NMR (500 MHz, DMSO-$d_6$) δ = 10.49 (s, 1H), 9.89 (d, NH), 9.44 (s, 1H), 8.65 (d, J = 8.0 Hz, 1H), 7.78 (d, J = 8.0 Hz, 2H), 7.76 (d, J = 8.0 Hz, 1H), 7.62 (d, J = 8.0 Hz, 2H), 7.23 (s, 1H), 5.51-5.40 (m, 1H), 1.64 (d, J = 8.0 Hz, 3H) MS m/z 450 [M + 1]$^+$. |

The compounds of the present invention provided in Table 2 were prepared by similar procedures as described in the synthesis of compound 15 using the corresponding acid (Compound 1-11) and amine (Compound A-Rb).

TABLE 2

| # | Structure | Characterization Data |
|---|---|---|
| 1P | 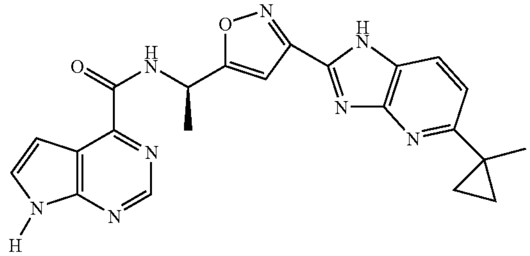 | $^1$H NMR (400.13 MHz, DMSO-$d_6$) δ 13.74 (s, 1H), 9.62 (d, J = 8.3 Hz, 1H), 8.89 (s, 1H), 8.01 (d, J = 8.5 Hz, 1H), 7.83 (d, J = 8.5 Hz, 1H), 7.77 (dd, J = 3.4, 2.4 Hz, 1H), 7.28 (d, J = 8.5 Hz, 1H), 7.05 (dd, J = 3.4, 1.8 Hz, 1H), 7.0 (s, 1H), 5.52 (m, 1H), 1.70 (d, J = 7.2 Hz, 1H), 1.54 (s, 3H), 1.21 (m, 2H), 0.86 (m, 2H) MS: m/z 429 [M + 1]$^+$. |

TABLE 2-continued

| # | Structure | Characterization Data |
|---|---|---|
| 5O | 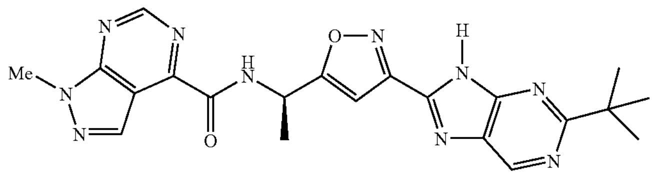 | $^1$H NMR (400.13 MHz, DMSO-d$_6$) δ 14.28 (s, 1H), 9.90 (d, J = 9.1Hz), 9.19 (s, 1H), 9.17 (s, 1H), 8.64 (s, 1H), 7.08 (s, 1H), 5.56 (m, 1H), 4.12 (s, 3H), 1.72 (d, J = 8.1 Hz, 3H), 1.42 (s, 3H) MS: m/z 447 [M + 1]$^+$. |
| 11O | 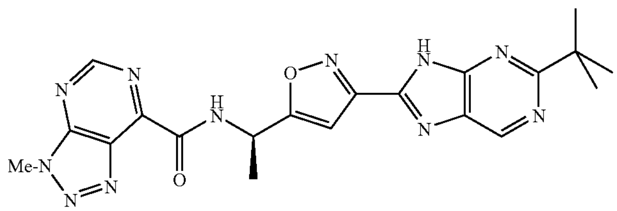 | $^1$H NMR (400 MHz, CDCl3) δ = 9.27 (s, 1H), 9.16 (s, 1H), 8.69 (d, J = 8.5 Hz, 1H), 7.05 (d, J = 0.8 Hz, 1H), 5.84-5.73 (m, 1H), 4.44 (s, 3H), 1.84 (d, J = 7.1 Hz, 3H), 1.46 (s, 9H) MS m/z 448 [M + 1]+. |
| 5P | 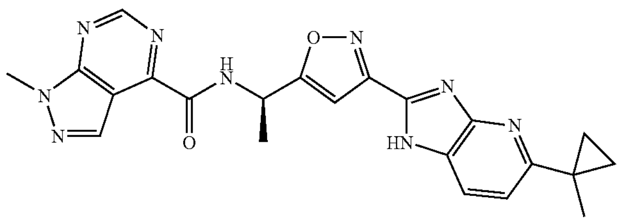 | $^1$H NMR (400 MHz, DMSO-d6) δ = 9.89 (d, J = 8.5 Hz, 1H), 9.19 (s, 1H), 8.64 (s, 1H), 7.97 (d, J = 8.5 Hz, 1H), 7.31 (d, J = 8.6 Hz, 1H), 7.03 (s, 1H), 5.63-5.45 (m, 2H), 4.12 (s, 3H), 1.71 (d, J = 7.1 Hz, 3H), 1.53 (s, 3H), 1.22-1.18 (m, 2H), 0.88-0.83 (m, 2H) MS m/z 444 [M + 1]+. |

The compounds of the present invention provided in Table 3 were prepared by similar procedures as described in the synthesis of compound 35 except the 3-bromo-5-(trifluoromethyl)aniline was replaced with the appropriate amine.

TABLE 3

| # | Structure | Characterization Data |
|---|---|---|
| 46 | 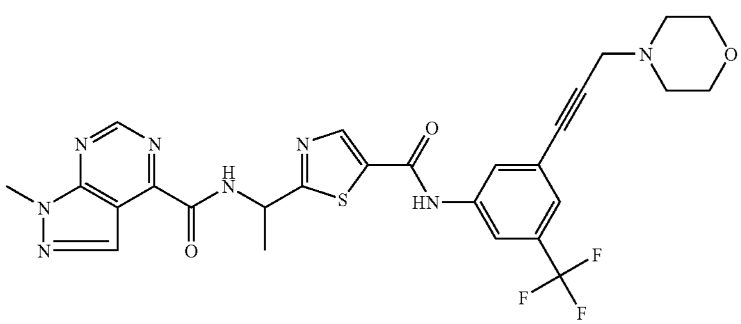 | $^1$H NMR (400 MHz, DMSO-d6) δ = 9.08 (s, 1H), 8.78 (br. s, 1H), 8.75 (s, 1H), 8.54 (s, 1H), 8.09 (s, 1H), 8.01 (1H, s), 7.43, (s, 1H), 5.69 (m, 1H), 4.21 (s 2H), 4.13 (m, 3H), 3.58 (m, 4H), 3.21 (m, 4H), 1.86 (d, J = 6.7Hz) MS m/z 599 [M + 1]$^+$. |
| 47 | 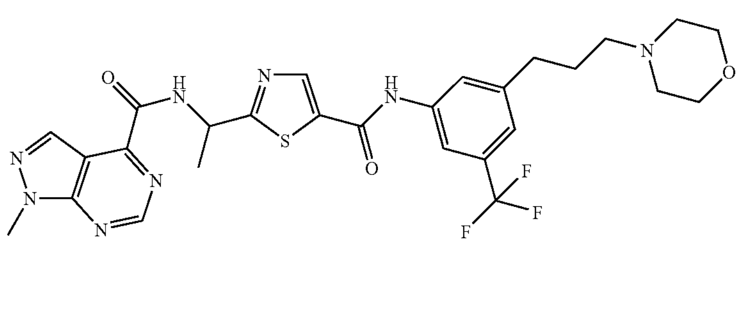 | $^1$H NMR (400 MHz, CDCl3) δ = 9.08 (s, 1H), 9.05 (s, 1H), 8.78 (d, J = 8.7 Hz, 1H), 8.73 (s, 1H), 8.49 (s, 1H), 8.15 (s, 1H), 7.56 (s, 1H), 7.14 (s, 1H), 5.73-5.61 (m, 1H), 4.19 (s, 3H), 4.07-3.90 (m, 4H), 3.32 (br. s, 4H) 3.00 (m, 2H), 2.92-2.76 (m, 2H), 2.29-2.16 (m, 2H), 1.84 (d, J = 6.7 Hz, 3H) MS m/z 603 [M + 1]$^+$. |

TABLE 3-continued

| # | Structure | Characterization Data |
|---|-----------|----------------------|
| 48 | 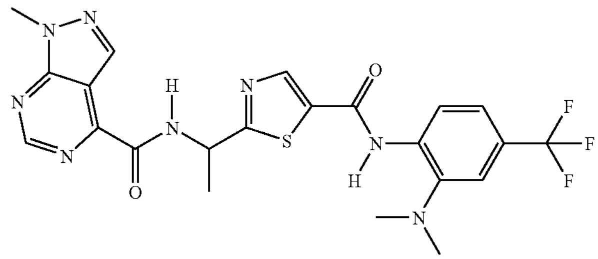 | $^1$H NMR (400 MHz, CDCl3) δ = 9.15 (br. s., 1H), 8.91 (s, 1H), 8.64 (d, J = 8.1 Hz, 1H), 8.60 (s, 1H), 8.33 (d, J = 8.7 Hz, 1H), 8.13 (s, 1H), 7.31 (s, 1H), 7.29 (s, 1H), 5.58-5.48 (m, 1H), 4.04 (s, 3H), 3.34 (s, 6H), 1.70 (d, J = 6.9 Hz, 3H) MS m/z 519 [M + 1]$^+$. |
| 49 | 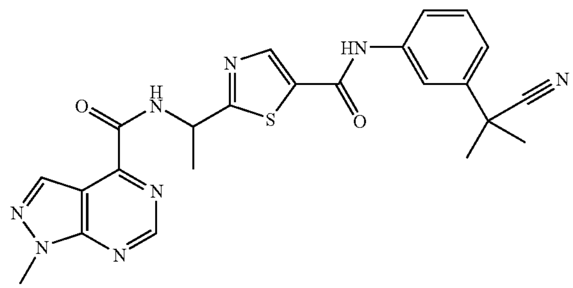 | $^1$H NMR (400 MHz, CDCl3) Shift = 8.89 (s, 1H), 8.62 (d, J = 8.5 Hz, 1H), 8.57 (s, 1H), 8.13 (s, 1H), 8.09 (s, 1H), 7.55 (t, J = 2.0 Hz, 1H), 7.49 (ddd, J = 0.9, 2.1, 8.1 Hz, 1H), 7.22 (t, J = 8.0 Hz, 1H), 7.10 (ddd, J = 0.9, 1.9, 7.9 Hz, 1H), 5.50 (dq, J = 7.0, 8.1 Hz, 1H), 4.04 (s, 3H), 1.68 (d, J = 6.9 Hz, 3H), 1.57 (s, 6H) MS m/z 475 [M + 1]$^+$. |
| 50 | 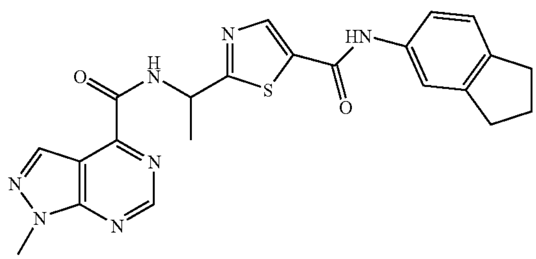 | $^1$H NMR (400 MHz, DMSO-d6) d = 10.25 (s, 1H), 9.98 (d, J = 8.1 Hz, 1H), 9.21 (s, 1H), 8.63 (s, 1H), 8.49 (s, 1H), 7.57 (s, 1H), 7.37 (d, J = 8.1 Hz, 1H), 7.18 (d, J = 8.1 Hz, 1H), 5.52 (quin, J = 7.3 Hz, 1H), 4.12 (s, 3H), 2.83 (dt, J = 7.5, 11.9 Hz, 4H), 2.01 (quin, J = 7.3 Hz, 2H), 1.72 (d, J = 7.1 Hz, 3H); m/z 448 [M + 1]$^+$. |
| 51 | 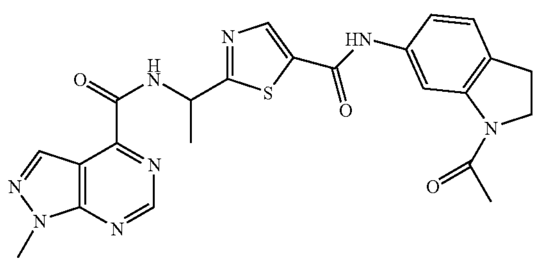 | $^1$H NMR (300 MHz, DMSO-d6) d = 10.36 (s, 1H), 9.97 (d, J = 7.9 Hz, 1H), 9.21 (s, 1H), 8.63 (s, 1H), 8.53 (s, 1H), 8.30 (d, J = 1.9 Hz, 1H), 7.48 (dd, J = 1.7, 8.1 Hz, 1H), 7.17 (d, J = 7.9 Hz, 1H), 5.61-5.45 (m, 1H), 4.18-4.03 (m, 5H), 3.09 (t, J = 8.3 Hz, 2H), 2.16 (s, 3H), 1.72 (d, 3H); m/z 491 [M + 1]$^+$. |
| 52 | 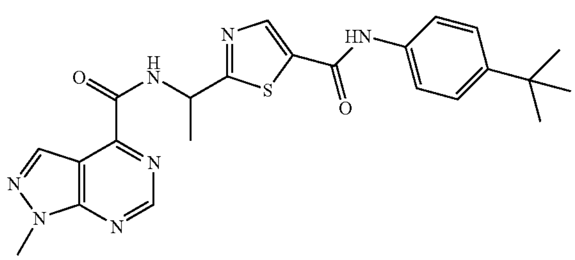 | $^1$H NMR (300 MHz, DMSO-d6) d = 10.30 (s, 1H), 9.98 (d, J = 8.3 Hz, 1H), 9.21 (s, 1H), 8.63 (s, 1H), 8.49 (s, 1H), 7.58 (d, J = 8.7 Hz, 2H), 7.36 (d, J = 8.7 Hz, 2H), 5.60-5.45 (m, 1H), 4.12 (s, 3H), 1.73 (d, J = 7.2 Hz, 3H), 1.27 (s, 9H); m/z 464 [M + 1]$^+$. |
| 53 | 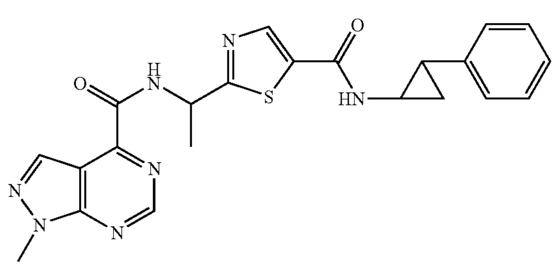 | $^1$H NMR (400 MHz, DMSO-d6) d = 9.95 (d, J = 8.1 Hz, 1H), 9.22-9.17 (m, 1H), 8.85 (d, J = 4.0 Hz, 1H), 8.62 (s, 1H), 8.29-8.22 (m, 1H), 7.31-7.22 (m, 2H), 7.20-7.10 (m, 3H), 5.55-5.43 (m, 1H), 4.17-4.06 (m, 3H), 3.00-2.90 (m, 1H), 2.07 (ddd, J = 3.5, 6.2, 9.5 Hz, 1H), 1.75-1.66 (m, 3H), 1.34-1.26 (m, 1H), 1.26-1.18 (m, 1H) MS m/z 448 [M + 1]$^+$. |

TABLE 3-continued

| # | Structure | Characterization Data |
|---|-----------|----------------------|
| 54 | 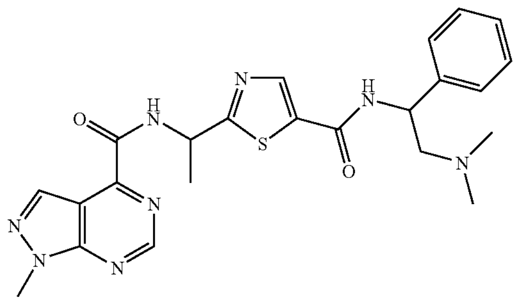 | ¹H-NMR (500 MHz, DMSO-d6): δ 9.10 (s, 1H), 8.61 (s, 1H), 8.35 (s, 1H), 7.37-7.25 (m, 7H), 5.60-5.58 (m, 1H), 5.28-5.25 (m, 1H), 4.15 (s, 3H), 3.00-2.95 (m, 2H), 2.36 (s, 6H), 1.79 (d, J = 7.0 Hz, 3H); m/z 479 [M + 1]⁺. |
| 55 | 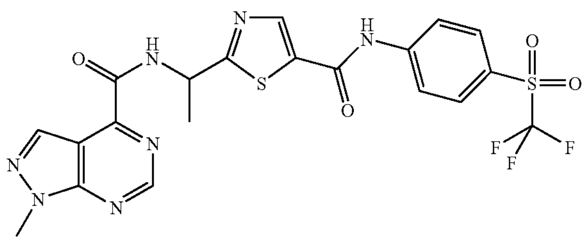 | ¹H-NMR (500 MHz, DMSO-d6): δ 10.99 (s, 1H), 10.02 (d, J = 7.5 Hz, 1H), 9.20 (s, 1H), 8.61 (d, J = 7.5 Hz, 2H), 8.12-8.10 (m, 4H), 5.53-5.52 (m, 1H), 4.11 (s, 3H), 1.73 (d, J = 8.0 Hz, 3H); m/z 540 [M + 1]⁺. |
| 56 | 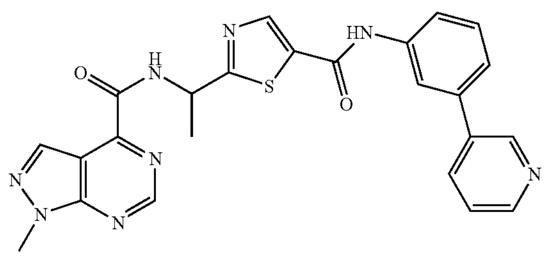 | ¹H NMR (400 MHz, DMSO-d6) d = 10.50 (s, 1H), 10.01 (d, J = 8.1 Hz, 1H), 9.22 (s, 1H), 8.86 (s, 1H), 8.63 (s, 1H), 8.59 (d, J = 3.5 Hz, 1H), 8.54 (s, 1H), 8.07-7.98 (m, 2H), 7.77 (d, J = 6.6 Hz, 1H), 7.55-7.44 (m, 3H), 5.54 (quin, J = 7.2 Hz, 1H), 4.12 (s, 3H), 1.74 (d, J = 7.1 Hz, 3H); m/z 485 [M + 1]⁺. |
| 57 | 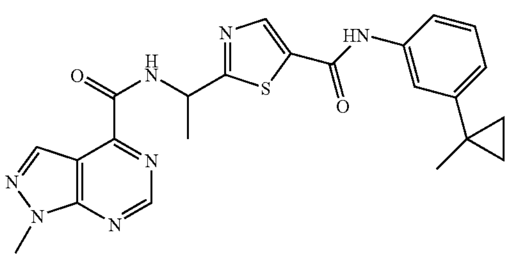 | ¹H NMR (400 MHz, DMSO-d6) d = 10.28 (s, 1H), 9.99 (d, J = 8.1 Hz, 1H), 9.21 (s, 1H), 8.63 (s, 1H), 8.50 (s, 1H), 7.60-7.49 (m, 2H), 7.24 (t, J = 7.8 Hz, 1H), 6.97 (d, J = 8.1 Hz, 1H), 5.53 (quin, J = 7.2 Hz, 1H), 4.12 (s, 3H), 1.73 (d, J = 7.1 Hz, 3H), 0.84-0.70 (m, 4H); m/z 462 [M + 1]⁺. |
| 58 | 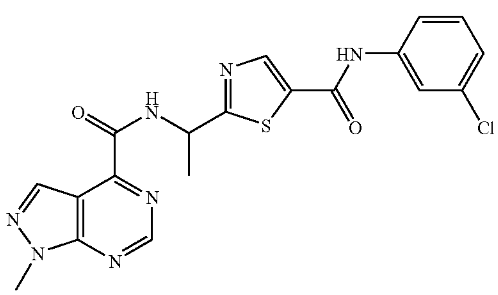 | ¹H-NMR (500 MHz, DMSO-d6): δ 10.51 (s, 1H), 10.01 (d, J = 5.0 Hz, 1H), 9.20 (s, 1H), 8.61 (s, 1H), 8.50 (s, 1H), 7.83 (s, 1H), 7.61 (d, J = 5.0 Hz, 1H), 7.39-7.36 (m, 1H), 7.17 (d, J = 8.0 Hz, 1H), 5.54-5.51 (m, 1H), 4.11 (s, 3H), 1.72 (d, J = 6.0 Hz, 3H); m/z 442 [M + 1]⁺. |

TABLE 3-continued

| # | Structure | Characterization Data |
|---|-----------|----------------------|
| 59 | 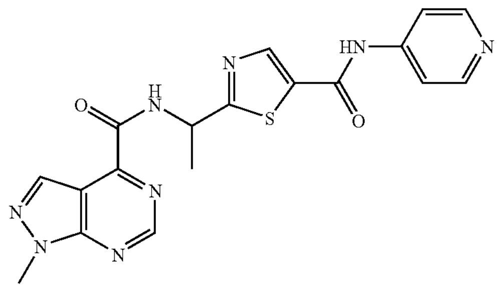 | ¹H-NMR (500 MHz, DMSO-d6): δ 10.67 (s, 1H), 10.02 (d, J = 8.0 Hz, 1H), 9.20 (s, 1H), 8.61 (s, 1H), 8.54 (s, 1H), 8.47 (d, J = 8.0 Hz, 2H), 7.67 (d, J = 8.0 Hz, 2H), 5.54-5.51 (m, 1H), 4.11 (s, 3H), 1.72 (d, J = 6.0 Hz, 3H); m/z 409 [M + 1]⁺. |
| 60 | 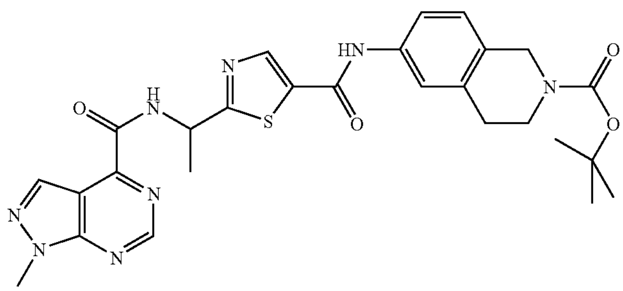 | ¹H-NMR (500 MHz, DMSO-d6): δ 10.33 (s, 1H), 9.99 (d, J = 10.0 Hz, 1H), 9.20 (s, 1H), 8.62 (s, 1H), 8.50 (s, 1H), 7.67 (d, J = 7.5 Hz, 2H), 7.34 (d, J = 7.5 Hz, 2H), 7.10-7.06 (m, 1H), 5.52-5.51 (m, 1H), 4.11 (s, 3H), 1.72 (d, J = 6.0 Hz, 3H); m/z 408 [M + 1]⁺. |
| 61 | 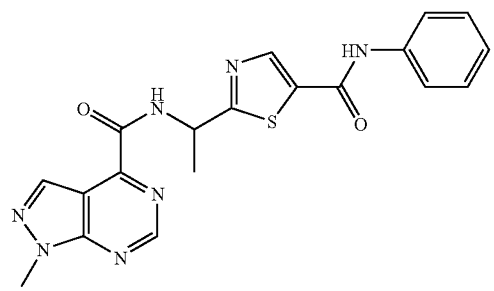 | ¹H-NMR (500 MHz, DMSO-d6): δ 10.37 (s, 1H), 9.96 (s, 1H), 9.20 (s, 1H), 8.61 (s, 1H), 8.49 (s, 1H), 7.57 (s, 1H), 7.52-7.50 (m, 1H), 7.20-7.18 (m, 1H), 5.53-5.50 (m, 1H), 4.23 (s, 2H), 4.11 (s, 3H), 3.36-3.35 (m, 2H), 2.98-2.97 (m, 2H), 1.72 (d, J = 5.0 Hz, 3H); m/z 463 [M + 1]⁺. |
| 62 | 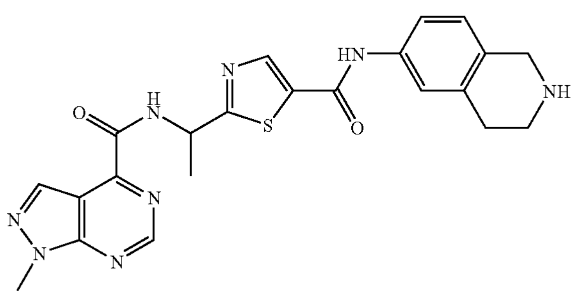 | ¹H-NMR (500 MHz, DMSO-d6): δ 10.31 (s, 1H), 9.99 (d, J = 5.0 Hz, 1H), 9.20 (s, 1H), 8.61 (s, 1H), 8.48 (s, 1H), 7.52 (m, 2H), 7.15 (d, J = 5.0 Hz, 1H), 5.52-5.50 (m, 1H), 4.58-4.53 (m, 2H), 4.11 (s, 3H), 3.64-3.61 (m, 2H), 2.72-2.49 (m, 2H), 2.06 (s, 3H), 1.72 (d, J = 5.0 Hz, 3H); m/z 505 [M + 1]⁺. |
| 63 | 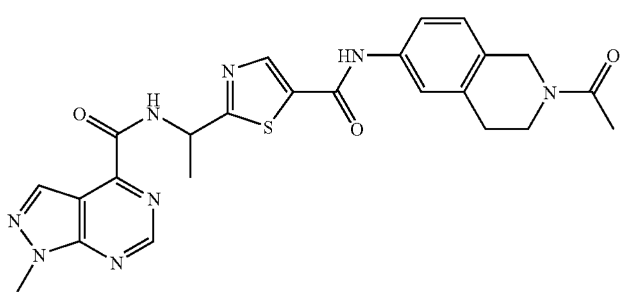 | ¹H-NMR (500 MHz, MeOD-d4): δ 9.02 (s, 1H), 8.53 (s, 1H), 8.31 (s, 1H), 7.32-7.28 (m, 2H), 7.17 (d, J = 10.0 Hz, 1H), 5.53-5.50 (m, 1H), 4.21 (s, 2H), 4.06 (s, 3H), 3.71-3.70 (m, 1H), 3.57-3.50 (m, 1H), 3.25-3.20 (m, 2H), 2.96-2.93 (m, 2H), 1.72 (d, J = 5.0 Hz, 3H); m/z 521 [M + 1]⁺. |

TABLE 3-continued

| # | Structure | Characterization Data |
|---|---|---|
| 64 | 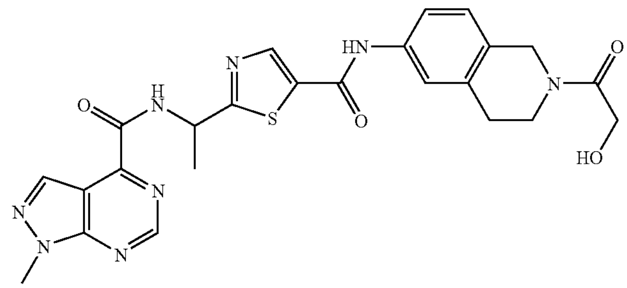 | $^1$H-NMR (500 MHz, DMSO-d6): δ 10.52 (s, 1H), 10.01 (d, J = 5.0 Hz, 1H), 9.20 (s, 1H), 8.62 (s, 1H), 8.50 (s, 1H), 7.63 (d, J = 11.5 Hz, 1H), 7.46 (d, J = 8.0 Hz, 1H), 7.39-7.37 (m, 1H), 6.94-6.91 (m, 1H), 5.54-5.51 (m, 1H), 4.11 (s, 3H), 1.72 (d, J = 6.0 Hz, 3H); m/z 426 [M + 1]$^+$. |
| 65 | 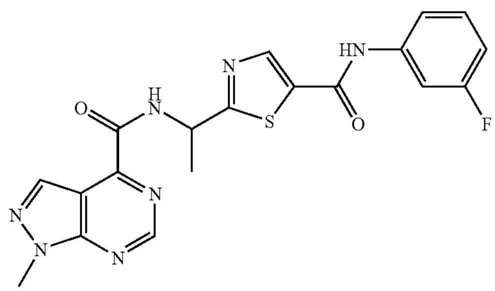 | $^1$H-NMR (500 MHz, DMSO-d6): δ 11.14 (s, 1H), 9.92 (d, J = 7.5 Hz, 1H), 9.15 (s, 1H), 8.78 (s, 1H), 8.57 (s, 1H), 8.47 (s, 1H), 8.05 (d, J = 5.0 Hz, 1H), 7.85 (t, J = 5.0 Hz, 1H), 7.20 (d, J = 5.0 Hz, 1H), 5.49-5.48 (m, 1H), 4.07 (s, 3H), 1.72 (d, J = 5.0 Hz, 3H); m/z 409 [M + 1]$^+$. |
| 66 | 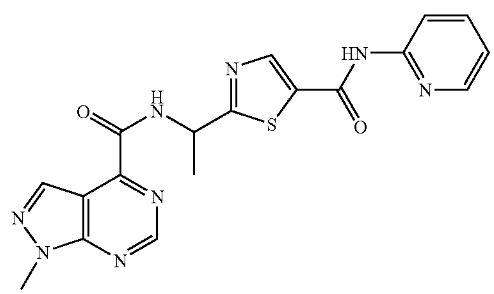 | $^1$H-NMR (500 MHz, DMSO-d6): δ 10.40 (s, 1H), 9.98 (d, J = 5.0 Hz, 1H), 9.20 (s, 1H), 8.61 (s, 1H), 8.49 (s, 1H), 7.53 (d, J = 10.0 Hz, 1H), 7.18 (d, J = 10.0 Hz, 1H), 5.53-5.50 (m, 1H), 4.11 (s, 3H), 3.64-3.05 (m, 6H), 2.92 (s, 3H), 1.72 (d, J = 5.0 Hz, 3H); m/z 477 [M + 1]$^+$. |
| 67 | 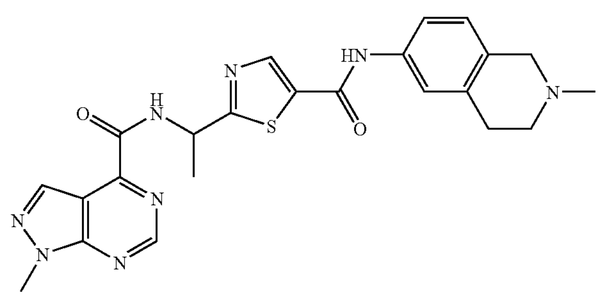 | $^1$H-NMR (500 MHz, DMSO-d6): δ 10.41 (s, 1H), 9.99 (d, J = 10 Hz, 1H), 9.20 (s, 1H), 8.61 (s, 1H), 8.50 (s, 1H), 7.62 (s, 1H), 7.54 (d, J = 5.0 Hz, 1H), 7.21 (d, J = 5.0 Hz, 1H), 5.51-5.50 (m, 1H), 4.11 (s, 3H), 3.63-3.12 (m, 7H), 1.72 (d, J = 5.0 Hz, 3H), 1.33-1.31 (q, 6H); m/z 505 [M + 1]$^+$. |
| 68 | 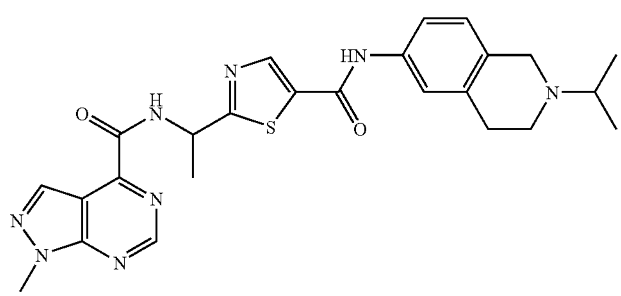 | $^1$H-NMR (500 MHz, DMSO-d6): δ 9.92 (d, J = 10.0 Hz, 1H), 9.19 (s, 1H), 8.60 (s, 1H), 8.35 (d, J = 10.0 Hz, 1H), 8.27 (s, 1H), 5.48-5.45 (m, 1H), 4.11 (s, 3H), 3.68 (bs, 1H), 1.78-1.77 (m, 2H), 1.68 (d, J = 5.0 Hz, 3H), 1.67-1.66 (m, 2H), 1.65-1.64 (m, 2H), 1.25-1.23 (m, 5H); m/z 414 [M + 1]$^+$. |

TABLE 3-continued

| # | Structure | Characterization Data |
|---|---|---|
| 69 | 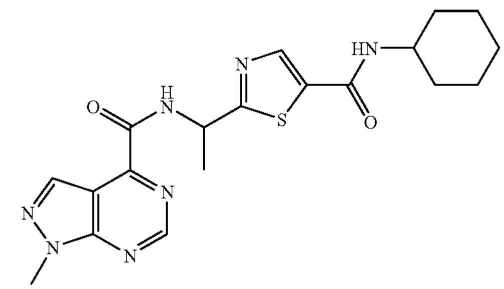 | ¹H-NMR (500 MHz, DMSO-d6): δ 10.47 (s, 1H), 10.00 (d, J = 5.0 Hz, 1H), 9.20 (s, 1H), 8.61 (s, 1H), 8.50 (s, 1H), 7.97 (s, 1H), 7.66 (d, J = 5.0 Hz, 1H), 7.31-7.30 (m, 2H), 5.53-5.51 (m, 1H), 4.11 (s, 3H), 1.72 (d, J = 6.0 Hz, 3H); m/z 486 [M + 1]⁺. |
| 70 | 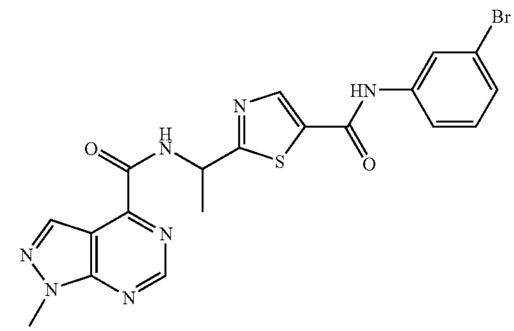 | ¹H-NMR (500 MHz, DMSO-d6): δ 11.05 (s, 1H), 10.27 (s, 1H), 9.98 (d, J = 10.0 Hz, 1H), 9.20 (s, 1H), 8.62 (s, 1H), 8.50 (s, 1H), 7.93 (s, 1H), 7.47 (d, J = 10.0 Hz, 1H), 7.28 (s, 1H), 7.19 (d, J = 10.0 Hz, 1H), 6.36 (s, 1H), 5.53-5.51 (m, 1H), 4.11 (s, 3H), 1.73 (d, J = 10.0 Hz, 3H); m/z 447 [M + 1]⁺. |
| 71 | 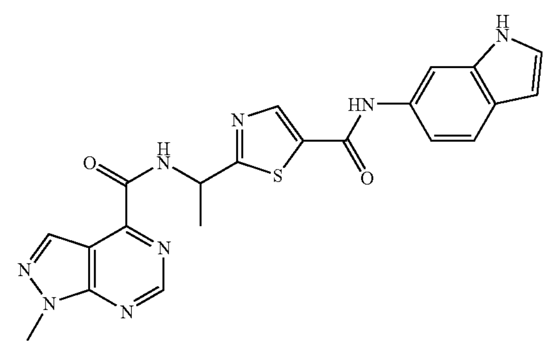 | ¹H-NMR (500 MHz, DMSO-d6): δ 10.27 (s, 1H), 9.98 (d, J = 5.0 Hz, 1H), 9.20 (s, 1H), 8.61 (s, 1H), 8.49 (s, 1H), 7.49-7.45 (m, 2H), 7.21 (t, J = 10.0 Hz, 1H), 6.93 (d, J = 10.0 Hz, 1H), 5.53-5.50 (m, 1H), 4.11 (s, 3H), 2.28 (s, 3H), 1.72 (d, J = 6.0 Hz, 3H); m/z 422 [M + 1]⁺. |
| 72 | 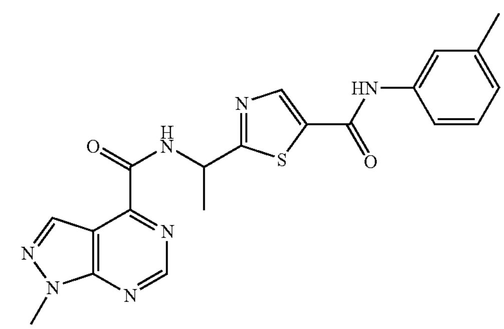 | ¹H-NMR (500 MHz, DMSO-d6): δ 9.15 (s, 1H), 8.78 (s, 1H), 8.57 (s, 1H), 8.47 (s, 1H), 8.29 (s, 1H), 8.05 (d, J = 5.0 Hz, 1H), 7.40 (d, J = 5.0 Hz, 1H), 5.49-5.48 (m, 1H), 4.07 (s, 3H), 1.70 (d, J = 5.0 Hz, 3H); m/z 409 [M + 1]⁺. |
| 73 | 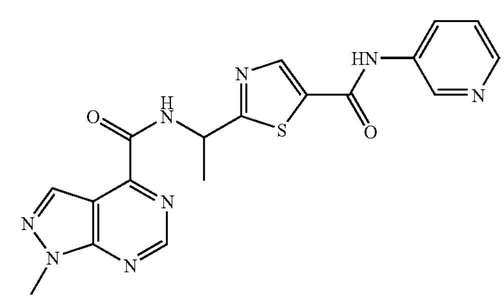 | ¹H-NMR (CDCl3, 200 MHz): δ 9.04 (s, 1H), 8.77-8.74 (m, 2H), 8.23 (s, 1H), 8.00-7.96 (m, 2H), 7.85 (d, J = 8 Hz, 1H), 7.14 (d, J = 8 Hz, 1H), 5.69-5.61 (m, 1H), 4.18 (s, 3H), 3.78 (s, 2H), 2.19 (s, 2H), 1.84 (d, J = 7 Hz, 3H), 1.35 (s, 6H); m/z 519 [M + 1]⁺. |

TABLE 3-continued

| # | Structure | Characterization Data |
|---|---|---|
| 74 | 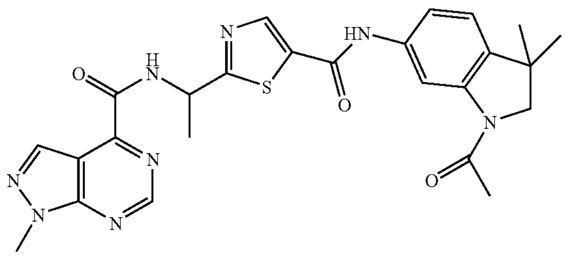 | ¹H-NMR (500 MHz, DMSO-d6): δ 10.42 (s, 1H), 9.99 (d, J = 10.0 Hz, 1H), 9.78 (s, 1H), 9.20 (s, 1H), 8.62 (s, 1H), 8.50 (s, 1H), 7.60 (s, 1H), 7.45 (d, J = 10.0 Hz, 1H), 7.29 (d, J = 10.0 Hz, 1H), 6.94 (d, J = 10.0 Hz, 1H), 5.52-5.51 (m, 1H), 4.11 (s, 3H), 2.98 (s, 3H), 1.72 (d, J = 5.0 Hz, 3H); m/z 501 [M + 1]⁺. |
| 75 | 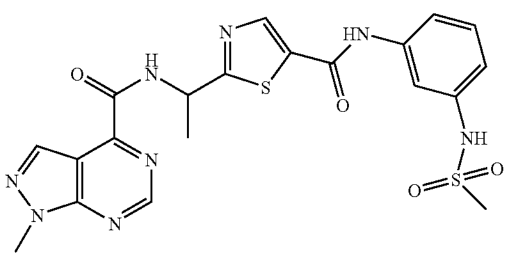 | ¹H-NMR (500 MHz, DMSO-d6): δ 10.23 (s, 1H), 9.90 (bs, 1H), 9.19 (s, 1H), 8.61 (s, 1H), 8.47 (s, 1H), 7.31 (s, 1H), 7.21-7.20 (m, 2H), 6.67 (d, J = 5.0 Hz, 1H), 5.54-5.51 (m, 1H), 4.56-4.52 (m, 1H), 4.11 (s, 3H), 1.73 (d, J = 5.0 Hz, 3H), 1.26-1.25 (m, 6H); m/z 466 [M + 1]⁺. |
| 76 | 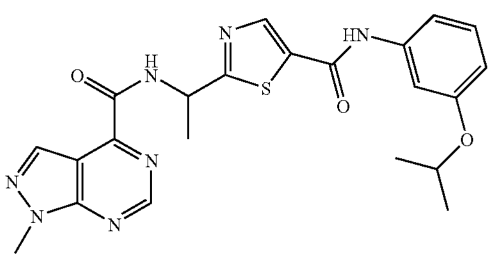 | ¹H-NMR (500 MHz, DMSO-d6): δ 9.14 (s, 1H), 8.56 (s, 1H), 8.44 (s, 1H), 7.53 (d, J = 10.0 Hz, 2H), 7.26 (d, J = 10.0 Hz, 1H), 7.03 (d, J = 10.0 Hz, 1H), 5.48-5.46 (m, 1H), 4.07 (s, 3H), 3.35 (s, 2H), 2.35-2.26 (m, 4H), 1.69 (d, J = 5.0 Hz, 3H), 1.43-1.42 (m, 4H), 1.32-1.31 (m, 2H); m/z 505 [M + 1]⁺. |
| 77 | 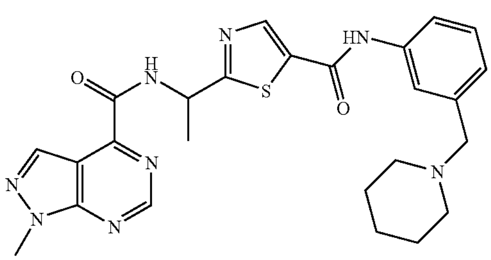 | ¹H-NMR (500 MHz, DMSO-d6): δ 10.59 (s, 1H), 10.00 (d, J = 5.0 Hz, 1H), 9.20 (s, 1H), 8.61 (s, 1H), 8.51 (s, 1H), 7.79 (s, 1H), 7.68 (d, J = 10.0 Hz, 1H), 7.47 (t, J = 5.0 Hz, 1H), 7.10 (d, J = 5.0 Hz, 1H), 5.54-5.51 (m, 1H), 4.11 (s, 3H), 1.73 (d, J = 10.0 Hz, 3H); m/z 492 [M + 1]⁺. |
| 78 | 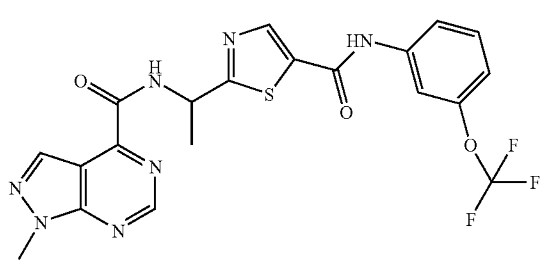 | ¹H-NMR (500 MHz, DMSO-d6): δ 10.20 (s, 1H), 9.98 (d, J = 5.0 Hz, 1H), 9.20 (s, 1H), 8.61 (s, 1H), 8.48 (s, 1H), 7.26 (s, 1H), 7.18 (d, J = 10.0 Hz, 2H), 6.71 (d, J = 5.0 Hz, 1H), 5.53-5.50 (m, 1H), 4.11 (s, 3H), 3.73-3.72 (m, 4H), 3.07-3.06 (m, 4H), 1.72 (d, J = 5.0 Hz, 3H); m/z 493 [M + 1]⁺. |
| 79 | 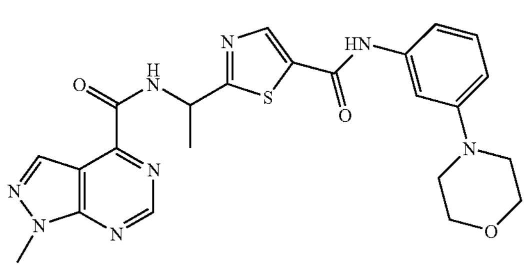 | ¹H-NMR (500 MHz, DMSO-d6): δ 10.34 (s, 1H), 9.99 (d, J = 7.5 Hz, 1H), 9.20 (s, 1H), 8.62 (s, 1H), 8.51 (s, 1H), 7.63 (d, J = 10.0 Hz, 2H), 7.28 (t, J = 5.0 Hz, 1H), 7.04 (d, J = 7.5 Hz, 1H), 5.53-5.50 (m, 1H), 4.11 (s, 3H), 3.55-3.42 (m, 4H), 3.41 (d, J = 7.5 Hz, 2H), 2.34-2.30 (m, 4H), 1.72 (d, J = 5.0 Hz, 3H); m/z 507 [M + 1]⁺. |

TABLE 3-continued

| # | Structure | Characterization Data |
|---|---|---|
| 80 | 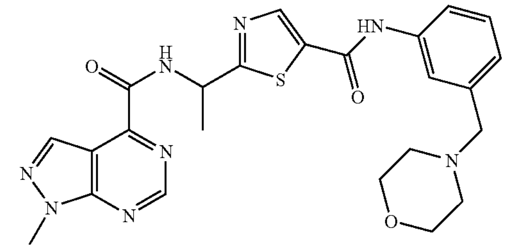 | ¹H-NMR (500 MHz, DMSO-d6): δ 10.30 (s, 1H), 9.98 (d, NH), 9.20 (s, 1H), 8.62 (s, 1H), 8.49 (s, 1H), 7.60-7.50 (m, 2H), 7.24 (s, 1H), 6.97 (s, 1H), 5.53-5.49 (m, 1H), 4.11 (s, 3H), 3.56 (s, 3H) 2.82-2.75 (m, 4H), 1.72 (d, J = 7 Hz, 3H); m/z 494 [M + 1]⁺. |
| 81 | 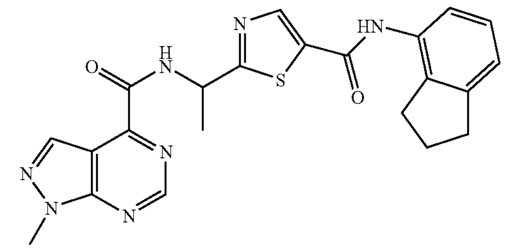 | ¹H NMR (300 MHz, DMSO-d6) d = 10.10 (s, 1H), 9.97 (d, J = 7.9 Hz, 1H), 9.21 (s, 1H), 8.63 (s, 1H), 8.46 (s, 1H), 7.19-7.05 (m, 3H), 5.61-5.44 (m, 1H), 4.12 (s, 3H), 2.94-2.74 (m, 4H), 1.97 (quin, J = 7.4 Hz, 2H), 1.73 (d, 3H); m/z 448 [M + 1]⁺. |
| 82 | 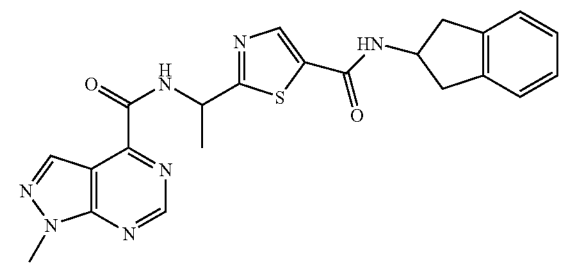 | ¹H NMR (300 MHz, DMSO-d6) d = 9.93 (d, J = 7.9 Hz, 1H), 9.20 (s, 1H), 8.81 (d. J = 6.8 Hz, 1H), 8.62 (s, 1H), 8.30 (s, 1H), 7.27-7.11 (m, 4H), 5.56-5.42 (m, 1H), 4.63 (sxt, J = 7.1 Hz, 1H), 4.12 (s, 3H), 3.23 (dd, J = 7.9, 15.9 Hz, 2H), 2.91 (dd, J = 6.2, 16.1 Hz, 2H), 1.69 (d, J = 7.2 Hz, 3H); m/z 448 [M + 1]⁺. |
| 83 | 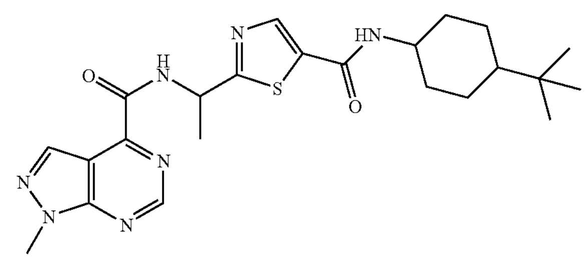 | ¹H NMR (300 MHz, DMSO-d6) d = 9.92 (d, J = 7.2 Hz, 1H), 9.20 (s, 1H), 8.62 (s, 1H), 8.38 (s, 1H), 8.35 (d, J = 7.9 Hz, 1H), 8.27 (s, 1H), 8.05 (d, J = 6.0 Hz, 1H), 5.55-5.41 (m, 1H), 4.12 (s, 3H), 4.02-3.52 (m, 1H), 1.99-0.89 (m, 12H), 0.84 (s, 9H); m/z 470 [M + 1]⁺. |
| 84 | 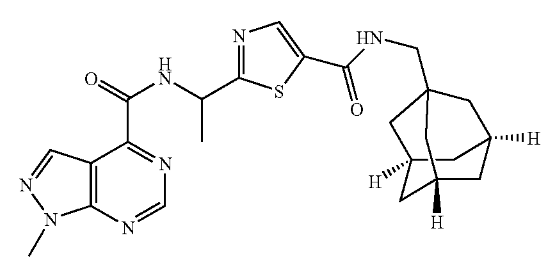 | ¹H NMR (300 MHz, DMSO-d6) d = 9.92 (d, J = 7.9 Hz, 1H), 9.20 (s, 1H), 8.62 (s, 1H), 8.44 (t, J = 6.2 Hz, 1H), 8.33 (s, 1H), 5.56-5.41 (m, 1H), 4.12 (s, 3H), 2.93 (d, J = 6.4 Hz, 2H), 1.91 (br. s., 3H), 1.74-1.51 (m, 9H), 1.45 (d, J = 2.3 Hz, 6H); m/z 480 [M + 1]⁺. |
| 85 | 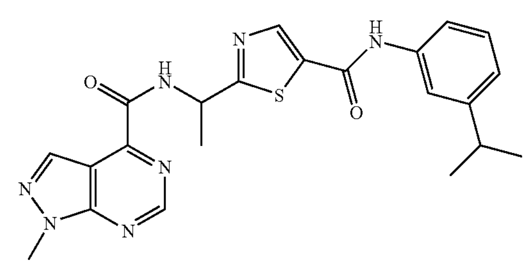 | ¹H-NMR (500 MHz, DMSO-d6): δ 10.28 (s, 1H), 9.98 (d, J = 10.0 Hz, 1H), 9.20 (s, 1H), 8.61 (s, 1H), 8.49 (s, 1H), 7.53-7.51 (m, 2H), 7.24 (t, J = 5.0 Hz, 1H), 6.99 (d, J = 5.0 Hz, 1H), 5.53-5.50 (m, 1H), 4.11 (s, 3H), 2.86-2.84 (m, 1H), 1.72 (d, J = 5.0 Hz, 3H), 1.19-1.18 (m, 6H); m/z 450 [M + 1]⁺. |

TABLE 3-continued

| # | Structure | Characterization Data |
|---|---|---|
| 86 | 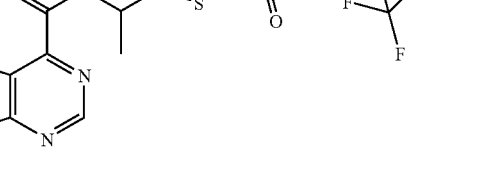 | $^1$H-NMR (500 MHz, DMSO-d6): δ 9.93 (d, J = 8.5 Hz, 1H), 9.18 (s, 1H), 8.69 (s, 1H), 8.60 (s, 1H), 8.19 (s, 1H), 7.56-7.49 (m, 4H), 5.48-5.45 (m, 1H), 4.10 (s, 3H), 3.47-3.45 (m, 2H), 2.91-2.88 (m, 2H), 1.68 (d, J = 7.0 Hz, 3H); m/z 504 [M + 1]$^+$. |
| 87 | 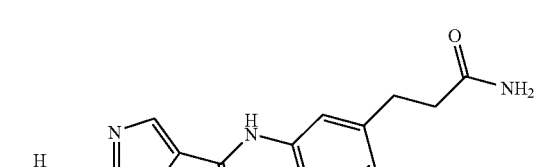 | $^1$H-NMR (500 MHz, DMSO-d6): δ 9.13 (s, 1H), 8.64 (s, 1H), 8.43 (s, 1H), 7.53 (s, 1H), 7.49 (d, J = 8 Hz, 1H), 7.28 (t, J = 7.5 Hz, 1H), 7.05 (d, J = 7.5 Hz, 1H), 5.65-5.63 (m, 1H), 4.17 (s, 3H), 2.94 (t, J = 8 Hz, 2H), 2.54 (t, J = 8 Hz, 2H), 1.83 (d, J = 7 Hz, 3H); m/z 479 [M + 1]$^+$. |
| 88 | 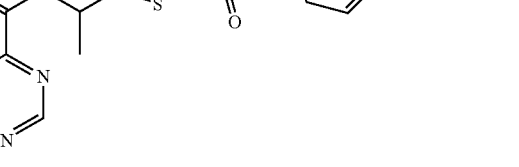 | $^1$H-NMR (500 MHz, MeOD-d4): δ 9.13 (s, 1H), 8.64 (s, 1H), 8.44 (s, 1H), 7.60 (d, J = 8 Hz, 1H), 7.53 (s, 1H), 7.28 (t, J = 8 Hz, 1H), 7.10 (d, J = 8 Hz, 1H), 5.66-5.62 (m, 1H), 4.17 (s, 3H), 3.56 (s, 2H) 1.83 (d, J = 7 Hz, 3H); m/z 466 [M + 1]$^+$. |
| 89 | 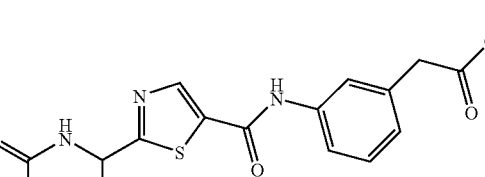 | $^1$H-NMR (500 MHz, DMSO-d6): δ 10.04 (s, 1H), 9.56 (d, J = 8.0 Hz, 1H), 9.19 (s, 1H), 8.61 (s, 1H), 8.45 (s, 1H), 6.19 (m, 2H), 6.79 (d, J = 7.0 Hz, 1H), 5.54 (s, 1H), 5.51 (q, J = 8.0 Hz, 1H), 4.11 (s, 3H), 3.15 (s, 2H), 1.71 (d, 3H), 1.18 (s, 9H); m/z 477 [M + 1]$^+$. |
| 90 | 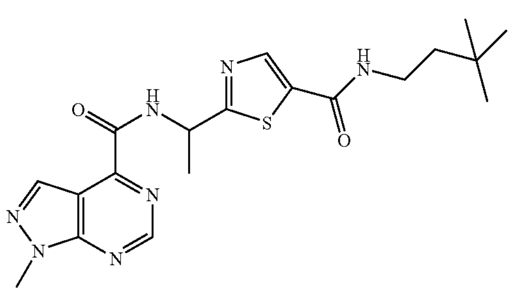 | $^1$H-NMR (500 MHz, DMSO-d6): δ 9.92 (d, J = 10.0 Hz, 1H), 9.18 (s, 1H), 8.60 (s, 1H), 8.52 (s, 1H), 8.22 (s, 1H), 5.45-5.41 (m, 1H), 4.10 (s, 3H), 3.21-3.19 (m, 2H), 1.68 (d, J = 5.0 Hz, 3H), 1.42-1.38 (m, 2H), 0.89 (s, 9H); m/z 416 [M + 1]$^+$. |

TABLE 3-continued

| # | Structure | Characterization Data |
|---|---|---|
| 91 | 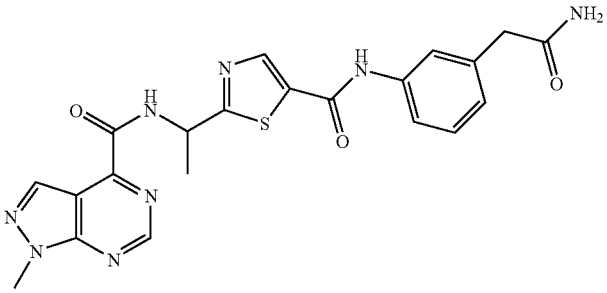 | ¹H-NMR (500 MHz, DMSO-d6): δ 10.35 (s, 1H), 9.98 (d, NH), 9.20 (s, 1H), 8.62 (s, 1H), 8.51 (s, 1H), 7.53-7.56 (m, 2H), 7.46 (s, 1H), 7.25 (t, J = 8 Hz, 1H), 7.00 (d, J = 8 Hz, 1H), 5.53-5.49 (m, 1H), 4.11 (s, 3H), 1.72 (d, J = 7 Hz, 3H); m/z 465 [M + 1]⁺. |
| 92 | 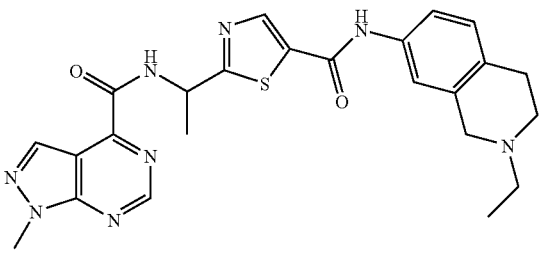 | ¹H-NMR (500 MHz, DMSO-d6): δ 10.41 (s, 1H), 9.99 (d, J = 5.0 Hz, 1H), 9.20 (s, 1H), 8.61 (s, 1H), 8.50 (s, 1H), 7.61 (s, 1H), 7.54 (d, J = 10.0 Hz, 1H), 7.20 (d, J = 10.0 Hz, 1H), 5.53-5.50 (m, 1H), 4.51-4.484 (m, 1H), 4.25-4.22 (m, 1H), 4.11 (s, 3H), 3.71-3.70 (m, 2H), 3.27-3.25 (m, 2H), 3.10-3.08 (m, 2H), 1.72 (d, J = 5.0 Hz, 3H), 1.31-1.28 (m, 3H); m/z 491 [M + 1]⁺. |
| 93 | 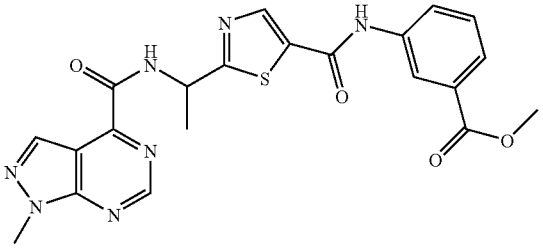 | ¹H-NMR (500 MHz, DMSO-d6): δ 10.56 (s, 1H), 10.00 (d, NH), 9.20 (s, 1H), 9.78 (s, 1H), 9.65 (s, 1H), 9.48 (s, 1H), 8.01 (d, J = 8 Hz, 1H), 7.78 (d, J = 8 Hz, 1H), 7.65 (t, J = 8 Hz, 1H), 5.55-5.50 (m, 1H), 4.11 (s, 3H), 3.82 (s, 3H), 1.72 (d, J = 7 Hz, 3H); m/z 466 [M + 1]⁺. |
| 94 | 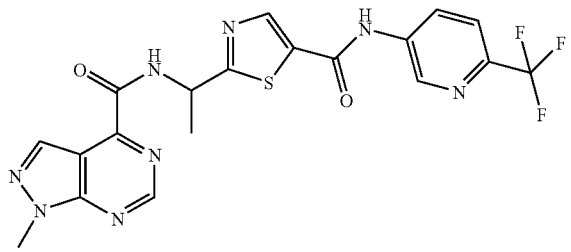 | ¹H-NMR (500 MHz, DMSO-d6): δ 10.89 (s, 1H), 10.02 (d, J = 5.0 Hz, 1H), 9.20 (s, 1H), 8.99 (s, 1H), 8.61 (s, 1H), 8.56 (s, 1H), 8.39 (d, J = 7.5 Hz, 1H), 7.91 (d, J = 5.0 Hz, 1H), 5.54-5.51 (m, 1H), 4.11 (s, 3H), 1.73 (d, J = 5.0 Hz, 3H); m/z 477 [M + 1]⁺. |
| 95 | 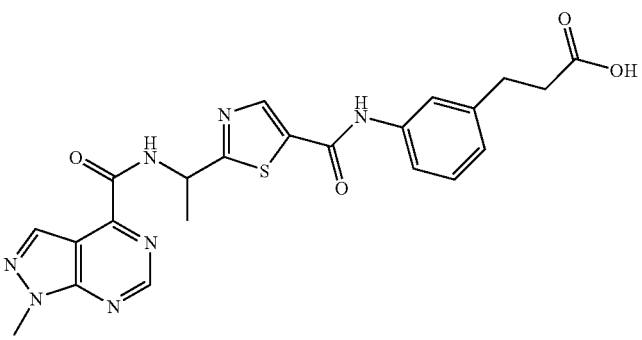 | ¹H-NMR (500 MHz, DMSO-d6): δ 12.05 (bs, 1H), 10.30 (s, 1H), 9.95 (s, 1H), 9.19 (s, 1H), 8.61 (s, 1H), 8.49 (s, 1H), 7.50-7.45 (m, 2H), 7.23 (s, 1H), 6.97 (s, 1H), 5.53-5.49 (m, 1H), 4.11 (s, 3H), 2.82-2.75 (m, 4H), 1.72 (d, J = 7 Hz, 3H); m/z 480 [M + 1]⁺. |

TABLE 3-continued

| # | Structure | Characterization Data |
|---|---|---|
| 96 | 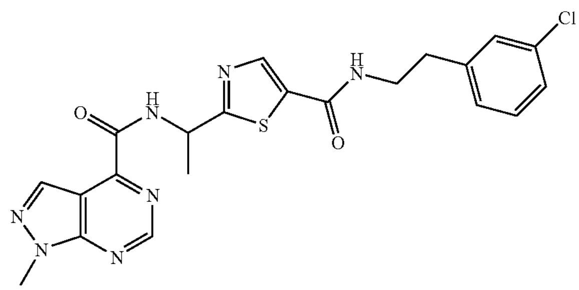 | ¹H-NMR (500 MHz, DMSO-d6): δ = 9.93 (d, J = 10.0 Hz, 1H), 9.18 (s, 1H), 8.69 (s, 1H), 8.68 (s, 1H), 8.21 (s, 1H), 7.30-7.15 (m, 4H), 5.48-5.45 (m, 1H), 4.10 (s, 3H), 3.44-3.42 (m, 2H), 2.81-2.78 (m, 2H), 1.68 (d, J = 5.0 Hz, 3H); m/z 470 [M + 1]⁺. |
| 97 | 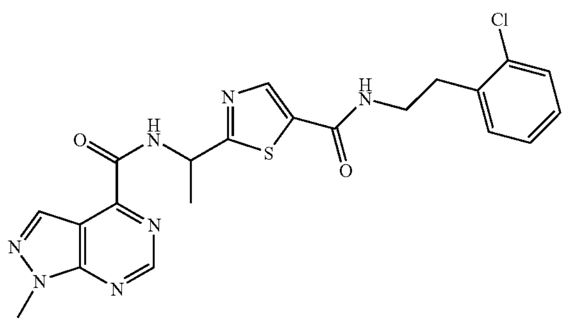 | ¹H-NMR (500 MHz, DMSO-d6): δ 9.93 (d, J = 10.0 Hz, 1H), 9.18 (s, 1H), 8.69 (s, 1H), 8.68 (s, 1H), 8.21 (s, 1H), 7.30-7.15 (m, 4H), 5.48-5.45 (m, 1H), 4.10 (s, 3H), 3.44-3.42 (m, 2H), 2.81-2.78 (m, 2H), 1.68 (d, J = 5.0 Hz, 3H); m/z 470 [M + 1]⁺. |
| 98 | 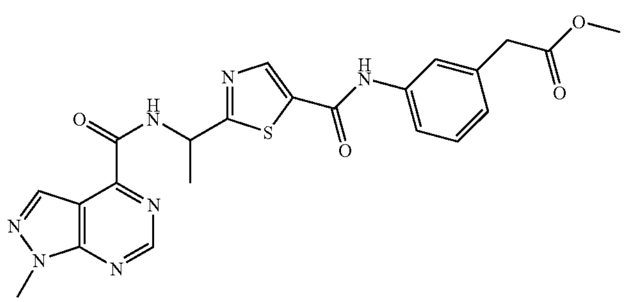 | ¹H-NMR (500 MHz, DMSO-d6): δ 10.36 (s, 1H), 9.98 (d, NH), 9.20 (s, 1H), 8.61 (s, 1H), 8.50 (s, 1H), 7.60-7.56 (m, 2H), 7.28 (t, J = 8 Hz, 1H), 7.00 (d, J = 7.5 Hz, 1H), 5.53-5.49 (m, 1H), 4.11 (s, 3H), 3.65 (s, 2H) 3.60 (s, 3H), 1.72 (d, J = 7 Hz, 3H); m/z 480 [M + 1]⁺. |
| 99 | 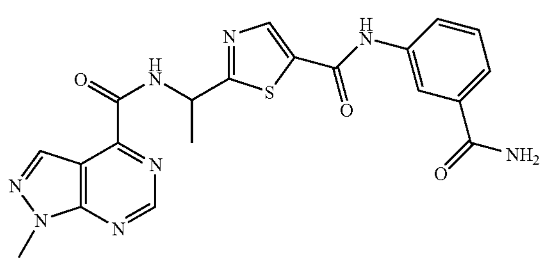 | ¹H-NMR (DMSO-D6 + D2O, 500 MHz): δ 9.15 (s, 1H), 8.57 (s, 1H), 8.48 (s, 1H), 8.06 (s, 1H), 7.81 (d, J = 8.5 Hz, 1H), 7.57 (d, J = 8.5 Hz, 1H), 7.42 (t, J = 8.5 Hz, 1H), 5.54-5.49 (m, 1H), 4.11 (s, 3H), 1.72 (d, J = 7 Hz, 3H); m/z 451 [M + 1]⁺. |
| 100 | 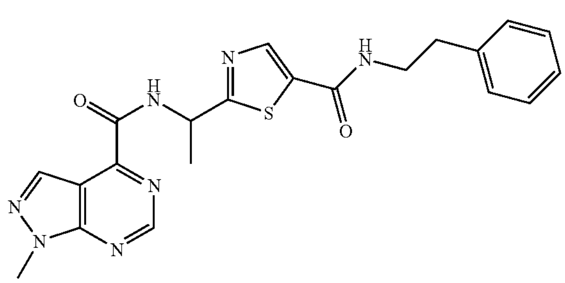 | ¹H-NMR (500 MHz, DMSO-d6): δ 9.98 (d, J = 8.5 Hz, 1H), 9.18 (s, 1H), 8.65 (s, 1H), 8.60 (s, 1H), 8.21 (s, 1H), 7.26-7.17 (m, 5H), 5.54-5.50 (m, 1H), 4.10 (s, 3H), 3.42-3.40 (m, 2H), 2.80-2.77 (m, 2H), 1.68 (d, J = 7.0 Hz, 3H); m/z 436 [M + 1]⁺. |

TABLE 3-continued

| # | Structure | Characterization Data |
|---|---|---|
| 101 | 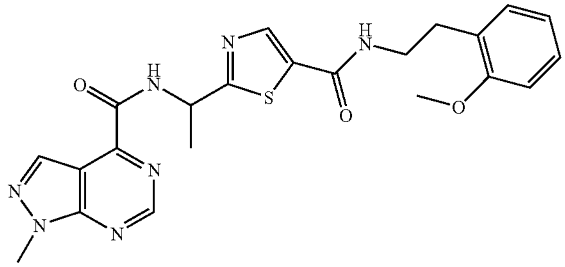 | ¹H-NMR (500 MHz, DMSO-d6): δ 9.93 (d, J = 10.0 Hz, 1H), 9.19 (s, 1H), 8.66 (s, 1H), 8.60 (s, 1H), 8.22 (s, 1H), 7.17-7.08 (m, 2H), 6.94 (d, J = 10.0 Hz, 1H), 6.85 (d, J = 10.0 Hz, 1H), 5.47-5.46 (m, 1H), 4.10 (s, 3H), 3.75 (s, 3H), 3.37-3.35 (m, 2H), 2.78-2.75 (m, 2H), 1.68 (d, J = 5.0 Hz, 3H); m/z 466 [M + 1]⁺. |
| 102 | 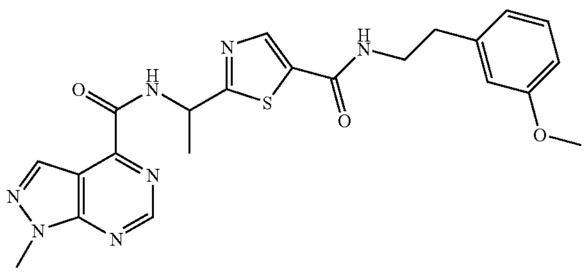 | ¹H-NMR (500 MHz, DMSO-d6): δ 9.80 (bs, 1H), 9.17 (s, 1H), 8.59 (s, 2H), 8.21 (s, 1H), 7.19-7.16 (m, 1H), 6.76-6.73 (m, 3H), 5.48-5.46 (m, 1H), 4.10 (s, 3H), 3.70 (s, 3H), 3.44-3.42 (m, 2H), 2.79-2.76 (m, 2H), 1.70 (d, J = 5.0 Hz, 3H); m/z 466 [M + 1]⁺. |
| 103 | 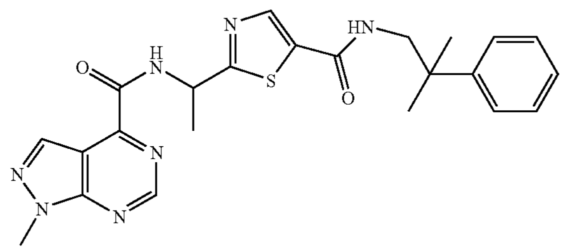 | ¹H-NMR (500 MHz, DMSO-d6): δ 9.93 (d, J = 8.5 Hz, 1H), 9.19 (s, 1H), 8.60 (s, 1H), 8.43 (s, 1H), 8.26 (s, 1H), 7.38 (d, J = 8.5 Hz, 2H), 7.30 (d, J = 8.5 Hz, 2H), 7.18-7.15 (m, 1H), 5.48-5.45 (m, 1H), 4.10 (s, 3H), 3.39 (d, J = 7.0 Hz, 2H), 1.68 (d, J = 7.0 Hz, 3H), 1.25 (s, 6H); m/z 464 [M + 1]⁺. |
| 104 | 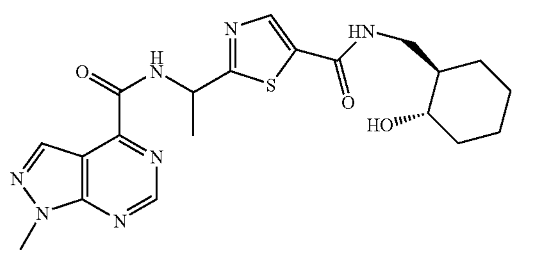 | ¹H-NMR (500 MHz, DMSO-d6): δ 9.92 (d, J = 7.5 Hz, 1H), 9.19 (s, 1H), 8.60 (s, 1H), 8.47 (bs, 1H), 8.26 (s, 1H), 5.48-5.45 (m, 1H), 4.61 (d, J = 5.0 Hz, 1H), 4.11 (s, 3H), 3.44-3.41 (m, 1H), 3.14-3.06 (m, 2H), 1.69 (d, J = 5.0 Hz, 3H), 1.60-1.56 (m, 2H), 1.41-1.37 (m, 2H), 1.15 (d, J = 5.0 Hz, 2H), 1.1-0.9 (m, 3H); m/z 444 [M + 1]⁺. |
| 105 | 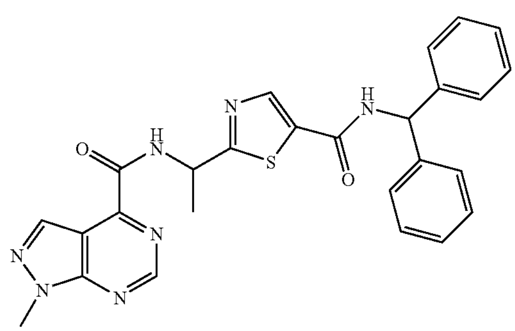 | ¹H-NMR (500 MHz, DMSO-d6): δ 9.94 (d, NH), 9.44 (d, NH), 9.18 (s, 1H), 8.60 (s, 1H), 8.48 (s, 1H), 7.35-7.24 (m, 10H), 6.30 (d, J = 8.5 Hz, 1H), 5.49-5.46 (m, 1H), 4.10 (s, 3H), 1.69 (d, J = 7.0 Hz, 3H); m/z 498 [M + 1]⁺. |

TABLE 3-continued

| # | Structure | Characterization Data |
|---|---|---|
| 106 | 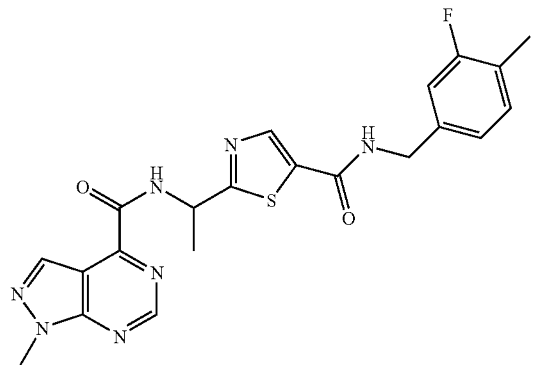 | ¹H-NMR (CDCl3, 500 MHz): δ 9.03 (s, 1H), 8.73-8.70 (m, 2H), 8.09 (s, 1H), 7.14 (t, J = 8.5 Hz, 1H), 6.99-6.96 (m, 2H), 6.14 (bs, 1H), 5.62-5.49 (m, 1H), 4.55 (d, J = 5.5 Hz, 2H), 4.18 (s, 3H), 2.25 (s, 3H), 1.81 (d, J = 7.0 Hz, 3H); m/z 454 [M + 1]⁺. |
| 107 | 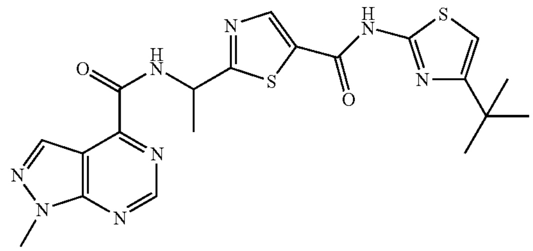 | ¹H-NMR (CDCL3, 500 MHz): δ 9.04 (s, 1H), 8.74 (s, 2H), 8.31 (s, 1H), 6.56 (s, 1H), 5.68-5.65 (m, 1H), 4.18 (s, 3H), 1.84 (d, J = 7.0 Hz, 3H), 1.30 (s, 9H); m/z 471 [M + 1]⁺. |
| 108 | 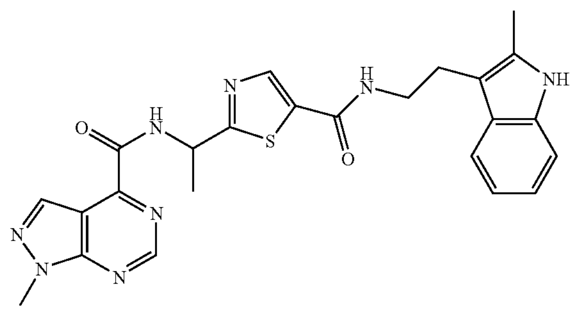 | ¹H-NMR (500 MHz, DMSO-d6): δ = 10.69 (s, 1H), 9.93 (d, J = 8.5 Hz, 1H), 9.19 (s, 1H), 8.71 (s, 1H), 8.61 (s, 1H), 8.20 (s, 1H), 7.42 (d, J = 8.5 Hz, 1H), 7.21 (d, J = 8.5 Hz, 1H), 6.94-6.89 (m, 2H), 5.48-5.47 (m, 1H), 4.11 (s, 3H), 3.32-3.30 (m, 2H), 2.88-2.83 (m, 2H), 2.35 (s, 3H), 1.70 (d, J = 7.0 Hz, 3H); m/z 488.7 [M + 1]⁺. |
| 109 | 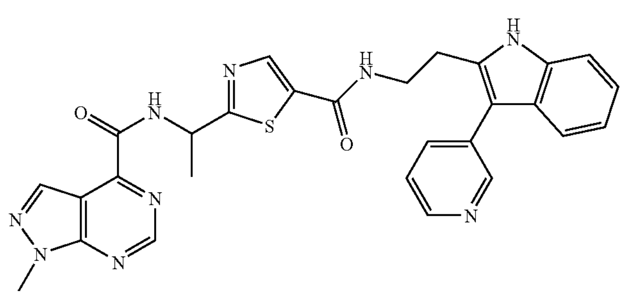 | ¹H-NMR (500 MHz, DMSO-d6): δ 11.35 (s, 1H), 9.94 (d, NH), 9.20 (s, 1H), 8.84 (s, 1H), 8.82 (s, 1H), 8.62 (s, 1H), 8.50 (s, 1H), 8.16 (s, 1H), 8.01 (d, J = 7.5 Hz, 1H), 7.65 (d, J = 7.5 Hz, 1H), 7.46 (d, J = 8.0 Hz, 1H), 7.37 (d, J = 8.0 Hz, 1H), 7.14-7.00 (m, 2H), 5.50-5.47 (m, 1H), 4.11 (s, 3H), 3.45-3.42 (m, 2H), 3.06-3.04 (m, 2H), 1.69 (d, J = 7.5 Hz, 3H); m/z 552 [M + 1]⁺. |
| 110 | 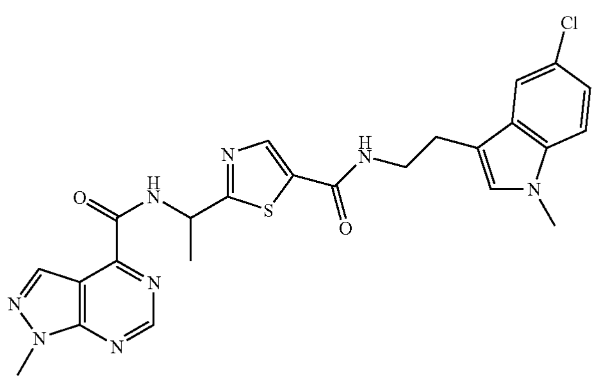 | ¹H-NMR (500 MHz, DMSO-d6): δ 9.93 (d, J = 9.5 Hz, 1H), 9.19 (s, 1H), 8.72 (s, 1H), 8.60 (s, 1H), 8.21 (s, 1H), 7.56 (s, 1H), 7.40 (d, J = 8.5 Hz, 1H), 7.21 (s, 1H), 7.10 (d, J = 9.0 Hz, 1H), 5.49-5.46 (m, 1H), 4.11 (s, 3H), 3.70 (s, 3H), 3.42-3.40 (m, 2H), 2.86 (t, J = 7.0 Hz, 2H), 1.69 (d, J = 7.0 Hz, 3H); m/z 523 [M + 1]⁺. |

TABLE 3-continued
| # | Structure | Characterization Data |
|---|---|---|
| 111 | 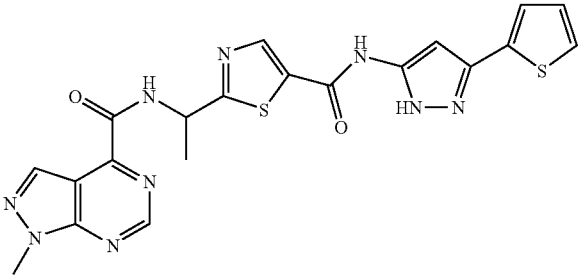 | ¹H-NMR (500 MHz, DMSO-d6): δ 10.09 (d, NH), 9.24 (s, 1H), 8.73 (s, 1H), 8.64 (s, 1H), 7.46 (s, 1H), 7.28 (s, 1H), 7.03 (s, 1H), 6.94 (s, 2H), 5.75 (s, 1H), 5.57-5.56 (m, 1H), 4.14 (s, 3H), 1.77 (d, J = 7.0 Hz, 3H); m/z 480 [M + 1]⁺. |
| 112 | 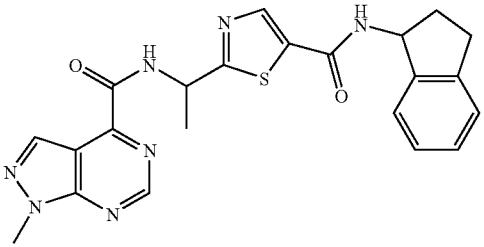 | ¹H NMR (300 MHz, DMSO-d6) d = 10.10 (s, 1H), 9.97 (d, J = 7.9 Hz, 1H), 9.21 (s, 1H), 8.63 (s, 1H), 8.46 (s, 1H), 7.19-7.05 (m, 3H), 5.61-5.44 (m, 1H), 4.12 (s, 3H), 2.94-2.74 (m, 4H), 1.97 (quin, J = 7.4 Hz, 2H), 1.73 (d, 3H); m/z 448 [M + 1]⁺. |
| 113 | 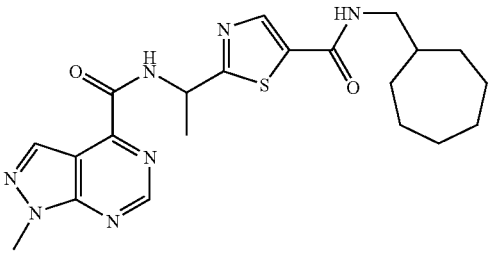 | (500 MHz, DMSO-d6): δ 9.92 (d, NH), 9.18 (s, 1H), 8.60-8.58 (m, 2H), 8.25 (s, 1H), 5.46-5.45 (m, 1H), 4.10 (s, 3H), 3.03-3.01 (m, 2H), 1.68 (d, J = 7.0 Hz, 3H), 1.63-1.10 (m, 13H); m/z 442 [M + 1]⁺. |
| 114 | 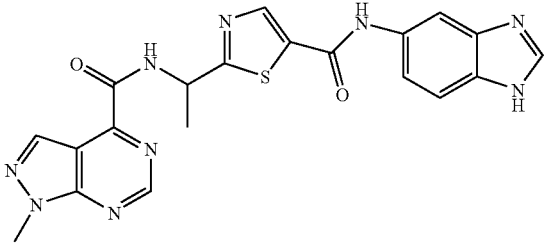 | ¹H-NMR (500 MHz, DMSO-d6): δ 9.94-9.92 (m, 1H), 9.18 (s, 1H), 9.03 (d, NH), 8.60 (s, 1H), 8.33 (s, 1H), 7.31-7.27 (m, 4H), 7.23-7.20 (m, 1H), 5.48-5.45 (m, 1H), 5.00-4.96 (m, 1H), 4.10 (s, 3H), 2.19-2.17 (m, 2H), 2.09 (s, 6H), 1.93-1.83 (m, 2H), 1.68 (d, J = 6.5 Hz, 3H); m/z 493 [M + 1]⁺. |
| 115 | 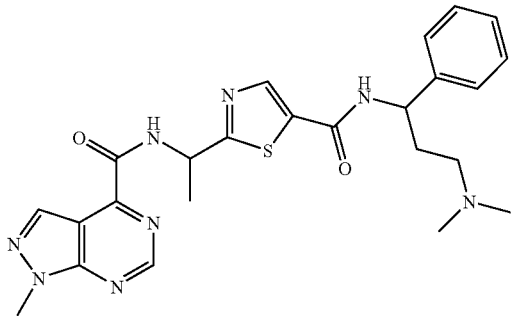 | ¹H-NMR (500 MHz, DMSO-d6): δ 9.90 (d, J = 7.5 Hz, 1H), 9.18 (s, 1H), 8.60 (s, 1H), 8.28 (s, 1H), 7.77 (s, 1H), 5.46-5.43 (m, 1H), 4.10 (s, 3H), 2.00 (s, 8H), 1.67-1.61 (m, 9H); m/z 466 [M + 1]⁺. |

TABLE 3-continued

| # | Structure | Characterization Data |
|---|---|---|
| 116 | 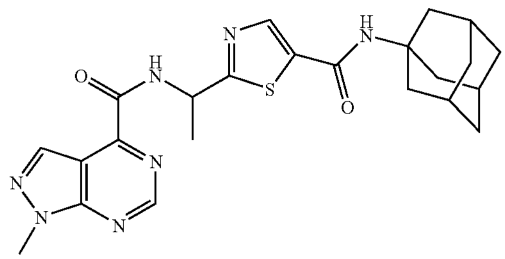 | ¹H-NMR (500 MHz, DMSO-d6): δ 9.92 (d, J = 7.5 Hz, 1H), 9.19 (s, 1H), 8.60 (s, 1H), 8.29 (s, 1H), 8.26 (d, J = 7.5 Hz, 1H), 5.48-5.45 (m, 1H), 4.10 (s, 3H), 3.76-3.71 (q, 1H), 1.68 (d, J = 5.0 Hz, 3H), 1.67-1.58 (m, 6H), 1.37-1.32 (m, 1H), 1.07-1.06 (m, 5H), 0.98-0.92 (m, 3H); m/z 442 [M + 1]⁺. |
| 117 | 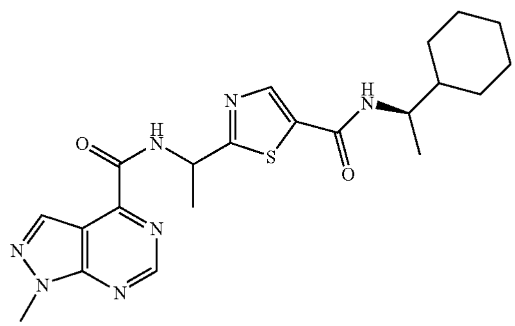 | ¹H-NMR (500 MHz, DMSO-d6): δ = 9.95 (d, J = 8.0 Hz, 1H), 9.19 (s, 1H), 8.82 (s, 1H), 8.61 (s, 1H), 8.29 (s, 1H), 7.18-7.05 (m, 4H), 5.50-5.47 (m, 1H), 4.11 (s, 3H), 3.45-3.42 (m, 2H), 2.98-2.96 (m, 1H), 2.70-2.65 (m, 3H), 1.74-1.71 (m, 3H), 1.70 (d, J = 7 Hz, 3H); m/z 476 [M + 1]⁺. |
| 118 | 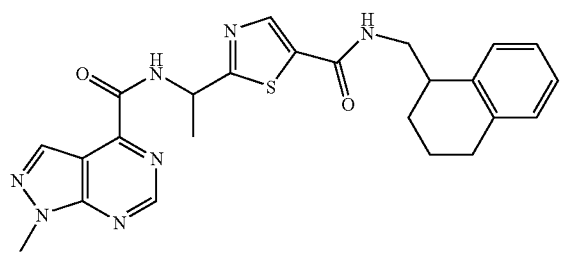 | ¹H-NMR (500 MHz, DMSO-d6): δ 9.19 (s, 1H), 8.60 (s, 1H), 8.29 (s, 1H), 8.26 (d, J = 7.5 Hz, 1H), 5.48-5.45 (m, 1H), 4.11 (s, 3H), 3.76-3.71 (q, 1H), 1.69 (d, J = 5.0 Hz, 3H), 1.67-1.62 (m, 6H), 1.37-1.32 (m, 1H), 1.07-1.06 (m, 5H), 0.98-0.92 (m, 3H); m/z 442 [M + 1]⁺. |
| 119 | 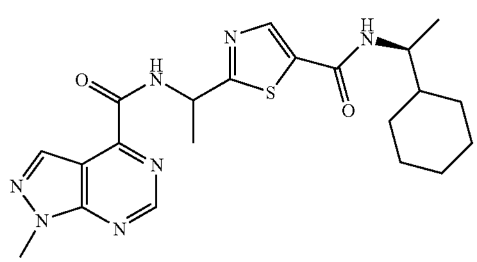 | ¹H-NMR (500 MHz, DMSO-d6): δ 9.94 (d, NH), 9.19 (s, 1H), 8.60 (s, 2H), 8.25 (s, 1H), 5.49-5.46 (m, 1H), 4.10 (s, 3H), 3.00-2.70 (m, 4H), 1.69 (d, J = 7.0 Hz, 3H), 1.61-1.59 (m, 6H), 1.05-0.95 (m, 6H); m/z 457 [M + 1]⁺. |
| 120 | 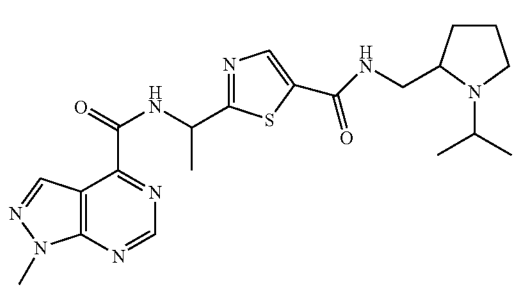 | ¹H-NMR (500 MHz, DMSO-d6): δ = 9.92 (d, J = 8.0 Hz, 1H), 9.18 (s, 1H), 8.59 (s, 1H), 8.52 (d, J = 1H), 8.19 (s, 1H), 6.28 (s, 1H), 5.48-5.45 (m 1H), 4.42-4.39 (m, 1H), 4.29-4.28 (m, 2H), 4.10 (s, 3H), 1.97-1.98 (m, 1H), 1.68 (d, J = 7 Hz, 3H), 1.15 (d, J = 6.5 Hz, 3H), 0.92-0.91 (m, 2H), 0.67-0.66 (m, 2H); m/z 548 [M + 1]⁺. |

TABLE 3-continued

| # | Structure | Characterization Data |
|---|-----------|----------------------|
| 121 | 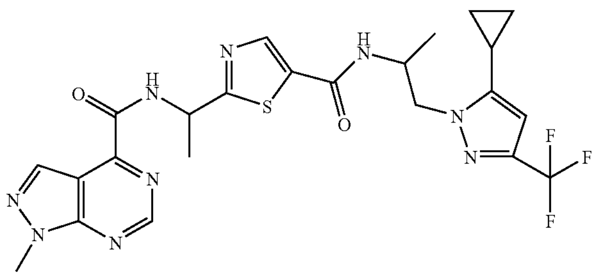 | ¹H-NMR (500 MHz, DMSO-d6): δ 10.55 (s, 1H), 9.94 (bs, 1H), 9.19 (s, 1H), 8.61 (s, 1H), 8.37 (s, 1H), 7.95 (s, 1H), 7.50 (s, 1H), 5.53-5.50 (m, 1H), 4.11 (s, 3H), 4.08-4.06 (m, 2H), 1.71 (d, J = 7.5 Hz, 3H), 1.34-1.31 (m, 3H); m/z 426 [M + 1]⁺. |
| 122 | 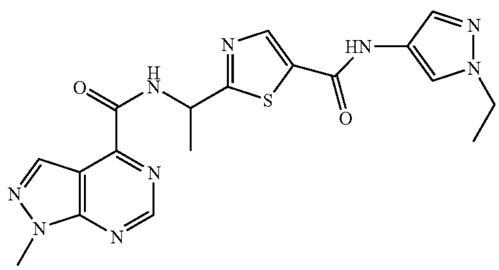 | ¹H-NMR (500 MHz, DMSO-d6): δ 9.93 (d, J = 8.0 Hz, 1H), 9.19 (s, 1H), 8.60 (s, 1H), 8.27-8.25 (m, 2H), 5.47-5.45 (m, 1H), 4.10 (s, 3H), 3.70-3.68 (m, 1H), 2.15-2.01 (m, 3H), 1.67 (d, J = 7 Hz, 3H), 1.55-1.10 (m, 11H); m/z 454 [M + 1]⁺. |
| 123 | 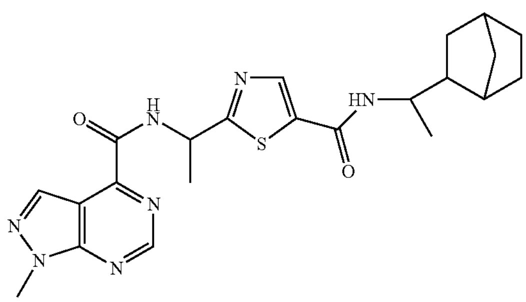 | ¹H-NMR (500 MHz, DMSO-d6): δ 9.92 (d, J = 7.5 Hz, 1H), 9.18 (s, 1H), 8.60 (s, 1H), 8.40 (bs, 1H), 8.25 (s, 1H), 6.92 (s, 1H), 6.74 (s, 1H), 5.48-5.47 (m, 1H), 4.11 (s, 3H), 3.26-3.24 (m, 2H), 1.88-1.86 (m, 2H), 1.69 (d, J = 5.0 Hz, 3H), 1.55-1.50 (m, 4H), 1.28-1.25 (m, 4H); m/z 544 [M + 1]⁺. |
| 124 | 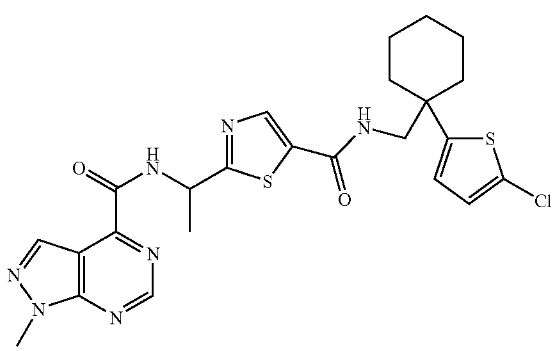 | ¹H-NMR (500 MHz, MeOD-d4): δ 9.14 (s, 1H), 8.64 (s, 1H), 8.47 (s, 1H), 8.15 (s, 1H), 7.90 (d, J = 8.5 Hz, 1H), 7.49 (d, J = 8.5 Hz, 1H), 5.65-5.64 (m, 1H), 4.17 (s, 3H), 3.64-3.55 (m, 2H), 3.42-3.37 (m, 2H), 1.82 (d, J = 6.5 Hz, 3H); m/z 498 [M + 1]⁺. |
| 125 | 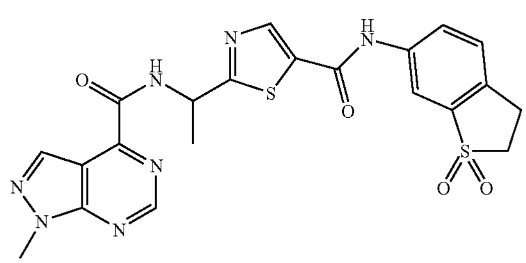 | ¹H-NMR (500 MHz, DMSO-d6): δ 9.93 (d, NH), 9.18 (s, 1H), 8.60 (s, 1H), 8.46 (d, NH), 8.26 (s, 1H), 5.48-5.47 (m, 1H), 4.10 (s, 3H), 3.82-3.80 (m, 1H), 1.97-1.70 (m, 9H), 1.67 (d, J = 7.0 Hz, 3H); m/z 482 [M + 1]⁺. |

TABLE 3-continued

| # | Structure | Characterization Data |
|---|-----------|----------------------|
| 126 | 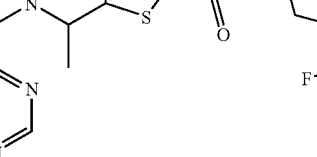 | ¹H-NMR (500 MHz, DMSO-d6): δ 10.09 (d, NH), 9.21 (s, 1H), 8.67 (s, 1H), 8.62 (s, 1H), 6.71 (s, 2H), 5.57-5.56 (m, 1H), 5.16 (s, 1H), 4.11 (s, 3H), 1.73 (d, J = 6.5 Hz, 3H), 1.72-1.70 (m, 1H), 0.80-0.75 (m, 2H), 0.68-0.58 (m, 2H); m/z 438 [M + 1]⁺. |
| 127 | 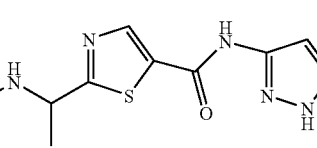 | ¹H-NMR (500 MHz, DMSO-d6): δ 9.93 (d, NH), 9.18 (s, 1H), 8.60 (s, 1H), 8.33 (s, 1H), 8.51 (d, NH), 8.19 (s, 1H), 6.41 (s, 1H), 5.48-5.45 (m, 1H), 4.33-4.30 (m, 1H), 4.17 (d, J = 6.5 Hz, 3H), 4.10 (s, 3H), 2.28 (s, 3H), 1.68 (d, J = 7.0 Hz, 3H), 1.14 (d, J = 6.0 Hz, 3H); m/z 522 [M + 1]⁺. |
| 128 | 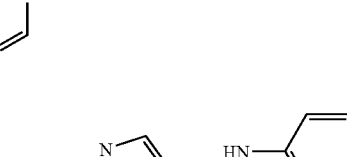 | ¹H-NMR (500 MHz, MeOD-d4): δ 9.14 (s, 1H), 8.65 (s, 1H), 8.48 (s, 1H), 8.11 (s, 1H), 7.92 (d, J = 10.0 Hz, 1H), 7.56 (t, J = 8.5 Hz, 1H), 7.45 (d, J = 10.0 Hz, 1H), 5.66-5.64 (m, 1H), 4.18 (s, 3H), 1.84 (d, J = 5.0 Hz, 3H); m/z 476 [M + 1]⁺. |
| 129 | 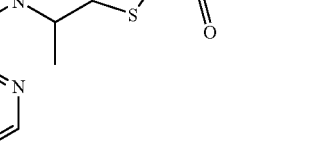 | ¹H-NMR (500 MHz, DMSO-d6): δ 10.37 (s, 1H), 9.93 (bs, 1H), 9.19 (s, 1H), 8.63 (d, J = 10.0 Hz, 2H), 8.48 (s, 1H), 7.64 (d, J = 7.5 Hz, 1H), 7.55 (s, 1H), 7.32 (t, J = 5.0 Hz, 1H), 7.03 (d, J = 7.5 Hz, 1H), 5.53-5.50 (m, 1H), 5.40 (s, 2H), 4.11 (s, 3H), 1.72 (d, J = 7.5 Hz, 3H); m/z 489 [M + 1]⁺. |

The compounds of the present invention provided in Table 4 were prepared by similar procedures as described in the synthesis of compound 39 except the 4-(2-chloroethyl)morpholin-4-ium chloride was replaced with the appropriate alkyl chloride.

TABLE 4

| # | Structure | Characterization Data |
|---|-----------|----------------------|
| 132 | 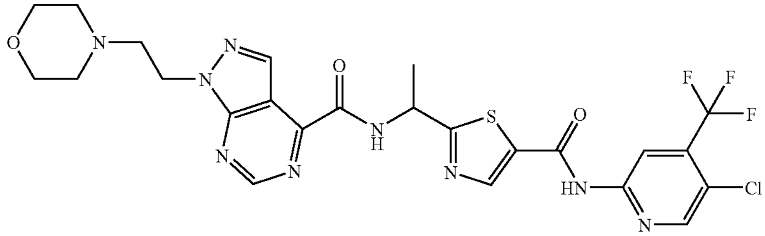 | 1+1 HNMR: (400.13 MHz, CDCl₃) δ = 9.06 (s, 1H), 8.78 (s, 1H), 8.77 (d, J = 8.0 Hz, 1H), 8.73, (s, 1H), 8.44 (s, 1H), 8.41 (s, 1H), 8.11 (s, 1H), 5.69 (dq, J = 8.0, 7.3 Hz, 1H), 5.87 (t, J = 6.4 Hz, 2H), 3.79 (m, 4H), 3.27 (t, J = 6.4 Hz, 2H), 2.85 (m, 4H), 1.87 (d, J = 7.3 Hz, 3H). MS m/z 610 [M + 1]⁺. |

TABLE 4-continued

| # | Structure | Characterization Data |
|---|---|---|
| 133 | 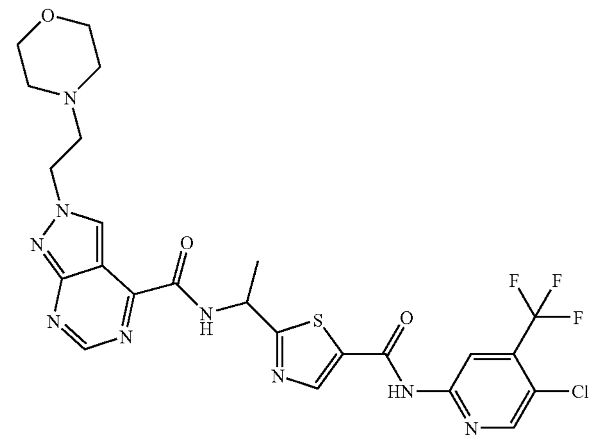 | +hu 1+l H NMR (400 MHz, CDCl$_3$) δ = 9.28 (d, 1H), 9.16 (s, 1H), 8.94 (s, 1H), 8.71 (d, J = 8.0 Hz, 2H), 8.70 (s, 1H) 8.42 (s, 1H), 8.41 (s, 1H), 5.65 (dq, J = 7.0, 8.1 Hz, 2H), 4.99 (br. s., 2H), 3.90-3.83 (m, 3H), 3.50 (s, 3H), 2.87 (br. s., 3H), 1.85(d, J = 6.9 Hz, 3H) |
| 134 | 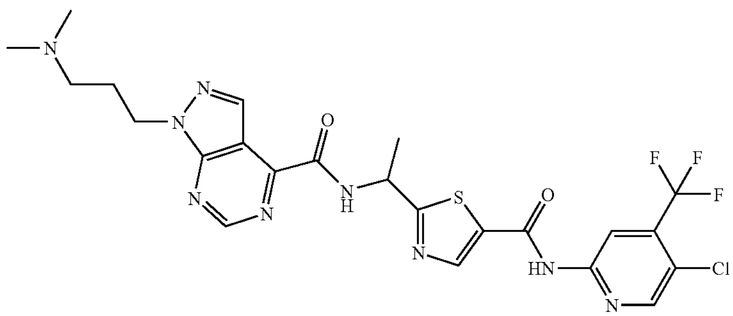 | 1+l H NMR (400.13 MHz, DMSO-d$_6$) δ = 10.02 (d, J = 8.0 Hz, 1H), 9.21 (s, 1H), 8.78 (s, 1H), 8.67 (s, 1H), 8.65 (s, 1H), 8.55 (s, 1H), 5.53 (dq, J = 8.0 7.0 Hz, 1H), 4.56 (t, J = 6.6+NL Hz, 2H), 2.32 (t, J = 6.6 Hz, 2H), 2.18 (s, 6H), 2.05 (quin, J = 6.6 Hz, 2H), 1.73 (d, J = 7.0 Hz, 3H), MS m/z 582 [M + 1]$^+$. |
| 135 | 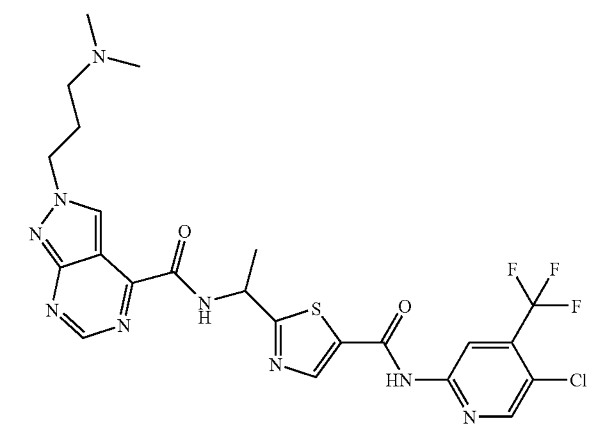 | +hu 1+l H NMR (400 MHz, DMSO-d6) δ = 9.97 (d, J = 8.2 Hz, 1H), 9.17 (s, 1H), 8.77 (s, 1H), 8.75 (s, 1H), 8.54 (s, 1H), 8.15 (s, 1H), 5.57-5.44 (m, 1H), 4.60 (t, J = 6.9 Hz, 2H), 3.33 (br. s., 7H), 2.36-2.31 (m, 2H), 2.22 (s, 7H), 2.17-2.09 (m, 2H), 1.72 (d, J = 7.1 Hz, 3H) MS m/z 582 [M + 1]$^+$. |
| 136 | 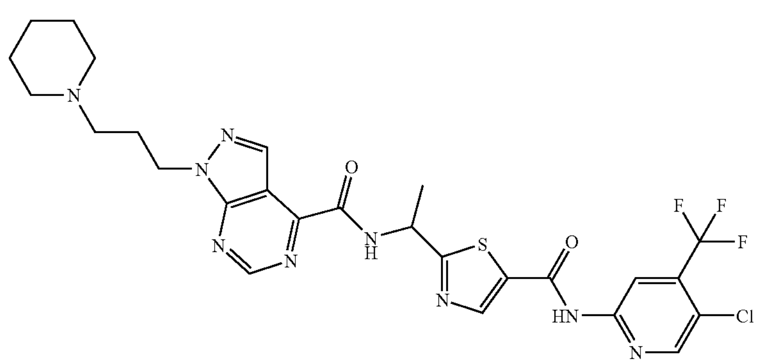 | 1+l H NMR (400.13 MHz, DMSO-d$_6$) δ = 10.01 (d, J = 8.0 Hz, 1H), 9.20 (s, 1H), 8.77 (s, 1H), 8.76 (s, 1H), 8.64 (s, 1H), 8.55 (s, 1H), 5.53 (dq, J = 8.0, 7.0 Hz, 1H). 4.56 (m, 2H), 2.31 (t, J = 7.0 Hz, 2H), 2.27 (m, 4H), 2.06 (quint, J = 7.0 Hz, 2), 1.73 (d, J = 8.0 Hz, 3H), 1.38 (m, 4H), 1.32 (m, 2H). MS m/z 622 [M + 1]$^+$. |

TABLE 4-continued
| # | Structure | Characterization Data |
|---|-----------|----------------------|
| 137 | 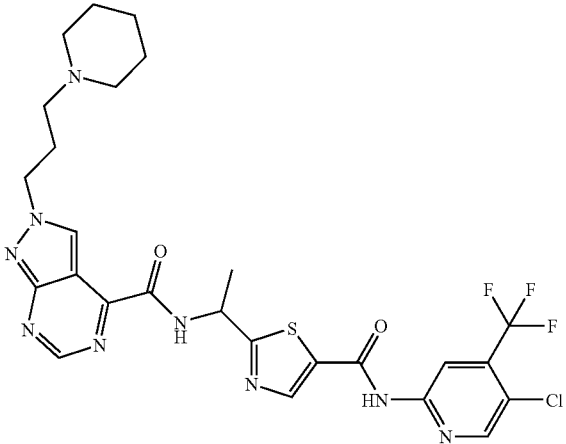 | +hu 1+l H NMR (400 MHz, DMSO-d6) δ = 9.96 (d, J = 8.2 Hz, 1H), 9.16 (s, 1H), 9.05 (s, 1H), 8.77 (s, 1H), 8.75 (s, 1H), 8.54 (s, 1H), 5.60-5.44 (m, 1H), 4.60 (t, J = 6.8 Hz, 2H), 2.33-2.21 (m, 6H), 2.12 (m, 2H), 1.72 (d, J = 6.9 Hz, 3H), 1.44 (m, 4H), 1.33 (m, 2H) MS m/z 622 [M + 1]+. |
Additional compounds of the present invention may be prepared according to general Scheme X. Such compounds are set forth in Table 5 below.
TABLE 5
Additional compounds
1A 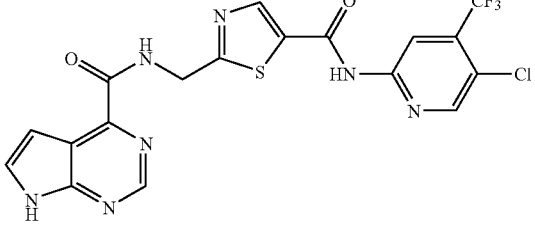
1C 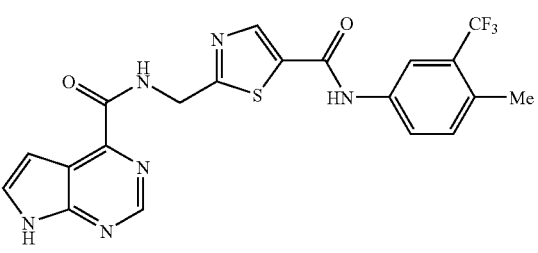
1Da 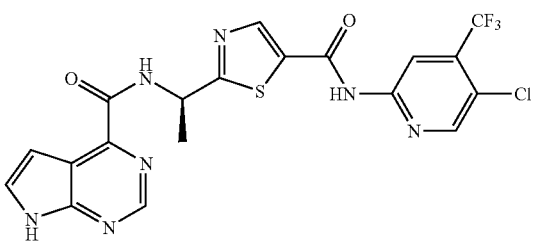

TABLE 5-continued
| Additional compounds |
1Db
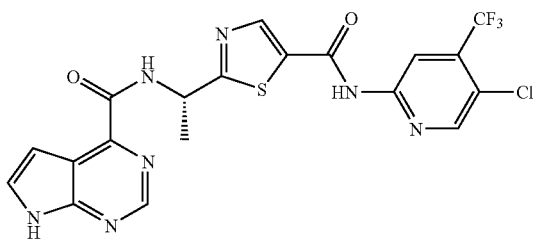
1Ea
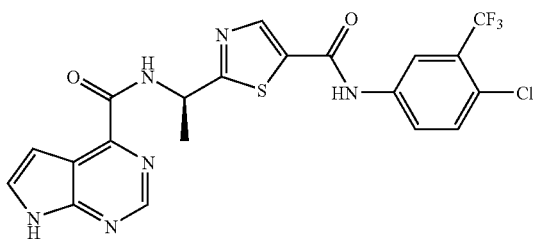
1Eb
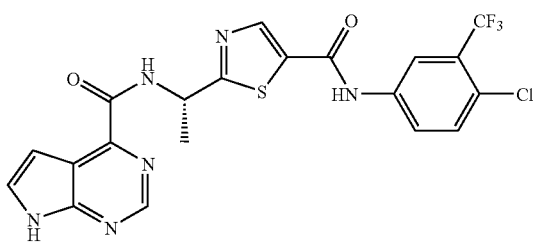
1F
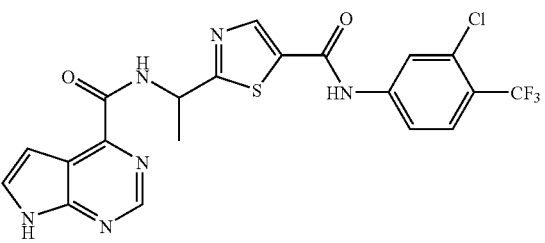
1G
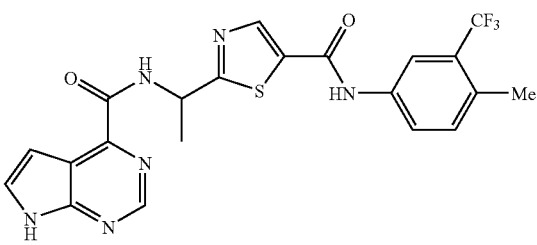
1H
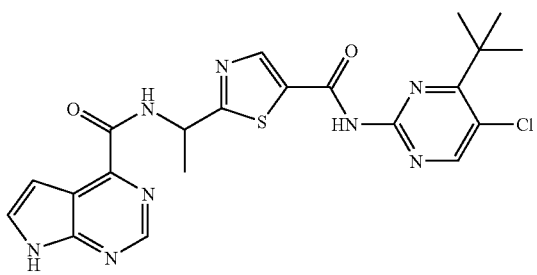

TABLE 5-continued
Additional compounds
1I
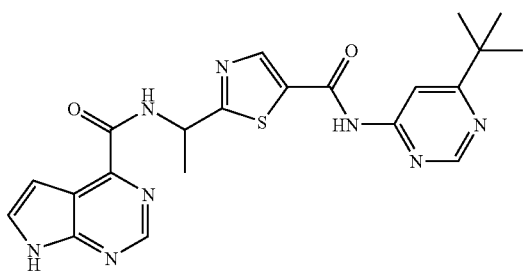
1J
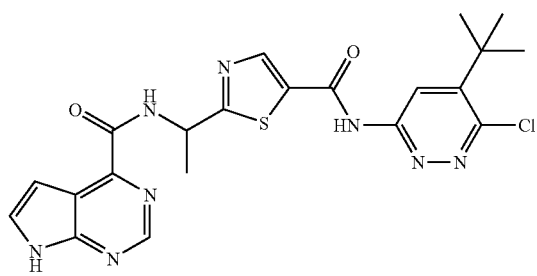
1K
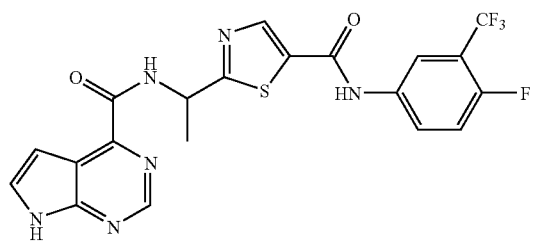
1L
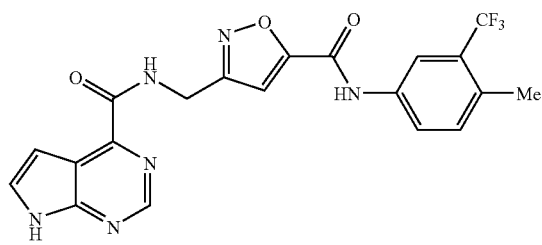
1Ma
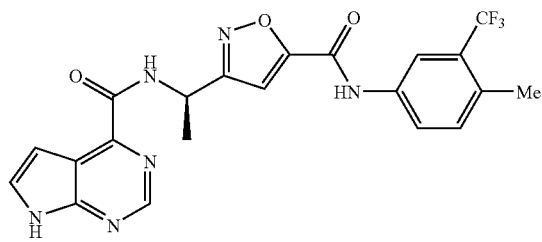
1Mb
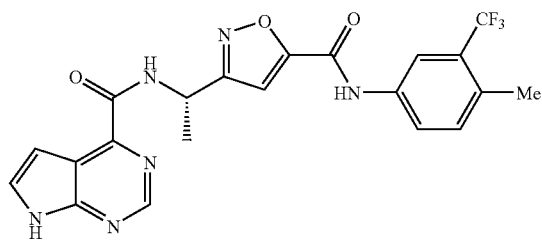

TABLE 5-continued
Additional compounds
1Nb 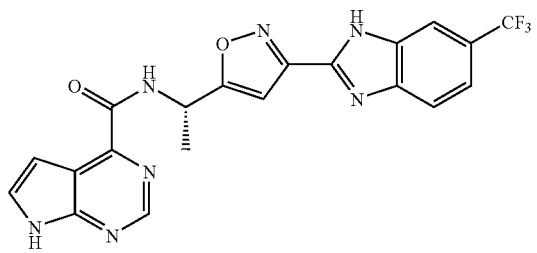
1O 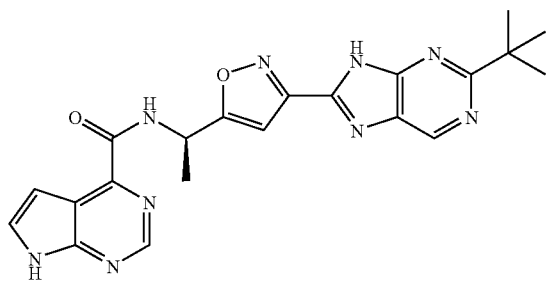
1Q 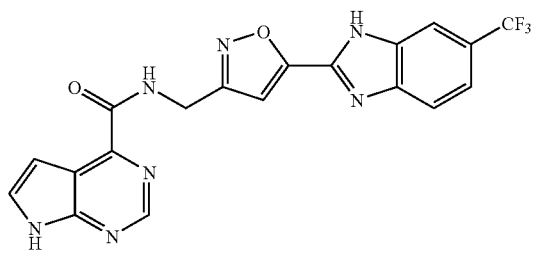
1Ra 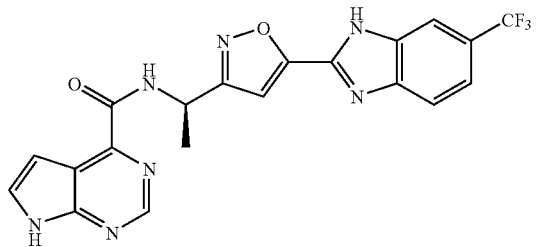
1Rb 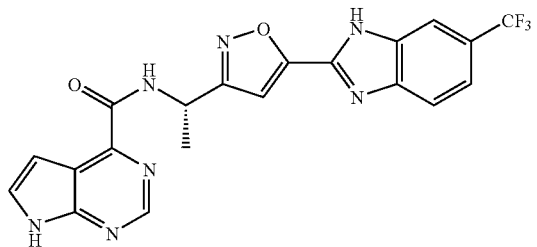
2A 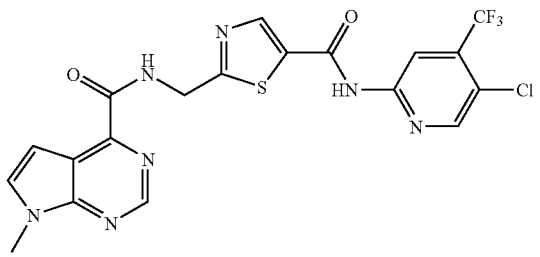

TABLE 5-continued
Additional compounds
2B 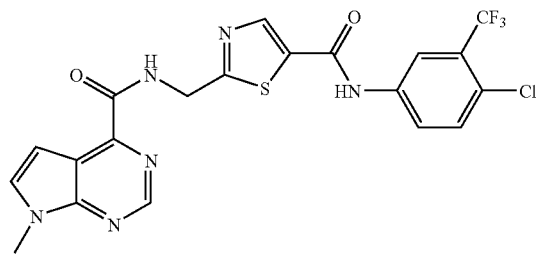
2C 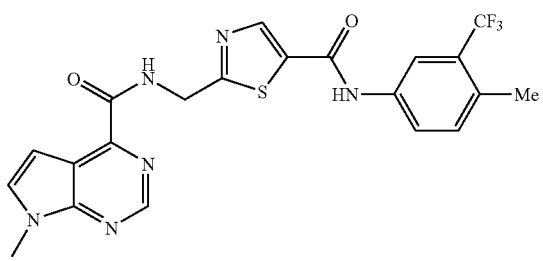
2D 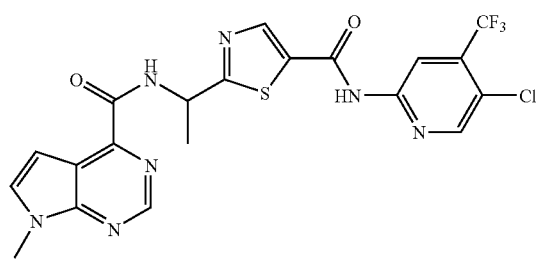
2Db 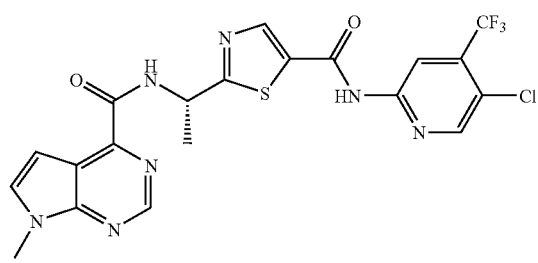
2E 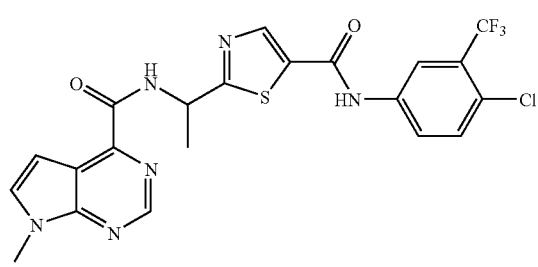
2Ea 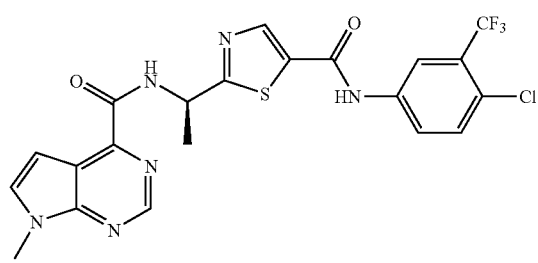

TABLE 5-continued
Additional compounds
2Eb
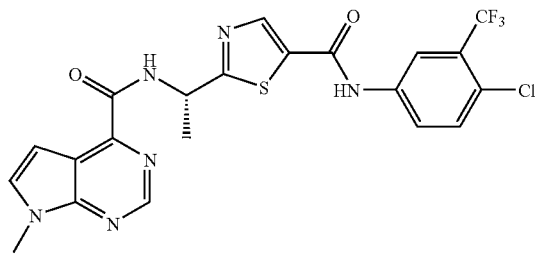
2F
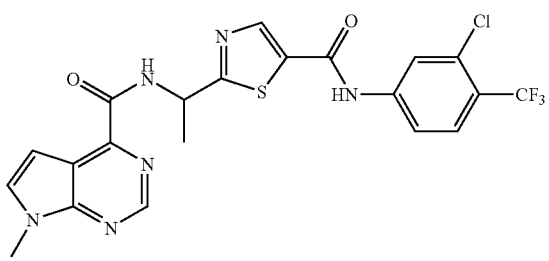
2G
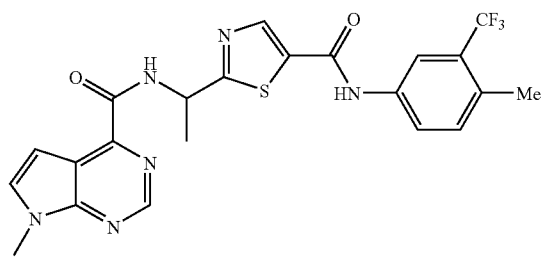
2H
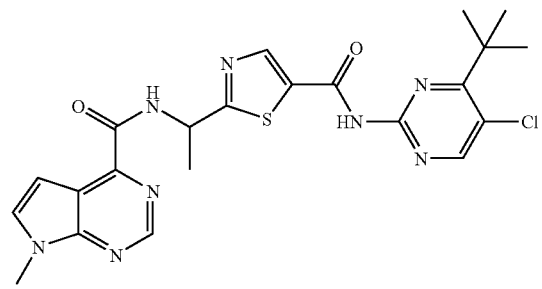
2I
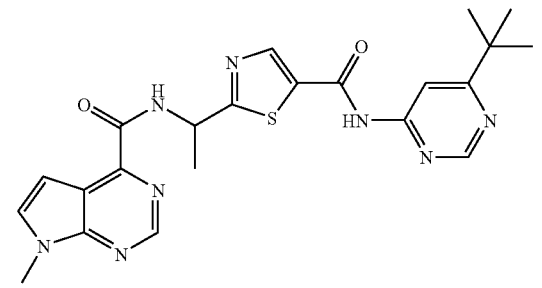

TABLE 5-continued
Additional compounds
2J
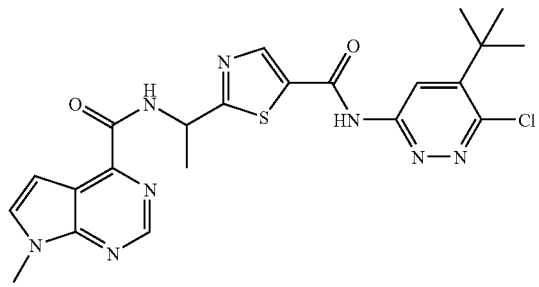
2K
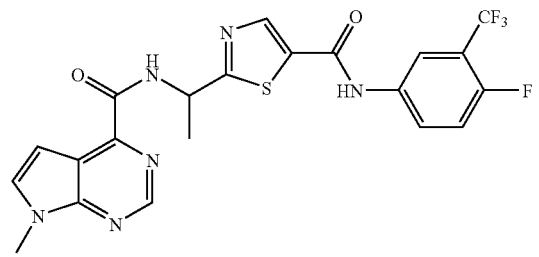
2L
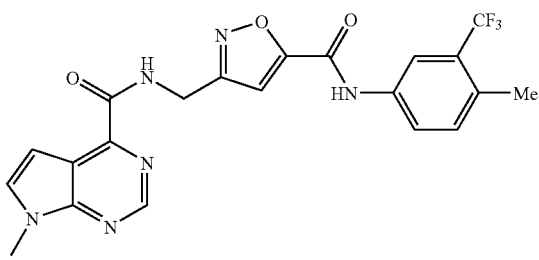
2Ma
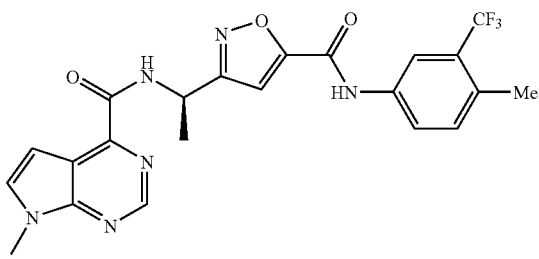
2Mb
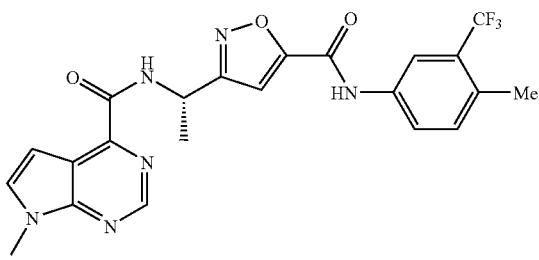
2Na
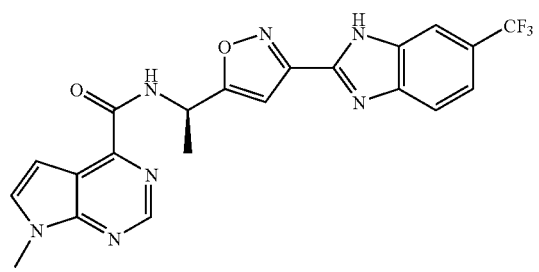

TABLE 5-continued
Additional compounds
2Nb
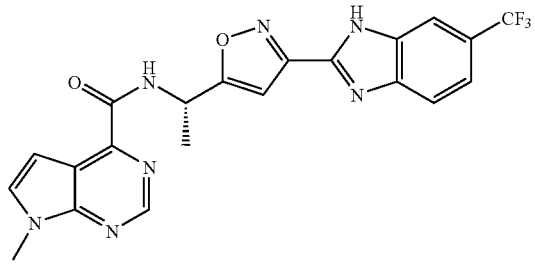
2O
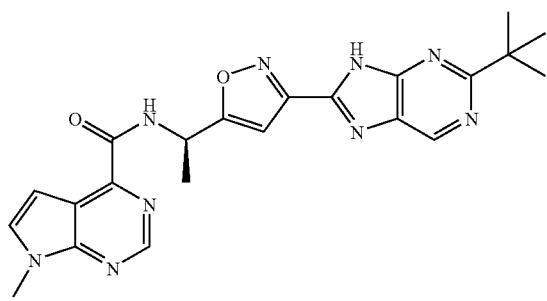
2P
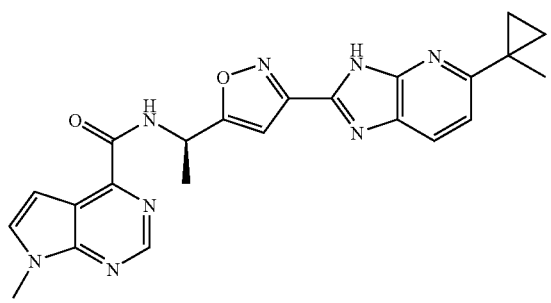
2Q
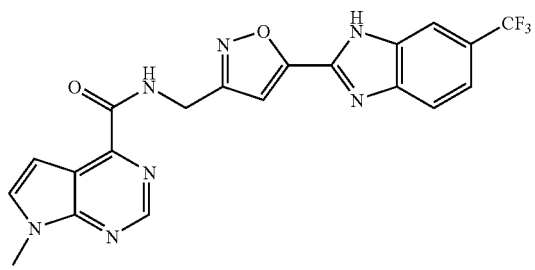
2Ra
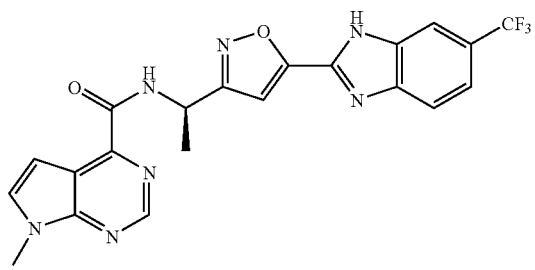

TABLE 5-continued
Additional compounds
2Rb 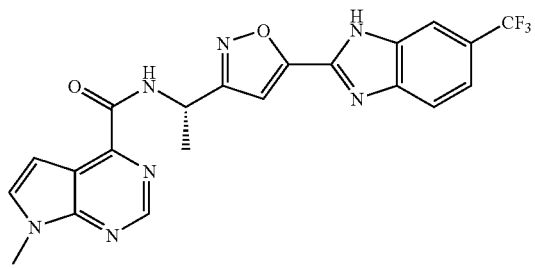
3A 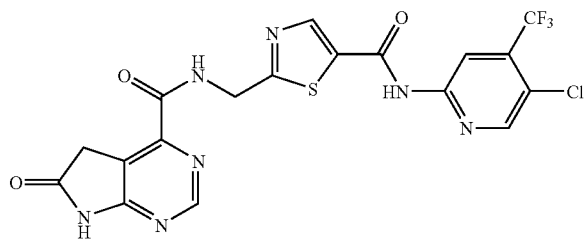
3B 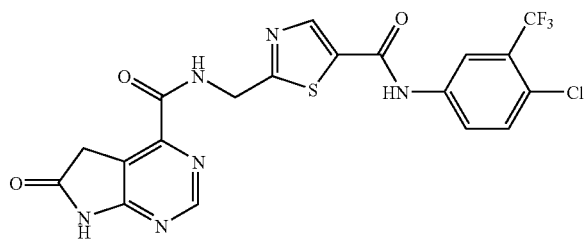
3C 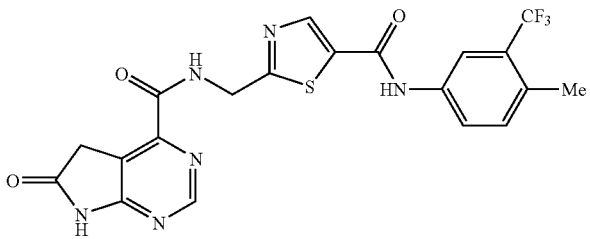
3D 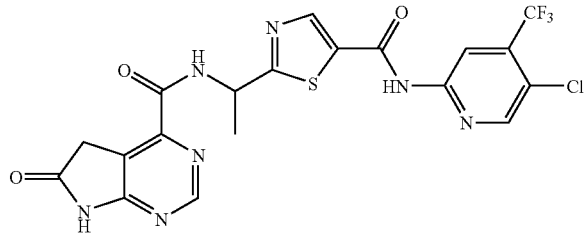
3Da 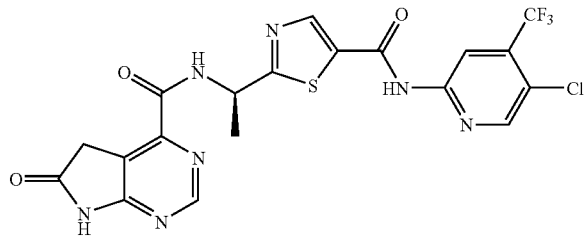

TABLE 5-continued
Additional compounds
3Db
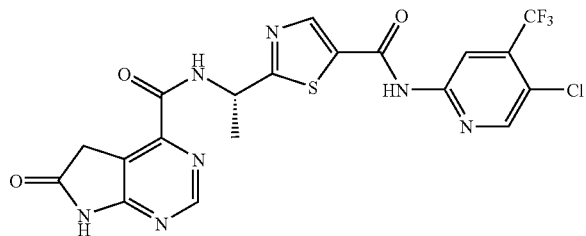
3E
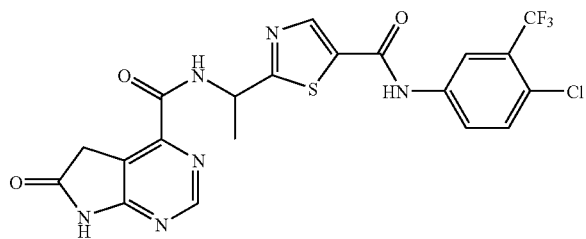
3Ea
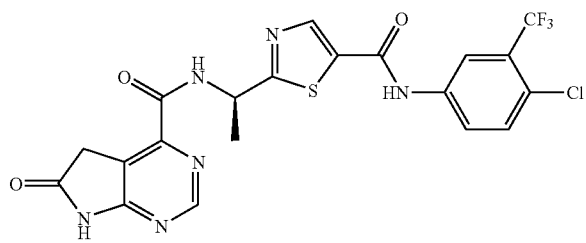
3Eb
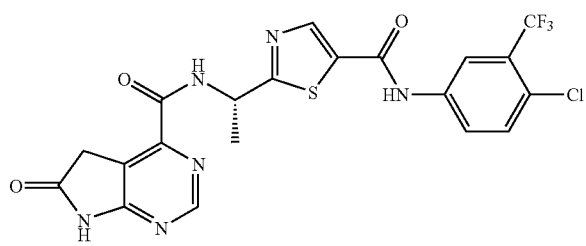
3F
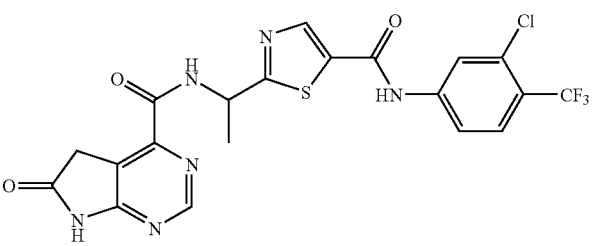
3H
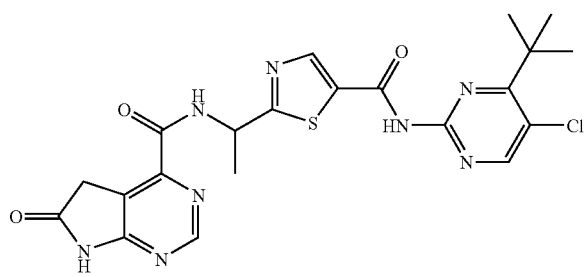

TABLE 5-continued
Additional compounds
3I
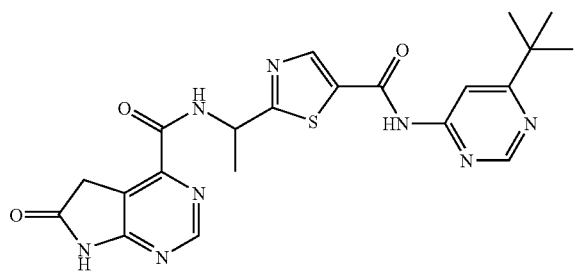
3J
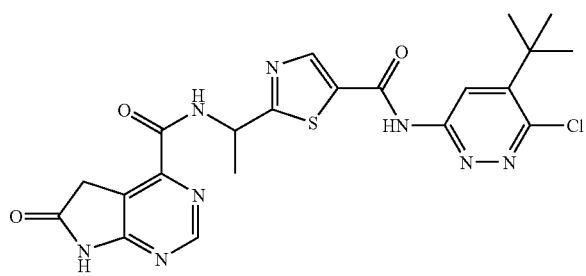
3K
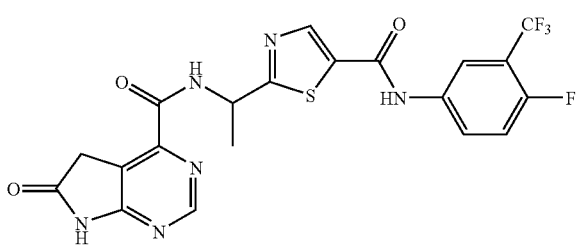
3L
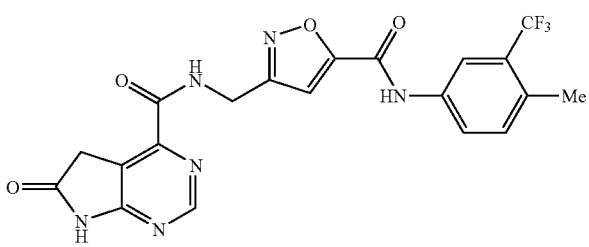
3Ma
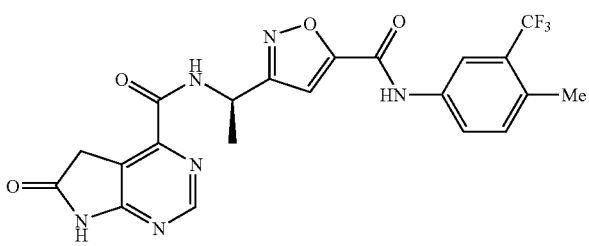
3Nb
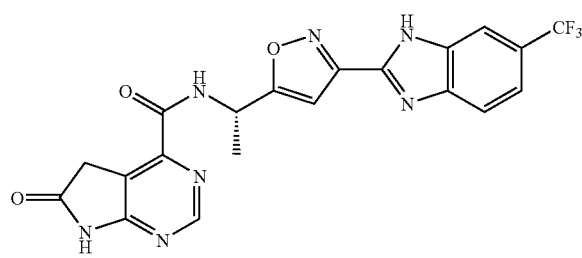

TABLE 5-continued
Additional compounds
3O
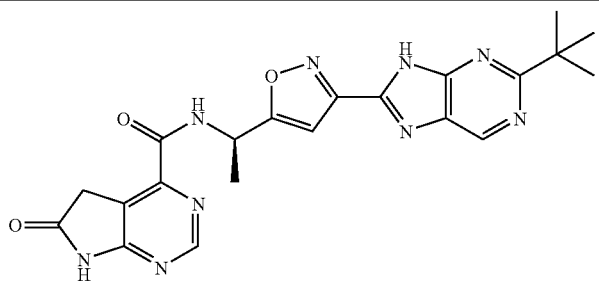
3P
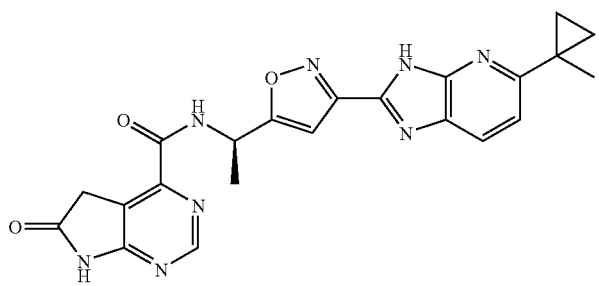
3Q
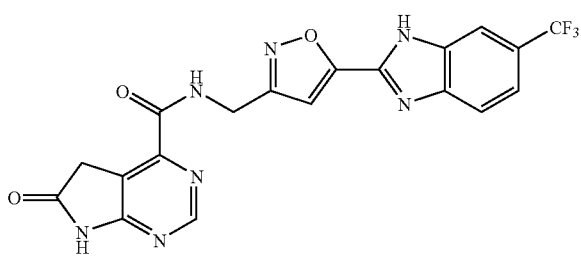
3Ra
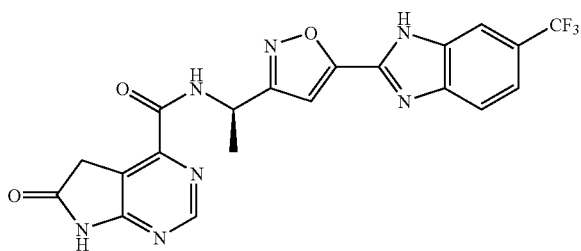
3Rb
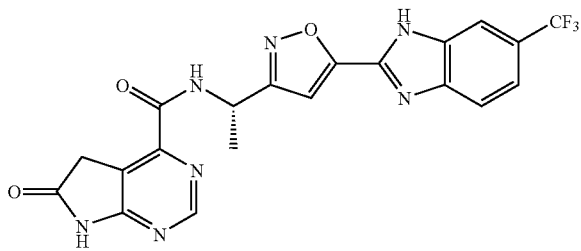
4B
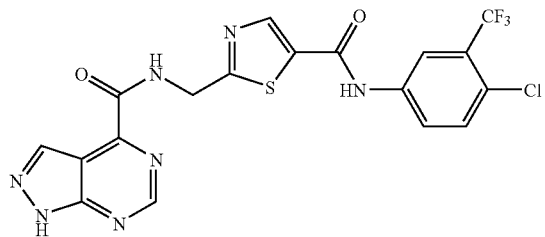

TABLE 5-continued
Additional compounds
4C
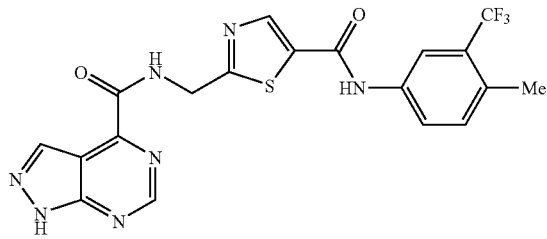
4D
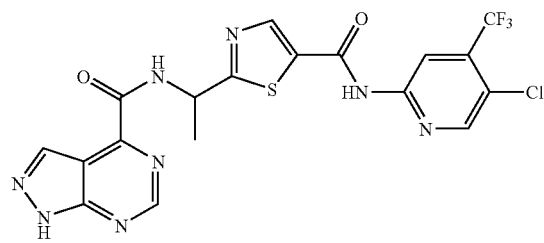
4Db
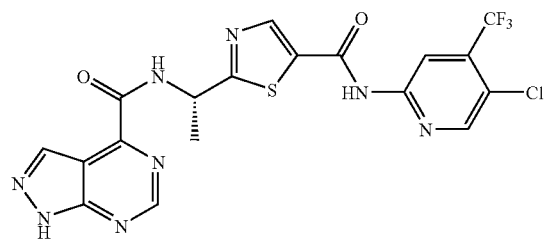
4Ea
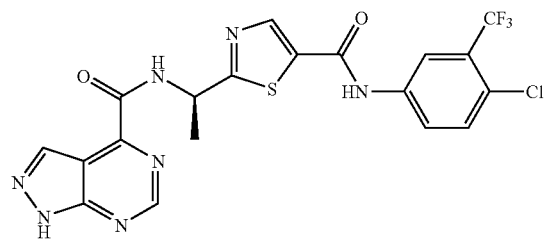
4Eb
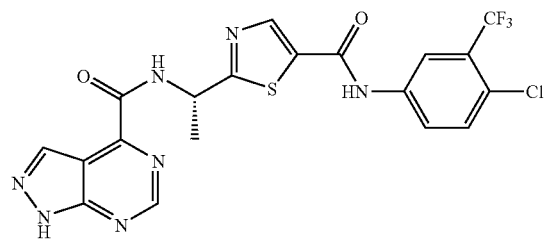
4G
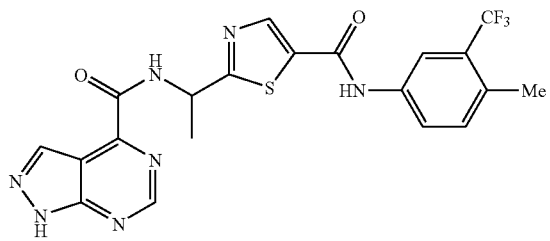

TABLE 5-continued
Additional compounds
4H 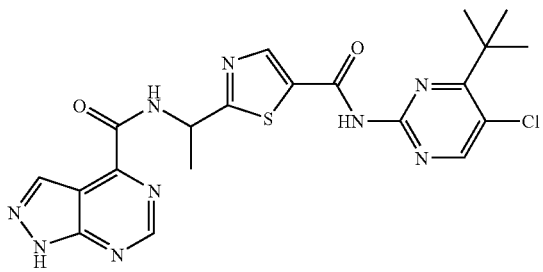
4I 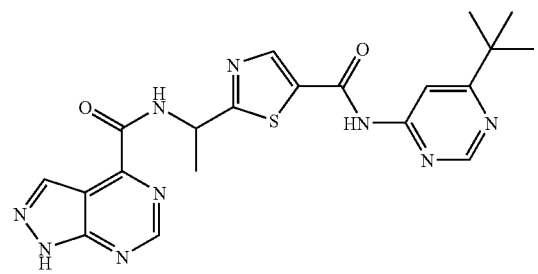
4J 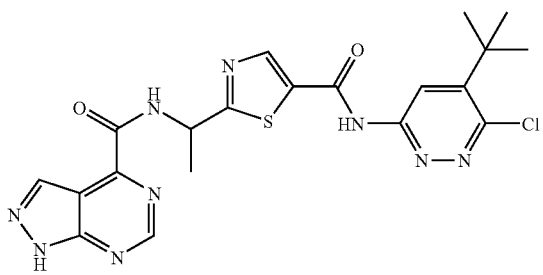
4K 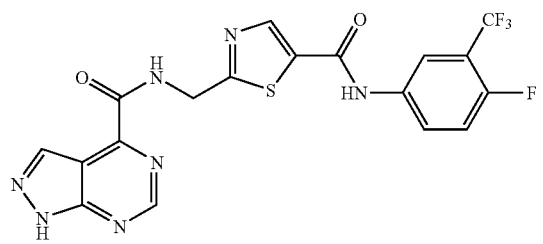
4L 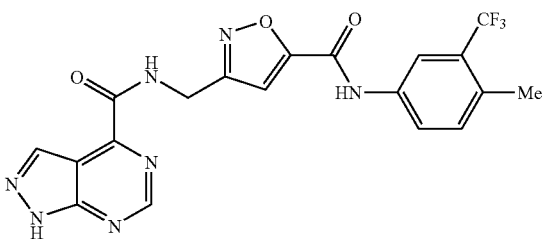
4Ma 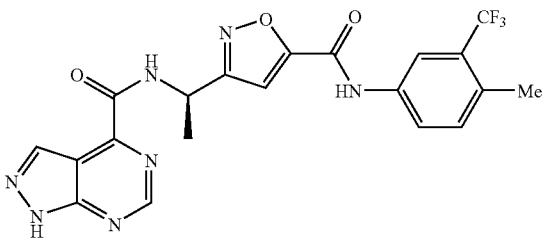

TABLE 5-continued

Additional compounds

4Mb, 4Nb, 4O, 4P, 4Q, 4Ra

TABLE 5-continued
Additional compounds
4Rb 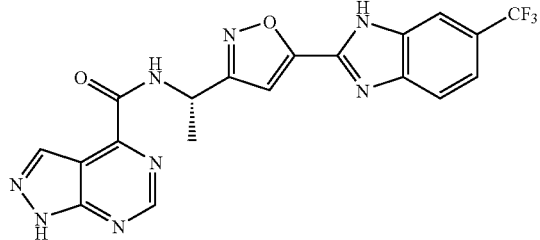
5A 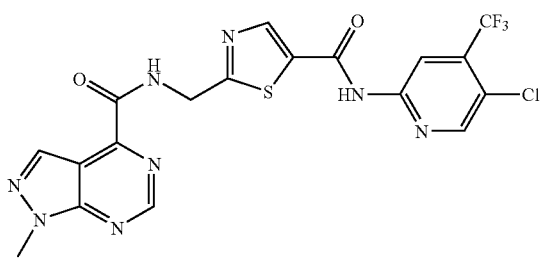
5B 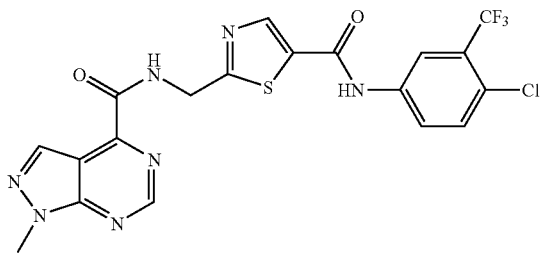
5C 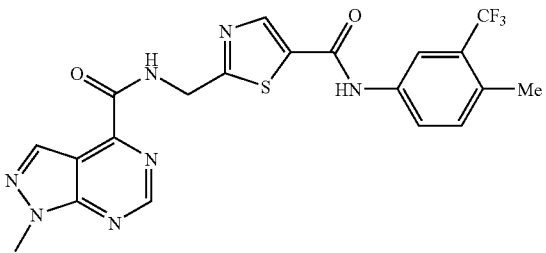
5D 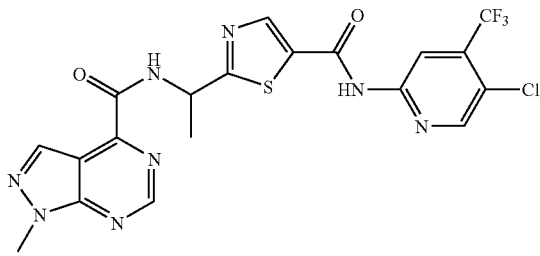
5Db 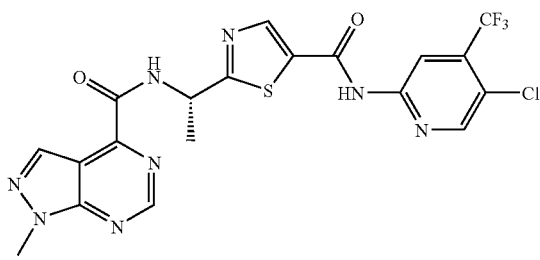

TABLE 5-continued
Additional compounds
5E 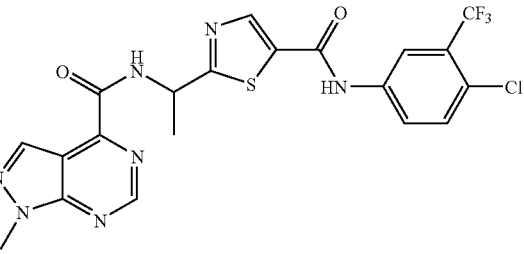
5Ea 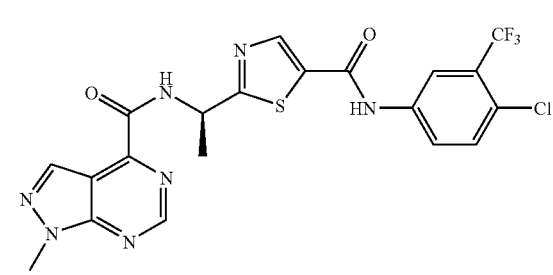
5Eb 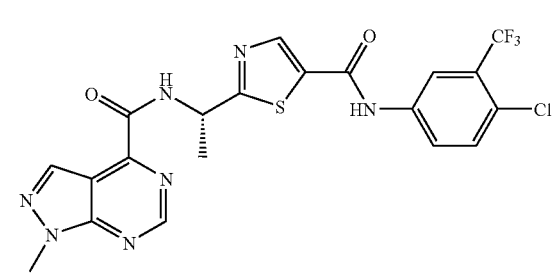
5F 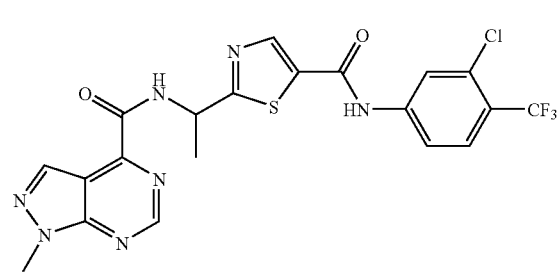
5G 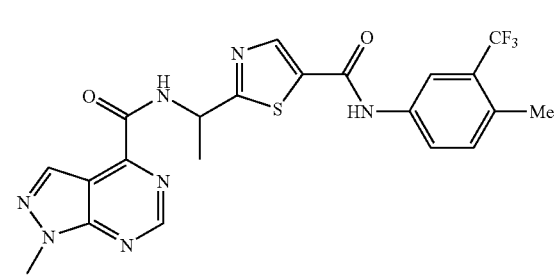
5H 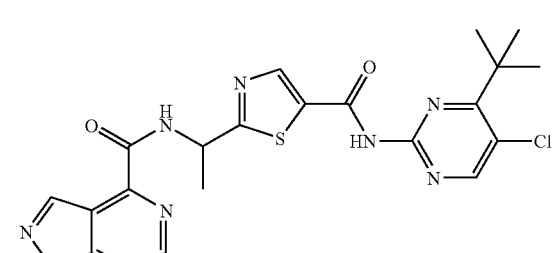

TABLE 5-continued
Additional compounds
5I
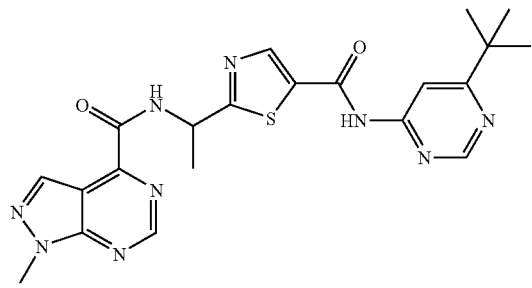
5J
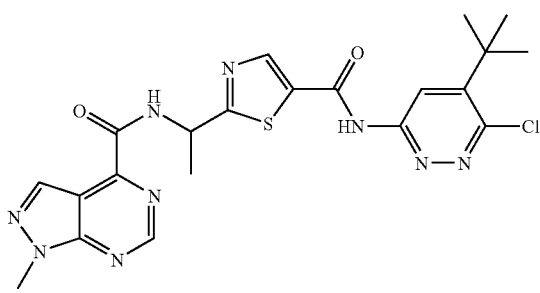
5K
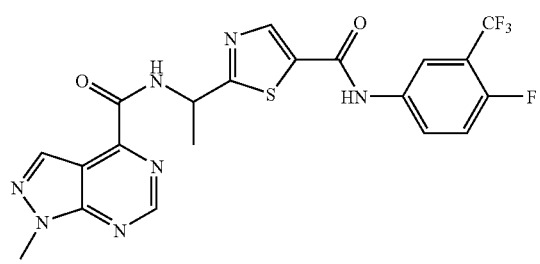
5L
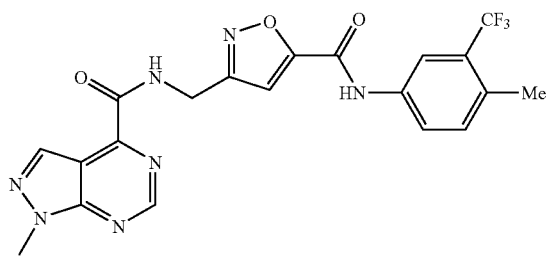
5Ma
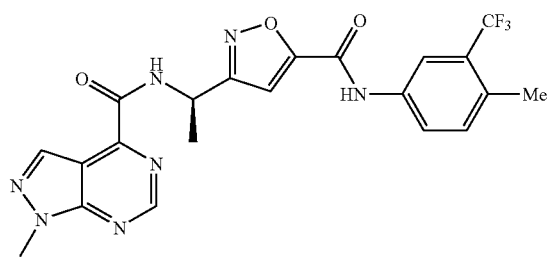

TABLE 5-continued
Additional compounds
5Mb
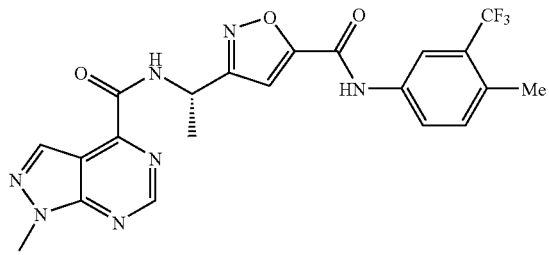
5Na
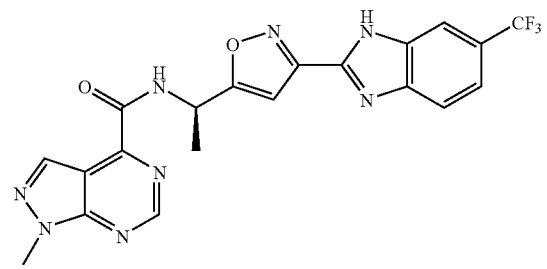
5Nb
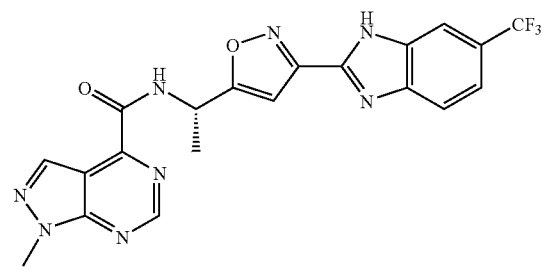
5O
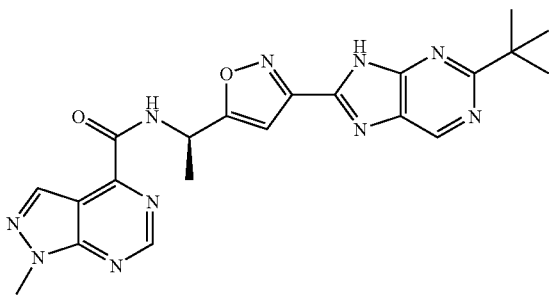
5P
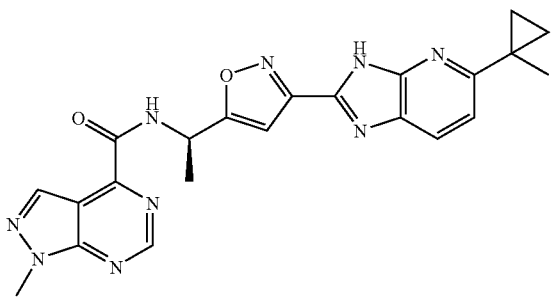

TABLE 5-continued
Additional compounds
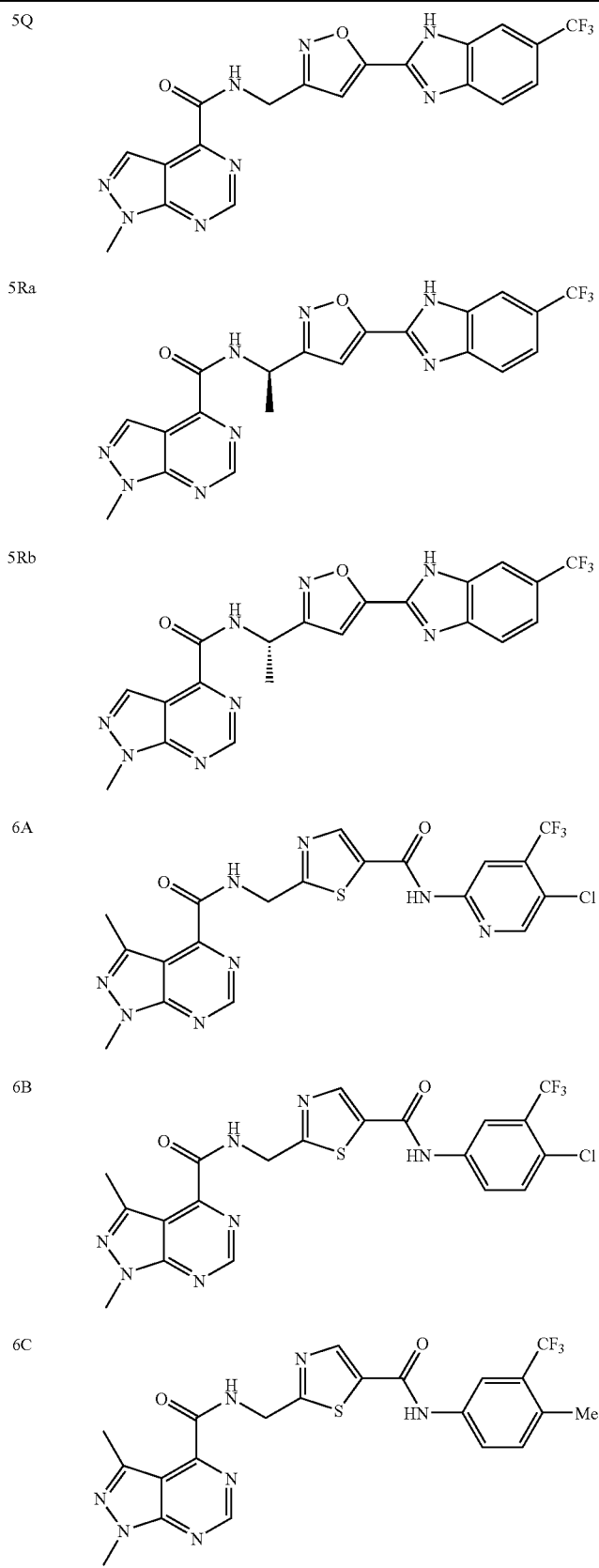

TABLE 5-continued
Additional compounds
6D 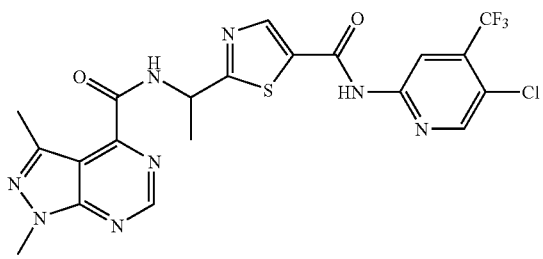
6Db 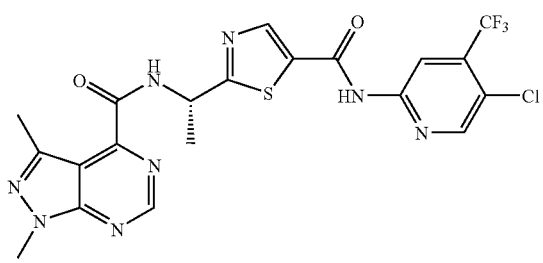
6E 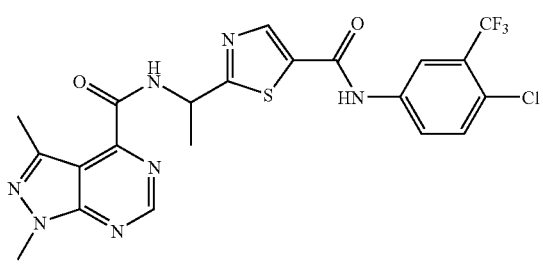
6Ea 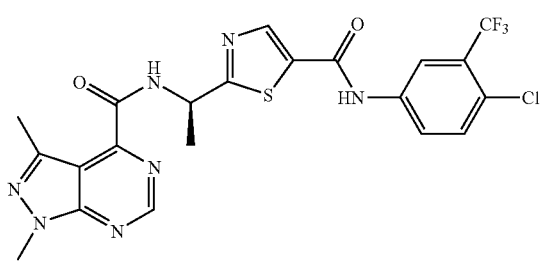
6Eb 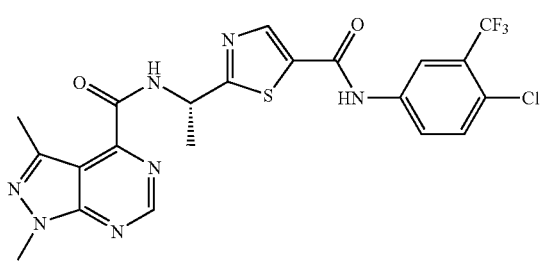
6F 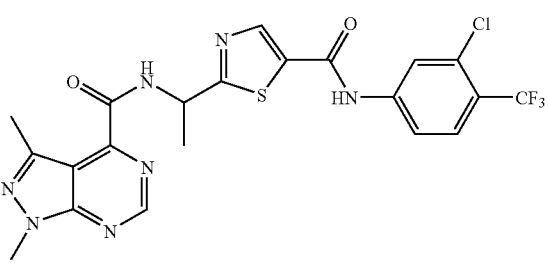

TABLE 5-continued
Additional compounds
6G 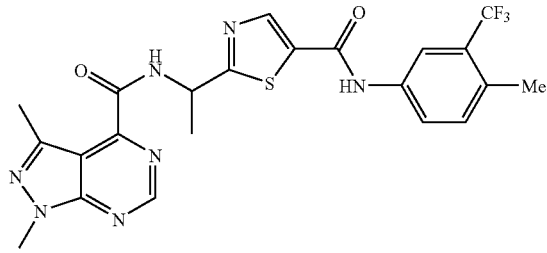
6H 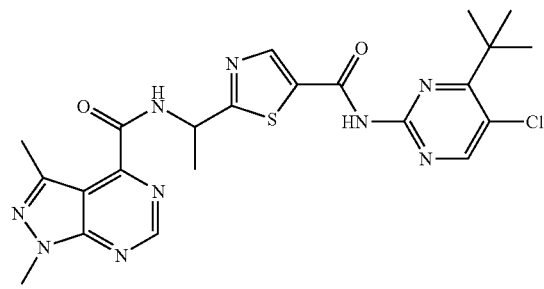
6I 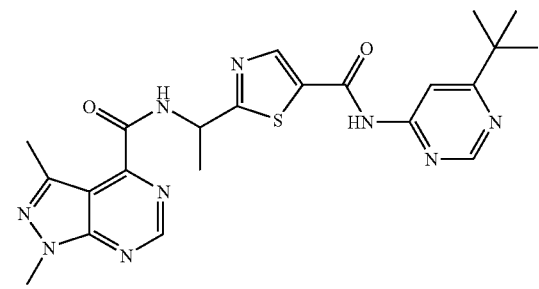
6J 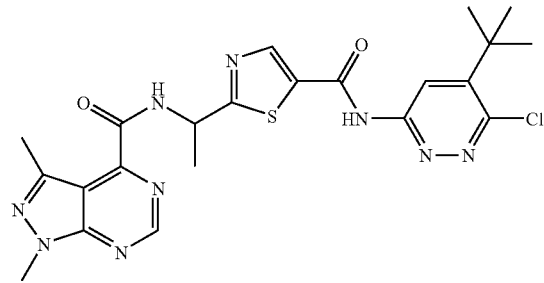
6K 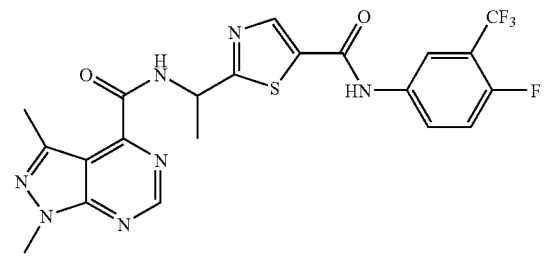

TABLE 5-continued
Additional compounds
6L
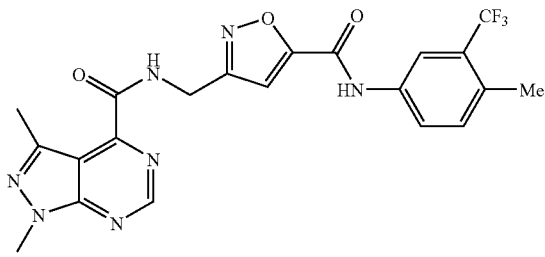
6Ma
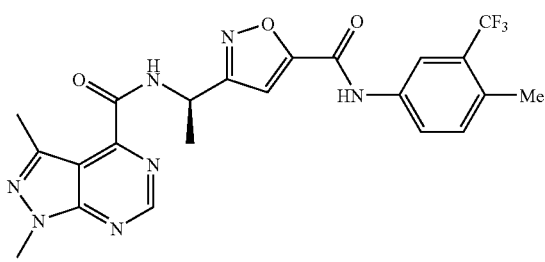
6Mb
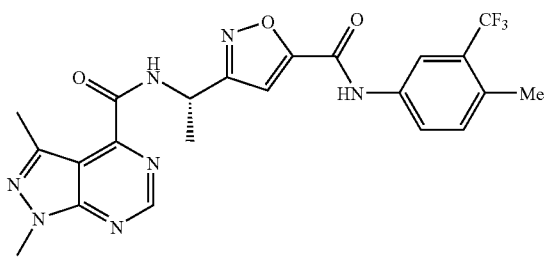
6Na
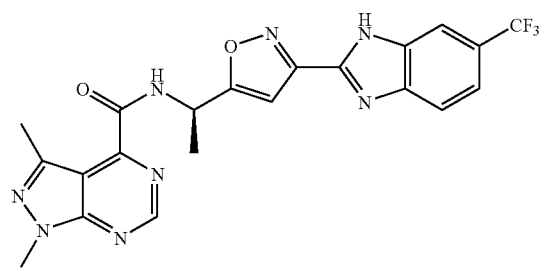
6Nb
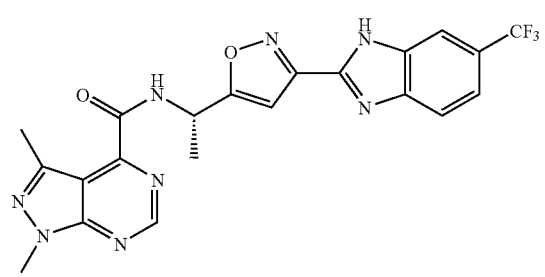

TABLE 5-continued
Additional compounds
6O
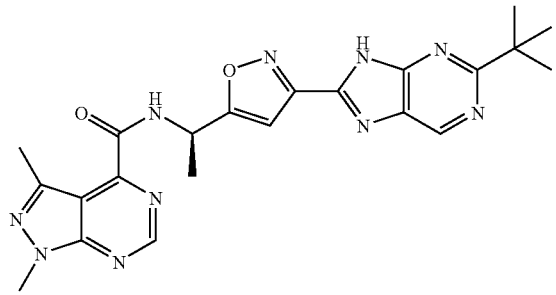
6P
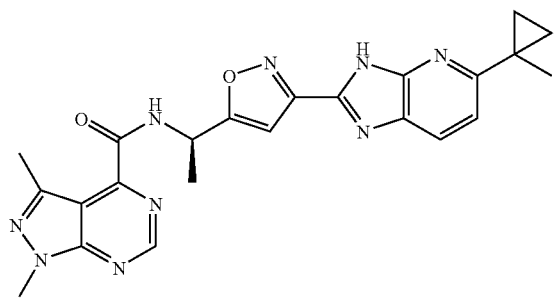
6Q
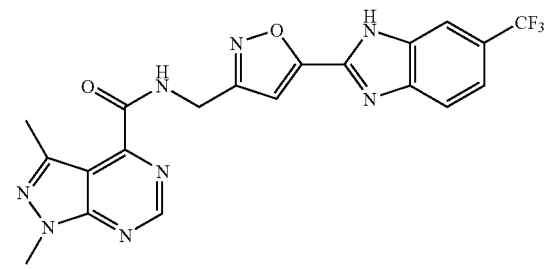
6Ra
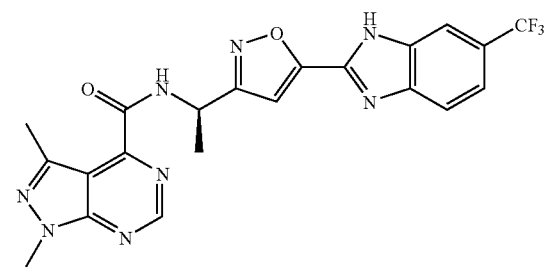
6Rb
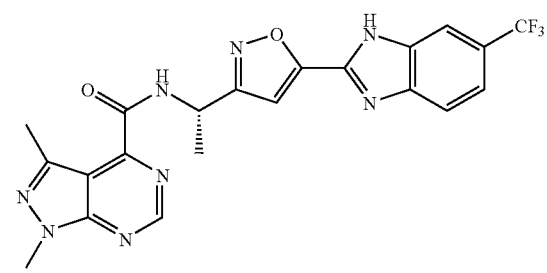

TABLE 5-continued

Additional compounds 8A, 8B, 8C, 8Da, 8Db, 8E

TABLE 5-continued
Additional compounds
8Ea 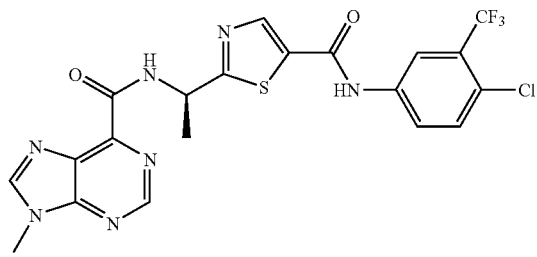
8Eb 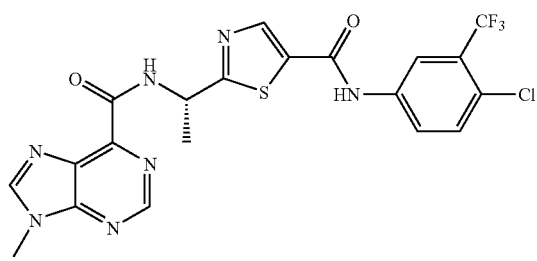
8F 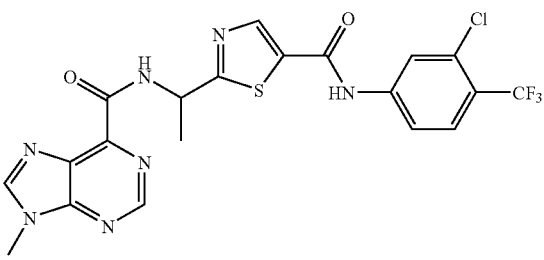
8G 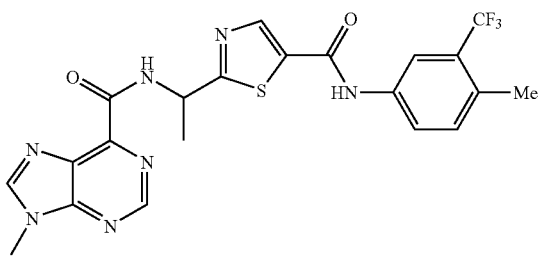
8H 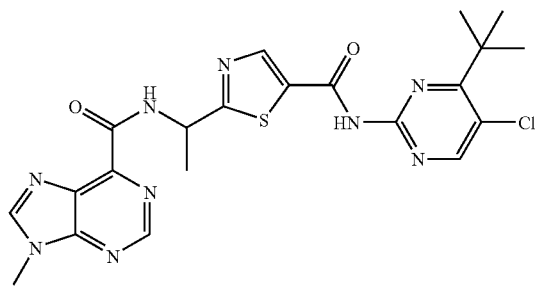

TABLE 5-continued
Additional compounds
8I
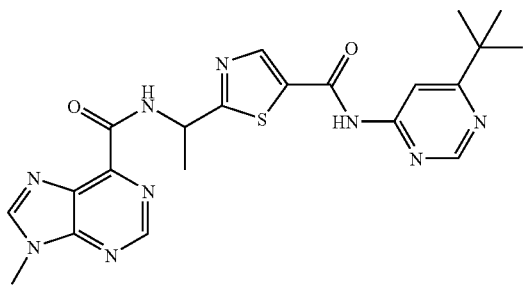
8J
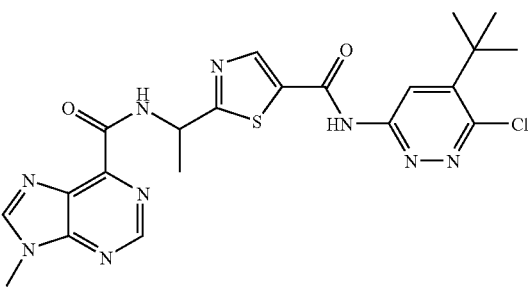
8K
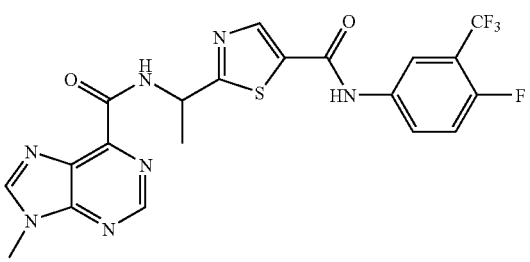
8L
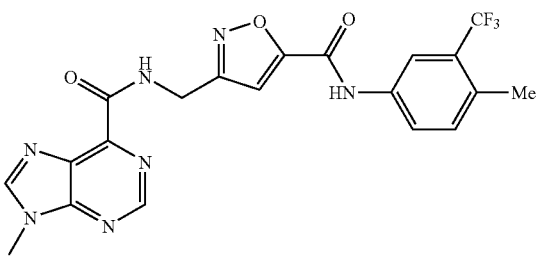
8Ma
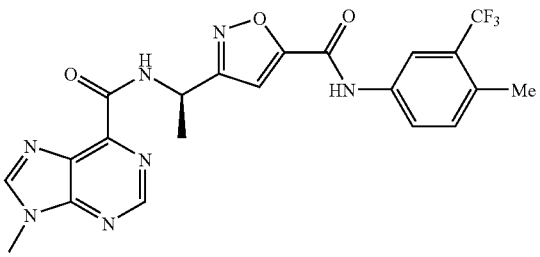

TABLE 5-continued
Additional compounds
8Mb
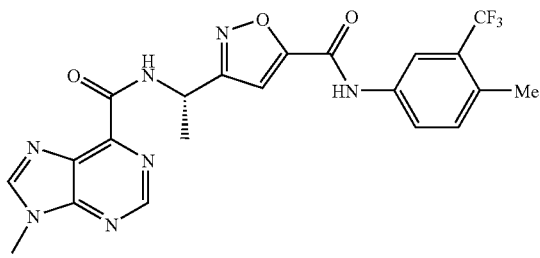
8Na
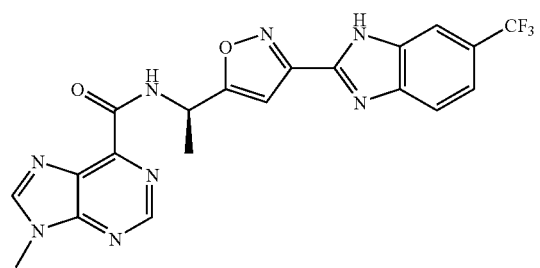
8Nb
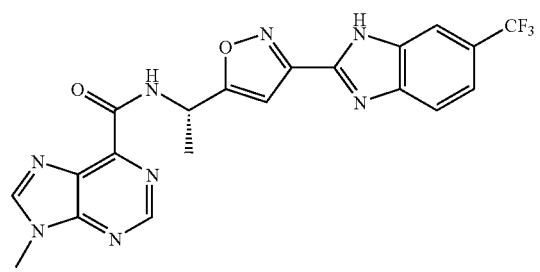
8O
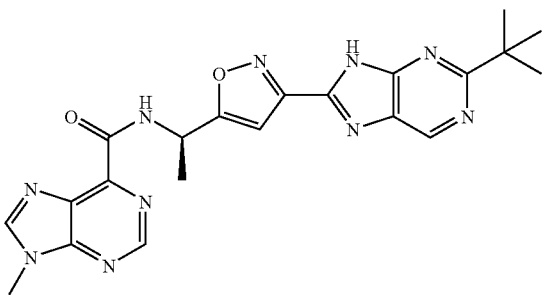
8P
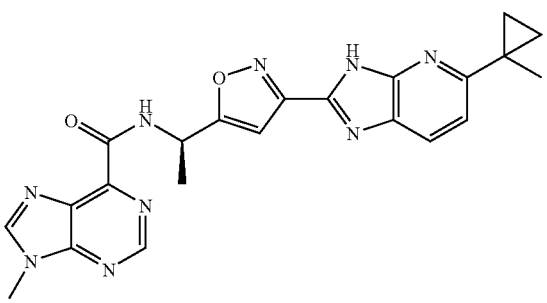

TABLE 5-continued
Additional compounds
8Q 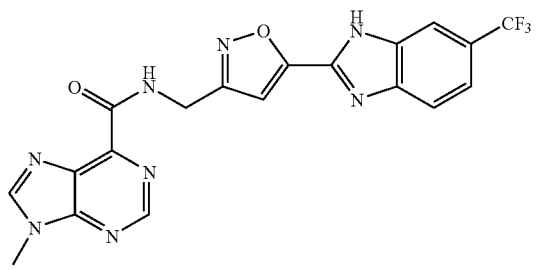
8Ra 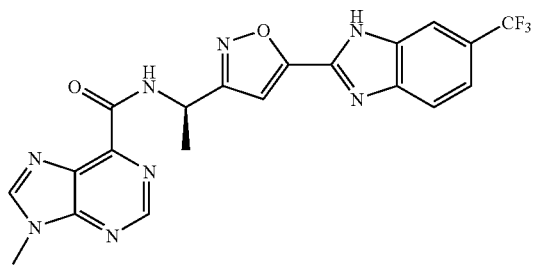
8Rb 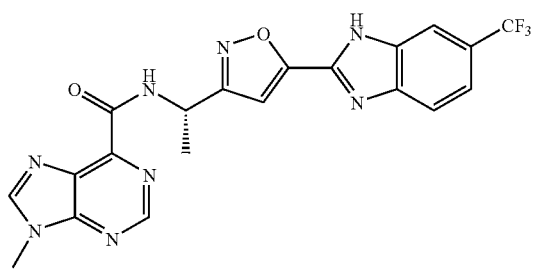
9A 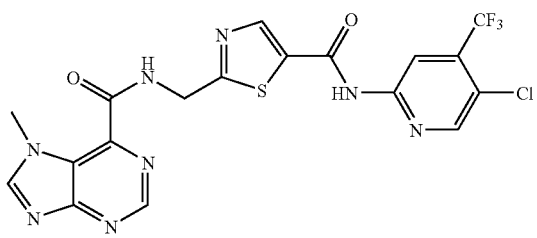
9B 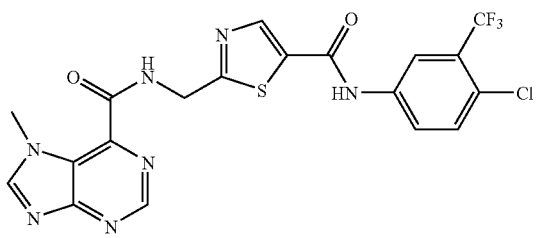
9C 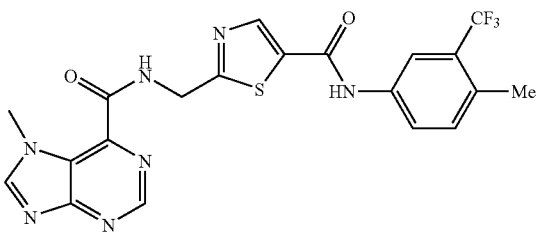

TABLE 5-continued
Additional compounds
9Da
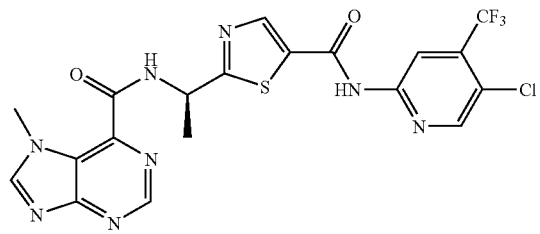
9Db
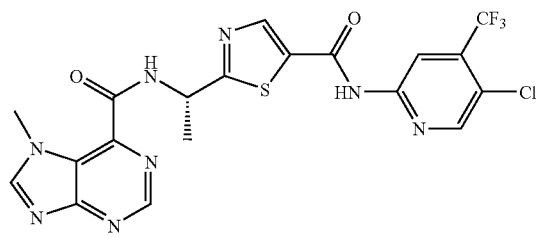
9E
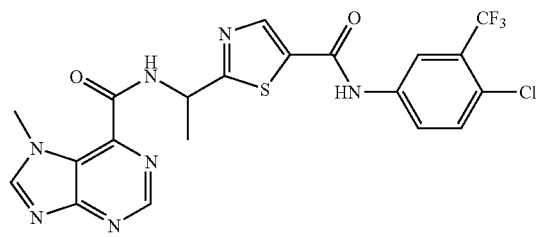
9Ea
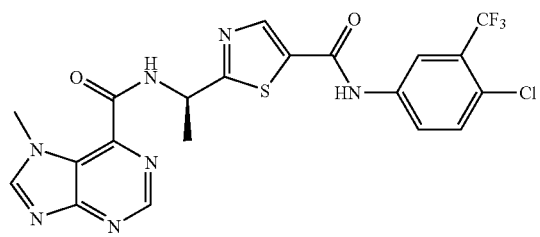
9Eb
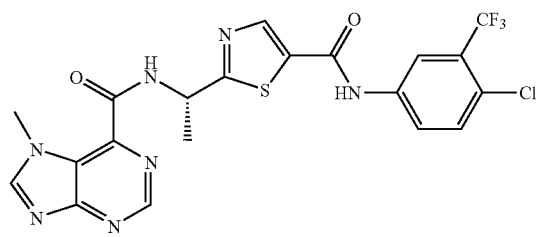
9F
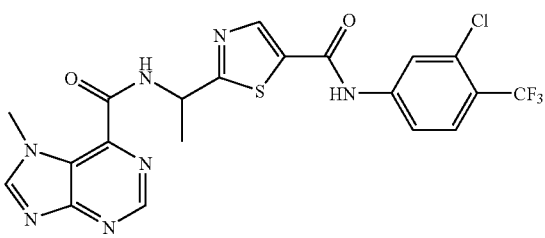

TABLE 5-continued
Additional compounds
9G 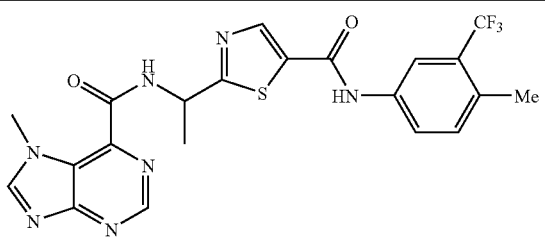
9H 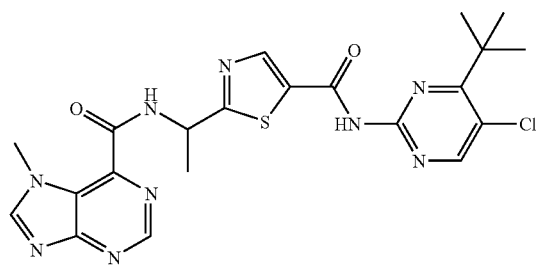
9I 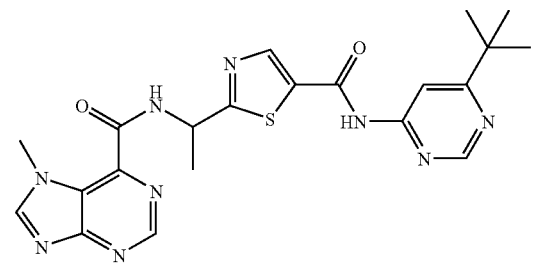
9J 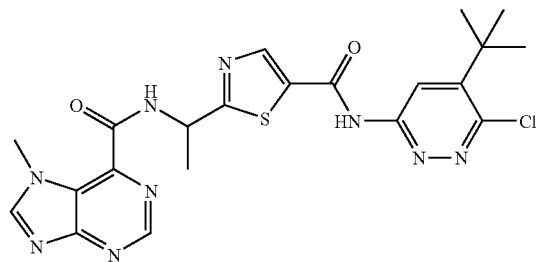
9K 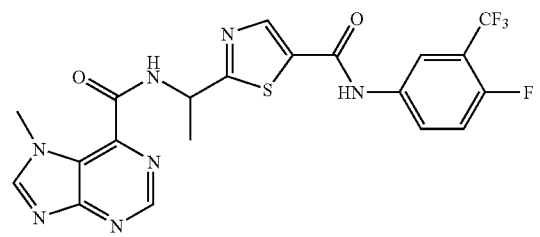
9L 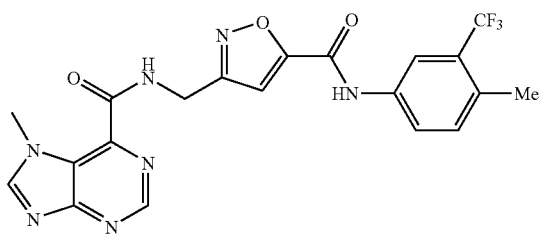

TABLE 5-continued
Additional compounds
9Ma
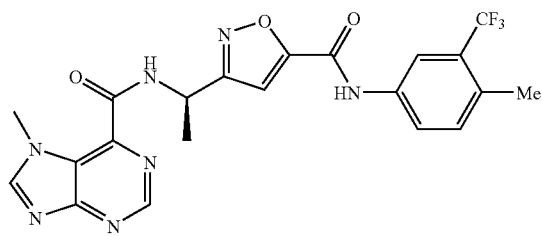
9Mb
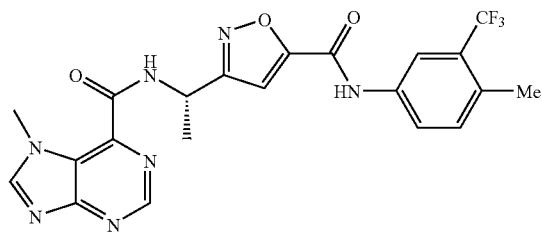
9Na
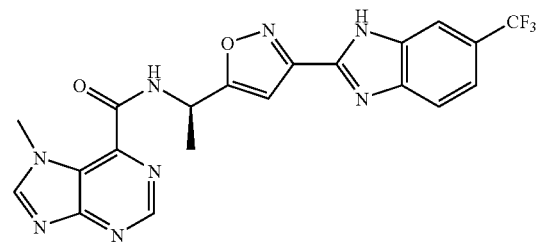
9Nb
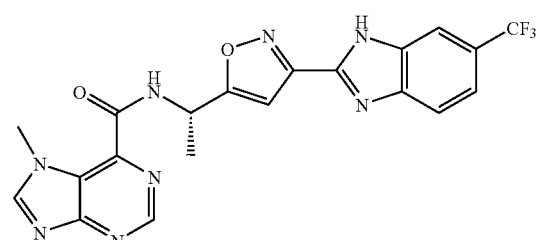
9O
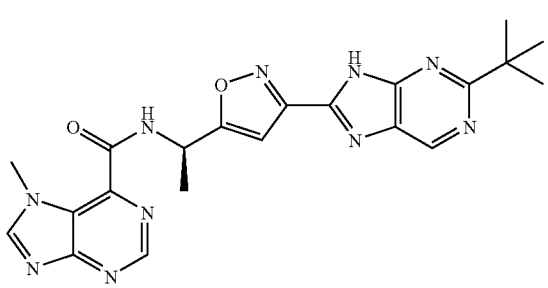
9P
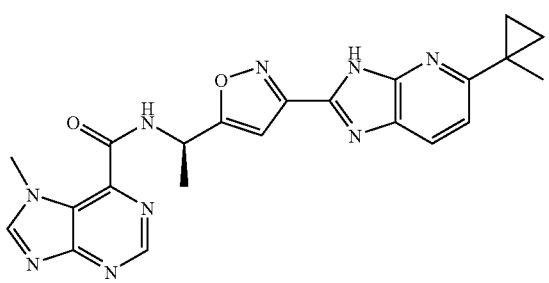

TABLE 5-continued
Additional compounds
9Q
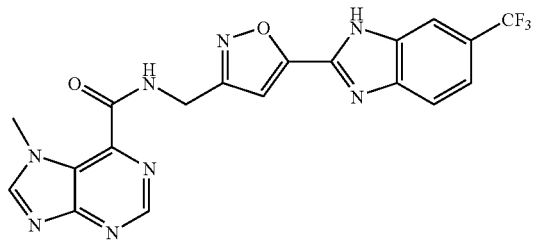
9Ra
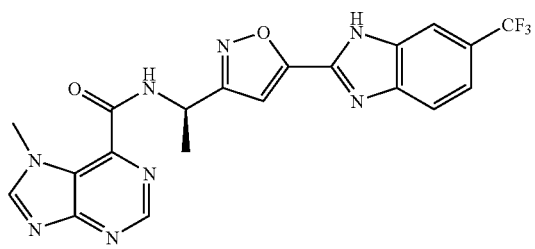
9Rb
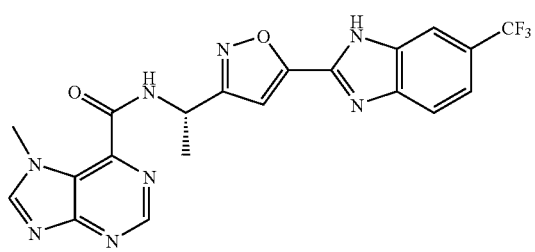
10A
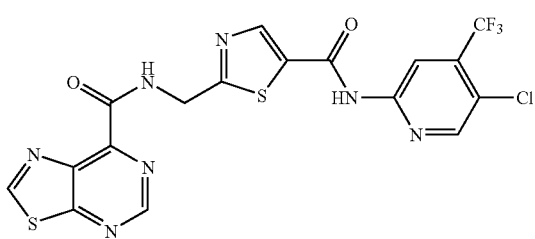
10B
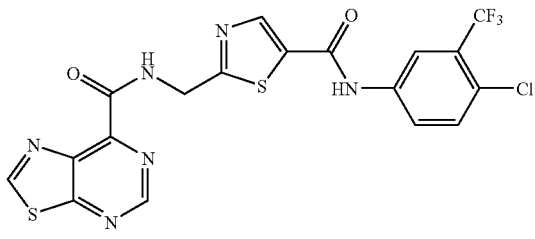
10C
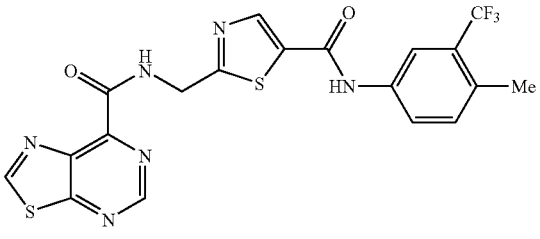

TABLE 5-continued
Additional compounds
10Da 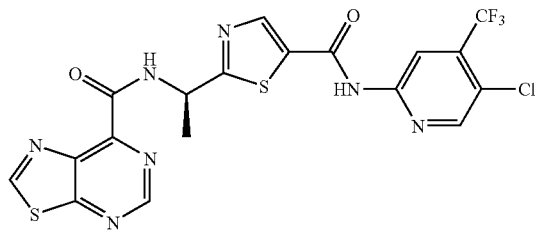
10Db 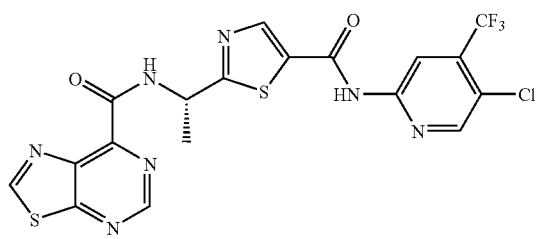
10E 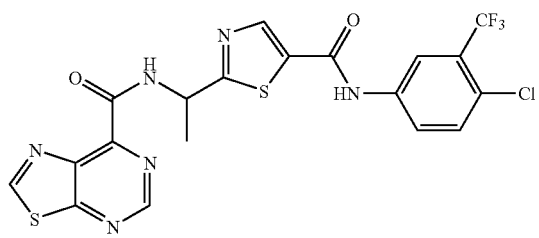
10Ea 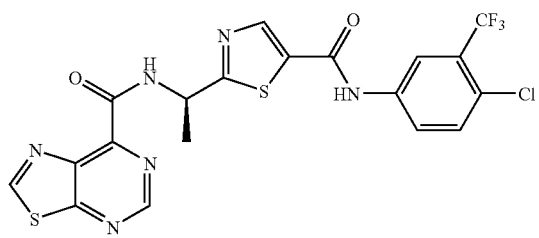
10Eb 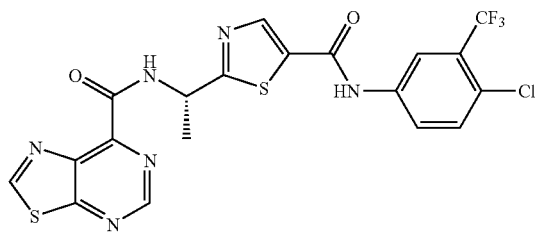
10F 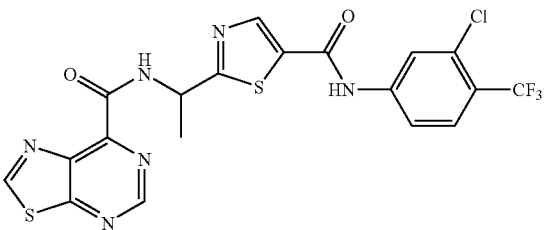

TABLE 5-continued
Additional compounds
10G
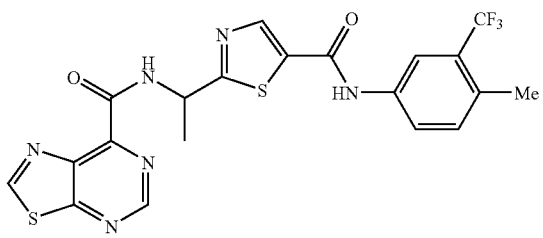
10H
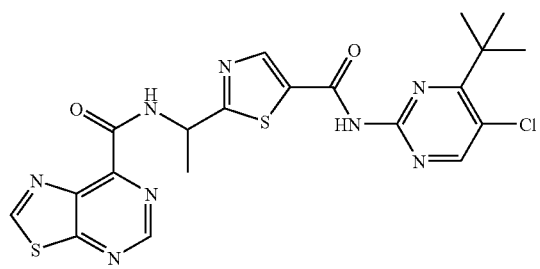
10I
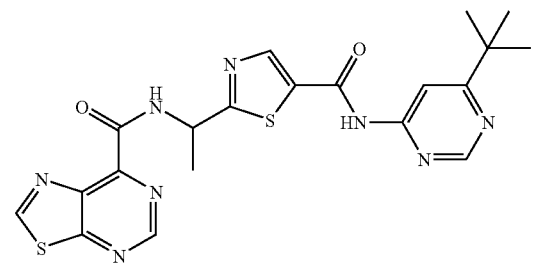
10J
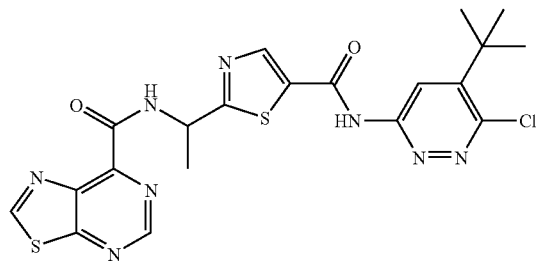
10K
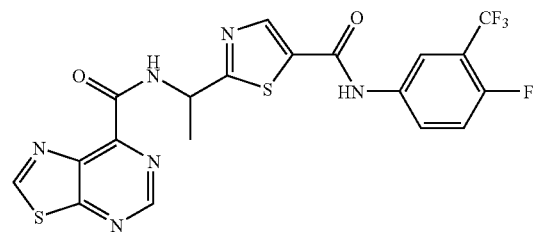
10L
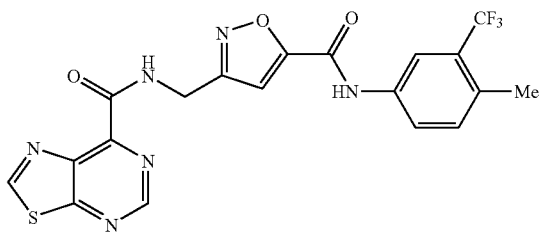

TABLE 5-continued
Additional compounds
10Ma
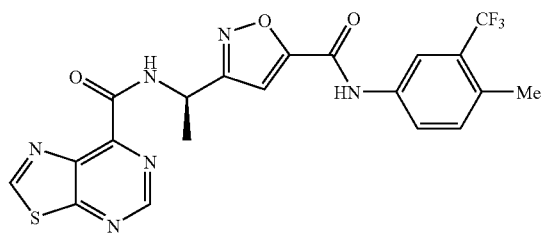
10Mb
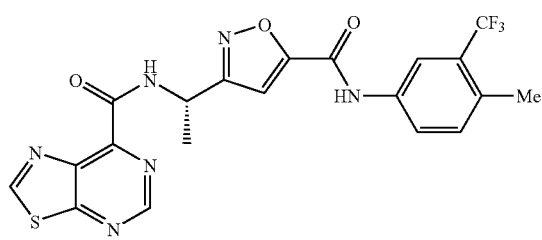
10Na
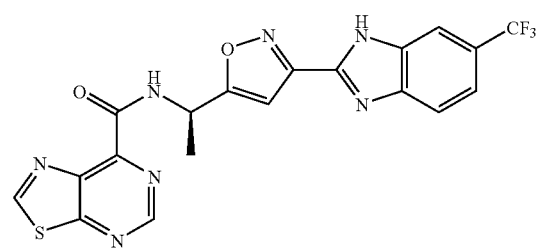
10Nb
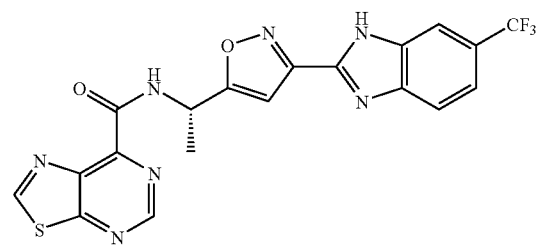
10O
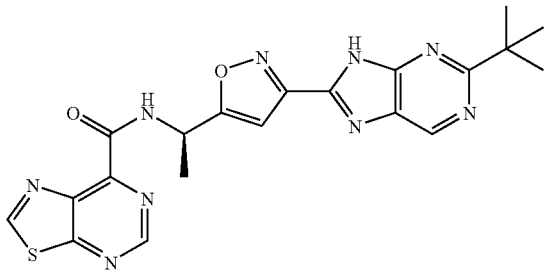
10P
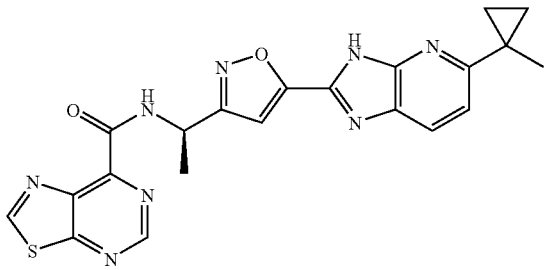

TABLE 5-continued
Additional compounds
10Q
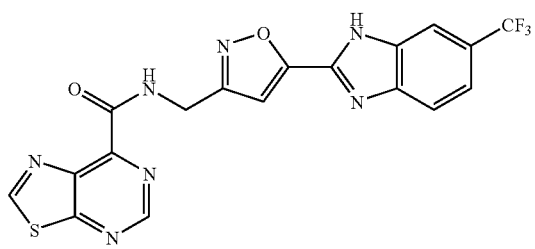
10Ra
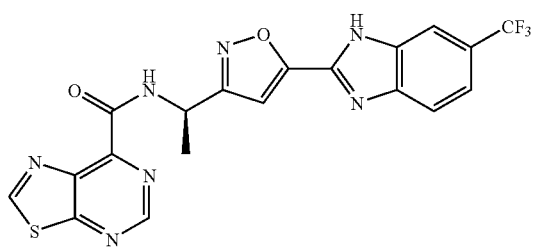
10Rb
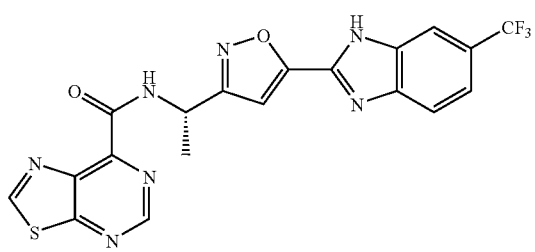
11A
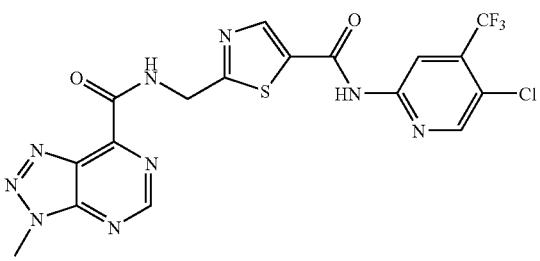
11B
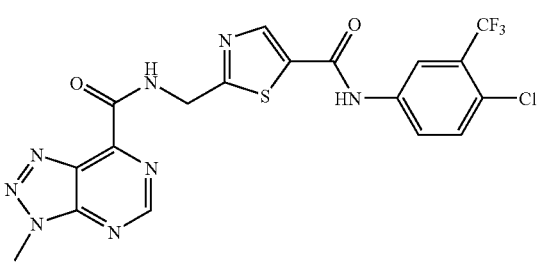
11C
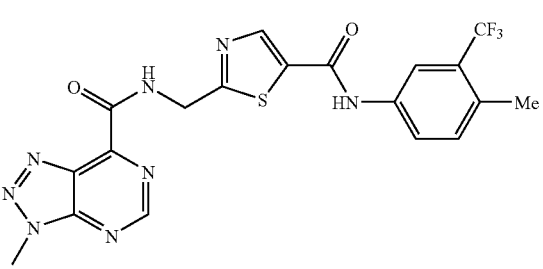

TABLE 5-continued
Additional compounds
11D
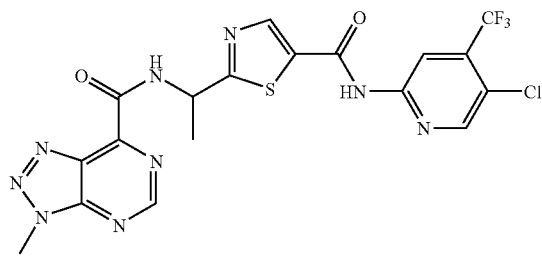
11Db
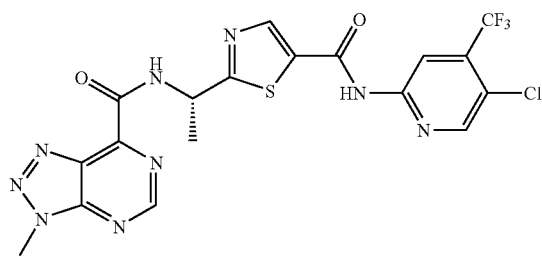
11E
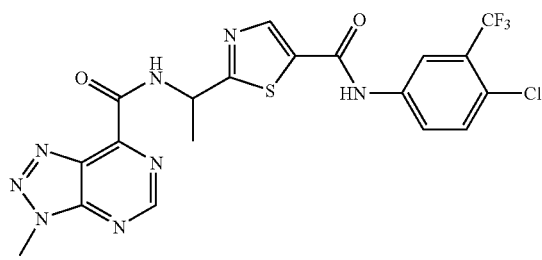
11Ea
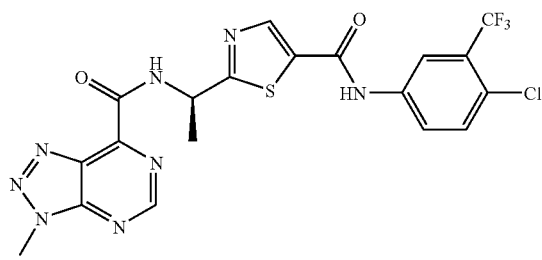
11Eb
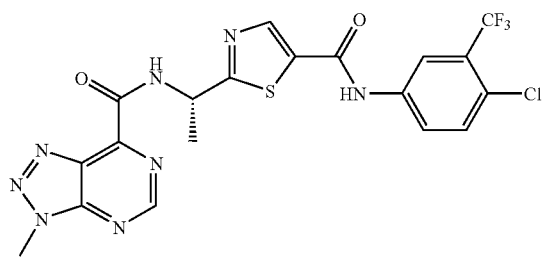
11F
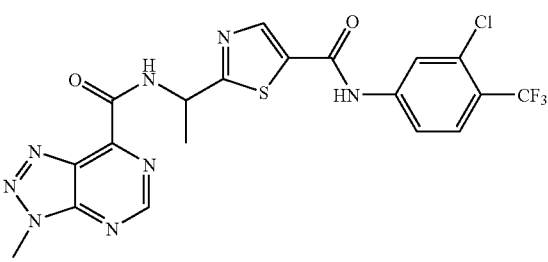

TABLE 5-continued
Additional compounds
11G
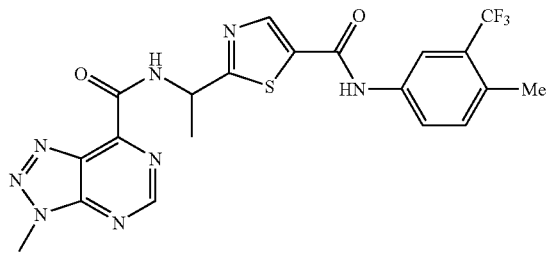
11H
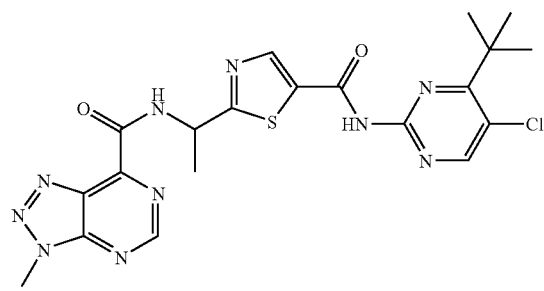
11I
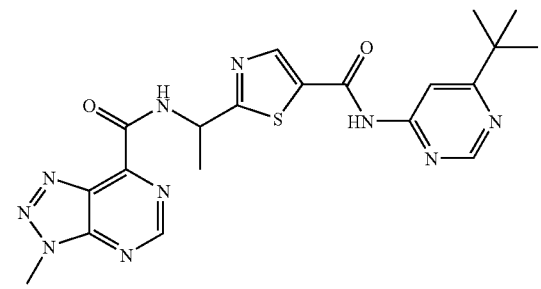
11J
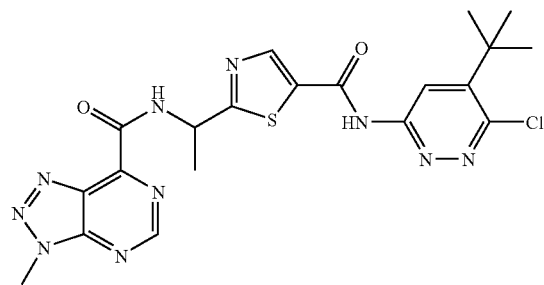
11K
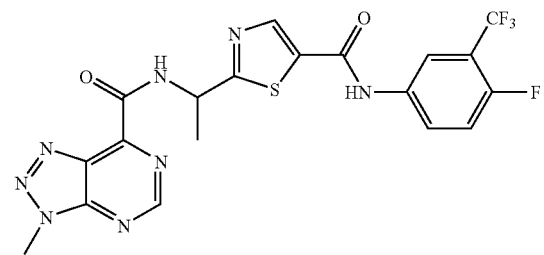

TABLE 5-continued
Additional compounds
11L
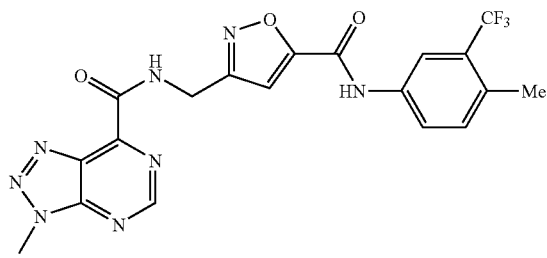
11Ma
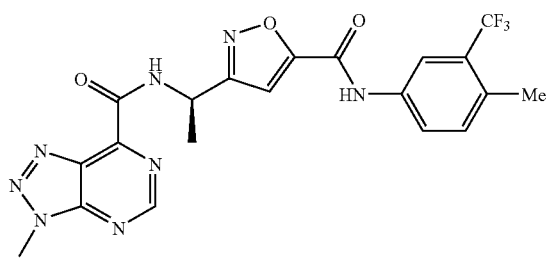
11Mb
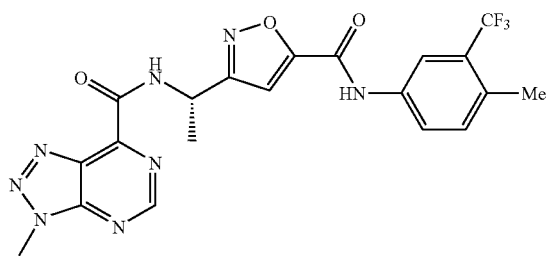
11Na
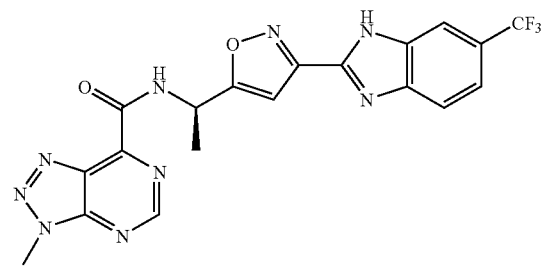
11Nb
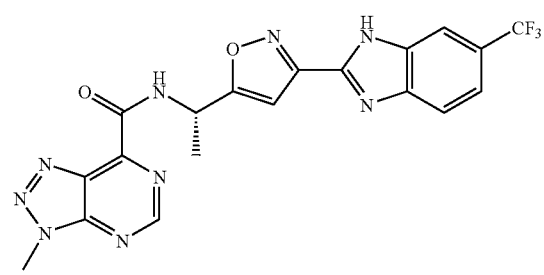

TABLE 5-continued
Additional compounds
11O
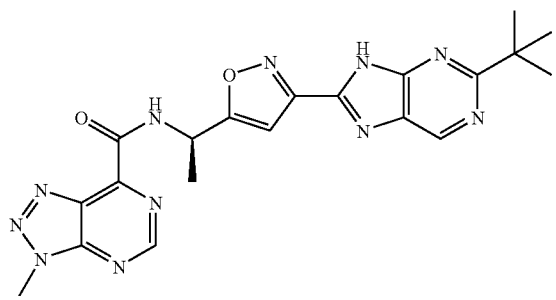
11P
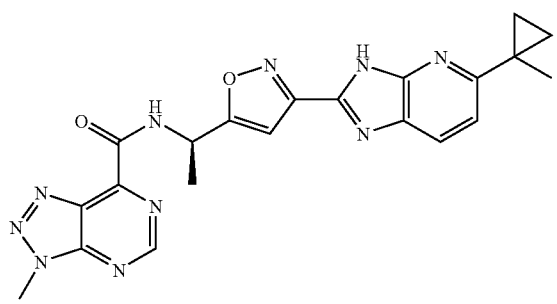
11Q
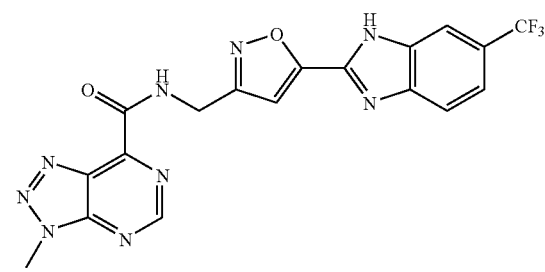
11Ra
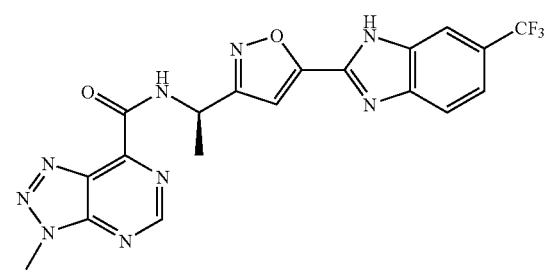
11Rb
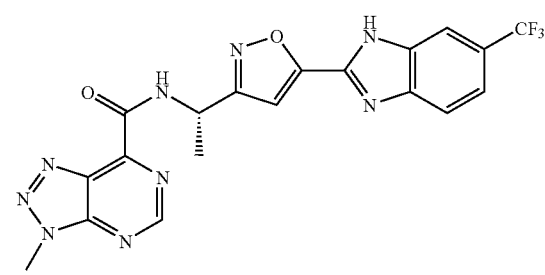

TABLE 5-continued
Additional compounds
12A
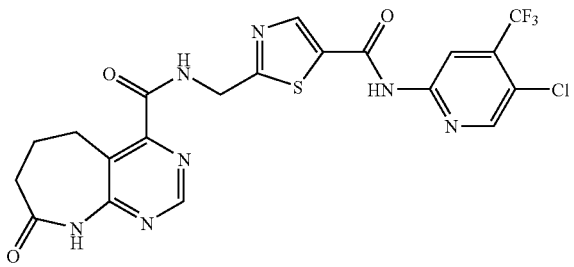
12B
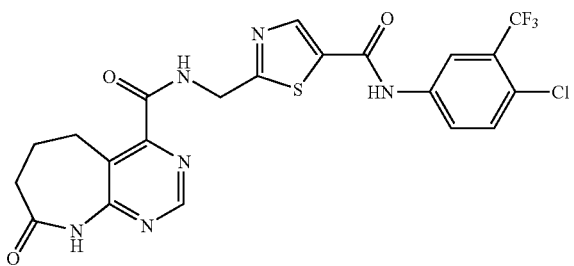
12C
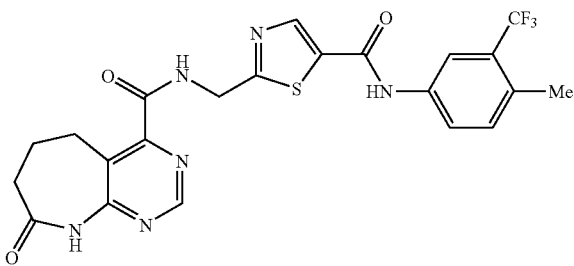
12D
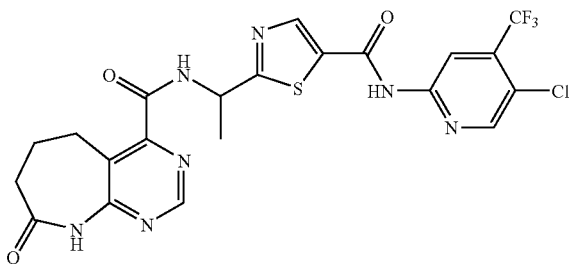
12Db
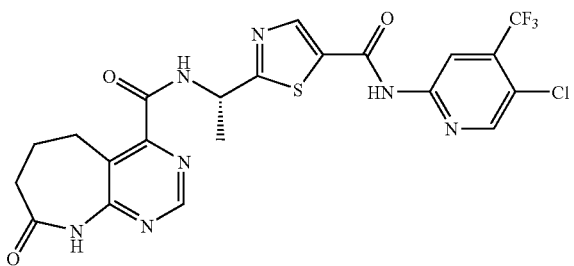

TABLE 5-continued
Additional compounds
12E
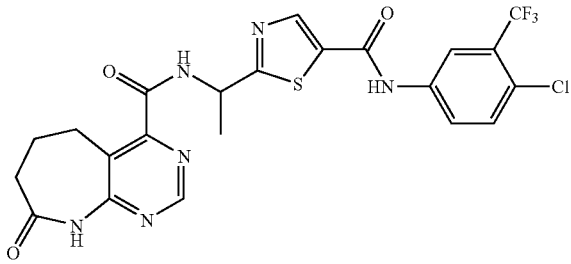
12Ea
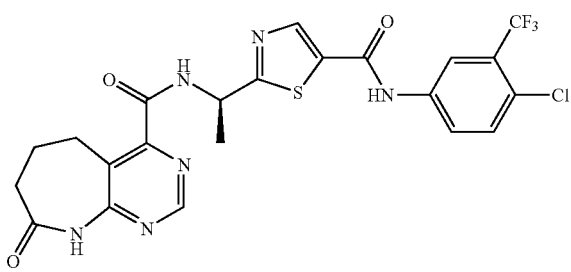
12Eb
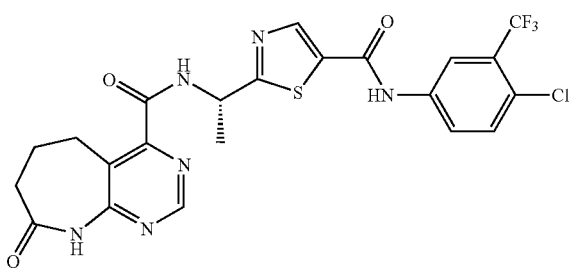
12F
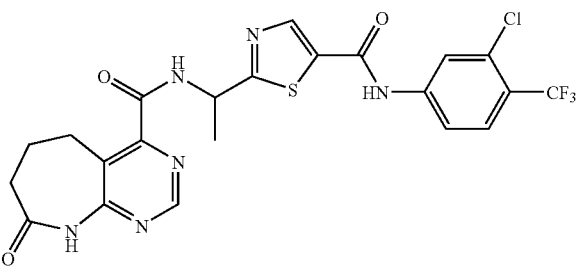
12G
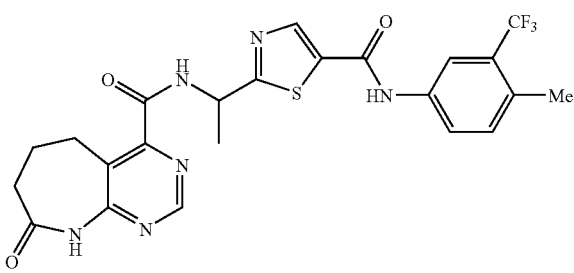

TABLE 5-continued
Additional compounds
12H
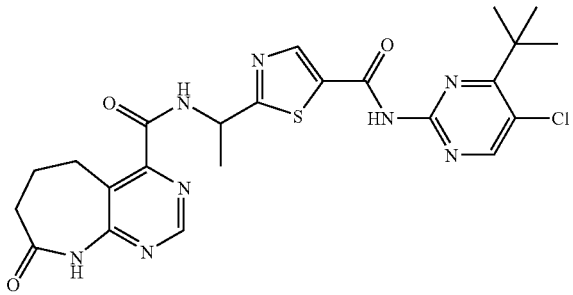
12I
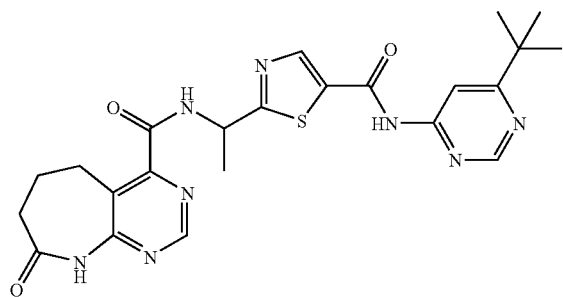
12J
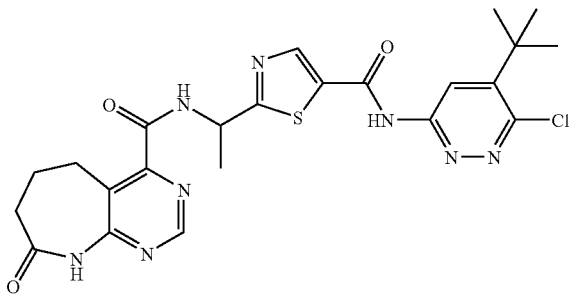
12K
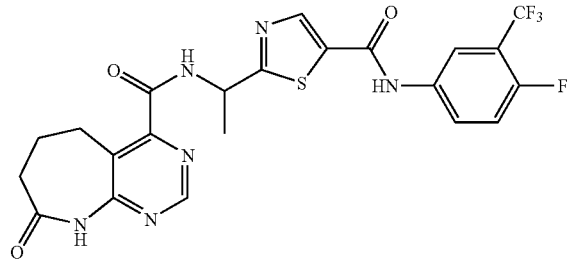
12L
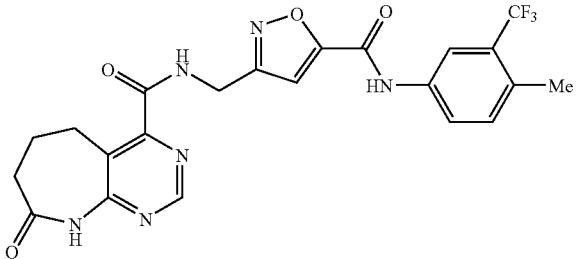

TABLE 5-continued
Additional compounds
12Ma
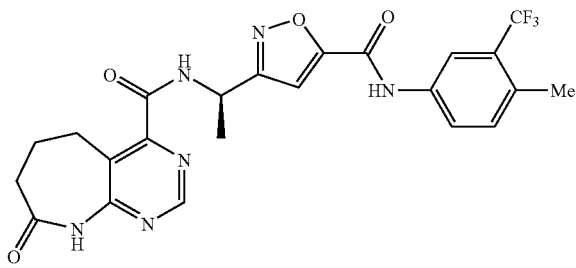
12Mb
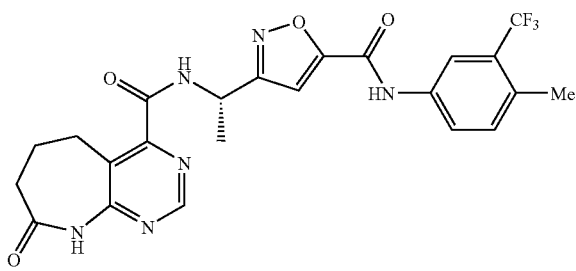
12Na
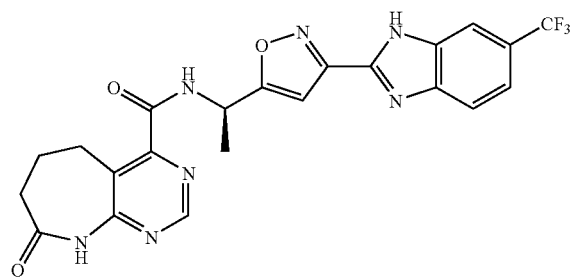
12Nb
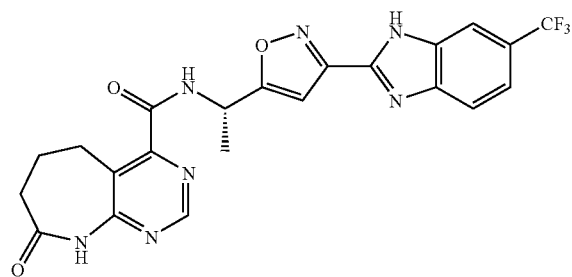
12O
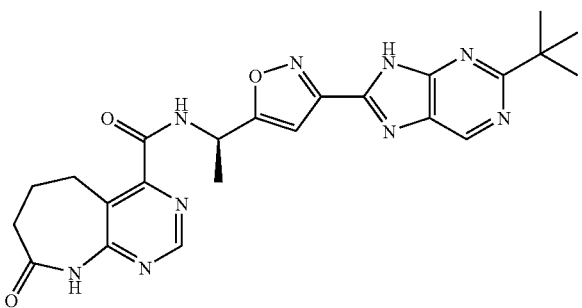

TABLE 5-continued
Additional compounds
12P
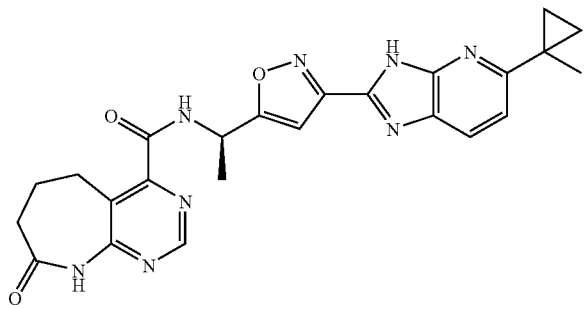
12Q
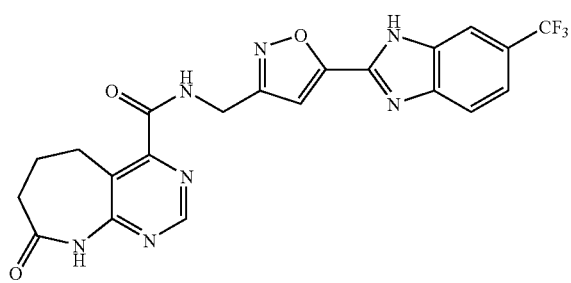
12Ra
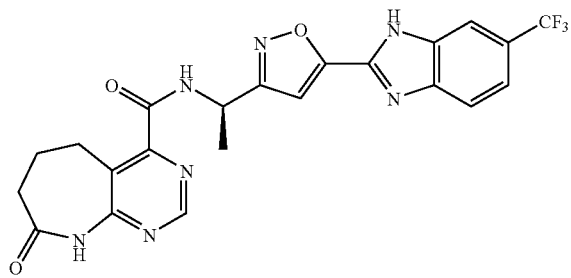
12Rb
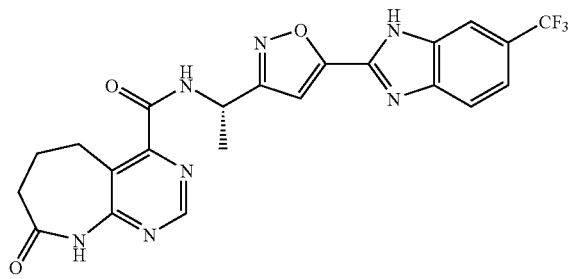
13A
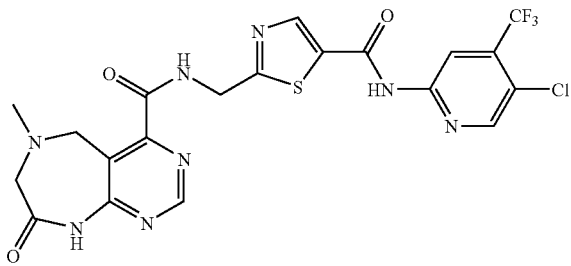

TABLE 5-continued
Additional compounds
13B
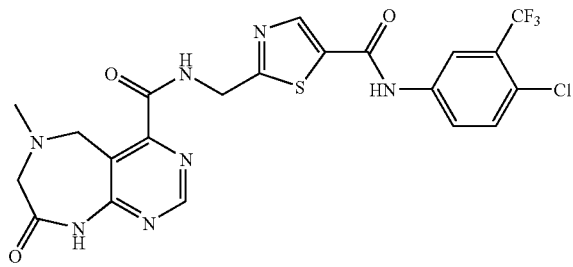
13C
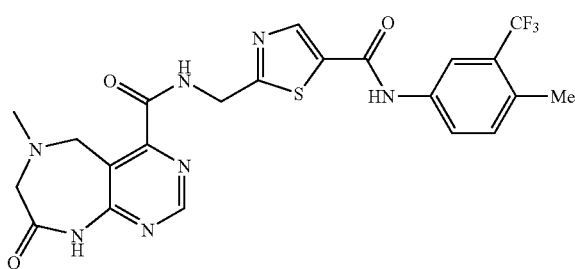
13D
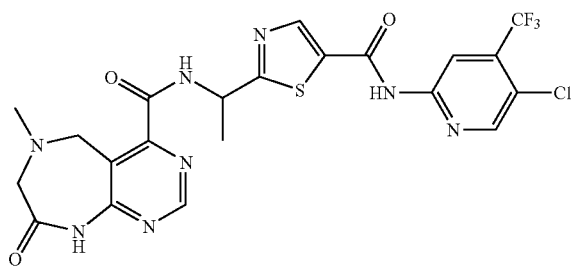
13Db
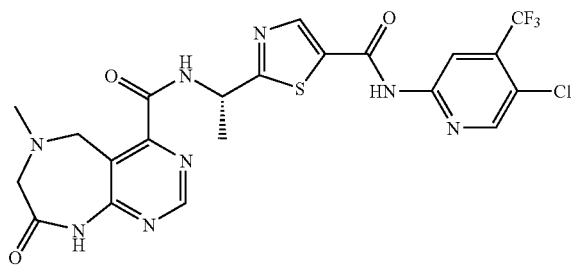
13E
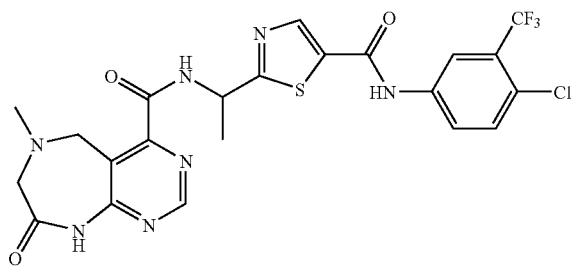

TABLE 5-continued
Additional compounds
13Ea
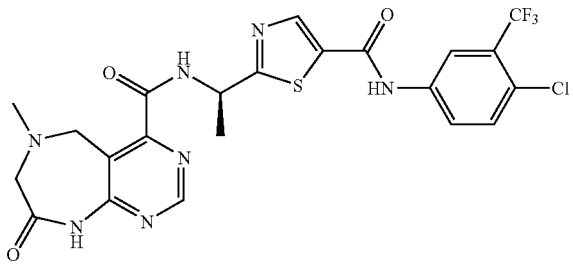
13Eb
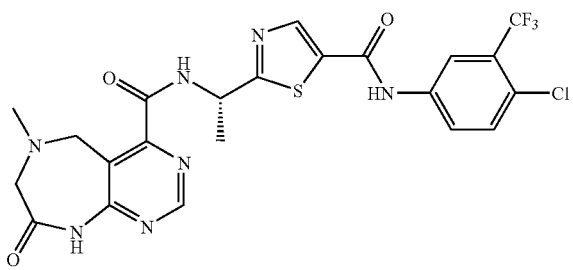
13F
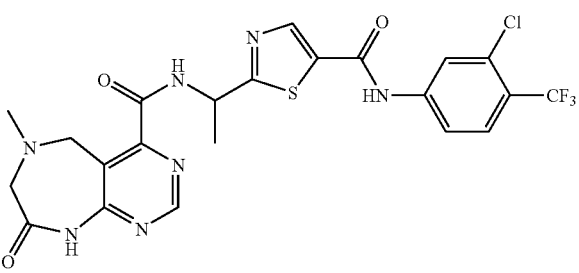
13G
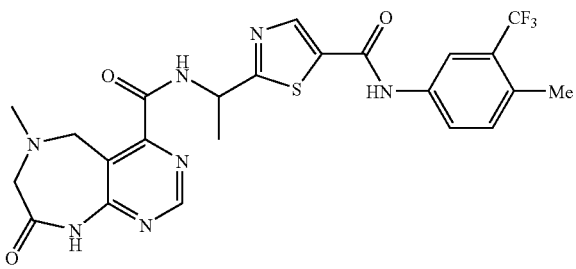
13H
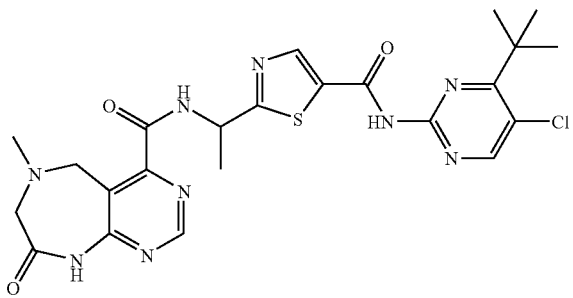

TABLE 5-continued
Additional compounds
13I
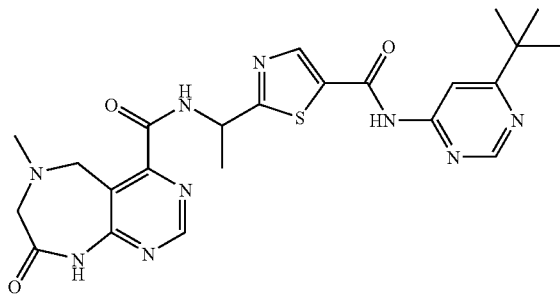
13J
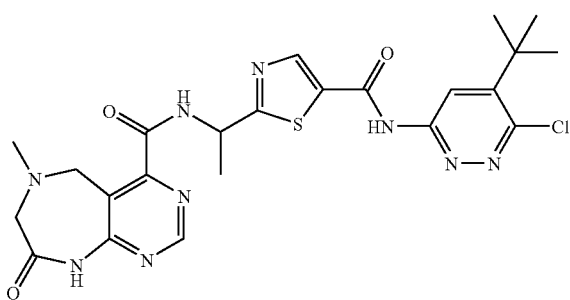
13K
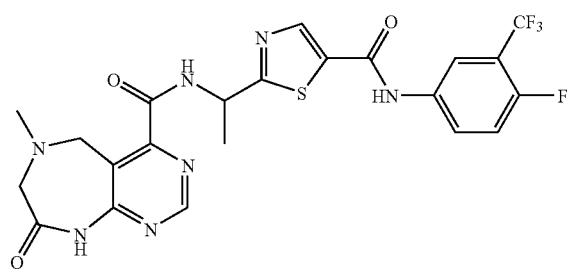
13L
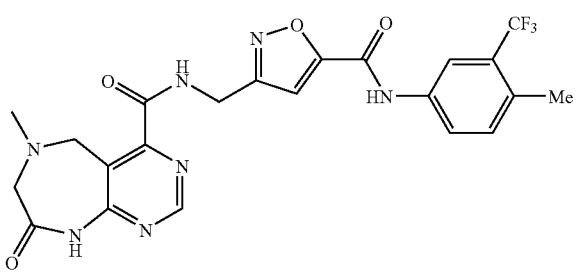
13Ma
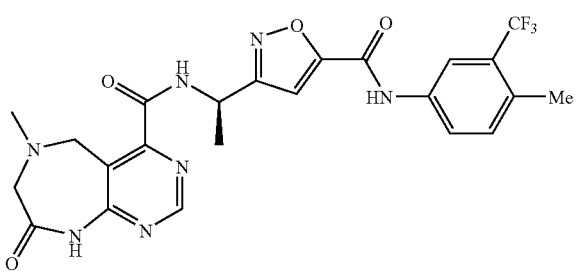

TABLE 5-continued
Additional compounds
13Mb
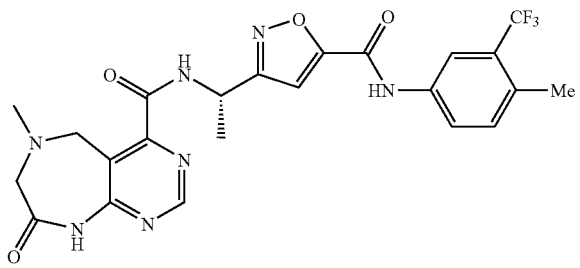
13Na
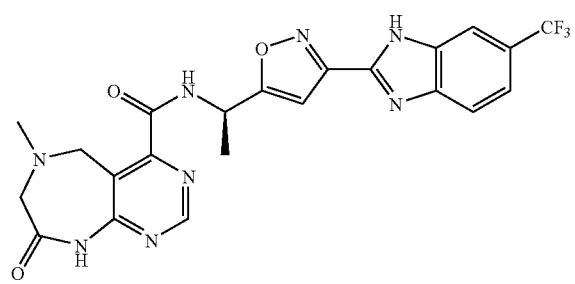
13Nb
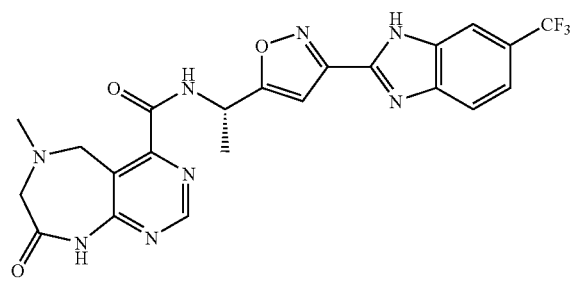
13O
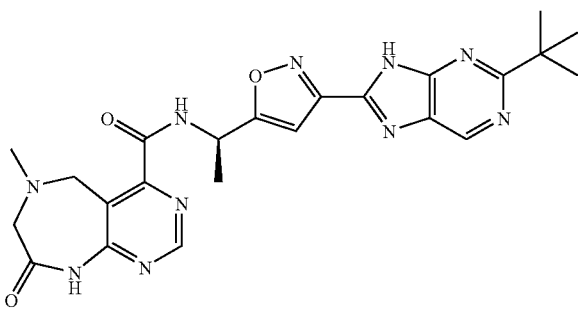
13P
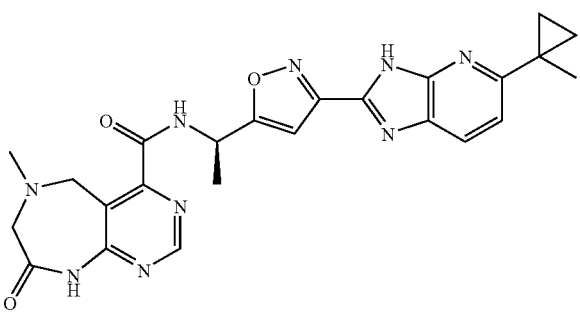

TABLE 5-continued

Additional compounds

13Q

13Ra

13Rb

Biological Assays
(1) Biochemical FRET Assay

Method utilized for measuring the phosphorylation of MEK by wild-type (WT) B-Raf as a method for quantifying the ability of molecules to inhibit the enzymatic activity of WT-B-Raf.

In the assay methods described below, the following definitions apply:

"HEPES" refers to 4-(2-hydroxyethyl)-1-piperazineethanesulfonic acid;

"MEK" refers to mitogen activated extracellular signal-related kinase kinase;

"DTT" refers to dithiothreitol;

"APC" refers to allophycocyanin;

"TR-FRET" refers to time resolved fluorescence energy transfer;

"PBS" refers to phosphate buffered saline;

"PMSF" refers to phenyl methyl sulfonamide; and

"BSA" refers to bovine serum albumin.

TABLE 6

Reagents

| Name | Units/Amount | Source | Catalog Number | Storage |
|---|---|---|---|---|
| Biotin-MEK1 (15:1) | DB021505 767 µg/mL (10.8 µM) | Biogen Idec. | In house | −80° C. |
| ATP | 10 mM, 500 µl | Gibco BRL | 8330-019 | −20° C. |
| B-Raf (WT) | 12 µg/480 µl 54% Pure (2.1 µM) | Upstate | 14-530M | −80° C. |
| DMSO | 100% | Fisher | D128-500 | RT |
| Streptavidin Allophycocyanin (SA-APC) | 14.8 µM SA (2.20 mg/ml) | Prozyme | PJ25S | 4° C., in the dark |
| Polyclonal Antiphospho MEK1/2(Ser 217/221) Antibody | 265 µg/ml (1.8 µM) | Cell Signaling Technologies Inc. | 9121 | −20° C. |

TABLE 6-continued

Reagents

| Name | Units/Amount | Source | Catalog Number | Storage |
|---|---|---|---|---|
| Lance Eu-W1024 Anti Rabbit IgG | 880 µg/ml (5.5 µM) | Perkin Elmer | AD083 | 4° C. |
| LANCE 10X Detection Buffer | N/A | Perkin Elmer | CR97-100 | 4° C. |
| SuperBlock in TBS | N/A | Pierce | 37535 | 4° C. |

TABLE 7

Buffers

| Master Buffer | Storage |
|---|---|
| 50 mM Hepes, 60 mM NaCl, 3 mM $MgCl_2$ | 4° C. |
| 1 M Dithiothreitol(DTT) | −20° C. in aliquots of 150 µl |
| 1 M $MnCl_2$ | 4° C. |
| 20% BSA, 0.002% Sodium Azide. | 4° C. |
| 20% Tween-20 | room temperature (~25° C.) |
| 1 M EDTA in $dH_2O$ | room temperature (~25° C.) |

Equipment and Materials: Analyst AD, LJL BioSystems, ID1615; 96 well ½ Area Black Polystyrene plates. Costar 3694.

Assay Protocol:
1. Add 10 µL 4.5× B-Raf WT
2. Add 10 µL 4.5× Test compound/DMSO
3. Add 25 µL mixture of 1.8×ATP/Biotin MEK
4. Incubate at room temperature for 90 minutes.
5. Add 5 µL of 150 mM EDTA to stop the reaction (final concentration of 15 mM; final volume of stopped reaction is 50 µl.).
6. Add 50 µL of 2× detection reagents (SA-APC, Anti p-MEK½, Eu-AntiRabbit IgG).
7. Incubate at room temperature for 90 minutes.
8. Read on Analyst.

TABLE 8

| Reagents used for Kinase reaction: |
|---|
| 50 µM ATP |
| 0.125 nM B-Raf (WT) |
| 12.5 nM Biotin-MEK (15:1) |
| 1% DMSO |
| 50 mM Hepes, 60 mM NaCl, 3 mM $MgCl_2$, |
| 2 mM DTT, 0.25 mM $MnCl_2$, 0.01% |
| BSA, 0.01% Tween-20 |
| Reagents used for Detection Reaction |
| 20 nM SA-APC |
| 2.5 nM Polyclonal Anti p-MEK1/2 (Ser217/221) |
| 2.5 nM Eu-AntiRabbit IgG |
| 1X Lance Detection Buffer |
| 10% Superblock in TBS |

WT Raf

Inhibitors were diluted 4-fold in 100% DMSO and added to a final concentration of 10 µM to 40 µM to a solution containing 12.5 nM biotin-MEK, 0.125 nM WT Raf in 50 mM HEPES, pH 7.4, 60 mM NaCl, 3 mM $MgCl_2$, 2 mM DTT, 0.25 mM $MnCl_2$, 0.01% BSA, and 0.01% Tween-20 and incubated for 2 hours at room temperature. The kinase reaction was started by the addition of 50 µM ATP to a final volume of 45 µl and allowed to progress for 60 minutes. The reaction was stopped with 15 mM EDTA and 20 nM Streptavidin-APC, 2.5 nM Polyclonal anti p-MEK½ (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

Mutant Raf

Inhibitors were diluted 4-fold in 100% DMSO and added to a final concentration of 10 µM to 40 pM to a solution containing 100 nM biotin-MEK, 0.125 nM V599E Raf in 50 mM HEPES, pH 7.4, 60 mM NaCl, 3 mM $MgCl_2$, 2 mM DTT, 0.25 mM $MnCl_2$, 0.01% BSA, and 0.01% Tween-20 and incubated for 20 minutes at room temperature. The kinase reaction was started by the addition of 25 µM ATP to a final volume of 45 µl and allowed to progress for 60 minutes. The reaction was stopped with 15 mM EDTA and 20 nM Streptavidin-APC, 2.5 nM Polyclonal anti p-MEK½ (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

C-Raf

Inhibitors were diluted 4-fold in 100% DMSO and added to a final concentration of 10 µM to 40 pM to a solution containing 50 nM biotin-MEK, 0.075 nM C-Raf in 50 mM HEPES, pH 7.4, 60 mM NaCl, 3 mM $MgCl_2$, 2 mM DTT, 0.25 mM $MnCl_2$, 0.01% BSA, and 0.01% Tween-20 and incubated for 20 minutes at room temperature. The kinase reaction was started by the addition of 10 µM ATP to a final volume of 45 µl and allowed to progress for 60 minutes. The reaction was stopped with 15 mM EDTA and 20 nM Streptavidin-APC, 2.5 nM Polyclonal anti p-MEK½ (Ser217/221), 2.5 nM Eu-labeled anti-rabbit IgG were added in Lance detection buffer and 5% Superblock in PBS for a final volume of 100 µl. The detection reaction was incubated for 90 minutes at room temperature and then read on an Analyst plate reader using standard TR-FRET (time resolved fluorescence resonance energy transfer) settings for Eu and APC.

Certain compounds of the present invention were assayed using the above Biochemical FRET assay and were found to be inhibitors of Raf kinase.

(2) Mechanistic Cellular Assay for Raf Kinase Activity

The following method was utilized for quantifying the amount of phospho-ERK in melanoma derived WM-266-4 cells (one allele each of wild type BRaf and mutant BRaf (V600D) as an indicator of Raf kinase activity in cells treated with various kinase inhibitors.

TABLE 9

| Materials Needed | Catalog Number |
|---|---|
| WM-266-4 cells | (ATCC number: CRL-1676) |
| RPMI 1640 cell culture medium | |
| Fetal Bovine Serum (FBS) | |
| Phosphate Buffered Saline (PBS) | |
| 96-well tissue culture plates | |
| Tissue culture 37° C. incubator | |
| 96-well V-bottom plates | |
| Rotary plate shaker (e.g., BELLCO GLASS Mini Orbital Shaker) | |
| Bio-Plex suspension array system | |
| Bio-Plex Cell Lysis Kit | (Bio Rad Catalog #171-304011) |
| Phenyl methyl sulphonyl fluoride (PMSF) | |
| Bio-Plex Phospho-ERK1/2 Assay Kit | (Bio Rad Catalog #171-V22238) |

Day 1: Cell Seeding (1) Detached adhered WM-266-4 cells from flask using 0.25% Trypsin. Resuspended cells in growth media (90% RPMI 1640, 10% FBS) and determine cell density.

(2) Seeded cells @10,000 cells/well in 96-well (flat bottom) tissue culture plates (36,000 cells/cm$^2$). Added growth media to a final volume of 200 uL/well and incubated overnight at 37° C.

Day 2: Cell Treatment (1) Prepared compound dilutions (1000× in DMSO) as follows. Starting with a stock of 5 mM compound in DMSO, diluted serially 3-fold in DMSO for a total of eight concentrations (5 mM, 1.67 mM, 0.556 mM, 0.185 mM, 0.062 mM, 0.021 mM, 0.007 mM, 0.002 mM).

(2) Prepared compound-containing media by adding 1 mL treatment media (100% RPMI 1640 without FBS) to 1 µL of compound dilution (from step 3).

(3) Removed plates (from step 2) from incubator. Aspirated media and replace with 150 µL compound-containing media. Incubate for 1-2 hr at 37° C.

(4) Removed plates (from step 5) from incubator and treated each as follows: aspirated compound-containing media and replaced with 300 µL ice-cold 1×PBS, aspirated PBS and replaced with 45 µL lysis buffer (Biorad Bio-Plex lysis buffer containing 0.4% v/v lysis buff. Factor 1, 0.2% v/v lysis buff. Factor 2, and PMSF to 2 mM final concentration), and then placed plate on ice until all plates were treated.

(5) After all plates were processed (step 6), placed plates on an orbital shaker and shook at room temperature for at least 15 min.

(6) Finally, removed plates from shaker, and transferred 40 µL/well of lysate from each to new corresponding 96-well V-bottom plates. At this point, samples may be frozen and stored @–80° C.

Day 2: Bioplex Assay (1) Thaw (if necessary) plates (from step 8) and added 40 µL of Phospho-Protein Assay Buffer to each 40 µL lysate for a 1:1 dilution.

(2) Prepared phospho-EEK1,2 Bioplex beads by diluting 1:50 with Bioplex Wash Buffer (mixing 49 µL Wash Buffer with 1 µL of phospho-EEK1,2 Bioplex beads for each sample to be analyzed). Protected from light by wrapping tube in aluminum foil and kept at room temperature.

(3) Prepared Filter Plate by adding 100 µL/well Bioplex Wash Buffer and removed by vacuum filtration.

(4) Add 50 µL of bead solution (from step 10) to each well of a prepared Filter Plate (from step 11) and vacuum filter. Wash/filter 2× with 100 µL/well Wash Buffer.

(5) Added 50 µL of each lysate to appropriate well of the Filter Plate (from step 12). For this and all subsequent plate incubation steps, placed plate on an inverted plate cover (reduces background), and wrapped in aluminum foil (to protect from light). Shook overnight at room temperature. Included positive (control lysate) and negative (lysis buffer) controls.

Day 3: Bioplex Assay Continued (1) Prepared detection antibody (phospho-EEK1,2 Ab) by diluting 1:25 with Detection Antibody Dilution Buffer (mixing 24 µL Detection Antibody Dilution Buffer with 1 µL of phospho-EEK1,2 Ab for each sample to be analyzed).

(2) Removed plate (from step 13) from shaker and vacuum filter. Washed/filter plate 3× with 100 µL/well Wash Buffer. Added 25 µL of diluted antibody to each well. Incubated on shaker at RT for 30-45 min.

(3) Prepared streptavidin-PE by diluting 1:100 with Wash Buffer (mixing 49.5 µL Wash Buffer with 0.5 µL of 100× streptavidin-PE for each sample to be analyzed). Protected from light.

(4) Removed plate (from step 15) from shaker and vacuum filter. Washed/filter plate 3× with 100 µL/well Wash Buffer. Add 50 µL of diluted streptavidin-PE solution (from step 16) to each sample well. Incubated on shaker for 10-20 min.

(5) Removed plate from shaker and vacuum filter. Wash/filter plate 3× with 100 µL/well Bead Resuspension Buffer. After last wash resuspended beads in 125 µL Bead Resuspension Buffer. Place plate on shaker for 2-3 minutes to ensure beads are well resuspended.

(6) Quantified phospho-ERK by reading plate in the Bio-Plex plate reader (run start-up and calibration programs before this step) using bead region 38 (pEEK1,2) and counting 50 beads per region.

WM-266-4 cells were seeded at a density of 10,000 cells/well in RPMI 1640 cell culture media containing 10% FBS in a 96-well flat bottom and incubated overnight at 37° C. Inhibitors were diluted 3-fold in DMSO, added to serum free RPMI 1640 cell culture media to a final concentration range of 5 µM to 2 nM, and used to treat the previously seeded WM-266-4 cells for 1-2 hr at 37° C. Cells were washed with ice-cold PBS, treated with 45 µl of lysis buffer (Bio-Rad Bio-Plex Lysis Buffer, Cat #171-304011, containing 0.4% v/v lysis buffer factor 1, 0.2% v/v lysis buffer Factor 2, and 2 mM PMSF) for 15 minutes on an orbital shaker at room temperature. Phosphorylated ERK was detected using a phospho-ERK Bioplex kit (Bio-Rad, Cat #171-304011) per the manufacturer's instructions and detected on a Bio-Plex plate reader counting 50 beads per region.

Certain compounds of the present invention were assayed using the above Cellular Assay for Raf Kinase Activity and were found to be inhibitors of Raf kinase.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I:

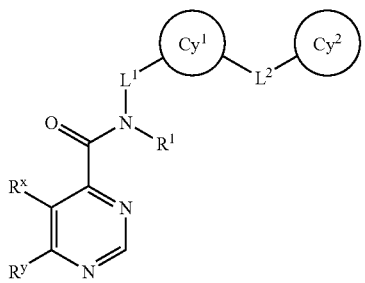

or a pharmaceutically acceptable salt thereof, wherein:
$Cy^1$ is an optionally substituted phenyl or an optionally substituted 5-6 membered partially unsaturated or aromatic ring having 1-3 heteroatoms independently selected from nitrogen, oxygen, or sulfur;
$Cy^2$ is an optionally substituted 5-10 membered saturated, partially unsaturated, or aromatic monocyclic or bicyclic ring having 0-4 heteroatoms, independently selected from nitrogen, oxygen, or sulfur;
$L^1$ is a direct bond or an optionally substituted, straight or branched $C_{1-6}$ alkylene chain;
$L^2$ is a direct bond, or is an optionally substituted, straight or branched $C_{1-6}$ alkylene chain wherein 1 or 2 methylene units of $L^2$ are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or a 3-6 membered cycloalkylene;
each R is independently hydrogen or an optionally substituted $C_{1-6}$ aliphatic group;
$R^1$ is hydrogen or an optionally substituted $C_{1-6}$ aliphatic group; and
$R^x$ and $R^y$ are taken together with their intervening atoms to form:
(a) a 5-membered partially unsaturated or aromatic fused ring having 0-3 heteroatoms independently selected from nitrogen, oxygen, or sulfur, or
(b) a 7-membered partially unsaturated fused ring having 0-3 heteroatoms independently selected from nitrogen, oxygen, or sulfur,
wherein any substitutable carbon on the ring formed by $R^x$ and $R^y$ is optionally substituted with —$R^2$, oxo, -halo, —NO$_2$, —CN, —OR$^2$, —SR$^2$, —N(R$^3$)$_2$, —C(O)R$^2$, —CO$_2$R$^2$, C(O)C(O)R$^2$, —C(O)CH$_2$C(O)R$^2$, —S(O)R$^2$, —S(O)$_2$R$^2$, —C(O)N(R$^3$)$_2$, —SO$_2$N(R$^3$)$_2$, —OC(O)R$^2$, —N(R$^3$)C(O)R$^2$, —N(R$^3$)N(R$^3$)$_2$, —C=NN(R$^3$)$_2$, —C=NOR$^2$, —N(R$^3$)C(O)N(R$^3$)$_2$, —N(R$^3$)SO$_2$N(R$^3$)$_2$, —N(R$^3$)SO$_2$R$^2$, or —OC(O)N(R$^3$)$_2$, and
wherein any substitutable nitrogen on the ring formed by $R^x$ and $R^y$ is optionally substituted with —$R^2$, —C(O)R$^2$, —CO$_2$R$^2$, C(O)C(O)R$^2$, —C(O)CH$_2$C(O)R$^2$, —S(O)R$^2$, —S(O)$_2$R$^2$, —C(O)N(R$^3$)$_2$, —SO$_2$N(R$^3$)$_2$, —OC(O)R$^2$, or —OC(O)N(R$^3$)$_2$;
each $R^2$ is independently hydrogen or an optionally substituted group selected from $C_{1-6}$ aliphatic, a $C_{6-10}$ monocyclic or bicyclic aryl ring, or a 5-10 membered saturated, partially unsaturated, or aromatic monocyclic or bicyclic ring having 1-4 heteroatoms independently selected from nitrogen, oxygen, or sulfur; and
each $R^3$ is independently $R^2$, or two $R^3$ on the same nitrogen are taken together with the nitrogen to form an optionally substituted 5-8 membered saturated, partially unsaturated, or aromatic ring having 1-4 heteroatoms independently selected from nitrogen, oxygen, or sulfur.

2. The compound according to claim 1, wherein $R^x$ and $R^y$ are taken together with their intervening atoms to form a 5-membered partially unsaturated or aromatic fused ring having 0-3 heteroatoms independently selected from nitrogen, oxygen, or sulfur.

3. The compound according to claim 2, wherein $R^x$ and $R^y$ are taken together with their intervening atoms to form a 5-membered partially unsaturated fused ring having 1-3 heteroatoms independently selected from nitrogen, oxygen, or sulfur.

4. The compound according to claim 3, wherein $R^x$ and $R^y$ are taken together with their intervening atoms to form a 5-membered aromatic fused ring having 1-3 heteroatoms independently selected from nitrogen, oxygen, or sulfur.

5. The compound according to claim 4, wherein $R^x$ and $R^y$ are taken together with their intervening atoms to form an optionally substituted imidazolidinone or pyrrolidinone ring.

6. The compound according to claim 5, wherein $R^x$ and $R^y$ are taken together with their intervening atoms to form a pyrrolo, pyrazolo, imidazolo, triazolo, thiopheno, furano, thiazolo, isothiazolo, thiadiazolo, oxazolo, isoxazolo, or oxadiaziolo fused ring.

7. The compound according to claim 1, wherein $R^x$ and $R^y$ are taken together with their intervening atoms to form a 7-membered partially unsaturated fused ring having 0-3 heteroatoms independently selected from nitrogen, oxygen, or sulfur.

8. The compound according to claim 7, wherein $R^x$ and $R^y$ are taken together with their intervening atoms to form a 7-membered partially unsaturated fused ring having 1-3 heteroatoms independently selected from nitrogen, oxygen, or sulfur.

9. The compound according to claim 8, wherein $R^x$ and $R^y$ are taken together with their intervening atoms to form a 7-membered partially unsaturated fused ring having 1-2 nitrogen atoms.

10. The compound according to claim 9, wherein $R^x$ and $R^y$ are taken together with their intervening atoms to form an azepino, diazepino, azepinono, or diazepinono fused ring.

11. The compound according to claim 1, wherein $R^1$ is hydrogen and $L^1$ is an optionally substituted, straight or branched $C_{1-4}$ alkylene chain.

12. The compound according to claim 11, wherein $L^1$ is an optionally substituted, branched $C_{1-4}$ alkylene chain.

13. The compound according to claim 1, wherein $Cy^1$ is an optionally substituted 5-membered saturated, partially unsaturated, or aromatic ring having 1-4 heteroatoms independently selected from nitrogen, oxygen, or sulfur.

14. The compound according claim 13, wherein $Cy^1$ is an optionally substituted pyrrolyl, pyrazolyl, imidazolyl, triazolyl, tetrazolyl, thiophenyl, furanyl, thiazolyl, isothiazolyl, thiadiazolyl, oxazolyl, isoxazolyl, or oxadiaziolyl group.

15. The compound according to claim 1, wherein $L^2$ is a direct bond or an optionally substituted, straight or branched $C_{1-4}$ alkylene chain wherein 1 or 2 methylene units of $L^2$ are replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, or —C(O)O—.

16. The compound according to claim 15, wherein $L^2$ is a direct bond.

17. The compound according to claim 15, wherein $L^2$ is —C(O)N(R)—, —N(R)C(O)—, —SO$_2$N(R)—, —N(R)SO$_2$—, —OC(O)—, or —C(O)O—.

18. The compound according to claim 17, wherein $L^2$ is —C(O)N(H)— or —N(H)C(O)—.

19. The compound according to claim 1, wherein $Cy^2$ is an optionally substituted group selected from:
   (a) a 5-membered saturated, partially unsaturated, or aromatic monocyclic ring having 1-3 heteroatoms, independently selected from nitrogen, oxygen, or sulfur;
   (b) phenyl or a 6-membered saturated, partially unsaturated, or aromatic monocyclic ring having 1-4 heteroatoms, independently selected from nitrogen, oxygen, or sulfur; or
   (c) a 5-10 membered saturated, partially unsaturated, or aromatic bicyclic ring having 0-4 heteroatoms, independently selected from nitrogen, oxygen, or sulfur.

20. The compound according to claim 19, wherein $Cy^2$ is an optionally substituted group selected from:
   (a) a 5-membered heteroaryl ring having 1-3 heteroatoms, independently selected from nitrogen, oxygen, or sulfur;
   (b) phenyl or a 6-membered heteroaryl ring having 1-3 nitrogen atoms; or
   (c) a 5,6-fused bicyclic heteroaryl ring having 1-4 heteroatoms selected from oxygen, sulfur or nitrogen.

21. The compound according to claim 20, wherein $Cy^2$ is an optionally substituted group selected from phenyl, pyrrolyl, pyrazolyl, imidazolyl, triazolyl, tetrazolyl, thiophenyl, furanyl, thiazolyl, isothiazolyl, thiadiazolyl, oxazolyl, isoxazolyl, oxadiazolyl, pyridinyl, pyrimidinyl, pyrazinyl, pyridazinyl, triazinyl, tetrazinyl, pyyrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl.

22. A compound of formula II:

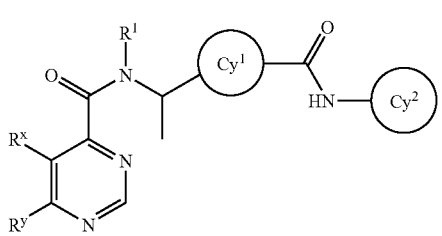

or a pharmaceutically acceptable salt thereof, wherein:
   each of $R^1$, $R^x$, and $R^y$ is as defined above and described in classes and subclasses herein;
   $Cy^1$ is an optionally substituted 5-6 membered saturated, partially unsaturated, or aromatic ring having 1-3 heteroatoms independently selected from nitrogen, oxygen, or sulfur; and
   $Cy^2$ is optionally substituted phenyl or an optionally substituted 6-membered aromatic ring having 1-3 nitrogen atoms.

23. The compound according to claim 22, wherein said compound is of formula II-a or II-b:

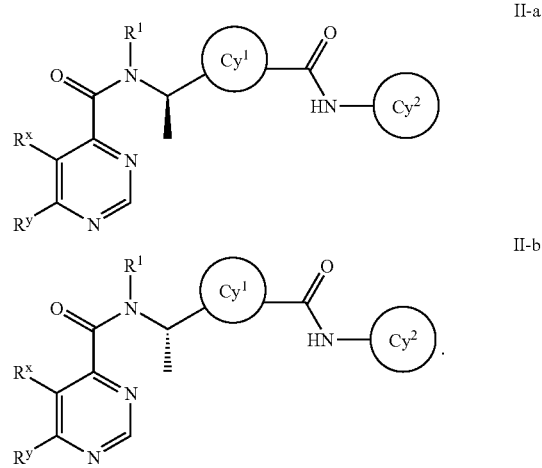

24. The compound according to claim 22, wherein $Cy^1$ is a 5-membered heteroaryl ring having 1-3 heteroatoms independently selected from nitrogen, oxygen, or sulfur.

25. The compound according to claim 23, wherein $Cy^1$ is a 5-membered heteroaryl ring having 1-3 heteroatoms independently selected from nitrogen, oxygen, or sulfur.

26. A compound of formula IV:

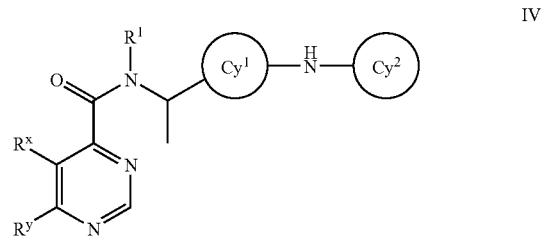

or a pharmaceutically acceptable salt thereof, wherein:
   $Cy^1$ is an optionally substituted 5-6 membered saturated, partially unsaturated, or aromatic ring having 1-3 heteroatoms independently selected from nitrogen, oxygen, or sulfur; and
   $Cy^2$ is optionally substituted phenyl or an optionally substituted 6-membered aromatic ring having 1-4 nitrogen atoms.

27. The compound according to claim 26, wherein said compound is of formula IV-a or IV-b:

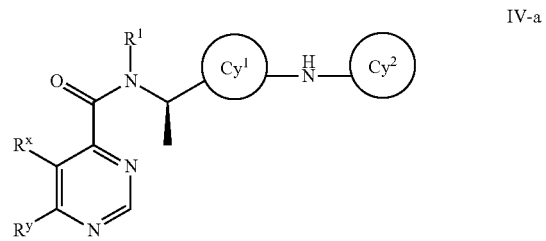

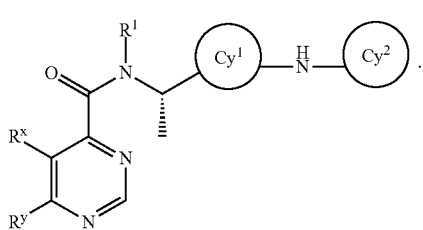

IV-b

28. The compound according to claim 27, wherein Cy¹ is a 5-membered heteroaryl ring having 1-3 heteroatoms independently selected from nitrogen, oxygen, or sulfur.

29. The compound according to claim 1, wherein said compound is selected from those depicted in Table 1, Table 2, Table 3, Table 4, or Table 5, or a pharmaceutically acceptable salt thereof.

30. A pharmaceutical composition comprising a compound according to claim 1 and a pharmaceutically acceptable carrier, adjuvant, or vehicle.

31. The composition of claim 30, in combination with a therapeutic agent selected from a chemotherapeutic or antiproliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

* * * * *